US010426967B2

(12) United States Patent
Pilla et al.

(10) Patent No.: US 10,426,967 B2
(45) Date of Patent: Oct. 1, 2019

(54) APPARATUS AND METHOD FOR ELECTROMAGNETIC TREATMENT OF NEUROLOGICAL INJURY OR CONDITION CAUSED BY A STROKE

(71) Applicant: Endonovo Therapeutics, Inc., Woodland Hills, CA (US)

(72) Inventors: Arthur A. Pilla, Oakland, NJ (US); Andre' A. Dimino, Woodcliff Lake, NJ (US); Iyer Viswanathan, Santa Clara, CA (US); Diana Casper, New York, NY (US); Berish Strauch, Rye, NY (US)

(73) Assignee: Endonovo Technology, Inc., Woodland Hills, CA (US)

( * ) Notice: Subject to any disclaimer, the term of this patent is extended or adjusted under 35 U.S.C. 154(b) by 0 days.

(21) Appl. No.: 15/217,855

(22) Filed: Jul. 22, 2016

(65) Prior Publication Data
US 2017/0165496 A1 Jun. 15, 2017

Related U.S. Application Data

(63) Continuation of application No. 14/171,553, filed on Feb. 3, 2014, now Pat. No. 9,440,089, which is a
(Continued)

(51) Int. Cl.
*A61N 2/00* (2006.01)
*A61N 1/36* (2006.01)

(52) U.S. Cl.
CPC .......... *A61N 2/006* (2013.01); *A61N 1/36014* (2013.01); *A61N 1/36025* (2013.01); *A61N 2/004* (2013.01)

(58) Field of Classification Search
CPC ... A61N 2/00; A61N 2/06; A61N 2/12; A61N 2/004; A61N 2/006; A61N 2/008;
(Continued)

(56) References Cited

U.S. PATENT DOCUMENTS

| 5,441,495 A * | 8/1995 | Liboff | A61N 2/02 600/13 |
| 6,463,336 B1 * | 10/2002 | Mawhinney | A61N 1/40 600/14 |

(Continued)

FOREIGN PATENT DOCUMENTS

WO WO-2010017249 A1 * 2/2010 ............. A61N 2/006

OTHER PUBLICATIONS

Rohde et al. "Effects of Pulsed Electromagnetic Fields on Interleukin-1β and Postoperative Pain: A Double-Blind, Placebo-Controlled, Pilot Study in Breast Reduction Patients" Plastic and Reconstructive Surgery (Jun. 2010), pp. 1-10.*

(Continued)

*Primary Examiner* — Kaylee R Wilson
(74) *Attorney, Agent, or Firm* — Roland J. Tong; Manning & Kass Ellrod Ramirez Trester LLP

(57) ABSTRACT

Described herein are methods of treating neurological injury and conditions, in particular symptoms and complications arising from or caused by a stroke. These treatment methods can include the steps of generating a pulsed electromagnetic field from a pulsed electromagnetic field source and applying the pulsed electromagnetic field in proximity to a target region.

9 Claims, 93 Drawing Sheets

Related U.S. Application Data continuation-in-part of application No. 13/252,114, filed on Oct. 3, 2011, now Pat. No. 9,427,598, said application No. 14/171,553 is a continuation-in-part of application No. 13/801,789, filed on Mar. 13, 2013, now abandoned, which is a continuation of application No. 12/819,956, filed on Jun. 21, 2010, now abandoned, which is a continuation-in-part of application No. 12/772,002, filed on Apr. 30, 2010, now abandoned, which is a continuation of application No. 11/003,108, filed on Dec. 3, 2004, now Pat. No. 7,744,524, said application No. 12/819,956 is a continuation-in-part of application No. 11/114,666, filed on Apr. 26, 2005, now Pat. No. 7,740,574, said application No. 12/819,956 is a continuation-in-part of application No. 11/110,000, filed on Apr. 19, 2005, now abandoned, said application No. 12/819,956 is a continuation-in-part of application No. 11/369,308, filed on Mar. 6, 2006, now abandoned, said application No. 12/819,956 is a continuation-in-part of application No. 11/369,309, filed on Mar. 6, 2006, now abandoned, said application No. 12/819,956 is a continuation-in-part of application No. 11/223,073, filed on Sep. 10, 2005, now Pat. No. 7,758,490, and a continuation-in-part of application No. 11/339,204, filed on Jan. 25, 2006, now abandoned, and a continuation-in-part of application No. 11/818,065, filed on Jun. 12, 2007, now abandoned, said application No. 12/819,956 is a continuation-in-part of application No. 11/903,294, filed on Sep. 20, 2007, now abandoned, said application No. 12/819,956 is a continuation-in-part of application No. 11/977,043, filed on Oct. 22, 2007, now abandoned.

(60) Provisional application No. 61/389,038, filed on Oct. 1, 2010, provisional application No. 61/456,310, filed on Nov. 4, 2010, provisional application No. 60/527,327, filed on Dec. 5, 2003, provisional application No. 60/564,887, filed on Apr. 26, 2004, provisional application No. 60/563,104, filed on Apr. 19, 2004, provisional application No. 60/658,967, filed on Mar. 7, 2005, provisional application No. 60/658,968, filed on Mar. 7, 2005, provisional application No. 60/812,841, filed on Jun. 12, 2006, provisional application No. 60/846,126, filed on Sep. 20, 2006, provisional application No. 60/852,927, filed on Oct. 20, 2006.

(58) Field of Classification Search
CPC .. A61N 1/36039; A61N 1/36025; A61N 1/40; A61N 1/36103; A61N 1/36082; A61N 2005/0645
See application file for complete search history.

(56) References Cited

U.S. PATENT DOCUMENTS

2009/0326315 A1* 12/2009 Nishi .................... A61N 2/004
  600/14
2010/0121407 A1* 5/2010 Pfaff .................. A61N 1/36082
  607/45

OTHER PUBLICATIONS

Czosnyka et al. "Monitoring and interpretation of intracranial pressure" J. Neurolo. Neurosurg. Psychiatry (2004) 75:813-821.*

* cited by examiner

*significantly different than null group, p<0.02

PMF pre-treatment increases neuronal survival after serum withdrawl.

Specific PMF signals increase neuronal survival after serum reduction

Chronic PMF partially protects dopaminergic neurons against 6-OHDA toxicity

Establishing baseline thermal fluctuations in voltage and electrical impedance at a respiratory target pathway structure. — Step 63101

Configuring at least one waveform to have sufficient signal to noise ratio to modulate at least one of ion and ligand interactions whereby the at least one of ion and ligand interactions are detectable in the respiratory target pathway structure above the established baseline thermal fluctuations in voltage and electrical impedance. — Step 63102

Generating an electromagnetic signal from the configured at least one waveform. — Step 63103

Coupling the electromagnetic signal to the respiratory target pathway structure using a coupling device. — Step 63104

FIG. 63

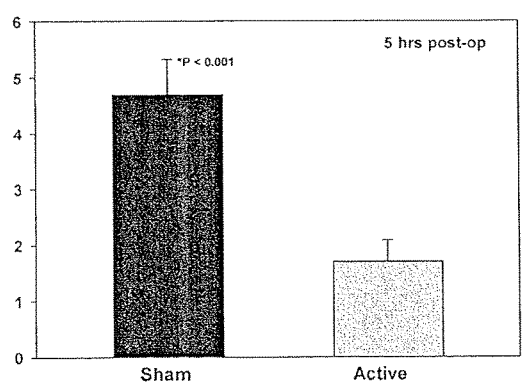
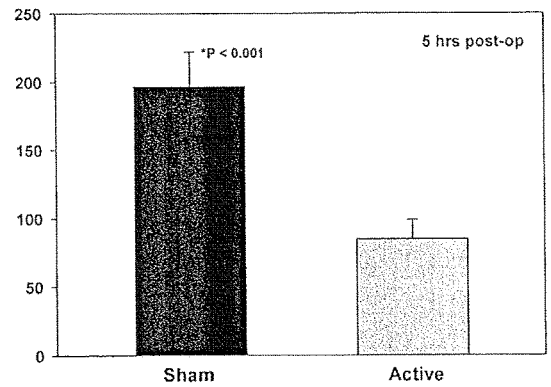
FIG. 83A
FIG. 83B

FIG. 86A
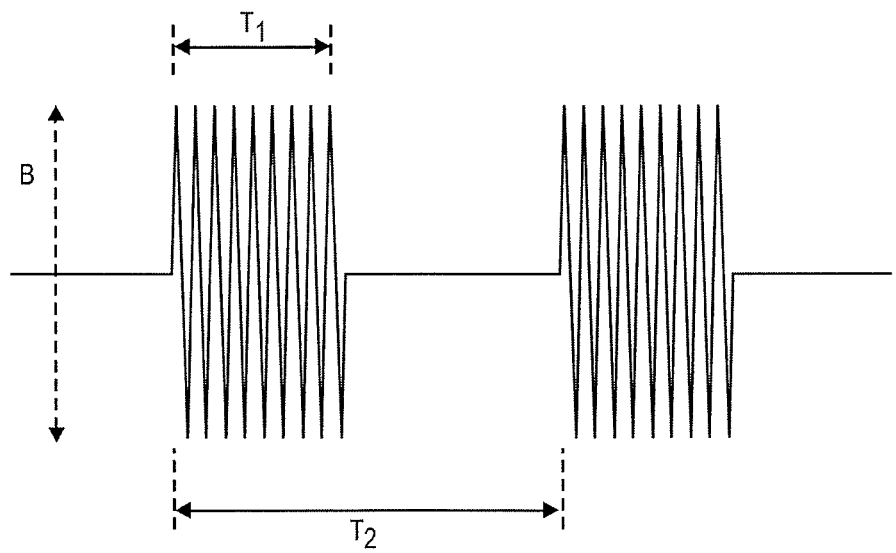
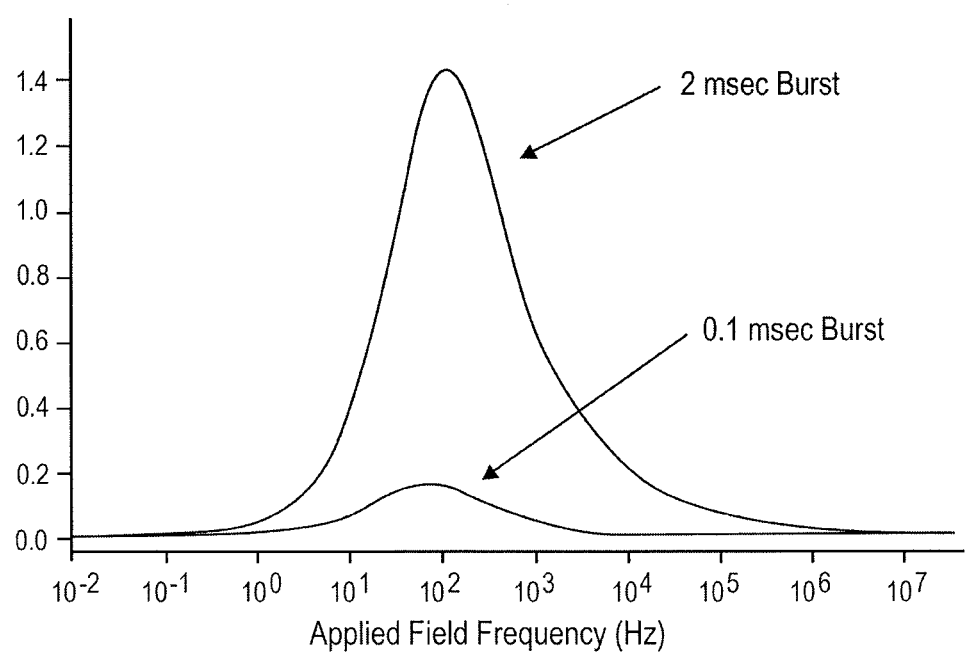
FIG. 86B

APPARATUS AND METHOD FOR ELECTROMAGNETIC TREATMENT OF NEUROLOGICAL INJURY OR CONDITION CAUSED BY A STROKE

CROSS REFERENCE TO RELATED APPLICATIONS

This application is a continuation of U.S. patent application Ser. No. 14/171,553, filed on Feb. 3, 2014, entitled "APPARATUS AND METHOD FOR ELECTROMAGNETIC TREATMENT OF NEUROLOGICAL INJURY OR CONDITION CAUSED BY A STROKE," Publication No. US-2014-0213843-A1, which is a continuation-in-part of U.S. patent application Ser. No. 13/252,114, filed on Oct. 3, 2011, entitled "METHOD AND APPARATUS FOR ELECTROMAGNETIC TREATMENT OF HEAD, CEREBRAL AND NEURAL INJURY IN ANIMALS AND HUMANS," Publication No. US-2012-0116149-A1, which claims the benefit under 35 U.S.C. § 119 of U.S. Provisional Application No. 61/389,038 filed on Oct. 1, 2010 and U.S. Provisional Application No. 61/456,310 filed on Nov. 4, 2010, the disclosures of which are incorporated by reference as if fully set forth herein.

U.S. patent application Ser. No. 14/171,553 is also a continuation-in-part of U.S. patent application Ser. No. 13/801,789 filed on Mar. 13, 2013, entitled "APPARATUS AND METHOD FOR ELECTROMAGNETIC TREATMENT," Publication No. US-2013-0274540-A1, which is a continuation of U.S. patent application Ser. No. 12/819,956, filed on Jun. 21, 2010, entitled "APPARATUS AND METHOD FOR ELECTROMAGNETIC TREATMENT," Publication No. US-2011-0112352-A1, which is a continuation-in-part of U.S. patent application Ser. No. 12/772,002, filed on Apr. 30, 2010, entitled "APPARATUS AND METHOD FOR ELECTROMAGNETIC TREATMENT OF PLANT, ANIMAL AND HUMAN TISSUE, ORGANS, CELLS AND MOLECULES," Publication No. US-2010-0222631-A1, which is a continuation of U.S. patent application Ser. No. 11/003,108, filed on Dec. 3, 2004, entitled "APPARATUS AND METHOD FOR ELECTROMAGNETIC TREATMENT OF PLANT, ANIMAL, AND HUMAN TISSUE, ORGANS, CELLS, AND MOLECULES," now U.S. Pat. No. 7,744,524, which claims the benefit under 35 U.S.C. § 119 of U.S. Provisional Patent Application No. 60/527,327, filed on Dec. 5, 2003, entitled "APPARATUS AND METHOD FOR ELECTROMAGNETIC TREATMENT OF PLANT, ANIMAL, AND HUMAN TISSUE, ORGANS, CELLS AND MOLECULES."

U.S. patent application Ser. No. 12/819,956 is also a continuation-in-part of U.S. patent application Ser. No. 11/114,666, filed on Apr. 26, 2005, entitled "ELECTROMAGNETIC TREATMENT INDUCTION APPARATUS AND METHOD FOR USING SAME," now U.S. Pat. No. 7,740,574, which claims the benefit under 35 U.S.C. § 119 of U.S. Provisional Patent Application No. 60/564,887, filed on Apr. 26, 2004, entitled "INDUCTION MEANS FOR THERAPEUTICALLY TREATING HUMAN AND ANIMAL CELLS, TISSUES AND ORGANS WITH ELECTROMAGNETIC FIELDS."

U.S. patent application Ser. No. 12/819,956 is also a continuation-in-part of U.S. patent application Ser. No. 11/110,000, filed on Apr. 19, 2005, entitled "ELECTROMAGNETIC TREATMENT APPARATUS AND METHOD FOR ANGIOGENESIS MODULATION OF LIVING TISSUES AND CELLS," Publication No. US-2005-0251229-A1, which claims the benefit under 35 U.S.C. § 119 of U.S. Provisional Patent Application No. 60/563,104, filed on Apr. 19, 2004, entitled "APPARATUS AND METHOD FOR THERAPEUTICALLY TREATING HUMAN AND ANIMAL CELLS, TISSUES AND ORGANS WITH ELECTROMAGNETIC FIELDS."

U.S. patent application Ser. No. 12/819,956 is also a continuation-in-part of U.S. patent application Ser. No. 11/369,308, filed on Mar. 6, 2006, entitled "ELECTROMAGNETIC TREATMENT APPARATUS FOR AUGMENTING WOUND REPAIR AND METHOD FOR USING SAME," Publication No. US-2006-0212077-A1, which claims the benefit under 35 U.S.C. § 119 of U.S. Provisional Patent Application No. 60/658,967, filed on Mar. 7, 2005, entitled "APPARATUS AND METHOD FOR THERAPEUTICALLY TREATING HUMAN, ANIMAL, AND PLANT CELLS, TISSUES, ORGANS, AND MOLECULES WITH ELECTROMAGNETIC FIELDS FOR WOUND REPAIR."

U.S. patent application Ser. No. 12/819,956 is also a continuation-in-part of U.S. patent application Ser. No. 11/369,309, filed on Mar. 6, 2006, entitled "ELECTROMAGNETIC TREATMENT APPARATUS FOR ENHANCING PHARMACOLOGICAL, CHEMICAL AND TOPICAL AGENT EFFECTIVENESS AND METHOD FOR USING SAME," Publication No. US-2007-0026514-A1, which claims the benefit under 35 U.S.C. § 119 of U.S. Provisional Patent Application No. 60/658,968, filed on Mar. 7, 2005, entitled "APPARATUS AND METHOD FOR TREATING HUMAN, ANIMAL AND PLANT CELLS, TISSUES, ORGANS AND MOLECULES WITH ELECTROMAGNETIC FIELDS BY ENHANCING THE EFFECTS OF PHARMACOLOGICAL, CHEMICAL, COSMETIC AND TOPICAL AGENTS."

U.S. patent application Ser. No. 12/819,956 is also a continuation-in-part of U.S. patent application Ser. No. 11/223,073, filed on Sep. 10, 2005, entitled "INTEGRATED COIL APPARATUS FOR THERAPEUTICALLY TREATING HUMAN AND ANIMAL CELLS, TISSUES AND ORGANS WITH ELECTROMAGNETIC FIELDS AND METHOD FOR USING SAME," now U.S. Pat. No. 7,758,490.

U.S. patent application Ser. No. 12/819,956 is also a continuation-in-part of U.S. patent application Ser. No. 11/339,204, filed on Jan. 25, 2006, entitled "SELF-CONTAINED ELECTROMAGNETIC APPARATUS FOR TREATMENT OF MOLECULES, CELLS, TISSUES, AND ORGANS WITHIN A CEREBROFACIAL AREA AND METHOD FOR USING SAME," Publication No. US-2007-0173904-A1, now abandoned.

U.S. patent application Ser. No. 12/819,956 is also a continuation-in-part of U.S. patent application Ser. No. 11/818,065, filed on Jun. 12, 2007, entitled "ELECTROMAGNETIC APPARATUS FOR PROPHYLAXIS AND REPAIR OF OPHTHALMIC TISSUE AND METHOD FOR USING SAME," Publication No. US-2008-0058793-A1, which claims the benefit under 35 U.S.C. § 119 of U.S. Provisional Patent Application No. 60/812,841, filed on Jun. 12, 2006, entitled "APPARATUS AND METHOD FOR THERAPEUTICALLY TREATING HUMAN AND ANIMAL CELLS, TISSUES, ORGANS AND MOLECULES WITH ELECTROMAGNETIC FIELDS FOR TREATMENT OF DISEASES OF THE EYE AND PROPHYLACTIC TREATMENT OF THE EYE."

U.S. patent application Ser. No. 12/819,956 is also a continuation-in-part of U.S. patent application Ser. No. 11/903,294, filed on Sep. 20, 2007, entitled "ELECTRO- MAGNETIC APPARATUS FOR RESPIRATORY DISEASE AND METHOD FOR USING SAME," Publication No. US-2008-0132971-A1, which claims the benefit under 35 U.S.C. § 119 of U.S. Provisional Patent Application No. 60/846,126, filed on Sep. 20, 2006, entitled "APPARATUS AND METHOD FOR THE TREATMENT OF DISEASES OF THE LUNGS WITH ELECTROMAGNETIC FIELDS."

U.S. patent application Ser. No. 12/819,956 is also a continuation-in-part of U.S. patent application Ser. No. 11/977,043, filed on Oct. 22, 2007, entitled "APPARATUS AND METHOD FOR THE TREATMENT OF EXCESSIVE FIBROUS CAPSULE FORMATION AND CAPSULAR CONTRACTURE WITH ELECTROMAGNETIC FIELDS," Publication No. US-2008-0140155-A1, which claims the benefit under 35 U.S.C. § 119 of U.S. Provisional Patent Application No. 60/852,927, filed on Oct. 20, 2006, entitled "APPARATUS AND METHOD FOR THE TREATMENT OF EXCESSIVE FIBROUS CAPSULE FORMATION AND CAPSULAR CONTRACTURE WITH ELECTROMAGNETIC FIELDS."

This application is related to U.S. patent application Ser. No. 14/171,613, filed on Feb. 3, 2014, entitled "APPARATUS AND METHOD FOR ELECTROMAGNETIC TREATMENT OF NEURODEGENERATIVE CONDITIONS," Publication No. US-2014-0221726-A1 and U.S. patent application Ser. No. 14/171,644, filed on Feb. 3, 2014, entitled "APPARATUS AND METHOD FOR ELECTROMAGNETIC TREATMENT OF NEUROLOGICAL PAIN," Publication No. US-2014-0213844-A1.

Each of the above applications are herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Field of the Invention

This invention pertains generally to an apparatus and a method for in vitro and in vivo therapeutic and prophylactic treatment of plant, animal, and human tissue, organs, cells and molecules. In particular, an embodiment according to the present invention pertains to use of non-thermal time-varying magnetic fields configured for optimal coupling to target pathway structures such as molecules, cells, tissue, and organs, using power and amplitude comparison analysis to evaluate a signal to thermal noise ratio ("SNR") in the target pathway structure. Another embodiment according to the present invention pertains to application of bursts of arbitrary waveform electromagnetic signals to target pathway structures such as molecules, cells, tissues, and organs using ultra lightweight portable coupling devices such as inductors and electrodes, and driver circuitry that can be incorporated into a positioning device such as knee, elbow, lower back, shoulder, foot, and other anatomical wraps, as well as apparel such as garments, footware, and fashion accessories.

Yet another embodiment according to the present invention pertains to application of steady state periodic signals of arbitrary waveform electromagnetic signals to target pathway structures such as molecules, cells, tissues, and organs. Examples of therapeutic and prophylactic applications of the present invention are musculoskeletal pain relief, edema reduction, increased local blood flow, microvascular blood perfusion, wound repair, bone repair, osteoporosis treatment and prevention, angiogenesis, neovascularization, enhanced immune response, tissue repair, enhanced transudation, and enhanced effectiveness of pharmacological agents. An embodiment according to the present invention can also be used in conjunction with other therapeutic and prophylactic procedures and modalities such as heat, cold, ultrasound, vacuum assisted wound closure, wound dressing, orthopedic fixation devices, and surgical interventions.

This invention may also pertain generally to an electromagnetic treatment induction apparatus and a method for using same to achieve modification of cellular and tissue growth, repair, maintenance, and general behavior by application of encoded electromagnetic information. More particularly this invention relates to the application of surgically non-invasive coupling of highly specific electromagnetic signal patterns to any number of body parts. In particular, an embodiment according to the present invention pertains to using an induction means such as a coil to deliver pulsing electromagnetic fields ("PEMF") to enhance living tissue growth and repair in conjunction with devices such as supports, wraps, beds, and wheelchairs, and in conjunction with other therapeutic and wellness physical modalities, such as ultrasound, negative or positive pressure, heat, cold, massage.

This invention may also pertain generally to an apparatus and a method for treatment of living tissues and cells by altering their interaction with their electromagnetic environment. This invention also relates to a method of modification of cellular and tissue growth, repair, maintenance, and general behavior by application of encoded electromagnetic information. More particularly this invention relates to the application of surgically non-invasive coupling of highly specific electromagnetic signal patterns to any number of body parts. In particular, an embodiment according to the present invention pertains to using pulsing electromagnetic fields ("PEMF") to enhance living tissue growth and repair via angiogenesis and neovascularization by affecting the precursors to growth factors and other cytokines, such as ion/ligand binding such as calcium binding to calmodoulin.

This invention may also generally relate to augmenting wound repair in humans, plants, and animals by altering the interaction with the electromagnetic environment of living tissues, cells, and molecules. The invention also relates to a method of modification of cellular and tissue growth, repair, maintenance and general behavior by the application of encoded electromagnetic information. More particularly, this invention provides for an application of highly specific electromagnetic frequency ("EMF") signal patterns to one or more body parts by surgically non-invasive reactive coupling of encoded electromagnetic information. Such application of electromagnetic waveforms to human, animal, and plant target pathway structures such as cells, organs, tissues and molecules, can serve to enhance wound repair.

The use of most low frequency EMF has been in conjunction with applications of bone repair and healing. As such, EMF waveforms and current orthopedic clinical use of EMF waveforms comprise relatively low frequency components and are of a very low power, inducing maximum electrical fields in a millivolts per centimeter (mV/cm) range at frequencies under five KHz. A linear physicochemical approach employing an electrochemical model of cell membranes to predict a range of EMF waveform patterns for which bioeffects might be expected is based upon an assumption that cell membranes, and specifically ion binding at structures in or on cell membranes, are a likely EMF target. Therefore, it is necessary to determine a range of waveform parameters for which an induced electric field could couple electrochemically at a cellular surface, such as by employing voltage-dependent kinetics. Extension of this linear model involves Lorentz force considerations that eventually demonstrated that the magnetic component of EMF could play a significant role in EMF therapeutics. This led to the ion cyclotron resonance and quantum models that predicts benefits from combined AC and DC magnetic field effects at very low frequency ranges.

The within invention is based upon biophysical and animal studies that attribute effectiveness of cell-to-cell communication on tissue structures' sensitivity to induced voltages and associated currents. A mathematical analysis using at least one of a Signal to Noise Ratio ("SNR") and a Power Signal to Noise Ratio ("Power SNR") evaluates whether EMF signals applied to target pathway structures such as cells, tissues, organs, and molecules, are detectable above thermal noise present at an ion binding location. Prior art of EMF dosimetry did not taken into account dielectric properties of tissue structures, rather the prior art utilized properties of isolated cells. By utilizing dielectric properties, reactive coupling of electromagnetic waveforms configured by optimizing SNR and Power SNR mathematical values evaluated at a target pathway structure can enhance repair of various wounds in human, animal and plant cells, organs, tissues and molecules for example post-surgical and traumatic wound repair, angiogenesis, improved blood perfusion, vasodilation, vasoconstriction, edema reduction, enhanced neovascularization, bone repair, tendon repair, ligament repair, organ regeneration and pain relief. Wound repair enhancement results from increased blood flow and modulation of angiogenesis and neovascularization as well as from other enhanced bioeffective processes.

Recent clinical use of non-invasive PRF at radio frequencies has used pulsed bursts of a 27.12 MHz sinusoidal wave, each pulse burst typically exhibiting a width of sixty five microseconds and having approximately 1,700 sinusoidal cycles per burst, and with various burst repetition rates.

Broad spectral density bursts of electromagnetic waveforms having a frequency in the range of one to one hundred megahertz (MHz), with 1 to 100,000 pulses per burst, and with a burst-repetition rate of 0.01 to 10,000 Hertz (Hz), are selectively applied to human, animal and plant cells, organs, tissues and molecules. The voltage-amplitude envelope of each pulse burst is a function of a random, irregular, or other like variable, effective to provide a broad spectral density within the burst envelope. The variables are defined by mathematical functions that take into account signal to thermal noise ratio and Power SNR in specific target pathway structures. The waveforms are designed to modulate living cell growth, condition and repair. Particular applications of these signals include, but are not limited to, enhancing treatment of organs, muscles, joints, skin and hair, post surgical and traumatic wound repair, angiogenesis, improved blood perfusion, vasodilation, vasoconstriction, edema reduction, enhanced neovascularization, bone repair, tendon repair, ligament repair, organ regeneration and pain relief. The application of the within electromagnetic waveforms can serve to enhance healing of various wounds.

According to an embodiment of the present invention a pulse burst envelope of higher spectral density can more efficiently couple to physiologically relevant dielectric pathways, such as cellular membrane receptors, ion binding to cellular enzymes, and general transmembrane potential changes. An embodiment according to the present invention increases the number of frequency components transmitted to relevant cellular pathways, resulting in a larger range of biophysical phenomena applicable to known healing mechanisms becoming accessible, including enhanced enzyme activity, growth factor release and cytokine release. By increasing burst duration and by applying a random, or other high spectral density envelope, to a pulse burst envelope of mono- or bi-polar rectangular or sinusoidal pulses that induce peak electric fields between $10^{-6}$ and 10 volts per centimeter (V/cm), and that satisfy detectability requirements according to SNR or Power SNR, a more efficient and greater effect could be achieved on biological healing processes applicable to both soft and hard tissues in humans, animals and plants resulting in an acceleration of wound repair.

The present invention relates to known mechanisms of wound repair that involve the naturally timed release of the appropriate growth factor or cytokine in each stage of wound repair as applied to humans, animals and plants. Specifically, wound repair involves an inflammatory phase, angiogenesis, cell proliferation, collagen production, and remodeling stages. There are timed releases of specific cytokines and growth factors in each stage. Electromagnetic fields can enhance blood flow and enhance the binding of ions which, in turn, can accelerate each healing phase. It is the specific intent of this invention to provide an improved means to enhance the action of exogenous factors and accelerate repair. An advantageous result of using the present invention is that wound repair can be accelerated due to enhanced blood flow or enhanced biochemical activity. It is an object of the present invention to provide an improved means to accelerate the intended effects or improve efficacy as well as other effects of the cytokines and growth factors relevant to each stage of wound repair.

Another object of the present invention is to cause and accelerate healing of chronic wounds such as diabetic ulcers, venous stasis ulcers, pressure sores and non-healing wounds of any origin.

Another object of the present invention is that by applying a high spectral density voltage envelope as a modulating or pulse-burst defining parameter according to SNR and Power SNR requirements, power requirements for such increased duration pulse bursts can be significantly lower than that of shorter pulse bursts having pulses within the same frequency range; this results from more efficient matching of frequency components to a relevant cellular/molecular process. Accordingly, the advantages, of enhanced transmitted dosimetry to relevant dielectric pathways and of decreased power requirements are achieved.

Therefore, a need exists for an apparatus and a method that more effectively accelerates wound repair in human, animal and plant cells, organs, tissues and molecules.

This invention may also relate to enhancing effectiveness of pharmacological, chemical, cosmetic and topical agents used to treat living tissues, cells and molecules by altering the interaction with the electromagnetic environment of the living tissues, cells, and molecules. The invention also relates to a method of modification of cellular and tissue growth, repair, maintenance and general behavior by the application of encoded electromagnetic information. More particularly, this invention provides for an application of highly specific electromagnetic frequency ("EMF") signal patterns to one or more body parts by surgically non-invasive reactive coupling of encoded electromagnetic information. Such application of electromagnetic waveforms in conjunction with pharmacological, chemical, cosmetic and topical agents as applied to, upon, or in human, animal, and plant target pathway structures such as cells, organs, tissues and molecules, can serve to enhance various effects of such agents.

By utilizing dielectric properties, reactive coupling of electromagnetic waveforms configured by optimizing SNR and Power SNR mathematical values evaluated at a target pathway structure can enhance various effects of pharmacological, chemical, cosmetic and topical agents that are applied to, upon or in human, animal and plant cells, organs, tissues and molecules. An enhancement results from increased blood flow and modulation of angiogenesis and neovascularization as well as from other enhanced bioeffective processes.

Particular applications of these signals include, but are not limited to, enhancing the effects of pharmacological, chemical, cosmetic and topical agents, prophylactic and wellness treatment of organs, muscles, joints, skin and hair, post surgical and traumatic wound repair, angiogenesis, improved blood perfusion, vasodilation, vasoconstriction, edema reduction, enhanced neovascularization, bone repair, tendon repair, ligament repair, organ regeneration and pain relief. The application of the within electromagnetic waveforms in conjunction with pharmacological, chemical, cosmetic and topical agents as applied to, upon or in human, animal and plant cells, organs, tissues and molecules can serve to enhance various effects of such compounds.

By increasing burst duration and by applying a random, or other high spectral density envelope, to a pulse burst envelope of mono- or bi-polar rectangular or sinusoidal pulses that induce peak electric fields between $10^{-6}$ and 10 volts percentimeter (V/cm), and that satisfy detectability requirements according to SNR or Power SNR, a more efficient and greater effect could be achieved on biological healing processes applicable to both soft and hard tissues in humans, animals and plants resulting in enhancement of the effectiveness of pharmacological, chemical, cosmetic, and topical agents.

The present invention relates to known mechanisms of pharmacological, chemical, cosmetic and topical agents as applied to, upon or in human, animal and plant cells, organs, tissues and molecules. Specifically, the agents' efficacy depends upon arrival of optimal dosages of the agents to intended target pathway structures, which can be accomplished either via enhanced blood flow or enhanced chemical activity catalyzed by an increase in active enzymes during a relevant biochemical cascade. Electromagnetic fields can enhance blood flow and ion binding which affect the agents' activity. An advantageous result of using the present invention is that the quantity of an agent may be able to be reduced due to the agents enhanced effectiveness. It is an object of the present invention to provide an improved means to enhance and accelerate the intended effects, and improve efficacy as well as other effects of pharmacological, chemical, cosmetic and topical agents applied to, upon or in human, animal and plant cells, organs, tissues and molecules.

Therefore, a need exists for an apparatus and a method that more effectively enhances and accelerates the intended effects, and improve efficacy as well as other bioeffective effects of pharmacological, chemical, cosmetic and topical agents applied to, upon or in human, animal and plant cells, organs, tissues and molecules.

This invention may also pertain generally to an electromagnetic treatment integrated coil apparatus and a method for using same to achieve modification of cellular and tissue growth, repair, maintenance, and general behavior by application of encoded electromagnetic information. More particularly this invention relates to the application of surgically non-invasive coupling of highly specific electromagnetic signal patterns to any number of body parts. This invention also relates to treatment of living tissues and cells by altering their interaction with their electromagnetic environment. The invention further relates to a method of modification of cellular and tissue growth, repair, maintenance, and general behavior by the application of encoded electromagnetic information. In particular, an embodiment according to the present invention pertains to using an induction means such as a coil to deliver pulsing electromagnetic fields ("PEMF") to enhance living tissue growth and repair integrated with devices such as supports, wraps, beds, and wheelchairs, and in conjunction with other therapeutic and wellness physical modalities, such as ultrasound, negative or positive pressure, heat, cold, massage.

This invention may also pertain generally to an apparatus and a method for using electromagnetic therapy treatment for hair maintenance and restoration and for treatment of degenerative neurological pathologies and other cerebrofacial conditions, including sleep disorders, by modulation of the interaction of hair, cerebral, neurological, and other tissues with their in situ electromagnetic environment. This invention also relates to a method of modification of cellular and tissue growth, repair, maintenance, and general behavior by application of encoded electromagnetic information to molecules, cells, tissues and organs on humans and animals. More particularly this invention relates to the application of surgically non-invasive coupling of highly specific electromagnetic signal patterns to hair and other cerebrofacial tissue. In particular, an embodiment according to the present invention pertains to using a self-contained apparatus that emits time varying magnetic fields ("PMF") configured using specific mathematical models to enhance hair and other tissue growth and repair by affecting the initial steps to growth factors and other cytokine release, such as ion/ligand binding for example calcium binding to calmodoulin.

This invention may relates to delivering electromagnetic signals to ophthalmic tissue of humans and animals that are injured or diseased whereby the interaction with the electromagnetic environment of living tissues, cells, and molecules is altered to achieve a therapeutic or wellness effect. The invention also relates to a method of modification of cellular and tissue growth, repair, maintenance and general behavior by the application of encoded electromagnetic information. More particularly, this invention provides for an application of highly specific electromagnetic frequency ("EMF") signal patterns to ophthalmic tissue by surgically non-invasive reactive coupling of encoded electromagnetic information. Such application of electromagnetic waveforms to human and animal target pathway structures such as cells, organs, tissues and molecules, can serve to remedy injured or diseased ophthalmic tissue or to prophylactically treat such tissue.

The use of most low frequency EMF has been in conjunction with applications of bone repair and healing. As such, EMF waveforms and current orthopedic clinical use of EMF waveforms comprise relatively low frequency components inducing maximum electrical fields in a millivolts per centimeter (mV/cm) range at frequencies under five KHz. A linear physicochemical approach employing an electrochemical model of cell membranes to predict a range of EMF waveform patterns for which bioeffects might be expected is based upon an assumption that cell membranes, and specifically ion binding at structures in or on cell membranes or surfaces, are a likely EMF target. Therefore, it is necessary to determine a range of waveform parameters for which an induced electric field could couple electrochemically at a cellular surface, such as by employing voltage-dependent kinetics.

The within invention is based upon biophysical and animal studies that attribute effectiveness of cell-to-cell communication on tissue structures' sensitivity to induced voltages and associated currents. A mathematical analysis using at least one of a Signal to Noise Ratio ("SNR") and a Power Signal to Noise Ratio ("Power SNR") evaluates whether EMF signals applied to target pathway structures such as cells, tissues, organs, and molecules, are detectable above thermal noise present at an ion binding location. Prior art of EMF dosimetry did not take into account dielectric properties of tissue structures, rather the prior art utilized properties of isolated cells. By utilizing dielectric properties, reactive coupling of electromagnetic waveforms configured by optimizing SNR and Power SNR mathematical values evaluated at a target pathway structure can enhance wellness of the ophthalmic system as well as repair of various ophthalmic injuries and diseases in human and animal cells, organs, tissues and molecules for example wet macular degeneration and dry macular degeneration. Cell, organ, tissue, and molecule repair enhancement results from increased blood flow and anti-inflammatory effects, and modulation of angiogenesis and neovascularization as well as from other enhanced bioeffective processes such as growth factor and cytokine release.

Broad spectral density bursts of electromagnetic waveforms having a frequency in the range of one hertz (Hz) to one hundred megahertz (MHz), with 1 to 100,000 pulses per burst, and with a burst-repetition rate of 0.01 to 10,000 Hertz (Hz), are selectively applied to human and animal cells, organs, tissues and molecules. The voltage-amplitude envelope of each pulse burst is a function of a random, irregular, or other like variable, effective to provide a broad spectral density within the burst envelope. The variables are defined by mathematical functions that take into account signal to thermal noise ratio and Power SNR in specific target pathway structures. The waveforms are designed to modulate living cell growth, condition and repair. Particular applications of these signals include, but are not limited to, enhancing treatment of organs, muscles, joints, eyes, skin and hair, post surgical and traumatic wound repair, angiogenesis, improved blood perfusion, vasodilation, vasoconstriction, edema reduction, enhanced neovascularization, bone repair, tendon repair, ligament repair, organ regeneration and pain relief. The application of the within electromagnetic waveforms can serve to enhance healing of various ophthalmic tissue injuries and diseases, as well as provide prophylactic treatment for such tissue.

According to an embodiment of the present invention a pulse burst envelope of higher spectral density can more efficiently couple to physiologically relevant dielectric pathways, such as cellular membrane receptors, ion binding to cellular enzymes, and general transmembrane potential changes. An embodiment according to the present invention increases the number of frequency components transmitted to relevant cellular pathways, resulting in different electromagnetic characteristics of healing tissue and a larger range of biophysical phenomena applicable to known healing mechanisms becoming accessible, including enhanced enzyme activity, second messenger, such as nitric oxide ("NO") release, growth factor release and cytokine release. By increasing burst duration and by applying a random, or other high spectral density envelope, to a pulse burst envelope of mono-polar or bi-polar rectangular or sinusoidal pulses that induce peak electric fields between $10^{-6}$ and 10 volts per centimeter (V/cm), and that satisfy detectability requirements according to SNR or Power SNR, a more efficient and greater effect could be achieved on biological healing processes applicable to both soft and hard tissues in humans and animals resulting in an acceleration of ophthalmic injury and disease repair.

The present invention relates to known mechanisms of ophthalmic injury and disease repair and healing that involve the naturally timed release of the appropriate anti-inflammatory cascade and growth factor or cytokine release in each stage of wound repair as applied to humans and animals. Specifically, ophthalmic injury and disease repair involves an inflammatory phase, angiogenesis, cell proliferation, collagen production, and remodeling stages. There are timed releases of second messengers, such as NO, specific cytokines and growth factors in each stage. Electromagnetic fields can enhance blood flow and enhance the binding of ions, which, in turn, can accelerate each healing phase. It is the specific intent of this invention to provide an improved means to enhance the action of endogenous factors and accelerate repair and to affect wellness. An advantageous result of using the present invention is that ophthalmic injury and disease repair, and healing can be accelerated due to enhanced blood flow or enhanced biochemical activity. In particular, an embodiment according to the present invention pertains to using an induction means such as a coil to deliver pulsing electromagnetic fields ("PEMF") for the maintenance of the ophthalmic system and the treatment of ophthalmic diseases such as macular degeneration, glaucoma, retinosa pigmentosa, repair and regeneration of optic nerve prophylaxis, and other related diseases. More particularly, this invention provides for the application, by surgically non-invasive reactive coupling, of highly specific electromagnetic signal patterns to one or more body parts. Such applications made on a non-invasive basis to the constituent tissues of the ophthalmic system and its surrounding tissues can serve to improve the physiological parameters of ophthalmic diseases.

An object of the present invention may be to provide an improved means to accelerate the intended effects or improve efficacy as well as other effects of the second messengers, cytokines and growth factors relevant to each stage of ophthalmic injury and disease repair and healing.

Another object of the present invention may be to cause and accelerate healing for treatment of ophthalmic diseases such as wet macular degeneration, dry macular degeneration, glaucoma, retinosa pigmentosa, repair and regeneration of optic nerve, prophylaxis, and other related diseases.

Another object of the present invention may be to accelerate healing of ophthalmic injuries of any type.

Another object of the present invention is to maintain wellness of the ophthalmic system.

Another object of the present invention is that by applying a high spectral density voltage envelope as a modulating or pulse-burst defining parameter according to SNR and Power SNR requirements, power requirements for such increased duration pulse bursts can be significantly lower than that of shorter pulse bursts having pulses within the same frequency range; this results from more efficient matching of frequency components to a relevant cellular/molecular process. Accordingly, the advantages of enhanced transmitted dosimetry to relevant dielectric pathways and of decreased power requirements, are achieved.

Therefore, a need exists for an apparatus and a method that effectively enhances wellness of the ophthalmic system and accelerates healing of ophthalmic injuries, ophthalmic diseases, areas around the ophthalmic system by modulating ion binding at cells, organs, tissues and molecules of humans and animals.

This invention may pertain to delivering electromagnetic signals to respiratory tissue such as lung tissue, of humans and animals that are injured or diseased whereby the interaction with the electromagnetic environment of living tissues, cells, and molecules is altered to achieve a therapeutic or wellness effect. The invention also relates to a method of modification of cellular and tissue growth, repair, maintenance and general behavior by the application of encoded electromagnetic information. More particularly, this invention provides for an application of highly specific electromagnetic frequency ("EMF") signal patterns to lung tissue by surgically non-invasive reactive coupling of encoded electromagnetic information. Such application of electromagnetic waveforms to human and animal target pathway structures such as cells, organs, tissues and molecules, can serve to remedy injured or diseased respiratory tissue or to prophylactically treat such tissue.

The use of most low frequency EMF has been in conjunction with applications of bone repair and healing. As such, EMF waveforms and current orthopedic clinical use of EMF waveforms comprise relatively low frequency components inducing maximum electrical fields in a millivolts per centimeter (mV/cm) range at frequencies under five KHz. A linear physicochemical approach employing an electrochemical model of cell membranes to predict a range of EMF waveform patterns for which bioeffects might be expected is based upon an assumption that cell membranes, and specifically ion binding at structures in or on cell membranes or surfaces, are a likely EMF target. Therefore, it is necessary to determine a range of waveform parameters for which an induced electric field could couple electrochemically at a cellular surface, such as by employing voltage-dependent kinetics.

A pulsed radio frequency ("PRF") signal derived from a 27.12 MHz continuous sine wave used for deep tissue healing is known in the prior art of diathermy. A pulsed successor of the diathermy signal was originally reported as an electromagnetic field capable of eliciting a non-thermal biological effect in the treatment of infections. Subsequently, PRF therapeutic applications have been reported for the reduction of post-traumatic and post-operative pain and edema in soft tissues, wound healing, burn treatment, and nerve regeneration. The application of PRF for resolution of traumatic and chronic edema has become increasingly used in recent years. Results to date using PRF in animal and clinical studies suggest that edema may be measurably reduced from such electromagnetic stimulus The within inventions may be based upon biophysical and animal studies that attribute effectiveness of cell-to-cell communication on tissue structures' sensitivity to induced voltages and associated currents. A mathematical power comparison analysis using at least one of a Signal to Noise Ratio ("SNR") and a Power Signal to Noise Ratio ("Power SNR") evaluates whether EMF signals applied to target pathway structures such as cells, tissues, organs, and molecules, are detectable above thermal noise present at an ion binding location. Prior art of EMF dosimetry did not take into account dielectric properties of tissue structures, rather the prior art utilized properties of isolated cells. By utilizing dielectric properties, reactive coupling of electromagnetic waveforms configured by optimizing SNR and Power SNR mathematical values evaluated at a target pathway structure can enhance wellness of the respiratory system as well as repair of various respiratory injuries and diseases in human and animal cells, organs, tissues and molecules for example sarcoidosis, granulomatous pneumonitis, pulmonary fibrosis, and "World Trade Center Cough." Cell, organ, tissue, and molecule repair enhancement results from increased blood flow and anti-inflammatory effects, and modulation of angiogenesis and neovascularization as well as from other enhanced bioeffective processes such as growth factor and cytokine release.

As mentioned above, broad spectral density bursts of electromagnetic waveforms having a frequency in the range of one hertz (Hz) to one hundred megahertz (MHz), with 1 to 100,000 pulses per burst, and with a burst-repetition rate of 0.01 to 10,000 Hertz (Hz), are selectively applied to human and animal cells, organs, tissues and molecules. The voltage-amplitude envelope of each pulse burst is a function of a random, irregular, or other like variable, effective to provide a broad spectral density within the burst envelope. The variables are defined by mathematical functions that take into account signal to thermal noise ratio and Power SNR in specific target pathway structures. The waveforms are designed to modulate living cell growth, condition and repair. Particular applications of these signals include, but are not limited to, enhancing treatment of organs, muscles, joints, eyes, skin and hair, post surgical and traumatic wound repair, angiogenesis, improved blood perfusion, vasodilation, vasoconstriction, edema reduction, enhanced neovascularization, bone repair, tendon repair, ligament repair, organ regeneration and pain relief. The application of the within electromagnetic waveforms can serve to enhance healing of various respiratory tissue injuries and diseases, as well as provide prophylactic treatment for such tissue. The present invention is a non-invasive, non-pharmacological treatment modality that can have a salutary impact on persons suffering from respiratory diseases or conditions or that can be used on a prophylactic basis for those individuals who may be prone to respiratory diseases or conditions.

An aspect of the present invention is that a pulse burst envelope of higher spectral density can more efficiently couple to physiologically relevant dielectric pathways, such as cellular membrane receptors, ion binding to cellular enzymes, and general transmembrane potential changes. Another aspect of the present invention increases the number of frequency components transmitted to relevant cellular pathways, resulting in different electromagnetic characteristics of healing tissue and a larger range of biophysical phenomena applicable to known healing mechanisms becoming accessible, including enhanced enzyme activity, second messenger, such as nitric oxide ("NO") release, growth factor release and cytokine release. By increasing burst duration and by applying a random, or other high spectral density envelope, to a pulse burst envelope of mono-polar or bi-polar rectangular or sinusoidal pulses that induce peak electric fields between $10^{-6}$ and 10 volts per centimeter (V/cm), and that satisfy detectability requirements according to SNR or Power SNR, a more efficient and greater effect could be achieved on biological healing processes applicable to both soft and hard tissues in humans and animals resulting in an acceleration of respiratory injury and disease repair.

The present invention relates to known mechanisms of respiratory injury and disease repair and healing that involve the naturally timed release of the appropriate anti-inflammatory cascade and growth factor or cytokine release in each stage of wound repair as applied to humans and animals. Specifically, respiratory injury and disease repair involves an inflammatory phase, angiogenesis, cell proliferation, collagen production, and remodeling stages. There are timed releases of second messengers, such as NO, specific cytokines and growth factors in each stage. Electromagnetic fields can enhance blood flow and enhance the binding of ions, which, in turn, can accelerate each healing phase. It is the specific intent of this invention to provide an improved means to enhance the action of endogenous factors and accelerate repair and to affect wellness. An advantageous result of using the present invention is that respiratory injury and disease repair, and healing can be accelerated due to enhanced blood flow or enhanced biochemical activity. In particular, an embodiment according to the present invention pertains to using an induction means such as a coil to deliver pulsing electromagnetic fields ("PEMF") for the maintenance of the respiratory system and the treatment of respiratory diseases such sarcoidosis, granulomatous pneumonitis, pulmonary fibrosis, and "World Trade Center Cough," and other related diseases. More particularly, this invention provides for the application, by surgically non-invasive reactive coupling, of highly specific electromagnetic signal patterns to one or more body parts. Such applications made on a non-invasive basis to the constituent tissues of the respiratory system and its surrounding tissues can serve to improve the physiological parameters of respiratory diseases.

Sarcoidosis, granulomatous pneumonitis, pulmonary fibrosis, and other related diseases result from inflammatory processes caused by inhalation of foreign material into lung tissue. The initiation of such diseases is the inflammation that occurs after particle inhalation. The within invention produces a physiological effect designed to reduce the inflammatory response, which in turn, may reduce the effects of inhaled foreign bodies on lung capacity and even prevent other systemic health problems. A number of physiological cascades that are accelerated or modified by the waveforms produced by the methods and apparatus of this invention serve to reduce the inflammatory processes. In particular, the PEMF signal can enhance the production of nitric oxide via modulation of Calcium ("$Ca^{2+}$") binding to calmodulin ("CaM"). This in turn can inhibit inflammatory leukotrienes that reduce the inflammatory process leading to excessive fibrous tissue for example scars, in lung tissue. Prophylactic use of the within invention by first responders may prevent or reduce the inflammatory processes leading to formation of fibrous tissue leading to lung disease.

Sarcoidosis involves inflammation that produces tiny agglomerations of cells in various organs of the body. These agglomerations are called glanulomas which are an aggregation and proliferation of macrophages to form nodules or granules. Such granulomas are of microscopic size and are not easily identifiable without significant magnification. Granulomas can grow and join together creating large and small groups of agglomerated cells. If there is a high prevalence of agglomerated granulomas in an organ, such as the lungs, the agglomerated granulomas can negatively impact the proper functioning of that organ. In the lungs, this negative impact can cause symptoms of sarcoidosis. Sarcoidosis can occur in almost any part of the body although it usually affects some organs such as the lungs and lymphnodes, more than others. It usually begins in one or two places, the lungs or lymphnodes especially the lymphnodes in the chest cavity. Sarcoidosis almost always occurs in more than one organ at a time. Exposure to pollutants or other particulates that are breathed into the lungs, such as dust and fibers present at the World Trade Center site after Sep. 11, 2001, can cause the scarring and resultant sarcoidosis.

Sarcoidosis involves both an active and a non-active phase. In the active phase, granulomas are formed and grow with symptoms developing. Scar tissue can form in the organs where such granulomas occur and inflammation is present. In the non-active phase, inflammation reduces, and the granulomas do not grow or may be reduced in size. If the non-active phase does occur, any scarring that occurred will remain and cause increased or continuing symptoms.

The course of the disease varies greatly. Sarcoidosis may be mild or severe. The inflammation that causes the granulomas may resolve without intervention and may stop growing or reduce in size. Symptoms may be reduced or alleviated within a few years after onset. In some cases, the inflammation remains but does not progress. There may be increased symptoms or flare-ups that require treatment on an intermittent basis. Although drug intervention can help, sarcoidosis may leave scar tissue in the lungs, skin, eyes or other organs and that scar tissue can permanently affect the functioning of the organs. Drug treatment usually does not affect scar tissue. The present invention has been shown in animal and clinical testing to reduce inflammation and accelerate angiogenesis and revascularization in organ tissue that may lead to improvement of vascularity of the tissue surrounding the scarring that may be the result of sarcoidosis in the lungs.

Sarcoidosis usually occurs slowly over many months and does not usually cause sudden illness. However, some symptoms may occur suddenly. These symptoms include disturbed heart rhythms, arthritis in the ankles, and eye symptoms. In some serious cases in which vital organs are affected, sarcoidosis can resulting death. However, sarcoidosis is not a form of cancer. Presently there is no way to prevent sarcoidosis. Sarcoidosis was once thought to be an uncommon condition. It is now known to affect tens of thousands of people throughout the United States. Since many people who have sarcoidosis exhibit no symptoms, it is difficult to determine the actual prevalence of sarcoidosis in populations, although there seems to be a higher incidence in certain cultures.

An aspect of the present invention is to provide an improved means to accelerate the intended effects or improve efficacy as well as other effects of the second messengers, cytokines and growth factors relevant to each stage of respiratory injury and disease repair and healing.

Another aspect of the present invention is to cause and accelerate healing for treatment of respiratory diseases such as, sarcoidosis, granulomatous pneumonitis, pulmonary fibrosis, and "World Trade Center Cough" and other related diseases.

Another aspect of the present invention is to accelerate healing of respiratory injuries of any type.

Another aspect of the present invention is to maintain wellness of the respiratory system.

Another aspect of the present invention is that by applying a high spectral density voltage envelope as a modulating or pulse-burst defining parameter according to SNR and Power SNR requirements, power requirements for such increased duration pulse bursts can be significantly lower than that of shorter pulse bursts having pulses within the same frequency range; this results from more efficient matching of frequency components to a relevant cellular/molecular process. Accordingly, the advantage of enhanced transmitted dosimetry to relevant dielectric pathways and the advantage of decreased power requirements, are achieved. This advantageously allows for implementation of the within invention in an easily transportable unit for ease of application to the lung area and is particularly suitable for prophylactic use by first responders.

Another aspect of the present invention allows application of specific waveforms in a convenient and comfortable configuration to a desired pulmonary area. In an embodiment according to the present invention, a portable generator with multiple coil applicators that are incorporated into a body-conforming garment is worn by the user during a posteriori treatment or worn prophylactically. This allows for the proper positioning of the output coils to the chest area thereby allowing the produced signals to be broadcast over the lungs in an efficient manner.

Therefore, a need exists for an apparatus and a method that effectively enhances wellness of the respiratory system and accelerates healing of respiratory injuries, respiratory diseases, and areas around the respiratory system by modulating ion binding at cells, organs, tissues and molecules of humans and animals.

This invention pertains generally to an electromagnetic coil apparatus and a method that configures and delivers electromagnetic signals to promote cell and tissue growth, repair, and maintenance. The electromagnetic environment of living tissues, cells, and molecules is altered by the electromagnetic signals generated by an embodiment of the present invention to achieve a therapeutic or wellness effect. Alteration of the electromagnetic environment can be particularly effective for alleviating pain and discomfort in individuals having capsular contracture or excessive fibrous capsule formation associated with any surgically implanted device. The invention also relates to a method of modification of cellular and tissue growth, repair, maintenance and general behavior by the application of encoded electromagnetic information. More particularly, this invention provides for an application of highly specific electromagnetic frequency ("EMF") signal patterns to excessive fibrous capsule tissue by non-invasive reactive coupling of encoded electromagnetic information. Such application of electromagnetic waveforms to human and animal fibrous capsule formation and capsular contracture target pathway structures such as cells, organs, tissues and molecules, can reduce the pain and edema associated with capsular contracture, can increase blood flow, neovascularization, vasculargenesis, and angiogenesis and can augment the release of growth factors and cytokines related to the prophylactic and a posteriori treatment of excessive fibrous capsule formation.

The present invention further relates to altering the cellular and molecular mechanisms of excessive fibrous capsule formation and to control capsular contracture generally associated with post surgical complications of implants such as breast augmentation.

Capsular contracture is a painful inflammatory condition which can occur at any time post surgically but usually occurs within the first several months after surgery. Capsular contracture is the most common complication of breast augmentation surgery but also can occur with other surgically implanted devices. At the time of initial breast augmentation surgery, a pocket is made for a breast implant in tissue covering the chest. During the healing process a capsule that is comprised of fibrous tissue forms. The body is genetically programmed to counteract that formation by attempting to shrink the scar tissue to a certain degree. Under normal circumstances, the pocket remains open thus allowing the implant to look and feel natural. However in a certain number of cases, the capsule will tighten thereby causing pressure by restricting the space for the implant. Furthermore this causes the implant to feel hard and rigid with concomitant distortion of the appearance of the breast. In later stages the implant feels extremely firm and may take on an unnatural "ball like" appearance. The present invention produces a physiological effect in the tissue of a capsular contracture. The physiological effect causes revascularization and inter-cellular modification tissue, to reduce in hardness and prevalence thereby reducing pain and discomfort for a patient. Waveforms produced by the within invention accelerate or modify a number of physiological cascades that either alleviate the propensity of the capsule to compress or harden, or produce a reduction in the existing capsule involvement with the physical area at which the waveforms have been applied to. In particular a pulsing electromagnetic field ("PEMF") signal can enhance production of nitric oxide ("NO") via modulation of Calcium ("$Ca2+$") binding to calmodulin ("CaM"). This in turn can inhibit inflammatory leukotrienes that reduce the inflammatory process leading to excessive fibrous capsule formation. At present, pharmacologic agents targeted to inhibit leukotrienes are employed for treating capsular contracture with limited success. Prophylactic use of the within invention prior to device implant in individuals that are deemed susceptible to capsular contracture formation may prevent or reduce the formation of excessive fibrous tissue.

An advantageous result of the within invention is that by applying a high spectral density voltage envelope as the modulating or pulse-burst defining parameter, the power requirement for such increased duration pulse bursts can be significantly lower than that of shorter pulse bursts containing pulses within the same frequency range. This is due to more efficient matching of the frequency components to relevant cellular and molecular processes. Accordingly the dual advantages of enhanced transmitted dosimetry to the relevant dielectric pathways and of decreased power requirements are achieved. This allows for the implementation of the within invention in an easily transportable unit for ease of application on capsular contracture patients.

Therefore, a need exists for an apparatus and a method that effectively accelerates or modifies a number of physiological cascades that alleviate the propensity of the capsule to compress or harden, that reduce excessive fibrous capsule formation, and that produce a reduction in the existing capsule involvement within the physical area to which the waveforms have been applied.

Described herein are also electromagnetic treatment devices, systems and methods. Some embodiments pertain generally to a method and apparatus for therapeutic and prophylactic treatment of animal and human nervous system. In particular, some embodiments pertain to use of non-thermal time-varying electromagnetic fields configured to accelerate the asymmetrical kinetics of the binding of intracellular ions to their respective binding proteins which regulate the biochemical signaling pathways living systems employ to contain and reduce the inflammatory response to injury. Other embodiments pertain to the non-thermal application of repetitive pulse bursts of sinusoidal, rectangular, chaotic or arbitrary waveform electromagnetic fields to instantaneously accelerate ion-buffer binding in signaling pathways in animal and human nervous system using ultra lightweight portable coupling devices such as inductors and electrodes, driven by miniature signal generator circuitry that can be incorporated into an anatomical positioning device such as a dressing, bandage, compression bandage, compression dressing; lumbar or cervical back, shoulder, head, neck and other body portion wraps and supports; garments, hats, caps, helmets, mattress pads, seat cushions, beds, stretchers, and other body supports in cars, motorcycles, buses, trains, airplanes, boats, ships and the like.

Yet another embodiment pertains to application of sinusoidal, rectangular, chaotic or arbitrary waveform electromagnetic signals, having frequency components below about 100 GHz, configured to accelerate the binding of intracellular $Ca^{2+}$ to a buffer, such as CaM, to enhance biochemical signaling pathways in animal and human nervous system. Signals configured according to additional embodiments produce a net increase in a bound ion, such as $Ca^{2+}$, at CaM binding sites because the asymmetrical kinetics of Ca/CaM binding allows such signals to accumulate voltage induced at the ion binding site, thereby accelerating voltage-dependent ion binding. Examples of therapeutic and prophylactic applications of the present invention are modulation of biochemical signaling in anti-inflammatory pathways, modulation of biochemical signaling in cytokine release pathways, modulation of biochemical signaling in growth factor release pathways; edema and lymph reduction, anti-inflammatory, post surgical and post operative pain and edema relief, nerve, bone and organ pain relief, increased local blood flow, microvascular blood perfusion, treatment of tissue and organ ischemia, brain tissue ischemia from stroke or traumatic brain injury, treatment of neurological injury and neurodegenerative diseases such as Alzheimer's and Parkinson's; angiogenesis, neovascularization; enhanced immune response; enhanced effectiveness of pharmacological agents; nerve regeneration; prevention of apoptosis; modulation of heat shock proteins for prophylaxis and response to injury or pathology.

Some embodiments can also be used in conjunction with other therapeutic and prophylactic procedures and modalities such as heat, cold, light, ultrasound, mechanical manipulation, massage, physical therapy, wound dressings, orthopedic and other surgical fixation devices, and surgical interventions. In addition, any of the variations described herein can also be used in conjunction with one or more pharmacological agents. Any of the variations described herein can also be used with imaging or non-imaging diagnostic procedures.

In some variations the systems, devices and/or methods generally relate to application of electromagnetic fields (EMF), and in particular, pulsed electromagnetic fields (PEMF), including a subset of PEMF in a radio frequency domain (e.g., pulsed radio frequency or PRF), for the treatment of head, cerebral and neural injury, including neurodegenerative conditions in animals and humans.

DISCUSSION OF RELATED ART

It is now well established that application of weak non-thermal electromagnetic fields ("EMF") can result in physiologically meaningful in vivo and in vitro bioeffects. Time-varying electromagnetic fields, comprising rectangular waveforms such as pulsing electromagnetic fields ("PEMF"), and sinusoidal waveforms such as pulsed radio frequency fields ("PRF") ranging from several Hertz to an about 15 to an about 40 MHz range, are clinically beneficial when used as an adjunctive therapy for a variety of musculoskeletal injuries and conditions.

Beginning in the 1960's, development of modern therapeutic and prophylactic devices was stimulated by clinical problems associated with non-union and delayed union bone fractures. Early work showed that an electrical pathway can be a means through which bone adaptively responds to mechanical input. Early therapeutic devices used implanted and semi-invasive electrodes delivering direct current ("DC") to a fracture site. Non-invasive technologies were subsequently developed using electrical and electromagnetic fields. These modalities were originally created to provide a non-invasive "no-touch" means of inducing an electrical/mechanical waveform at a cell/tissue level. Clinical applications of these technologies in orthopaedics have led to approved applications by regulatory bodies worldwide for treatment of fractures such as non-unions and fresh fractures, as well as spine fusion. Presently several EMF devices constitute the standard armamentarium of orthopaedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

Cellular studies have addressed effects of weak low frequency electromagnetic fields on both signal transduction pathways and growth factor synthesis. It can be shown that EMF stimulates secretion of growth factors after a short, trigger-like duration. Ion/ligand binding processes at a cell membrane are generally considered an initial EMF target pathway structure. The clinical relevance to treatments for example of bone repair, is upregulation such as modulation, of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Stimulation of transforming growth factor beta ("TGF-$\beta$") messenger RNA ("mRNA") with PEMF in a bone induction model in a rat has been shown. Studies have also demonstrated upregulation of TGF-$\beta$ mRNA by PEMF in human osteoblast-like cell line designated MG-63, wherein there were increases in TGF-$\beta$1, collagen, and osteocalcin synthesis. PEMF stimulated an increase in TGF-$\beta$1 in both hypertrophic and atrophic cells from human non-union tissue. Further studies demonstrated an increase in both TGF-$\beta$1 mRNA and protein in osteoblast cultures resulting from a direct effect of EMF on a calcium/calmodulin-dependent pathway. Cartilage cell studies have shown similar increases in TGF-$\beta$1 mRNA and protein synthesis from EMF, demonstrating a therapeutic application to joint repair. U.S. Pat. No. 4,315,503 (1982) to Ryaby and U.S. Pat. No. 5,723,001 (1998) to Pilla typify the research conducted in this field.

However, prior art in this field applies unnecessarily high amplitude and power to a target pathway structure, requires unnecessarily long treatment time, and is not portable.

Therefore, a need exists for an apparatus and a method that more effectively modulates biochemical processes that regulate tissue growth and repair, shortens treatment times, and incorporates miniaturized circuitry and light weight applicators thus allowing the apparatus to be portable and if desired disposable. A further need exists for an apparatus and method that more effectively modulates biochemical processes that regulate tissue growth and repair, shortens treatment times, and incorporates miniaturized circuitry and light weight applicators that can be constructed to be implantable.

EMF has been used in applications of bone repair and bone healing. Waveforms comprising low frequency components and low power are currently used in orthopedic clinics. Origins of using bone repair signals began by considering that an electrical pathway may constitute a means through which bone can adaptively respond to EMF signals. A linear physicochemical approach employing an electrochemical model of a cell membrane predicted a range of EMF waveform patterns for which bioeffects might be expected. Since a cell membrane was a likely EMF target, it became necessary to find a range of waveform parameters for which an induced electric field could couple electrochemically at the cellular surface, such as voltage-dependent kinetics. Extension of this linear model also involved Lorentz force analysis.

A pulsed radio frequency ("PRF") signal derived from a 27.12 MHz continuous sine wave used for deep tissue healing is known in the prior art of diathermy. A pulsed successor of the diathermy signal was originally reported as an electromagnetic field capable of eliciting a non-thermal biological effect in the treatment of infections. PRF therapeutic applications have been reported for reduction of post-traumatic and post-operative pain and edema in soft tissues, wound healing, burn treatment and nerve regeneration. Application of EMF for the resolution of traumatic edema has become increasingly used in recent years. Results to date using PRF in animal and clinical studies suggest that edema may be measurably reduced from such electromagnetic stimulus.

Prior art considerations of EMF dosimetry have not taken into account dielectric properties of tissue structure as opposed to the properties of isolated cells.

In recent years, clinical use of non-invasive PRF at radio frequencies comprised using pulsed bursts of a 27.12 MHz sinusoidal wave, wherein each pulse burst comprises a width of sixty-five microseconds, having approximately 1,700 sinusoidal cycles per burst, and various burst repetition rates. This limited frequency components that could couple to relevant dielectric pathways in cells and tissue.

Time-varying electromagnetic fields, comprising rectangular waveforms such as pulsing electromagnetic fields, and sinusoidal waveforms such as pulsed radio frequency fields ranging from several Hertz to an about 15 to an about 40 MHz range, are clinically beneficial when used as an adjunctive therapy for a variety of musculoskeletal injuries and conditions.

Beginning in the 1960's, development of modern therapeutic and prophylactic devices was stimulated by clinical problems associated with non-union and delayed union bone fractures. Early work showed that an electrical pathway can be a means through which bone adaptively responds to mechanical input. Early therapeutic devices used implanted and semi-invasive electrodes delivering direct current ("DC") to a fracture site. Non-invasive technologies were subsequently developed using electrical and electromagnetic fields. These modalities were originally created to provide a non-invasive "no-touch" means of inducing an electrical/mechanical waveform at a cell/tissue level. Clinical applications of these technologies in orthopaedics have led to approved applications by regulatory bodies worldwide for treatment of fractures such as non-unions and fresh fractures, as well as spine fusion. Presently several EMF devices constitute the standard armamentarium of orthopaedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

Cellular studies have addressed effects of weak low frequency electromagnetic fields on both signal transduction pathways and growth factor synthesis. It can be shown that EMF stimulates secretion of growth factors after a short, trigger-like duration. Ion/ligand binding processes at a cell membrane are generally considered an initial EMF target pathway structure. The clinical relevance to treatments for example of bone repair, is upregulation such as modulation, of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Stimulation of transforming growth factor beta ("TGF-β") messenger RNA ("mRNA") with PEMF in a bone induction model in a rat has been shown. Studies have also demonstrated upregulation of TGF-β mRNA by PEMF in human osteoblast-like cell line designated MG-63, wherein there were increases in TGF-β1, collagen, and osteocalcin synthesis. PEMF stimulated an increase in TGF-β1 in both hypertrophic and atrophic cells from human non-union tissue. Further studies demonstrated an increase in both TGF-β1 mRNA and protein in osteoblast cultures resulting from a direct effect of EMF on a calcium/calmodulin-dependent pathway. Cartilage cell studies have shown similar increases in TGF-β1 mRNA and protein synthesis from EMF, demonstrating a therapeutic application to joint repair. Various studies conclude that upregulation of growth factor production may be a common denominator in the tissue level mechanisms underlying electromagnetic stimulation. When using specific inhibitors, EMF can act through a calmodulin-dependent pathway. It has been previously reported that specific PEMF and PRF signals, as well as weak static magnetic fields, modulate $Ca^{2+}$ binding to CaM in a cell-free enzyme preparation. Additionally, upregulation of mRNA for BMP2 and BMP4 with PEMF in osteoblast cultures and upregulation of TGF-β1 in bone and cartilage with PEMF have been demonstrated.

However, prior art in this field does not use an induction apparatus that is lightweight, portable, disposable, implantable, and configured with, integrated into, or attached to at least one of garments, fashion accessories, footwear, bandages, anatomical supports, an anatomical wraps, apparel, cushions, mattresses, pads, wheelchairs, therapeutic beds, therapeutic chairs, therapeutic and health maintenance devices such as vacuum assisted wound closure devices, mechanical and functional electrical stimulation devices and exercise devices, ultrasound, heat, cold, massage, and exercise.

Therefore, a need exists for an electromagnetic treatment induction apparatus and a method for using same that is lightweight, portable, implantable, and can be disposable. A further need exists for an electromagnetic treatment induction apparatus and method that can be used more effectively with miniaturized circuitry that optimally configures electromagnetic waveforms to be inductively coupled with plant, animal, and human tissue, organs, cells, and molecules for therapeutic treatment.

As mentioned above, by use of a substantially single voltage amplitude envelope with each PRF burst, one was limiting frequency components that could couple to relevant dielectric pathways in cells and tissue.

However, prior art in this field does not configure waveforms based upon a ion/ligand binding transduction pathway. Prior art waveforms are inefficient since prior art waveforms apply unnecessarily high amplitude and power to living tissues and cells, require unnecessarily long treatment time, and cannot be generated by a portable device.

Therefore, a need exists for an apparatus and a method that more effectively modulates angiogenesis and other biochemical processes that regulate tissue growth and repair, shortens treatment times, and incorporates miniaturized circuitry and light weight applicators thus allowing the apparatus to be portable and if desired disposable. A further need exists for an apparatus and method that more effectively modulates angiogenesis and other biochemical processes that regulate tissue growth and repair, shortens treatment times, and incorporates miniaturized circuitry and light weight applicators that can be constructed to be implantable.

Time-varying electromagnetic fields, comprising either rectangular, pseudo-rectangular, or both rectangular and pseudo-rectangular waveforms, such as pulse modulated electromagnetic fields, and sinusoidal waveforms such as pulsed radio frequency fields ranging from several Hertz to an about 15 to an about 40 MHz range, are clinically beneficial when used as an adjunctive therapy for a variety of musculoskeletal injuries and conditions.

However, prior art in this field does not use an induction apparatus that delivers a signal according to a mathematical model, is programmable, lightweight, portable, disposable, implantable, and configured with, integrated into, or attached to at least one of garments, fashion accessories, footware, bandages, anatomical supports, an anatomical wraps, apparel, cushions, mattresses, pads, wheelchairs, therapeutic beds, therapeutic chairs, therapeutic and health maintenance devices such as vacuum assisted wound closure devices, mechanical and functional electrical stimulation devices and exercise devices, ultrasound, heat, cold, massage, and exercise. A further need exists for an electromagnetic treatment induction apparatus and a method for using same that is lightweight, portable, implantable, and can be disposable. A further need exists for an electromagnetic treatment induction apparatus and method having decreased power requirements and non-invasive characteristics that allow an enhanced signal to be integrated into surgical dressings, wound dressings, pads, seat cushions, mattress pads, shoes, and any other garment and structure juxtaposed to living tissue and cells, even to be integral to creation of a garment to deliver an enhanced EMF signal to any body parts and that delivers a signal according to a mathematical model and is programmable.

Prior art equipment in this field is bulky, not designed for outdoor use, and not self-contained.

Therefore, a need exists for an apparatus and a method that more effectively modulates biochemical processes that regulate hair and other cerebrofacial tissue growth and repair, shortens treatment times, and incorporates miniaturized circuitry and light weight applicators thus allowing the apparatus to be portable and if desired disposable. A further need exists for an apparatus and method that more effectively modulates biochemical processes that regulate hair and other cerebrofacial tissue growth and repair, shortens treatment times, and incorporates miniaturized circuitry and light weight applicators that can be constructed to be implantable.

Traumatic brain injury (hereinafter known as TBI) remains as one of the leading causes of morbidity and mortality for civilians and for soldiers on the battlefield and is a major health and socio-economic problem throughout the world. In currently deployed war-fighters, head injuries, the majority of which include the brain, account for 22% of all injuries and 56% of those are classified as moderate to severe. In January 2008, the Department of Defense reported that over 5,500 soldiers had suffered traumatic brain injury caused by explosive weaponry, including suicide bombings, mines that explode on impact, and missiles. In addition to the immediate needs of the wounded, traumatic brain injury may create long-term or even permanent cognitive, motor, and sensory disabilities that require ongoing support, rehabilitation, and treatment.

Additionally, traumatic brain injury is also a significant cause of death in civilians. Epidemiological data indicate that in the US, at least 1.4 to 2 million people are treated for traumatic brain injury every year, resulting in 56,000 deaths and 18,000 survivors suffering from neurological impairment. Annual costs in the US are estimated at $60 billion. The World Health Organization projected that by 2020, road traffic accidents, a major cause of traumatic brain injury, will rank third as a cause of the global burden of disease and disablement, behind only ischemic heart disease and unipolar depression. Recently, the demographics of traumatic brain injury have shifted to include more cases due to falls in middle-aged and older subjects. It is predicted that there will be 5 million head injuries over the next decade and 30 million worldwide.

Tissue damage from head injuries such as traumatic brain injury generally arises from the mechanical damage of the trauma event and subsequent secondary physiological responses to the trauma event. For example, moderate to severe traumatic brain injury can produce mechanical damage by direct trauma to brain tissue that can cause the disruption of cell membranes and blood vessels, resulting in direct and ischemic neuronal death. Then, secondary physiological responses such as inflammation and swelling can result in further damage and even death of healthy brain tissue. Importantly, even in the absence of direct mechanical injury (i.e. diffuse brain trauma), such secondary physiological responses can still occur and result in injury to healthy brain tissue. For example, astrocytes and microglia often react to head injury conditions and by secreting destructive cytokines (e.g. IL-1$\beta$, TNF-$\alpha$, IFN-$\gamma$, and IL-6) as well as other inflammatory molecules, such as glutamate, reactive oxygen and nitrogen species, which, alone, or in combination, can be neurotoxic.

While the primary and immediate consequences of mechanical trauma to neurons cannot be undone, secondary pathological sequelae, specifically brain swelling and inflammation, are situational candidates for intervention. The toll of neurological deficits and mortality from TBI continue in the military and private sectors and, to date, there are no widely successful medical or surgical interventions to prevent neuronal death.

Current medical practice has attempted to use pharmaceuticals to mitigate and prevent tissue damage and injury resulting from secondary physiological responses of traumatic brain injury with little success. For example, intravenous, high-dose corticosteroids have been administered to reduce cerebral inflammation after traumatic brain injury, but several studies have demonstrated that steroids can be neurotoxic. In fact, results from a clinical randomized trial in 2005 tested whether a high dose regimen of the steroid methylprednisolone sodium succinate (MPSS), administered within 8 hours after injury, would improve survival after head injury. This trial was planned to randomize 20,000 patients and was powered to detect a drop in mortality from 15% to 13%, a small, but important improvement in outcome. However, the data and safety monitoring board halted the trial after half of the patients were enrolled as it became apparent that MPSS significantly increased mortality of severe injuries from 17.9% to 21.1% (p=0.0001).

The search for alternatives to improve morbidity and mortality from traumatic brain injury has not been fruitful. At least 21 multi-center clinical trials, aimed to determine the clinical value of a range of approaches, from steroids to calcium and glutamate antagonists to antioxidants and antifibrinolytic agents and hypothermia were conducted from 1985 to 2006, but unfortunately none have demonstrated a convincing benefit in the overall traumatic brain injury population. In spite of extremely promising pre-clinical data and early phase trials, no agent has yet been shown convincingly in a phase III trial to have clear benefit in terms of improving functional outcome after traumatic brain injury. Importantly, a common problem in these pharmacological approaches is that all of the candidate drugs had potential deleterious side effects on non-target tissue. In fact, the development of pharmaceutical agents for traumatic brain injury has all but ceased with increasing reluctance of the pharmaceutical industry to sponsor the testing of new candidate therapies as uncertainty remains regarding benefit.

Given the absence of treatment options for head trauma, there is a need for a therapy that can target and reduce secondary physiological responses such as inflammation, swelling, and intracranial pressure while also promoting repair and regrowth in and around the injured area. While EMF treatments have been explored for a variety of uses, the possible benefits of PEMF in treating or preventing neurological injury and degenerative conditions such as TBI, subarachnoid hemorrhage, brain ischemia, stroke, and Alzheimer's or Parkinson's Disease are relatively unknown. This is in part due to the fact that the secondary physiological responses (e.g. inflammatory) in the central nervous system (CNS) differ from that of the periphery systems for which PEMF is currently used. Moreover, attention has been focused on pharmaceutical treatments until recently. Accordingly, embodiments of the present invention address this need and provide methods and devices using PEMF to treat patients suffering from neurological injury (such as traumatic brain injury) and secondary physiological responses arising from that injury.

Transient elevations in cytosolic $Ca^{2+}$, from external stimuli as simple as changes in temperature and receptor activation, or as complex as mechanical disruption of tissue, will activate CaM. Once $Ca^{2+}$ ions are bound, a conformational change will allow CaM bind to and activate a number of key enzymes involved in cell viability and function, such as the endothelial and neuronal constitutive nitric oxide synthases (cNOS); eNOS and nNOS, respectively. As a consequence, NO is rapidly produced, albeit in lower concentrations than the explosive increases in NO produced by inducible NOS (iNOS), during the inflammatory response. In contrast, these smaller, transient increases in NO produced by Ca/CaM-binding will activate soluble guanylyl cyclase (sGC), which will catalyze the formation of cyclic guanosine monophosphate (cGMP). The CaM/NO/cGMP signaling pathway can rapidly modulate blood flow in response to normal physiologic demands, as well as to inflammation. Importantly, this same pathway will also rapidly attenuate expression of cytokines such as interleukin-1beta (IL-1β), and iNOS and stimulate anti-apoptotic pathways in neurons. All of these effects are mediated by calcium and cyclic nucleotides, which in turn regulate growth factors such as basic fibroblast growth factor (FGF-2) and vascular endothelial growth factor (VEGF), resulting in pleiotropic effects on cells involved in tissue repair and maintenance.

In general, inflammatory response in the brain differs from that in other organs. It is exemplified by a more modest and delayed recruitment of leukocytes into the brain than into peripheral organs. Brain microglia, in contrast, are activated and release inflammatory mediators beginning within minutes to hours after TBI. The mediators often express neurotoxic and neuroprotective properties. For example, cytokines may either promote damage or support recovery processes; in some cases, cytokines, such as interleukin-6, may perform both functions.

This invention teaches that rapid intervention after traumatic head, cerebral and neural injury with electromagnetic fields configured to rapidly modulate the biochemical signaling cascades animals and humans employ in response to physical and chemical perturbations will significantly reduce the pathological consequences of such injuries, thereby reducing morbidity and the cost of health care.

Bone growth stimulator (hereinafter known as BGS) electromagnetic fields are now part of the standard armamentarium of orthopedic practice worldwide for the treatment of recalcitrant bone fractures. Radio frequency signals, originally developed for deep tissue heating (diathermy), were shown to produce biological effects when applied at non-thermal levels using pulse-modulation techniques to produce pulsed radio frequency (hereinafter known as PRF) signals, which is a subset frequency band within PEMF. At the cellular level, numerous studies demonstrate that BGS, PRF and other electromagnetic field (hereinafter known as EMF) signals modulate the release of growth factors and cytokines.

Stimulation of transforming growth factor beta ("TGF-b") messenger RNA ("mRNA") with EMF in a bone induction model in a rat has been shown. Studies have also demonstrated upregulation of TGF-b mRNA by PEMF in human osteoblast-like cell line designated MG-63, wherein there were increases in TGF-b1, collagen, and osteocalcin synthesis. EMF stimulated an increase in TGF-b1 in both hypertrophic and atrophic cells from human non-union tissue. Further studies demonstrated an increase in both TGF-b1 mRNA and protein in osteoblast cultures resulting from a direct effect of EMF on a calcium/calmodulin-dependent pathway. Cartilage cell studies have shown similar increases in TGF-b1 mRNA and protein synthesis from EMF, demonstrating a therapeutic application to joint repair.

However, prior art in this field has not produced electromagnetic signals configured specifically to instantaneously accelerate the asymmetrical kinetics of the binding of intracellular ions to their associated buffers which regulate the biochemical signaling pathways living systems employ in response to brain tissue ischemia from stroke, traumatic brain injury, head injury, cerebral injury, neurological injury and neurodegenerative diseases. The result is that there are no devices currently in use for clinical applications of electromagnetic fields for the treatment of brain tissue ischemia from stroke, traumatic brain injury, head injury, cerebral injury, neurological injury and neurodegenerative diseases.

Therefore, a need exists for an apparatus and a method that modulates the biochemical pathways that regulate animal and human tissue response to brain tissue ischemia from stroke, traumatic brain injury, head injury, cerebral injury, neurological injury and neurodegenerative diseases by configuring EMF signals specifically to accelerate the asymmetrical kinetics of ion binding to intracellular buffers which regulate the relevant biochemical signaling pathways. Some embodiments provide for a method that employs electromagnetic fields for rapid treatment of brain tissue ischemia from stroke, traumatic brain injury, head injury, cerebral injury, neurological injury and neurodegenerative diseases. In another embodiment, an apparatus incorporates miniaturized circuitry and light weight coil applicators or electrodes thus allowing the apparatus to be low cost, portable and, if desired, disposable. A further need exists for an apparatus and method that incorporates the asymmetrical kinetics of ion binding to intracellular buffers to configure electromagnetic waveforms to increase the rate of ion binding and enhance the biochemical signaling pathways living systems employ in response to brain tissue ischemia from stroke, traumatic brain injury, head injury, cerebral injury, neurological injury and neurodegenerative diseases, and incorporates miniaturized circuitry and light weight applicators that can be constructed to be implantable.

SUMMARY OF THE DISCLOSURE

Various apparatus, methods, devices, and systems are described herein. The summary, FIGS., and detailed descriptions are set forth in ten parts (parts 1-10). Each part may be considered internally consistent, however, embodiments, ranges, features, elements, and illustrations from one part may be used in combination (in whole or in part) with embodiments, ranges, features, elements, and illustrations from another part or parts. Although there is some repetition in the FIGS. and languages in each of these parts, this disclosure is intended to illustrate different variations and embodiments of the devices, systems, and methods for electrically stimulating tissue to treat various disorders, as described in greater detail herein.

Part 1

Described herein are apparatus and methods for delivering electromagnetic signals to human, animal and plant target pathway structures such as molecules, cells, tissue and organs for therapeutic and prophylactic purposes. A preferred embodiment according to the present invention utilizes a Power Signal to Noise Ratio ("Power SNR") approach to configure bioeffective waveforms and incorporates miniaturized circuitry and lightweight flexible coils. This advantageously allows a device that utilizes a Power SNR approach, miniaturized circuitry, and lightweight flexible coils, to be completely portable and if desired to be constructed as disposable and if further desired to be constructed as implantable.

Specifically, broad spectral density bursts of electromagnetic waveforms, configured to achieve maximum signal power within a bandpass of a biological target, are selectively applied to target pathway structures such as living organs, tissues, cells and molecules. Waveforms are selected using a unique amplitude/power comparison with that of thermal noise in a target pathway structure. Signals comprise bursts of at least one of sinusoidal, rectangular, chaotic and random wave shapes, have frequency content in a range of about 0.01 Hz to about 100 MHz at about 1 to about 100,000 bursts per second, and have a burst repetition rate from about 0.01 to about 1000 bursts/second. Peak signal amplitude at a target pathway structure such as tissue, lies in a range of about 1 µV/cm to about 100 mV/cm. Each signal burst envelope may be a random function providing a means to accommodate different electromagnetic characteristics of healing tissue. A preferred embodiment according to the present invention comprises a 20 millisecond pulse burst comprising about 5 to about 20 microsecond symmetrical or asymmetrical pulses repeating at about 1 to about 100 kilohertz within the burst. The burst envelope is a modified 1/f function and is applied at random repetition rates. A resulting waveform can be delivered via inductive or capacitive coupling.

It is an object of the present invention to configure a power spectrum of a waveform by mathematical simulation by using signal to noise ratio ("SNR") analysis to configure an optimized, bioeffective waveform then coupling the configured waveform using a generating device such as ultra lightweight wire coils that are powered by a waveform configuration device such as miniaturized electronic circuitry.

It is another object of the present invention to evaluate Power SNR for any target pathway structure such as molecules, cells, tissues and organs of plants, animals and humans using any input waveform, even if the electrical equivalents are non-linear as in a Hodgkin-Huxley membrane model.

It is another object of the present invention to provide a method and apparatus for treating plants, animals and humans using electromagnetic fields selected by optimizing a power spectrum of a waveform to be applied to a chosen biochemical target pathway structure such as a molecule, cell, tissue and organ of a plant, animal, and human.

It is another object of the present invention to employ significantly lower peak amplitudes and shorter pulse duration. This can be accomplished by matching via Power SNR, a frequency range in a signal to frequency response and sensitivity of a target pathway structure such as a molecule, cell, tissue, and organ, of plants, animals and humans.

Part 2

An electromagnetic treatment induction apparatus and a method for using same for therapeutic treatment of living tissues and cells by inductively coupling optimally configured waveforms to alter the living tissues and cells' interaction with their electromagnetic environment.

According to an embodiment of the present invention, by treating a selectable body region with a flux path comprising a succession of EMF pulses having a minimum width characteristic of at least about 0.01 microseconds in a pulse burst envelope having between about 1 and about 100,000 pulses per burst, in which a voltage amplitude envelope of said pulse burst is defined by a randomly varying parameter in which instantaneous minimum amplitude thereof is not smaller than the maximum amplitude thereof by a factor of one ten-thousandth. The pulse burst repetition rate can vary from about 0.01 to about 10,000 Hz. A mathematically definable parameter can also be employed to define an amplitude envelope of said pulse bursts.

By increasing a range of frequency components transmitted to relevant cellular pathways, access to a large range of biophysical phenomena applicable to known healing mechanisms, including enhanced enzyme activity and growth factor and cytokine release, is advantageously achieved.

According to an embodiment of the present invention, by applying a random, or other high spectral density envelope, to a pulse burst envelope of mono- or bi-polar rectangular or sinusoidal pulses which induce peak electric fields between $10^{-6}$ and 10 volts per centimeter (V/cm), a more efficient and greater effect can be achieved on biological healing processes applicable to both soft and hard tissues in humans, animals and plants. A pulse burst envelope of higher spectral density can advantageously and efficiently couple to physiologically relevant dielectric pathways, such as, cellular membrane receptors, ion binding to cellular enzymes, and general transmembrane potential changes thereby modulating angiogenesis and neovascularization.

By advantageously applying a high spectral density voltage envelope as a modulating or pulse-burst defining parameter, power requirements for such modulated pulse bursts can be significantly lower than that of an unmodulated pulse. This is due to more efficient matching of the frequency components to the relevant cellular/molecular process. Accordingly, the dual advantages of enhanced transmitting dosimetry to relevant dielectric pathways and of decreasing power requirements are achieved.

A preferred embodiment according to the present invention comprises about 0.1 to about 100 millisecond pulse burst comprising about 1 to about 200 microsecond symmetrical or asymmetrical pulses repeating at about 0.1 to about 100 kilohertz within the burst. The burst envelope is a modified 1/f function and is applied at random repetition rates between about 0.1 and about 1000 Hz. Fixed repetition rates can also be used between about 0.1 Hz and about 1000 Hz. An induced electric field from about 0.001 mV/cm to about 100 mV/cm is generated. Another embodiment according to the present invention comprises an about 0.01 millisecond to an about 10 millisecond burst of high frequency sinusoidal waves, such as 27.12 MHz, repeating at about 1 to about 100 bursts per second. An induced electric field from about 0.001 mV/cm to about 100 mV/cm is generated. Resulting waveforms can be delivered via inductive or capacitive coupling.

It is another object of the present invention to provide an electromagnetic method of treatment of living cells and tissues comprising a broad-band, high spectral density electromagnetic field.

It is a further object of the present invention to provide an electromagnetic method of treatment of living cells and tissues comprising amplitude modulation of a pulse burst envelope of an electromagnetic signal that will induce coupling with a maximum number of relevant EMF-sensitive pathways in cells or tissues.

It is an object of the present invention to configure a power spectrum of a waveform by mathematical simulation by using signal to noise ratio ("SNR") analysis to configure a waveform optimized to modulate angiogensis and neovascualarization then coupling the configured waveform using a generating device such as ultra lightweight wire coils that are powered by a waveform configuration device such as miniaturized electronic circuitry.

It is an object of the present invention to provide lightweight flexible coils, that can be placed in at least one of garments, fashion accessories, footwear, bandages, anatomical supports, an anatomical wraps, apparel, cushions, mattresses, pads, wheelchairs, therapeutic beds, therapeutic chairs, therapeutic and health maintenance devices such as vacuum assisted wound closure devices, mechanical and functional electrical stimulation devices and exercise devices and dressings to deliver the optimum dose of non-invasive pulsed electromagnetic treatment configured as shown above, for enhanced repair and growth of living tissue in animals, humans and plants.

It is another object of the present invention to provide multiple coils, delivering a waveform configured by SNR/Power analysis of a target pathway, to increase area of treatment coverage.

It is another object of the present invention to provide multiple coils that are simultaneously driven or that are sequentially driven such as multiplexed, with the same or different optimally configured waveforms as shown above.

It is a further object of the present invention to provide flexible, lightweight coils that focus the EMF signal to the affected tissue by incorporating the coils, delivering a waveform configured by SNR/Power analysis of a target pathway, into ergonomic support garments.

It is yet a further object of the present invention to utilize conductive thread to create daily wear, and exercise and sports garments having integrated coils, delivering a waveform configured by SNR/Power analysis of a target pathway, positioned in proximity to an anatomical target.

It is yet a further object of the present invention to utilize lightweight flexible coils or conductive thread to deliver the EMF signal to affected tissue by incorporating such coils or conductive threads as an integral part of various types of bandages, such as, compression, elastic, cold compress and hot compress and delivering a waveform configured by SNR/Power analysis of a target pathway.

It is another object of the present invention to employ several coils, delivering a waveform configured by SNR/Power analysis of a target pathway, to increase EMF coverage area.

It is another object of the present invention to construct a coil, delivering a waveform configured by SNR/Power analysis of a target pathway, using conductive thread.

It is another object of the present invention to construct a coil, delivering a waveform configured by SNR/Power analysis of a target pathway, using fine flexible conductive wire.

It is another object of the present invention to supply the same or different waveforms configured by SNR/Power analysis of a target pathway, simultaneously or sequentially to single or multiple coils.

It is yet a further object of the present invention to incorporate at least one coil in a surgical wound dressing to apply an enhanced EMF signal non-invasively and non-surgically, the surgical wound dressing to be used in combination with standard wound treatment.

It is another object of the present invention to construct the coils delivering a waveform configured by SNR/Power analysis of a target pathway, for easy attachment and detachment to dressings, garments and supports by using an attachment means such as Velcro, an adhesive and any other such temporary attachment means.

It is another object of the present invention to provide coils delivering a waveform configured by SNR/Power analysis of a target pathway, that are integrated with therapeutic beds, therapeutic chairs, and wheelchairs.

It is another object of the present invention to provide coils delivering a waveform configured by SNR/Power analysis of a target pathway, that are integrated with various therapy surfaces, such as pressure relieving, inflatable, fluid, visco-elastic and air fluidized bed and other support surfaces.

It is another object of the present invention to provide coils delivering a waveform configured by SNR/Power analysis of a target pathway that are integrated with therapeutic seat cushions such as inflatable, fluidized, foam cushions.

It is another object of the present invention to provide coils delivering a waveform configured by SNR/Power analysis of a target pathway, that are integrated with at least one of therapeutic mattress overlays, sheets, blankets, pillows, pillow cases, and therapeutic devices that can apply steady or intermittent pressure such as air clearance vests.

It is another object of the present invention to provide for the inclusion of a flux path to any therapeutic surface, structure, or device to enhance the effectiveness of such therapeutic surfaces, structures or devices by delivering a waveform configured by SNR/Power analysis of a target pathway.

It is another object of the present invention to incorporate coils delivering a waveform configured by SNR/Power analysis of a target pathway, in footware such as shoes.

It is another object of the present invention to integrate at least one coil delivering a waveform configured by SNR/Power analysis of a target pathway, with a therapeutic surface, structure or device to enhance the effectiveness of such therapeutic surface, structure or device.

Part 3

Also described herein are apparatus and methods for electromagnetic treatment of living tissues and cells by altering their interaction with their electromagnetic environment.

It is an object of the present invention to provide modulation of electromagnetically sensitive regulatory processes at the cell membrane and at junctional interfaces between cells.

It is another object of the present invention to provide increased blood flow to affected tissues by modulating angiogenesis and neovascualarization.

It is another object of the present invention to provide increased blood flow to enhance viability, growth, and differentiation of implanted cells, such as stem cells, tissues and organs.

It is another object of the present invention to provide increased blood flow in cardiovascular diseases by modulating angiogenesis and neovascualarization.

It is another object of the present invention to improve micro-vascular blood perfusion and reduced transudation.

It is another object of the present invention to provide a treatment of maladies of the bone and other hard tissue by modulating angiogenesis and neovascularization.

It is a still further object of the present invention to provide a treatment of edema and swelling of soft tissue by increased blood flow through modulation of angiogenesis and neovascularization.

It is another object of the present invention to provide an electromagnetic method of treatment of living cells and tissues that can be used for repair of damaged soft tissue.

It is yet another object of the present invention to increase blood flow to damaged tissue by modulation of vasodilation and stimulating neovascularization.

It is a yet further object of the present invention to provide an apparatus for modulation of angiogenesis and neovascularization that can be operated at reduced power levels and still possess benefits of safety, economics, portability, and reduced electromagnetic interference.

It is another object of the present invention to modulate angiogenesis and neovascularization by evaluating Power SNR for any target pathway structure such as molecules, cells, tissues and organs of plants, animals and humans using any input waveform, even if electrical equivalents are non-linear as in a Hodgkin-Huxley membrane model.

It is another object of the present invention to provide a method and apparatus for treating plants, animals and humans using electromagnetic fields selected by optimizing a power spectrum of a waveform to be applied to a biochemical target pathway structure to enable modulation of angiogenesis and neovascularization within molecules, cells, tissues and organs of a plant, animal, and human.

It is another object of the present invention to significantly lower peak amplitudes and shorter pulse duration. This can be accomplished by matching via Power SNR, a frequency range in a signal to frequency response and sensitivity of a target pathway structure such as a molecule, cell, tissue, and organ, of plants, animals and humans to enable modulation of angiogenesis and neovascularization.

Part 4

The present invention relates to accelerating wound repair of living tissues, cells and molecules by providing a therapeutic, prophylactic and wellness apparatus and method for non-invasive pulsed electromagnetic treatment to enhance condition, repair and growth of living tissue in animals, humans and plants. This beneficial method operates to selectively change a bio-electromagnetic environment associated with cellular and tissue environments by using electromagnetic means such as EMF generators and applicator heads. An embodiment according to the present invention comprises introducing a flux path to a selectable body region, comprising a succession of EMF pulses having a minimum width characteristic of at least 0.01 microseconds in a pulse burst envelope having between 1 and 100,000 pulses per burst, in which a voltage amplitude envelope of said pulse burst is defined by a randomly varying parameter in which an instantaneous minimum amplitude thereof is not smaller than a maximum amplitude thereof by a factor of one ten thousandth. Further, the repetition rate of such pulse bursts may vary from 0.01 to 10,000 Hertz. A mathematically definable parameter satisfying SNR and/or Power SNR detectability requirements in a target structure is employed to define the configuration of the pulse bursts.

It is another object of the present invention to provide a method of treating living cells and tissue by electromagnetically modulating sensitive regulatory processes at a cell membrane and at junctional interfaces between cells, using waveforms configured to satisfy SNR and Power SNR detectability requirements in a target pathway structure.

Specifically, broad spectral density bursts of electromagnetic waveforms, configured to achieve maximum signal power within a bandpass of a biological target, are selectively applied to target pathway structures such as tissues, to enhance effectiveness of pharmacological, chemical, cosmetic and topical agents. Waveforms are selected using a unique amplitude/power comparison with that of thermal noise in a target pathway structure. Signals comprise bursts of at least one of sinusoidal, rectangular, chaotic and random wave shapes, have frequency content in a range of about 0.01 Hz to about 100 MHz at about 1 to about 100,000 bursts per second, and have a burst repetition rate from about 0.01 to about 1000 bursts/second. Peak signal amplitude at a target pathway structure such as organs, cells, tissues, and molecules, lies in a range of about 1 µV/cm to about 100 mV/cm. Each signal burst envelope may be a random function providing a means to accommodate different electromagnetic characteristics of enhancing bioeffective processes. A preferred embodiment according to the present invention comprises about 0.1 to about 100 millisecond pulse burst comprising about 1 to about 200 microsecond symmetrical or asymmetrical pulses repeating at about 0.1 to about 100 kilohertz within the burst. The burst envelope is a modified 1/f function and is applied at random repetition rates between about 0.1 and about 1000 Hz. Fixed repetition rates can also be used between about 0.1 Hz and about 1000 Hz. An induced electric field from about 0.001 mV/cm to about 100 mV/cm is generated. Another embodiment according to the present invention comprises an about 0.01 millisecond to an about 10 millisecond burst of high frequency sinusoidal waves, such as 27.12 MHz, repeating at about 1 to about 100 bursts per second. An induced electric field from about 0.001 mV/cm to about 100 mV/cm is generated. Resulting waveforms can be delivered via inductive or capacitive coupling.

It is another object of the present invention to provide electromagnetic treatment for wound repair having a broadband, high spectral density electromagnetic field configured according to at least one of SNR and Power SNR.

It is another object of the present invention to accelerate wound repair by configuring a power spectrum of a waveform by mathematical simulation by using signal to noise ratio ("SNR") analysis to configure a waveform optimized to modulate angiogensis and neovascualarization, then coupling the configured waveform using a generating device such as ultra lightweight wire coils that are powered by a waveform configuration device such as miniaturized electronic circuitry.

It is another object of the present invention to modulate angiogenesis and neovascularization by evaluating Power SNR at any target pathway structure such as molecules, cells, tissues and organs to accelerate wound repair by using any input waveform, even if electrical equivalents are non-linear as in a Hodgkin-Huxley membrane model.

It is another object of the present invention to provide an apparatus that incorporates use of Power SNR in which amplitude modulation of the pulse burst envelope of the electromagnetic signal will induce coupling with a maximum number of relevant EMF-sensitive pathways in cells and tissues to enhance wound repair in humans, animals and plants.

It is another object of the present invention to provide a method and apparatus for enhancing wound repair using electromagnetic fields selected by optimizing a power spectrum of a waveform to be applied to a biochemical target pathway structure to enable modulation of angiogenesis and neovascularization within molecules, cells, tissues and organs.

It is another object of the present invention to significantly lower peak amplitudes and shorter pulse duration by matching via Power SNR, a frequency range in a signal to frequency response and sensitivity of a target pathway structure such as a molecule, cell, tissue, and organ thereby enabling modulation of angiogenesis and neovascularization for accelerating wound repair.

It is another object of the invention to provide a method of enhancing soft tissue and hard tissue repair.

It is another object of the invention to provide a method of increasing blood flow to affected tissues by modulating angiogenesis.

It is another object of the invention to provide an improved method of increasing blood flow to enhance the viability and growth or differentiation of implanted cells, tissues and organs.

It is another object of the invention to provide an improved method of increasing blood flow in cardiovascular diseases by modulating angiogenesis.

It is another object of the invention to provide beneficial physiological effects through improvement of micro-vascular blood perfusion and reduced transudation.

It is another object of the invention to provide an improved method of treatment of maladies of the bone and other hard tissue.

It is a still further object of the invention to provide an improved means of the treatment of edema and swelling of soft tissue.

It is another object to provide a means of repair of damaged soft tissue.

It is yet another object to provide a means of increasing blood flow to damaged tissue by modulation of vasodilation and stimulating neovascularization.

It is yet another object to enhance healing of post-surgical wounds by reducing the inflammatory phase and modulating growth factor release.

It is yet another object of the instant invention to reduce the inflammatory phase post-cosmetic surgery.

It is yet another object of the instant invention to reduce or eliminate the post-surgical complications of breast augmentation, such as capsular contractions.

It is yet another object of the instant invention to reduce post-surgical pain, edema and discoloration.

It is yet a further object of the present invention to treat chronic wounds such as diabetic ulcers, venous stasis ulcers, pressure sores and any non-healing wound with EMF signals configured according to an embodiment of the present invention.

It is a yet a further object to provide apparatus for use of an electromagnetic method of the character indicated, wherein operation of the apparatus can proceed at reduced power levels as compared to those of related methods known in electromedicine and respective biofield technologies, with attendant benefits of safety, economics, portability, and reduced electromagnetic interference.

It is a further object of the present invention to provide a method for treatment to enhance wellness.

It is a further object of the present invention to provide a method in which electromagnetic waveforms are configured according to SNR and Power SNR detectability requirements in a target pathway structure.

It is another object of the present invention to provide a method for electromagnetic treatment comprising a broadband, high spectral density electromagnetic field.

It is another object of the present invention to provide a method of enhancing soft tissue and hard tissue repair by using EMF.

It is another object of the present invention to provide a method to increase blood flow to affected tissues by using electromagnetic treatment to modulate angiogenesis.

It is yet a further object of the present invention to provide a method of treatment of chronic wounds such as diabetic ulcers, venous stasis ulcers, pressure sores and any non-healing wound.

It is another object of the present invention to provide a method to increase blood flow to regulate viability, growth, and differentiation of implanted cells, tissues and organs.

It is another object of the present invention to provide a method to treat cardiovascular diseases by modulating angiogensis and increasing blood flow.

It is another object of the present invention to provide a method to improve micro-vascular blood perfusion and reduce transudation.

It is another object of the present invention to provide a method to increase blood flow to treat maladies of bone and hard tissue.

It is another object of the present invention to provide a method to increase blood flow to treat edema and swelling of soft tissue.

It is another object of the present invention to provide a method to increase blood flow to repair damaged soft tissue.

It is another object of the present invention to provide a method to increase blood flow to damaged tissue by modulation of vasodilation and stimulating neovascularization.

It is a further object of the present invention to provide an electromagnetic treatment apparatus wherein the apparatus operates using reduced power levels.

It is a yet further object of the present invention to provide an electromagnetic treatment apparatus wherein the apparatus is inexpensive, portable, and produces reduced electromagnetic interference.

Part 5

The present invention relates to enhancing effectiveness of pharmacological, chemical, cosmetic and topical agents used to treat living tissues, cells and molecules by providing a therapeutic, prophylactic and wellness apparatus and method for non-invasive pulsed electromagnetic treatment to enhance condition, repair and growth of living tissue in animals, humans and plants. This beneficial method operates to selectively change a bio-electromagnetic environment associated with cellular and tissue environments by using electromagnetic means such as EMF generators and applicator heads. An embodiment according to the present invention comprises introducing a flux path to a selectable body region, comprising a succession of EMF pulses having a minimum width characteristic of at least 0.01 microseconds in a pulse burst envelope having between 1 and 100,000 pulses per burst, in which a voltage amplitude envelope of said pulse burst is defined by a randomly varying parameter in which an instantaneous minimum amplitude thereof is not smaller than a maximum amplitude thereof by a factor of one ten thousandth. Further, the repetition rate of such pulse bursts may vary from 0.01 to 10,000 Hertz. A mathematically definable parameter satisfying SNR and/or Power SNR detectability requirements in a target structure is employed to define the configuration of the pulse bursts. Mathematically defined parameters are selected by considering the dielectric properties of the target pathway structure, and the ratio of the induced electric field amplitude with respect to voltage due to thermal noise or other baseline cellular activity.

It is another object of the present invention to provide a method of treating living cells and tissue by electromagnetically modulating sensitive regulatory processes at a cell membrane and at junctional interfaces between cells, using waveforms configured to satisfy SNR and Power SNR detectability requirements in a target pathway structure.

It is another object of the present invention to enhance effectiveness of pharmacological, chemical, cosmetic and topical agents by configuring a power spectrum of a waveform by mathematical simulation by using signal to noise ratio ("SNR") analysis to configure a waveform optimized to modulate angiogensis and neovascualarization, then coupling the configured waveform using a generating device such as ultra lightweight wire coils that are powered by a waveform configuration device such as miniaturized electronic circuitry.

It is another object of the present invention to modulate angiogenesis and neovascularization by evaluating Power SNR at any target pathway structure such as molecules, cells, tissues and organs to enhance effectiveness of pharmacological, chemical, cosmetic and topical agents, by using any input waveform, even if electrical equivalents are non-linear as in a Hodgkin-Huxley membrane model.

It is another object of the present invention to provide an apparatus that incorporates use of Power SNR to regulate and adjust electromagnetic therapy treatment to enhance effectiveness of pharmacological, chemical, cosmetic and topical agents.

It is another object of the present invention to provide a method and apparatus for enhancing effectiveness of pharmacological, chemical, cosmetic and topical agents using electromagnetic fields selected by optimizing a power spectrum of a waveform to be applied to a biochemical target pathway structure to enable modulation of angiogenesis and neovascularization within molecules, cells, tissues and organs.

It is another object of the present invention to significantly lower peak amplitudes and shorter pulse duration by matching via Power SNR, a frequency range in a signal to frequency response and sensitivity of a target pathway structure such as a molecule, cell, tissue, and organ thereby enabling modulation of angiogenesis and neovascularization for enhancing effectiveness of pharmacological, chemical, cosmetic and topical agents.

It is a further object of the present invention to provide an apparatus for application of electromagnetic waveforms, to be used in conjunction with pharmacological, chemical, cosmetic and topical agents applied to, upon or in human, animal and plant cells, organs, tissues and molecules so that bioeffective processes of such compounds can be enhanced.

It is a further object of the present invention to provide a method to enhance effectiveness of pharmacological, chemical, cosmetic and topical agents for therapeutic, prophylactic and wellness ends.

It is a further object of the present invention to provide a method for treatment of organs, muscles, joints, skin and hair using EMF in conjunction with pharmacological, chemical, cosmetic and topical agents to improve the agents' effectiveness.

It is a further object of the present invention to provide a method for treatment of organs, muscles, joints, skin and hair using EMF in conjunction with pharmacological, chemical, cosmetic and topical agents to enhance wellness.

It is a further object of the present invention to provide a method in which electromagnetic waveforms are configured according to SNR and Power SNR detectability requirements in a target pathway structure.

It is another object of the present invention to provide a method for electromagnetic treatment comprising a broadband, high spectral density electromagnetic field.

It is another object of the present invention to provide a method of enhancing soft tissue and hard tissue repair by using EMF in conjunction with pharmacological, chemical, cosmetic and topical agents.

It is another object of the present invention to provide a method to enhance effectiveness of pharmacological, chemical, cosmetic and topical agents by increasing blood flow to affected tissues by using electromagnetic treatment to modulate angiogenesis.

It is another object of the present invention to provide a method to increase blood flow for enhancing effectiveness of pharmacological, chemical, cosmetic and topical agents that regulate viability, growth, and differentiation of implanted cells, tissues and organs.

It is another object of the present invention to provide a method to treat cardiovascular diseases by modulating angiogensis and increasing blood flow to enhance effectiveness of pharmacological, chemical, cosmetic and topical agents.

It is another object of the present invention to provide a method that increases physiological effectiveness of pharmacological, chemical, cosmetic and topical agents by improving micro-vascular blood perfusion and reduced transudation.

It is another object of the present invention to provide a method to increase blood flow to enhance effectiveness of pharmacological, chemical, cosmetic and topical agents used for treating maladies of bone and hard tissue.

It is another object of the present invention to provide a method to increase blood flow to enhance effectiveness of pharmacological, chemical, cosmetic and topical agents used for treating edema and swelling of soft tissue.

It is another object of the present invention to provide a method to increase blood flow to enhance effectiveness of pharmacological, chemical, cosmetic and topical agents used for repairing damaged soft tissue.

It is another object of the present invention to provide a method to increase blood flow to damaged tissue by modulation of vasodilation and stimulating neovascularization whereby enhanced effectiveness of pharmacological, chemical, cosmetic and topical agents is achieved.

It is a further object of the present invention to provide an electromagnetic treatment apparatus wherein the apparatus operates using reduced power levels.

It is a yet further object of the present invention to provide an electromagnetic treatment apparatus wherein the apparatus is inexpensive, portable, and produces reduced electromagnetic interference.

Part 6

An electromagnetic treatment induction apparatus integrated into therapeutic and non-therapeutic devices and a method for using same for therapeutic treatment of living tissues and cells by inductively coupling optimally configured waveforms to alter the living tissues and cells' interaction with their electromagnetic environment.

The lightweight flexible coils can be an integral portion of a positioning device such as surgical dressings, wound dressings, pads, seat cushions, mattress pads, shoes, wheelchairs, chairs, and any other garment and structure juxtaposed to living tissue and cells. By advantageously integrating a coil into a positioning device therapeutic treatment can be provided to living tissue and cells in an inconspicuous and convenient manner.

Specifically, broad spectral density bursts of electromagnetic waveforms, configured to achieve maximum signal power within a bandpass of a biological target, are selectively applied to target pathway structures such as living organs, tissues, cells and molecules. Waveforms are selected using a unique amplitude/power comparison with that of thermal noise in a target pathway structure. Signals comprise bursts of at least one of sinusoidal, rectangular, chaotic and random wave shapes, have frequency content in a range of about 0.01 Hz to about 100 MHz at about 1 to about 100,000 bursts per second, and have a burst repetition rate from about 0.01 to about 1000 bursts/second. Peak signal amplitude at a target pathway structure such as tissue, lies in a range of about 1 µV/cm to about 100 mV/cm. Each signal burst envelope may be a random function providing a means to accommodate different electromagnetic characteristics of healing tissue. A preferred embodiment according to the present invention comprises about 0.1 to about 100 millisecond pulse burst comprising about 1 to about 200 microsecond symmetrical or asymmetrical pulses repeating at about 0.1 to about 100 kilohertz within the burst. The burst envelope is a modified 1/f function and is applied at random repetition rates between about 0.1 and about 1000 Hz. Fixed repetition rates can also be used between about 0.1 Hz and about 1000 Hz. An induced electric field from about 0.001 mV/cm to about 100 mV/cm is generated. Another embodiment according to the present invention comprises an about 0.01 millisecond to an about 10 millisecond burst of high frequency sinusoidal waves, such as 27.12 MHz, repeating at about 1 to about 100 bursts per second. An induced electric field from about 0.001 mV/cm to about 100 mV/cm is generated. Resulting waveforms can be delivered via inductive or capacitive coupling.

It is another object of the present invention to deliver a waveform configured by SNR/Power analysis of a target pathway structure, in a programmable manner for example according to a time-dose program, a series of pulses, or some other sequence random or patterned.

It is another object of the present invention to generate a signal from a waveform configured by SNR/Power analysis of a target pathway structure, in a programmable manner for example according to a time-dose program, a series of pulses, or some other sequence random or patterned.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to prevent the loss and deterioration of cells and tissues.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to augment cell and tissue activity.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to increase cell population.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to prevent neuron deterioration.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to increase neuron population.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to prevent deterioration of adrenergic neurons in a cerebrofacial area.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to increase adrenergic neuron population in a cerebrofacial area.

Part 7

An apparatus and a method for electromagnetic treatment of hair and other cerebrofacial molecules, cells, organs, tissue, ions, and ligands by altering their interaction with their electromagnetic environment.

By increasing a range of frequency components transmitted to relevant cellular pathways, hair and other cerebrofacial tissue restoration is advantageously achieved.

According to an embodiment of the present invention, by applying a random, or other high spectral density envelope, to a pulse burst envelope of mono- or bi-polar rectangular or sinusoidal pulses which induce peak electric fields between $10^{-8}$ and 10 volts per centimeter (V/cm), a more efficient and greater effect can be achieved on biological healing processes applicable to both soft and hard tissues in humans, animals and plants. A pulse burst envelope of higher spectral density can advantageously and efficiently couple to physiologically relevant dielectric pathways, such as, cellular membrane receptors, ion binding to cellular enzymes, and general transmembrane potential changes thereby growing, restoring and maintaining hair and other cerebrofacial tissue.

Specifically, broad spectral density bursts of electromagnetic waveforms, configured to achieve maximum signal power within a bandpass of a biological target, are selectively applied to target pathway structures such as hair and other cerebrofacial tissues. Waveforms are selected using a unique amplitude/power comparison with that of thermal noise in a target pathway structure. Signals comprise bursts of at least one of sinusoidal, rectangular, chaotic and random wave shapes, have frequency content in a range of about 0.01 Hz to about 100 MHz at about 1 to about 100,000 bursts per second, and have a burst repetition rate from about 0.01 to about 1000 bursts/second. Peak signal amplitude at a target pathway structure such as hair and or cerebrofacial tissue, lies in a range of about 1 µV/cm to about 100 mV/cm. Each signal burst envelope may be a random function providing a means to accommodate different electromagnetic characteristics of healing tissue. A preferred embodiment according to the present invention comprises about 0.1 to about 100 millisecond pulse burst comprising about 1 to about 200 microsecond symmetrical or asymmetrical pulses repeating at about 0.1 to about 100 kilohertz within the burst. The burst envelope is a modified 1/f function and is applied at random repetition rates between about 0.1 and about 1000 Hz. Fixed repetition rates can also be used between about 0.1 Hz and about 1000 Hz. An induced electric field from about 0.001 mV/cm to about 100 mV/cm is generated. Another embodiment according to the present invention comprises an about 0.01 millisecond to an about 10 millisecond burst of high frequency sinusoidal waves, such as 27.12 MHz, repeating at about 1 to about 100 bursts per second. An induced electric field from about 0.001 mV/cm to about 100 mV/cm is generated. Resulting waveforms can be delivered via inductive or capacitive coupling.

It is another object of the present invention to provide an electromagnetic method of treatment of hair and other cerebrofacial tissues comprising a broad-band, high spectral density electromagnetic field.

It is a further object of the present invention to provide an electromagnetic method of treatment of hair and other cerebrofacial tissues comprising amplitude modulation of a pulse burst envelope of an electromagnetic signal that will induce coupling with a maximum number of relevant EMF-sensitive pathways in cells or tissues.

It is another object of the present invention to provide enhanced hair and other cerebrofacial tissue growth and repair in individuals that have experienced hair loss due to medical conditions such as psoriasis, and hair loss as a result of medication shock and usage.

It is another object of the present invention to provide an apparatus and method that may be used in conjunction with pharmacological and herbal agents, and in conjunction with standard physical therapy and medical treatments.

It is another object of the present invention to provide enhanced hair and other cerebrofacial tissue growth and repair in conjunction with topical and medication treatments.

It is another object of the present invention to provide a self-contained hair restoration and cerebrofacial condition apparatus that can be portable, fashionable, and worn whenever and wherever an individual so desires.

It is another object of the present invention to provide a self-contained hair restoration and cerebrofacial condition apparatus that can be programmed to release electromagnetic therapy treatment at, at least one of specific and random time intervals.

It is a still further object of the present invention to provide a self-contained hair restoration and cerebrofacial condition apparatus for use in any type of headware, for example a hat, sweatband, and flexible knit cap.

It is yet another object of the present invention to increase blood flow to damaged cerebrofacial tissue by modulation of vasodilation and stimulating neovascularization.

It is yet another object of the present invention to prevent the loss and deterioration of cells and tissues of any type in the cerebrofacial area.

A further object of the present invention is to augment the activity of cells and tissues in the cerebrofacial area.

Yet a further object of the present invention is to increase cell population in the cerebrofacial area.

It is yet a further object of the present invention to prevent the deterioration of neurons in the cerebrofacial area.

It is yet another object of the present invention to increase neuron population in the cerebrofacial area.

It is yet a further object of the present invention to prevent the deterioration of adrenergic neurons in the cerebrofacial area.

It is yet another object of the present invention to increase adrenergic neuron population in the cerebrofacial area.

It is a yet another object of the present invention to provide an apparatus for cerebrofacial conditions that modulates angiogenesis and neovascularization that can be operated at reduced power levels and still possess benefits of safety, economics, portability, and reduced electromagnetic interference.

It is an object of the present invention to configure a power spectrum of a waveform by mathematical simulation by using signal to noise ratio ("SNR") analysis to configure a waveform optimized to modulate angiogensis and neovascualarization in a cerebrofacial area then coupling the configured waveform using a generating device such as ultra lightweight wire coils that are powered by a waveform configuration device such as miniaturized electronic circuitry.

It is another object of the present invention to modulate angiogenesis and neovascularization by evaluating Power SNR for any target pathway structure such as molecules, cells, tissues and organs in a cerebrofacial area using any input waveform, even if electrical equivalents are non-linear as in a Hodgkin-Huxley membrane model.

It is another object of the present invention to provide a self-contained hair restoration and cerebrofacial apparatus that incorporates use of Power SNR to regulate and adjust electromagnetic therapy treatment.

It is another object of the present invention to provide a method and apparatus for treating hair loss and other cerebrofacial conditions occurring in animals and humans using electromagnetic fields selected by optimizing a power spectrum of a waveform to be applied to a biochemical target pathway structure to enable modulation of angiogenesis and neovascularization within molecules, cells, tissues and organs in a cerebrofacial area.

It is another object of the present invention to significantly lower peak amplitudes and shorter pulse duration. This can be accomplished by matching via Power SNR, a frequency range in a signal to frequency response and sensitivity of a target pathway structure such as a molecule, cell, tissue, and organ, in a cerebrofacial area to enable modulation of angiogenesis and neovascularization.

Part 8

An embodiment according to the present invention comprises an electromagnetic signal having a pulse burst envelope of spectral density to efficiently couple to physiologically relevant dielectric pathways, such as cellular membrane receptors, ion binding to cellular enzymes, and general transmembrane potential changes. The use of a burst duration which is generally below 100 microseconds for each PRF burst, limits the frequency components that could couple to the relevant dielectric pathways in cells and tissue. An embodiment according to the present invention increases the number of frequency components transmitted to relevant cellular pathways whereby access to a larger range of biophysical phenomena applicable to known healing mechanisms, including enhanced second messenger release, enzyme activity and growth factor and cytokine release can be achieved. By increasing burst duration and applying a random, or other envelope, to the pulse burst envelope of mono-polar or bi-polar rectangular or sinusoidal pulses which induce peak electric fields between $10^{-6}$ and 10 V/cm, a more efficient and greater effect can be achieved on biological healing processes applicable to both soft and hard tissues in humans, animals and plants.

Another embodiment according to the present invention comprises known cellular responses to weak external stimuli such as heat, light, sound, ultrasound and electromagnetic fields. Cellular responses to such stimuli result in the production of protective proteins, for example, heat shock proteins, which enhance the ability of the cell, tissue, organ to withstand and respond to such external stimuli. Electromagnetic fields configured according to an embodiment of the present invention enhance the release of such compounds thus advantageously providing an improved means to enhance prophylactic protection and wellness of living organisms. In certain ophthalmic diseases there are physiological deficiencies and disease states that can have a lasting and deleterious effect on the proper functioning of the ophthalmic system. Those physiological deficiencies and disease states can be positively affected on a non-invasive basis by the therapeutic application of waveforms configured according to an embodiment of the present invention. In addition, electromagnetic waveforms configured according to an embodiment of the present invention can have a prophylactic effect on the ophthalmic system whereby a disease condition can be prevented, and if a disease condition already exists in its earliest stages, that condition can be prevented from developing into a more advanced state.

An example of an ophthalmic disease that can be positively affected by an embodiment according to the present invention, both on a chronic disease as well on a prophylactic basis, is macular degeneration. Age-related macular degeneration ("ARMD") is the most common cause of irreversible vision loss those over the age of 60. Macular degeneration is a disorder of the retina, the light-sensitive inner lining of the back of the eye. There are a number of abnormalities associated with the term "age-related macular degeneration." They range from mild changes with no decrease in vision to abnormalities severe enough to result in the loss of all "straight ahead" vision. Macular degeneration does not cause total blindness because the remaining and undamaged parts of the retina around the macula continue to provide "side" vision.

There are two main types of macular degeneration, "dry" and "wet." With respect to dry macular degeneration, aging causes the cells in the retina to become less efficient. Deposits of tissue, called drusen, appear under the retina which can be identified through visual examination. A few small drusen may cause no decrease in vision. However, if too many large drusen develop, vision will decrease. The application of electromagnetic waveforms configured according to an embodiment of the present invention can positively effect tissue present in the retina and modify the propensity to form drusen, thereby having an effect on the progression of dry macular degeneration. Conversely, wet macular degeneration is a function of leaking of the capillaries in the layer of cells below the retina called the retinal pigment epithelium. Electromagnetic waveforms configured according to an embodiment of the present invention, have proven to have a positive effect on circulatory vessels and other tissues which can lead to an improvement in the disease state of wet macular degeneration.

Another advantage of electromagnetic waveforms configured according to an embodiment of the present invention is that by applying a high spectral density voltage envelope as the modulating or pulse-burst defining parameter, the power requirement for such increased duration pulse bursts can be significantly lower than that of shorter pulse bursts containing pulses within the same frequency range; this is due to more efficient matching of the frequency components to the relevant cellular/molecular process. Accordingly, the dual advantages, of enhanced transmitted dosimetry to the relevant dielectric pathways and of decreased power requirement are achieved.

The present invention relates to a therapeutically beneficial method of and apparatus for non-invasive pulsed electromagnetic treatment for enhanced condition, repair and growth of living tissue in animals, humans and plants. This beneficial method operates to selectively change the bio-electromagnetic environment associated with the cellular and tissue environment through the use of electromagnetic means such as PRF generators and applicator heads. An embodiment of the present invention more particularly includes the provision of a flux path, to a selectable body region, of a succession of EMF pulses having a minimum width characteristic of at least 0.01 microseconds in a pulse burst envelope having between 1 and 100,000 pulses per burst, in which a voltage amplitude envelope of said pulse burst is defined by a randomly varying parameter in which the instantaneous minimum amplitude thereof is not smaller than the maximum amplitude thereof by a factor of one ten-thousandth. Further, the repetition rate of such pulse bursts may vary from 0.01 to 10,000 Hz. Additionally a mathematically-definable parameter can be employed in lieu of said random amplitude envelope of the pulse bursts.

By increasing a range of frequency components transmitted to relevant cellular pathways, access to a large range of biophysical phenomena applicable to known healing mechanisms, including enhanced second messenger release, enzyme activity and growth factor and cytokine release, is advantageously achieved.

Another advantage of an embodiment according to the present invention is that by applying a high spectral density voltage envelope as a modulating or pulse-burst defining parameter, power requirements for such modulated pulse bursts can be significantly lower than that of an unmodulated pulse. This is due to more efficient matching of the frequency components to the relevant cellular/molecular process. Accordingly, the dual advantages of enhanced transmitting dosimetry to relevant dielectric pathways and of decreasing power requirements are achieved.

A further object of the present invention is to integrate at least one coil delivering a waveform configured by SNR/Power analysis of a target pathway structure, with a therapeutic surface, structure or device to enhance the effectiveness of such therapeutic surface, structure or device to augment the activity of cells and tissues of any type in any living target area.

It is yet a further object of the present invention to provide an improved electromagnetic method of the beneficial treatment of living cells and tissue by the modulation of electromagnetically sensitive regulatory processes at the cell membrane and at junctional interfaces between cells.

A further object of the present invention is to provide a means for the use of electromagnetic waveforms to cause a beneficial effect in the treatment of ophthalmic diseases.

It is a further object of the present invention to provide improved means for the prophylactic treatment of the ophthalmic system to improve function and to prevent or arrest diseases of the ophthalmic system.

It is another object to provide an electromagnetic treatment method of the above type having a broad-band, high spectral density electromagnetic field.

It is a further object of the present invention to provide a method of the above type in which amplitude modulation of the pulse burst envelope of the electromagnetic signal will induce coupling with a maximum number of relevant EMF-sensitive pathways in cells or tissues.

It is another object of the present invention to provide an improved method of enhancing soft tissue and hard tissue repair.

It is another object of the present invention to provide an improved method of increasing blood flow to affected tissues by modulating angiogenesis.

It is another object of the present invention to provide an improved method of increasing blood flow to enhance the viability and growth or differentiation of implanted cells, tissues and organs.

It is another object of the present invention to provide an improved method of increasing blood flow in cardiovascular diseases by modulating angiogenesis.

It is another object of the present invention to provide beneficial physiological effects through improvement of micro-vascular blood perfusion and reduced transudation.

It is another object of the present invention to provide an improved method of treatment of maladies of the bone and other hard tissue.

It is a still further object of the present invention to provide an improved means of the treatment of edema and swelling of soft tissue.

It is a still further object of the present invention to provide an improved means to enhance second messenger release.

It is another object of the present invention to provide a means of repair of damaged soft tissue.

It is yet another object of the present invention to provide a means of increasing blood flow to damaged tissue by modulation of vasodilation and stimulating neovascularization.

It is a yet further object of the present invention to provide an apparatus that can operate at reduced power levels as compared to those of related methods known in electromedicine and respective biofield technologies, with attendant benefits of safety, economics, portability, and Part 9

The methods and apparatus according to present invention, comprises delivering electromagnetic signals to respiratory target pathway structures, such as respiratory molecules, respiratory cells, respiratory tissues, and respiratory organs for treatment of inflammatory processes leading to excessive fibrous tissue formation such as scar tissue, associated with the inhalation of foreign particles into lung tissue. An embodiment according to the present invention utilizes SNR and Power SNR approaches to configure bioeffective waveforms and incorporates miniaturized circuitry and lightweight flexible coils. This advantageously allows a device that utilizes the SNR and Power SNR approaches, miniaturized circuitry, and lightweight flexible coils to be completely portable and if desired to be constructed as disposable.

An embodiment according to the present invention comprises an electromagnetic signal having a pulse burst envelope of spectral density to efficiently couple to physiologically relevant dielectric pathways, such as cellular membrane receptors, ion binding to cellular enzymes, and general transmembrane potential changes. The use of a burst duration which is generally below 100 microseconds for each PRF burst, limits the frequency components that could couple to the relevant dielectric pathways in cells and tissue. An embodiment according to the present invention increases the number of frequency components transmitted to relevant cellular pathways whereby access to a larger range of biophysical phenomena applicable to known healing mechanisms, including enhanced second messenger release, enzyme activity and growth factor and cytokine release can be achieved. By increasing burst duration and applying a random, or other envelope, to the pulse burst envelope of mono-polar or bi-polar rectangular or sinusoidal pulses which induce peak electric fields between $10^{-6}$ and 10 V/cm, a more efficient and greater effect can be achieved on biological healing processes applicable to both soft and hard tissues in humans, animals and plants.

Another embodiment according to the present invention comprises known cellular responses to weak external stimuli such as heat, light, sound, ultrasound and electromagnetic fields. Cellular responses to such stimuli result in the production of protective proteins, for example, heat shock proteins, which enhance the ability of the cell, tissue, organ to withstand and respond to such external stimuli. Electromagnetic fields configured according to an embodiment of the present invention enhance the release of such compounds thus advantageously providing an improved means to enhance prophylactic protection and wellness of living organisms. In certain respiratory diseases there are physiological deficiencies and disease states that can have a lasting and deleterious effect on the proper functioning of the respiratory system. Those physiological deficiencies and disease states can be positively affected on a non-invasive basis by the therapeutic application of waveforms configured according to an embodiment of the present invention. In addition, electromagnetic waveforms configured according to an embodiment of the present invention can have a prophylactic effect on the respiratory system whereby a disease condition can be prevented, and if a disease condition already exists in its earliest stages, that condition can be prevented from developing into a more advanced state.

An example of a respiratory disease that can be positively affected by an embodiment according to the present invention, both on a chronic disease as well on a prophylactic basis, is inflammation in lung tissue resulting from inhalation of foreign particles that remain in lung tissue. Electromagnetic waveforms configured according to an embodiment of the present invention, have proven to have a positive effect on circulatory vessels and other tissues which can lead to reducing inflammation that can lead to lung disease.

Another advantage of electromagnetic waveforms configured according to an embodiment of the present invention is that by applying a high spectral density voltage envelope as the modulating or pulse-burst defining parameter, the power requirement for such increased duration pulse bursts can be significantly lower than that of shorter pulse bursts containing pulses within the same frequency range; this is due to more efficient matching of the frequency components to the relevant cellular/molecular process. Accordingly, the dual advantages, of enhanced transmitted dosimetry to the relevant dielectric pathways and of decreased power requirement are achieved.

The present invention relates to a therapeutically beneficial method of and apparatus for non-invasive pulsed electromagnetic treatment for enhanced condition, repair and growth of living tissue in animals, humans and plants. This beneficial method operates to selectively change the bio-electromagnetic environment associated with the cellular and tissue environment through the use of electromagnetic means such as PRF generators and applicator heads. An embodiment of the present invention more particularly includes the provision of a flux path, to a selectable body region, of a succession of EMF pulses having a minimum width characteristic of at least 0.01 microseconds in a pulse burst envelope having between 1 and 100,000 pulses per burst, in which a voltage amplitude envelope of said pulse burst is defined by a randomly varying parameter in which the instantaneous minimum amplitude thereof is not smaller than the maximum amplitude thereof by a factor of one ten-thousandth. Further, the repetition rate of such pulse bursts may vary from 0.01 to 10,000 Hz. Additionally a mathematically-definable parameter can be employed in lieu of said random amplitude envelope of the pulse bursts.

Another advantage of an embodiment according to the present invention is that by applying a high spectral density voltage envelope as a modulating or pulse-burst defining parameter, power requirements for such modulated pulse bursts can be significantly lower than that of an unmodulated pulse. This is due to more efficient matching of the frequency components to the relevant cellular/molecular process. Accordingly, the dual advantages of enhanced transmitting dosimetry to relevant dielectric pathways and of decreasing power requirements are achieved.

Specifically, broad spectral density bursts of electromagnetic waveforms, configured to achieve maximum signal power within a bandpass of a biological target, are selectively applied to target pathway structures such as living organs, tissues, cells and molecules. Waveforms are selected using a novel amplitude/power comparison with that of thermal noise in a target pathway structure. Signals comprise bursts of at least one of sinusoidal, rectangular, chaotic and random wave shapes have frequency content in a range of 0.01 Hz to 100 MHz at 1 to 100,000 bursts per second, with a burst duration from 0.01 to 100 milliseconds, and a burst repetition rate from 0.01 to 1000 bursts/second. Peak signal amplitude at a target pathway structure such as tissue, lies in a range of 1 µV/cm to 100 mV/cm. Each signal burst envelope may be a random function providing a means to accommodate different electromagnetic characteristics of healing tissue. Preferably the present invention comprises a 20 millisecond pulse burst, repeating at 1 to 10 burst/second and comprising 5 to 200 microsecond symmetrical or asymmetrical pulses repeating at 0.1 to 100 kilohertz within the burst. The burst envelope is a modified 1/f function and is applied at random repetition rates. Fixed repetition rates can also be used between about 0.1 Hz and about 1000 Hz. An induced electric field from about 0.001 mV/cm to about 100 mV/cm is generated. Another embodiment according to the present invention comprises a 4 millisecond of high frequency sinusoidal waves, such as 27.12 MHz, repeating at 1 to 100 bursts per second. An induced electric field from about 0.001 mV/cm to about 100 mV/cm is generated. Resulting waveforms can be delivered via inductive or capacitive coupling for 1 to 30 minute treatment sessions delivered according to predefined regimes by which PEMF treatment may be applied for 1 to 12 daily sessions, repeated daily. The treatment regimens for any waveform configured according to the instant invention may be fully automated. The number of daily treatments may be programmed to vary on a daily basis according to any predefined protocol.

In another aspect of the present invention, an electromagnetic method of treatment of living cells and tissues comprising modulation of electromagnetically sensitive regulatory processes at a cell membrane and at junctional interfaces between cells is provided.

In another aspect of the present invention, multiple coils deliver a waveform configured by SNR/Power analysis of a target pathway structure, to increase area of treatment coverage.

In another aspect of the present invention, multiple coils that are simultaneously driven or that are sequentially driven such as multiplexed, deliver the same or different optimally configured waveforms as illustrated above.

In still another aspect of the present invention, flexible, lightweight coils that focus the EMF signal to the affected tissue delivering a waveform configured by SNR/Power analysis of a target pathway structure, are incorporated into dressings and ergonomic support garments.

In a further aspect of the present invention, at least one coil delivering a waveform configured by SNR/Power analysis of a target pathway structure, is integrated with a therapeutic surface, structure or device to enhance the effectiveness of such therapeutic surface, structure or device to augment the activity of cells and tissues of any type in any living target area.

In yet a further aspect of the present invention, an improved electromagnetic method of the beneficial treatment of living cells and tissue by the modulation of electromagnetically sensitive regulatory processes at the cell membrane and at junctional interfaces between cells is provided.

In a further aspect of the present invention, a means for the use of electromagnetic waveforms to cause a beneficial effect in the treatment of respiratory diseases is provided.

In a further aspect of the present invention, improved means for the prophylactic treatment of the respiratory system to improve function and to prevent or arrest diseases of the respiratory system is provided.

In another aspect of the present invention, an electromagnetic treatment method of the above type having a broadband, high spectral density electromagnetic field is provided.

In a further aspect of the present invention, a method of the above type in which amplitude modulation of the pulse burst envelope of the electromagnetic signal will induce coupling with a maximum number of relevant EMF-sensitive pathways in cells or tissues is provided.

In another aspect of the present invention, an improved method of enhancing soft tissue and hard tissue repair is provided.

In another aspect of the present invention, an improved method of increasing blood flow to affected tissues by modulating angiogenesis is provided.

In another aspect of the present invention, an improved method of increasing blood flow to enhance the viability and growth or differentiation of implanted cells, tissues and organs is provided.

In another aspect of the present invention, an improved method of increasing blood flow in cardiovascular diseases by modulating angiogenesis is provided.

In another aspect of the present invention, beneficial physiological effects through improvement of micro-vascular blood perfusion and reduced transudation are provided.

In another aspect of the present invention, an improved method of treatment of maladies of the bone and other hard tissue is provided.

In still further aspect of the present invention, an improved means of the treatment of edema and swelling of soft tissue is provided.

In a further aspect of the present invention, an improved means to enhance second messenger release is provided.

In another aspect of the present invention, a means of repair of damaged soft tissue is provided.

In yet another aspect of the present invention, a means of increasing blood flow to damaged tissue by modulation of vasodilation and stimulating neovascularization is provided.

In yet a further aspect of the present invention, an apparatus that can operate at reduced power levels as compared to those of related methods known in electromedicine and respective biofield technologies, with attendant benefits of safety, economics, portability, and reduced electromagnetic interference is provided.

"About" for purposes of the invention means a variation of plus or minus 0.1%.

"Respiratory" for purposes of the invention means any organs and structures such as nose, nasal passages, nasopharynx, larynx, trachea, bronchi, lungs and airways in which gas exchange takes.

Part 10

The apparatus and method according to present invention, comprise delivering electromagnetic signals to fibrous capsule formation and capsular contracture target pathway structures, such as capsular molecules, capsular cells, capsular tissues, and capsular organs for alleviation of the propensity of a capsule to compress or harden, for reduction of excessive fibrous capsule formation, and for reduction in existing capsule involvement with a physical area of a body. An embodiment according to the present invention utilizes SNR and Power SNR approaches to configure bioeffective waveforms and incorporates miniaturized circuitry and lightweight flexible coils. This advantageously allows a device that utilizes the SNR and Power SNR approaches, miniaturized circuitry, and lightweight flexible coils to be completely portable and if desired to be constructed as disposable.

An apparatus comprising an electromagnetic signal generating means for emitting signals comprising bursts of at least one of sinusoidal, rectangular, chaotic, and random waveforms, having a frequency content in a range of about 0.01 Hz to about 100 MHz at about 1 to about 100,000 waveforms per second, having a burst duration from about 1 usec to about 100 msec, and having a burst repetition rate from about 0.01 to about 1000 bursts/second, wherein the waveforms are adapted to have sufficient signal to noise ratio of at least about 0.2 in respect of a given fibrous capsule formation and capsular contracture target pathway structure to modulate at least one of ion and ligand interactions in that fibrous capsule formation and capsular contracture target pathway structure, wherein the signal to noise ratio is evaluated by calculating a frequency response of the impedance of the target path structure divided by a calculated frequency response of baseline thermal fluctuations in voltage across the target path structure, an electromagnetic signal coupling means wherein the coupling means comprises at least one of an inductive coupling means and a capacitive coupling means, connected to the electromagnetic signal generating means for delivering the electromagnetic signal to the fibrous capsule formation and capsular contracture target pathway structure, and a garment wherein the electromagnetic signal generating means and electromagnetic signal coupling means are incorporated into the garment.

An apparatus comprising a waveform configuration means for configuring at least one waveform to have sufficient signal to noise ratio or power signal to noise ratio of at least about 0.2, to modulate at least one of ion and ligand interactions whereby the at least one of ion and ligand interactions are detectable in a fibrous capsule formation and capsular contracture target pathway structure above baseline thermal fluctuations in voltage and electrical impedance at the fibrous capsule formation and capsular contracture target pathway structure, wherein the signal to noise ratio is evaluated by calculating a frequency response of the impedance of the target path structure divided by a calculated frequency response of baseline thermal fluctuations in voltage across the target path structure, a coupling device connected to the waveform configuration means by at least one connecting means for generating an electromagnetic signal from the configured at least one waveform and for coupling the electromagnetic signal to the fibrous capsule formation and capsular contracture target pathway structure whereby the at least one of ion and ligand interactions are modulated, and a garment incorporating the waveform configuration means, the at least one connecting means, and the coupling device.

A method comprising establishing baseline thermal fluctuations in voltage and electrical impedance at a fibrous capsule formation and capsular contracture target pathway structure depending on a state of the fibrous capsule tissue, evaluating a signal to noise ratio by calculating a frequency response of the impedance of the target pathway structure divided by a calculated frequency response of baseline thermal fluctuations in voltage across the target pathway structure, configuring at least one waveform to have sufficient signal to noise ratio of at least about 0.2 to modulate at least one of ion and ligand interactions whereby the at least one of ion and ligand interactions are detectable in the fibrous capsule formation and capsular contracture target pathway structure above the evaluated baseline thermal fluctuations in voltage, generating an electromagnetic signal from the configured at least one waveform; and coupling the electromagnetic signal to the fibrous capsule formation and capsular contracture target pathway structure using a coupling device.

Part 11

Described herein are devices, systems and methods for delivering electromagnetic signals and fields configured specifically to accelerate the asymmetrical kinetics of the binding of intracellular ions to their respective intracellular buffers, to enhance the biochemical signaling pathways animals and humans employ to respond to brain tissue ischemia from stroke, traumatic brain injury, head injury, cerebral injury, neurological injury and neurodegenerative diseases.

One variation according to the present invention utilizes a repetitive burst of arbitrary non-thermal EMF waveforms configured to maximize the bound concentration of intracellular ions at their associated molecular buffers to enhance the biochemical signaling pathways living systems employ in response to brain tissue ischemia from stroke, traumatic brain injury, head injury, cerebral injury, neurological injury and neurodegenerative diseases. Non-thermal electromagnetic waveforms are selected first by choosing the ion and the intracellular binding protein, for example $Ca^{2+}$ and CaM, among the many ion-buffer combinations within the living cell, which determines the frequency range within which the signal must have non-thermal frequency components of sufficient, but non-destructive, amplitude to accelerate the kinetics of ion binding. Signals comprise a pulse duration, random signal duration or carrier period which is less than half of the ion bound time to increase the voltage in the target pathway so as to maximally accelerate ion binding to maximally modulate biochemical signaling pathways to enhance specific cellular and tissue responses to brain tissue ischemia from stroke, traumatic brain injury, head injury, cerebral injury, neurological injury and neurodegenerative diseases.

In some variations, signals comprise bursts of at least one of sinusoidal, rectangular, chaotic or random EMF wave shapes; have burst duration less than about 100 msec, with frequency content less than about 100 MHz, repeating at less than about 1000 bursts per second. Peak signal amplitude in the ion-buffer binding pathway is less than about 1000 V/m. Another embodiment comprises about a 1 to about a 50 millisecond burst of radio frequency sinusoidal waves in the range of about 1 to about 100 MHz, incorporating radio frequencies in the industrial, scientific and medical (hereinafter known as ISM) band, for example 27.12 MHz, but it may be 6.78 MHz, 13.56 MHz or 40.68 MHz in the short wave frequency band, repeating between about 0.1 and about 10 bursts/sec. Such waveforms can be delivered via inductive coupling with a coil applicator or via capacitive coupling with electrodes in electrochemical contact with the conductive outer surface of the target.

Some embodiments described provide for a waveform configuration that accelerates the kinetics of $Ca^{2+}$ binding to CaM, consisting of about a 1 to about a 10 msec burst of between about 5 MHz to about 50 MHz in the ISM band, repeating between about 1 and about 5 bursts/sec and inducing a peak electric field between about 1 and about 100 V/m, then coupling the configured waveform using a generating device such as ultra lightweight wire or printed circuit coils that are powered by a waveform configuration device such as miniaturized electronic circuitry.

Other embodiments described provide for a waveform configuration that accelerates the kinetics of $Ca^{2+}$ binding to CaM, consisting of about a 1 to about a 10 msec burst of 27.12 MHz radio frequency sinusoidal waves, repeating between about 1 and about 5 bursts/sec and inducing a peak electric field between about 1 and about 100 V/m, then coupling the configured waveform using a generating device such as ultra lightweight wire, printed circuit coils or conductive garments that are powered by a waveform configuration device such as miniaturized electronic circuitry which is programmed to apply the aforementioned waveform at fixed or variable intervals, for example for 1 minute every 10 minutes, or for 10 minutes every hour, or for any other regimen found to be beneficial for a prescribed treatment.

Further embodiments provide for methods and devices for applying electromagnetic waveforms to animals and humans that accelerate the asymmetrical kinetics of the binding of intracellular ions to their associated intracellular buffers, by configuring the waveforms to contain repetitive frequency components of sufficient amplitude to maximize the bound concentration of the intracellular ion to its associated intracellular buffer, thereby to enhance the biochemical signaling pathways living tissue employ in response to brain tissue ischemia from stroke, traumatic brain injury, head injury, cerebral injury, neurological injury and neurodegenerative diseases.

Additional embodiments provide for methods and devices for applying electromagnetic waveforms to animals and humans which match the asymmetrical kinetics of the binding of $Ca^{2+}$ to CaM by configuring the waveforms to contain repetitive frequency components of sufficient amplitude to accelerate and increase the binding of $Ca^{2+}$ to CaM, thereby enhancing the CaM-dependent nitric oxide (NO)/cyclic guanosine monophosphate (cGMP) signaling pathway.

Further embodiments provide for electromagnetic waveform configurations to contain repetitive frequency components of sufficient amplitude to accelerate and increase the binding of $Ca^{2+}$ to CaM, thereby enhancing the CaM-dependent NO/cGMP signaling pathway to accelerate blood and lymph vessel dilation for relief of post-operative and post traumatic pain and edema.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to enhance angiogenesis and microvascularization for hard and soft tissue repair.

A further aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to accelerate deoxyribonucleic acid (hereinafter known as DNA) synthesis by living cells.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway to modulate growth factor release, such as basic fibroblast growth factor (bFGF), vascular endothelial growth factor (VGEF), bone morphogenic protein (BMP), or any other growth factor production by living cells.

It is yet another aspect of the present invention to configure electromagnetic waveforms to contain repetitive frequency components of sufficient amplitude to accelerate and increase the binding of $Ca^{2+}$ to CaM, thereby enhancing the CaM-dependent NO/cGMP signaling pathway to modulate growth factor release, such as basic fibroblast growth factor (bFGF), vascular endothelial growth factor (VGEF), bone morphogenic protein (BMP), or any other growth factor production by living cells employ in response to brain tissue ischemia from stroke, traumatic brain injury, head injury, cerebral injury, neurological injury and neurodegenerative diseases.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to modulate cytokine, such as interleukin 1-beta (IL-1β), interleukin-6 (IL-6), or any other cytokine production by living cells.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to modulate cytokine, such as interleukin 1-beta (IL-1β), interleukin-6 (IL-6), or any other cytokine production by living cells in response to brain tissue ischemia from stroke, traumatic brain injury, head injury, cerebral injury, neurological injury and neurodegenerative diseases.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to accelerate the production of extracellular proteins for tissue repair and maintenance.

It is another aspect of the present invention to configure electromagnetic waveforms to contain repetitive frequency components of sufficient amplitude to accelerate and increase the binding of $Ca^{2+}$ to CaM, thereby enhancing the CaM-dependent NO/cyclic adenosine monophosphate (cAMP) signaling pathway, or any other signaling pathway, to modulate cell and tissue differentiation.

It is yet another aspect of the present invention to configure electromagnetic waveforms to contain repetitive frequency components of sufficient amplitude to accelerate and increase the binding of $Ca^{2+}$ to CaM, thereby enhancing the CaM-dependent NO/cAMP signaling pathway, or any other signaling pathway, to prevent or reverse neurodegeneration.

Another aspect of the present invention is to configure electromagnetic waveforms to contain frequency components of sufficient amplitude to accelerate the binding of $Ca^{2+}$ to CaM, thereby enhancing the CaM-dependent NO/cGMP signaling pathway to modulate heat shock protein release from living cells.

Yet another aspect of the invention provides for a method for treating a neurological injury or condition in a patient in need thereof including the steps of generating a pulsed electromagnetic field from a pulsed electromagnetic field source and applying the pulsed electromagnetic field in proximity to a target region affected by the neurological injury or condition to reduce a physiological response to the neurological injury or condition. Optionally, in any of the preceding embodiments, the physiological response can be inflammation and/or increased intracranial pressure.

Optionally, in any of the preceding embodiments, the method may also include monitoring the physiological response and continuing to apply the pulsed electromagnetic field until an acceptable level of the physiological response is reached. Optionally, in any of the preceding embodiments, the physiological response can be increased intracranial pressure and the acceptable level is below about 20 mmHg.

In further variations, the method may include a pulsed electromagnetic field comprising a 2 msec burst of 27.12 MHz sinusoidal waves repeating at 2 Hz. In other variations, the method may include a pulsed electromagnetic field comprising a 3 msec burst of 27.12 MHz sinusoidal waves repeating at 2 Hz. In further embodiments, the pulsed electromagnetic field may comprise a 4 msec burst of 27.12 MHz sinusoidal waves repeating at 2 Hz.

A further aspect of the invention provides for a method for treating a neurological injury or condition in a patient in need thereof where the method includes generating a first pulsed electromagnetic field from a pulsed electromagnetic field source; applying the first pulsed electromagnetic field in proximity to a target region affected by the neurological injury or condition to reduce a physiological response to the neurological injury or condition for a first treatment interval; discontinuing the application of the first pulsed electromagnetic field for an inter-treatment period greater than zero; and applying a second pulsed electromagnetic field in proximity to the target region. Optionally, in any of the preceding embodiments, the first and second pulsed electromagnetic fields are substantially the same.

Optionally, in any of the preceding embodiments, the method may include monitoring the physiological response; and modifying the first pulsed electromagnetic field to the second pulsed electromagnetic field in response to the monitoring step.

Moreover, optionally, in any of the preceding embodiments, the method may also include monitoring the physiological response; and discontinuing treatment once an acceptable level of the physiological response is reached.

Optionally, in any of the preceding embodiments, the method may also include attenuating inflammatory cytokines and growth factors at the target region by applying the first pulsed electromagnetic field or the second pulsed electromagnetic field to the target region.

Optionally, in any of the preceding embodiments, the method may also include accelerating the healing of the target region by applying the first pulsed electromagnetic field or the second pulsed electromagnetic field to the target region.

Furthermore, in other embodiments, applying the first pulsed electromagnetic field in proximity to a target region affected by the neurological injury or condition to reduce a physiological response may comprise reducing a concentration of IL-1β. In further embodiments, the neurological injury or condition may be a neurodegenerative disease.

In further embodiments, the neurological injury or condition is TBI.

Another aspect of the invention provides for a method for treating a neurological injury or condition in a patient in need thereof, the method including generating a pulsed electromagnetic field from a pulsed electromagnetic field source; and applying the pulsed electromagnetic field in proximity to a target brain region affected by the neurological injury or condition to reduce a physiological response to the neurological injury or condition by modulating microglia activation in the target brain region. In some embodiments, modulating microglia activation includes reducing microglia activation in the target brain region.

Another aspect of the invention provides for a method of promoting neurological repair or growth following a neurological injury or condition including placing a treatment coil of a self-contained, lightweight, and portable treatment apparatus externally to a target treatment site in need of repair or development, wherein the treatment apparatus comprises a conformable coil having one or more turns of wire and a control circuit; generating an electromagnetic field using the treatment coil; delivering the electromagnetic field to the target treatment site using the treatment coil; and reducing a physiological response to the neurological injury or condition.

Optionally, in any of the preceding embodiments, generating an electromagnetic field comprises generating at least one burst of sinusoidal, rectangular, chaotic, or random waveforms, having a frequency content in a range of about 0.01 Hz to about 10,000 MHz at about 1 to about 100,000 bursts per second, having a burst duration from about 0.01 to about 1000 bursts per second, and having a burst repetition rate from about 0.01 to about 1000 bursts/second.

Generating an electromagnetic field may comprise generating at least one burst of sinusoidal, rectangular, chaotic, or random waveforms, having a frequency content in a range of about 0.01 Hz to about 10,000 MHz, having a burst duration from about 0.1 to about 100 msec, at a peak amplitude of 0.001 G to about 0.1 G, and having a burst repetition rate from about 0.01 to about 100 bursts/second.

Optionally, in any of the preceding embodiments, the method may also include delivering the electromagnetic field for a period of about 1 minute to about 240 minutes.

Optionally, in any of the preceding embodiments, the physiological response can be a cognitive deficiency.

Optionally, in any of the preceding embodiments, the pulsed electromagnetic field comprises about a 1 msec to about a 10 msec burst of 27.12 MHz sinusoidal waves repeating at about 1 Hz to about 10 Hz.

Optionally, in any of the preceding embodiments, the pulsed electromagnetic field comprises an ISM carrier frequency modulated at about a 1 msec to about a 10 msec burst repeating at about 1 Hz to about 10 Hz.

Optionally, in any of the preceding embodiments, the pulsed electromagnetic field comprises an ISM carrier or any other radio frequency up to 10,000 GHz, configured to modulate a rhythm of a physiological system.

Optionally, in any of the preceding embodiments, the physiological system is the central nervous system. Moreover, optionally, in any of the preceding embodiments, the physiological system is the peripheral nervous system. Additionally, optionally, in any of the preceding embodiments, the physiological system is the cardiac system.

Optionally, in any of the preceding embodiments, the physiological system is the pulmonary system.

Optionally, in any of the preceding embodiments, the pulsed electromagnetic field comprises an ISM carrier or any other radio frequency up to 10,000 GHz, configured to modulate a rhythm of a physiological process Optionally, in any of the preceding embodiments, the pulsed electromagnetic field comprises an ISM carrier or any other radio frequency up to 10,000 GHz, configured to modulate a rhythm of a brain.

Optionally, in any of the preceding embodiments, the pulsed electromagnetic field comprises an ISM carrier or any other radio frequency up to 10,000 GHz, configured to modulate a circadian rhythm.

Optionally, in any of the preceding embodiments, the pulsed electromagnetic field comprises an ISM carrier frequency configured to modulate quality of sleep.

Optionally, in any of the preceding embodiments, the pulsed electromagnetic field is configured to modulate calmodulin-dependent signaling in a biological system.

Optionally, in any of the preceding embodiments, the electromagnetic field comprises a waveform that produces an effect upon calmodulin-dependent signaling in a biological system.

Optionally, in any of the preceding embodiments, the electromagnetic field comprises a waveform that modulates at least one biological signaling pathway.

Optionally, in any of the preceding embodiments, the method may also include increasing a growth factor in the target region.

Optionally, in any of the preceding embodiments, increasing a growth factor in the target region enhances angiogenesis.

Optionally, in any of the preceding embodiments, increasing a growth factor in the target region enhances nervous tissue regeneration.

Optionally, in any of the preceding embodiments, the growth factor is selected from the group consisting of FGF-2, VEGF, and BMP.

Optionally, in any of the preceding embodiments, the pulsed electromagnetic field comprises an ISM carrier or any other radio frequency up to 10,000 GHz, configured to modulate a sleep pattern.

Optionally, in any of the preceding embodiments, the pulsed electromagnetic field comprises an ISM carrier or any other radio frequency up to 10,000 GHz, configured to modulate slow-wave sleep in a sleep cycle to effect the production of human growth hormone. The above and yet other embodiments and advantages of the present invention will become apparent from the hereinafter set forth Brief Description of the Drawings and Detailed Description of the Invention.

"About" for purposes of the invention means a variation of plus or minus 50%.

The above and yet other aspects and advantages of the present invention will become apparent from the hereinafter set forth Brief Description of the Drawings and Detailed Description of the Invention.

BRIEF DESCRIPTION OF THE DRAWINGS

Preferred embodiments of the present invention will be described below in more detail, with reference to the accompanying drawings.

Part 1

Part 2

Figure 9:
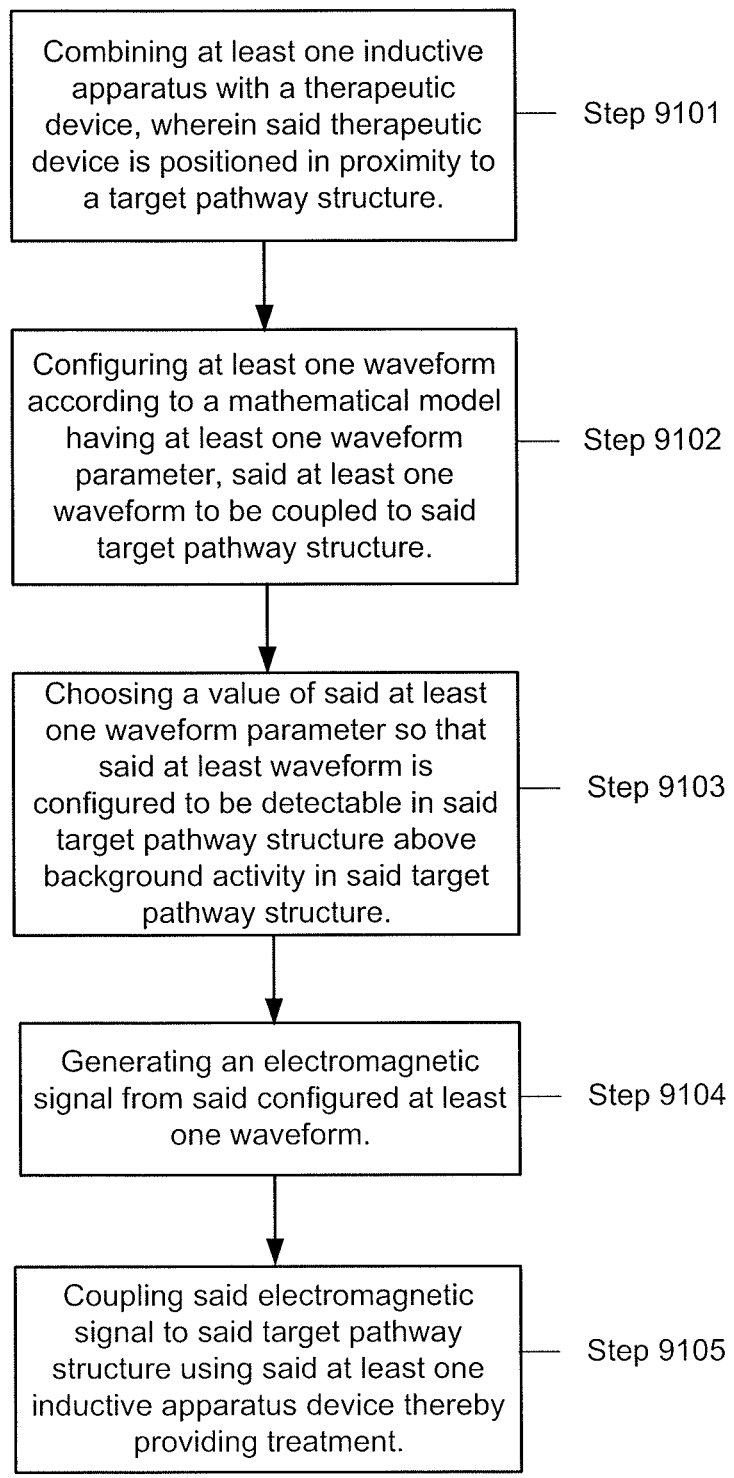
Figure 10:
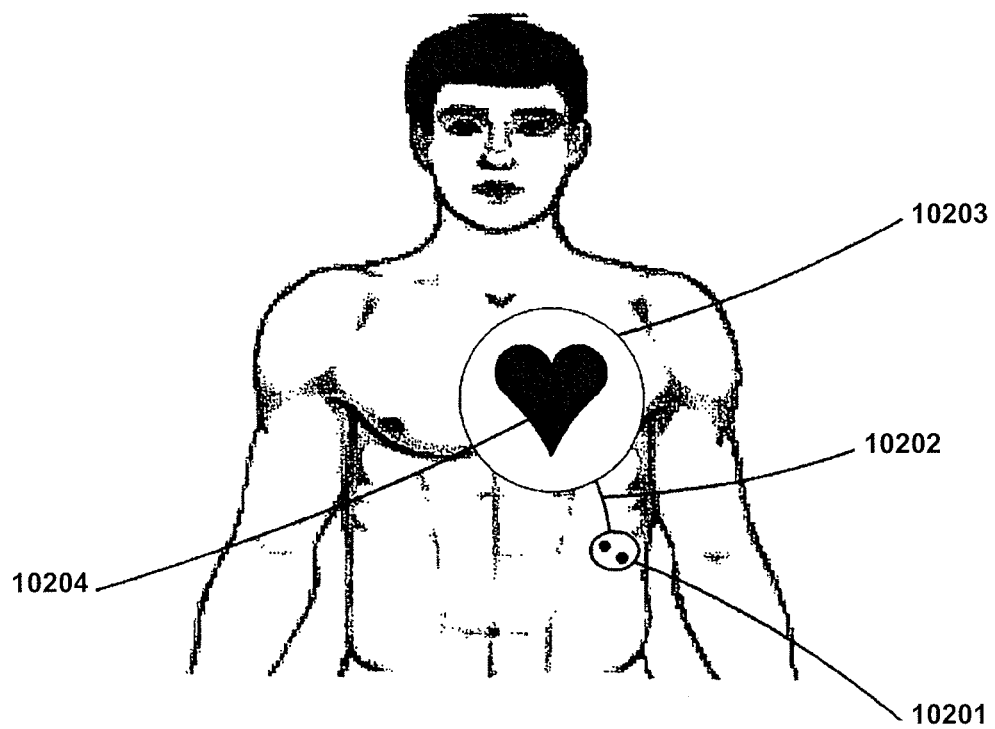
Figure 11:
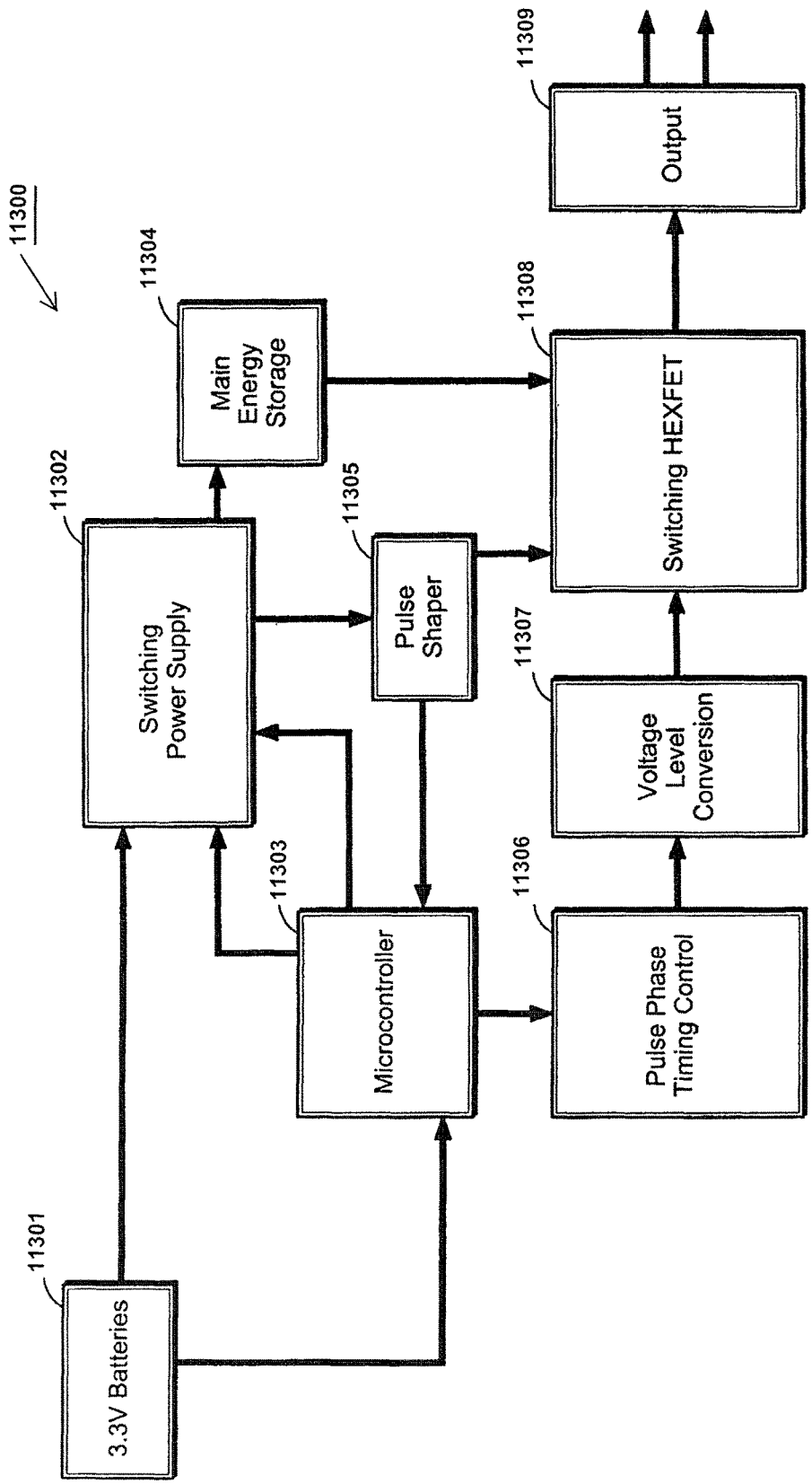
Figure 12:
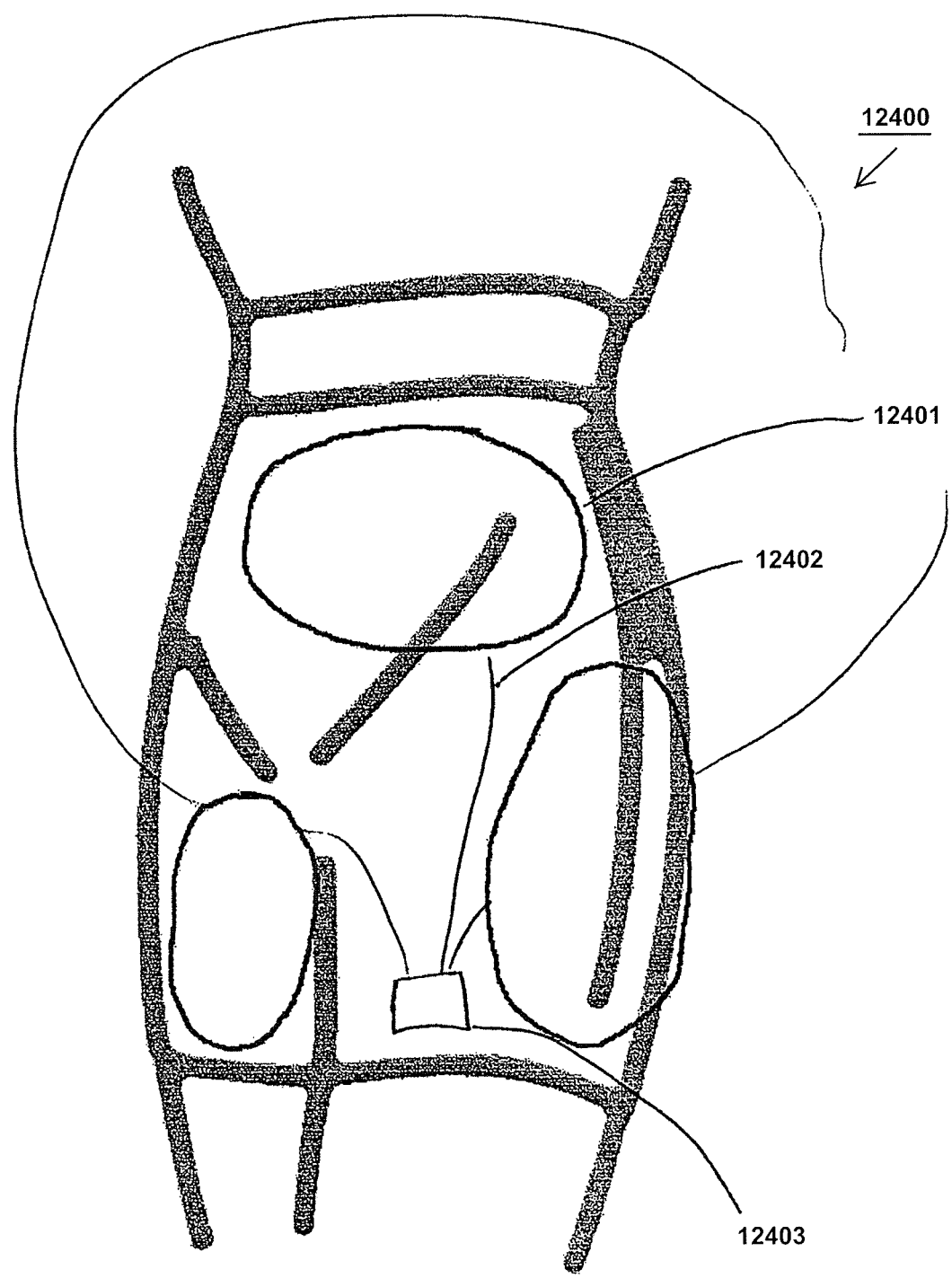
Figure 13:
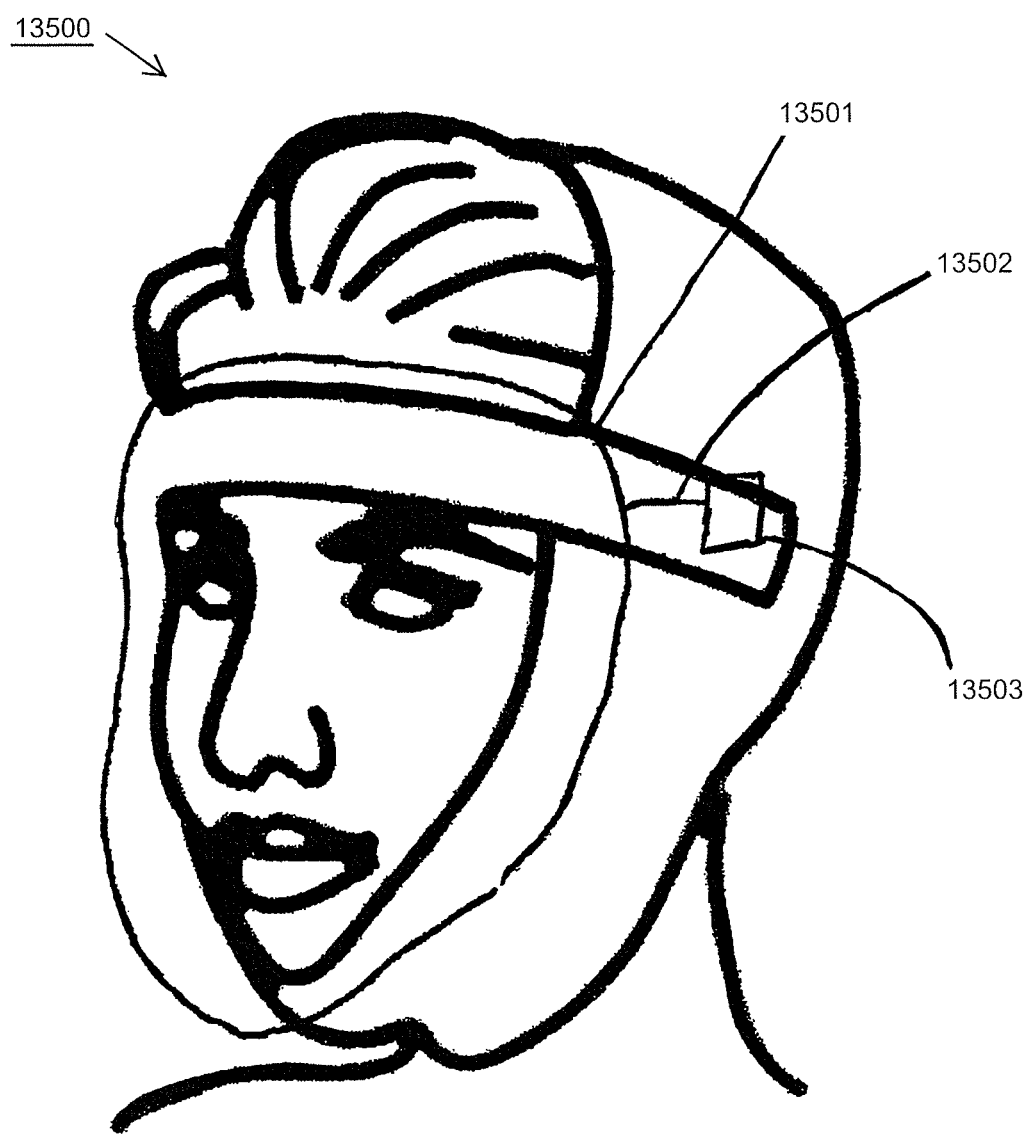
Figure 14:
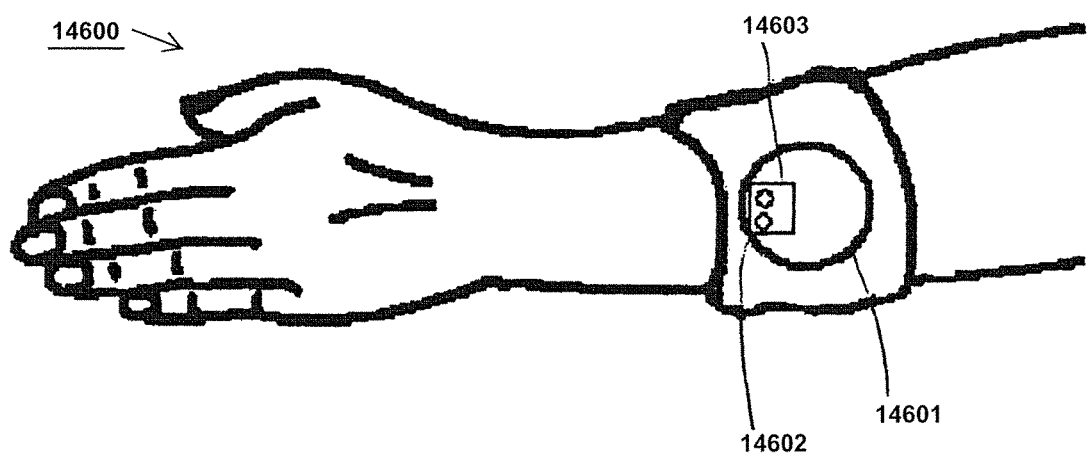
Figure 15:
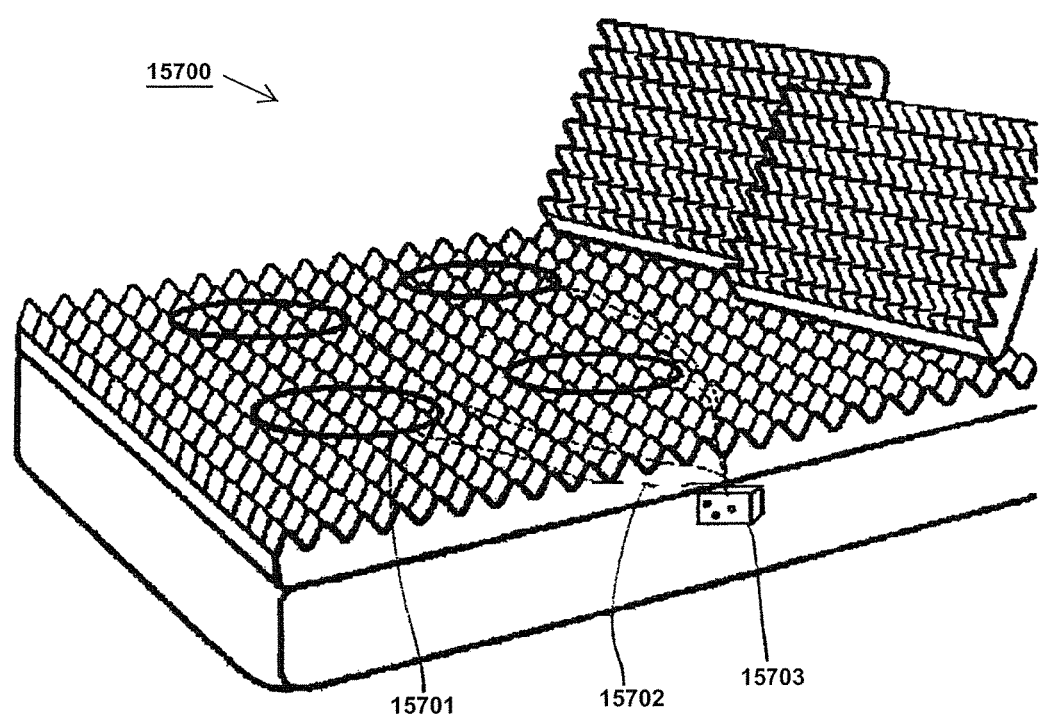
Figure 16A:
Figure 16B:
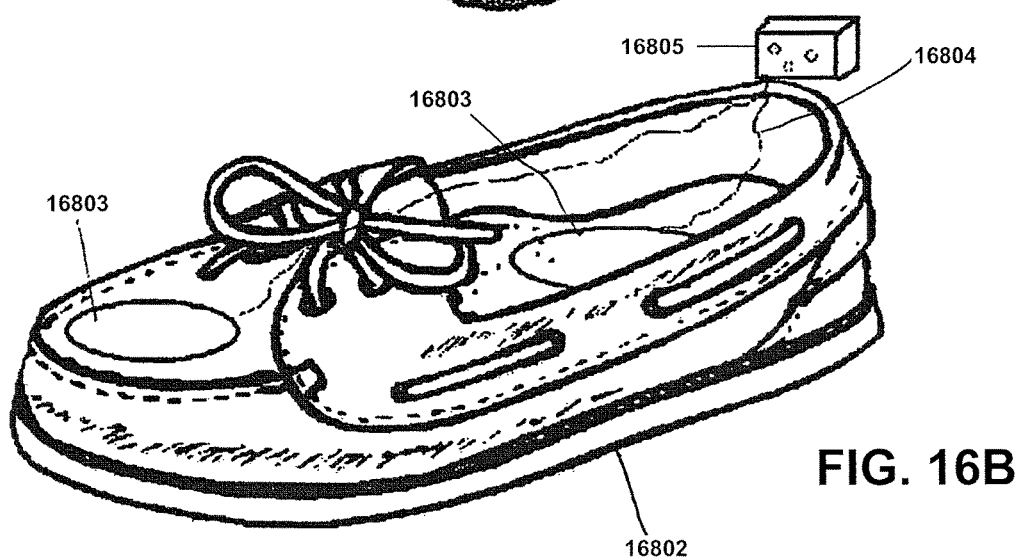
Figure 17:
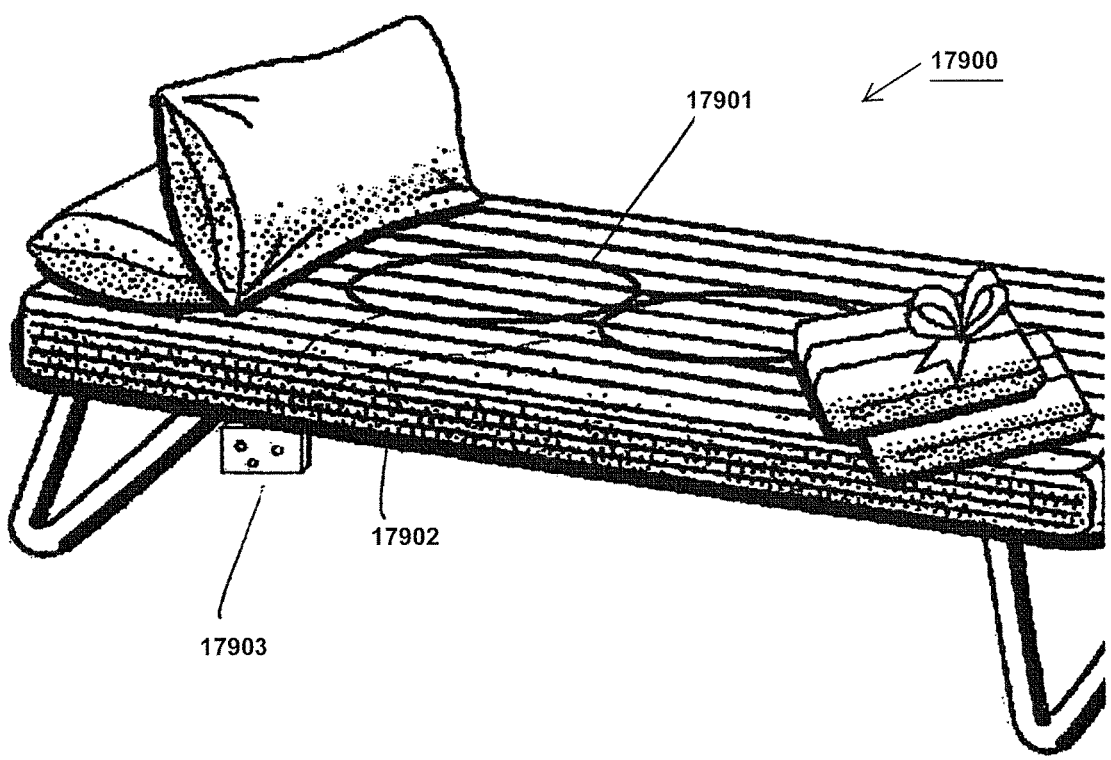
Figure 18:
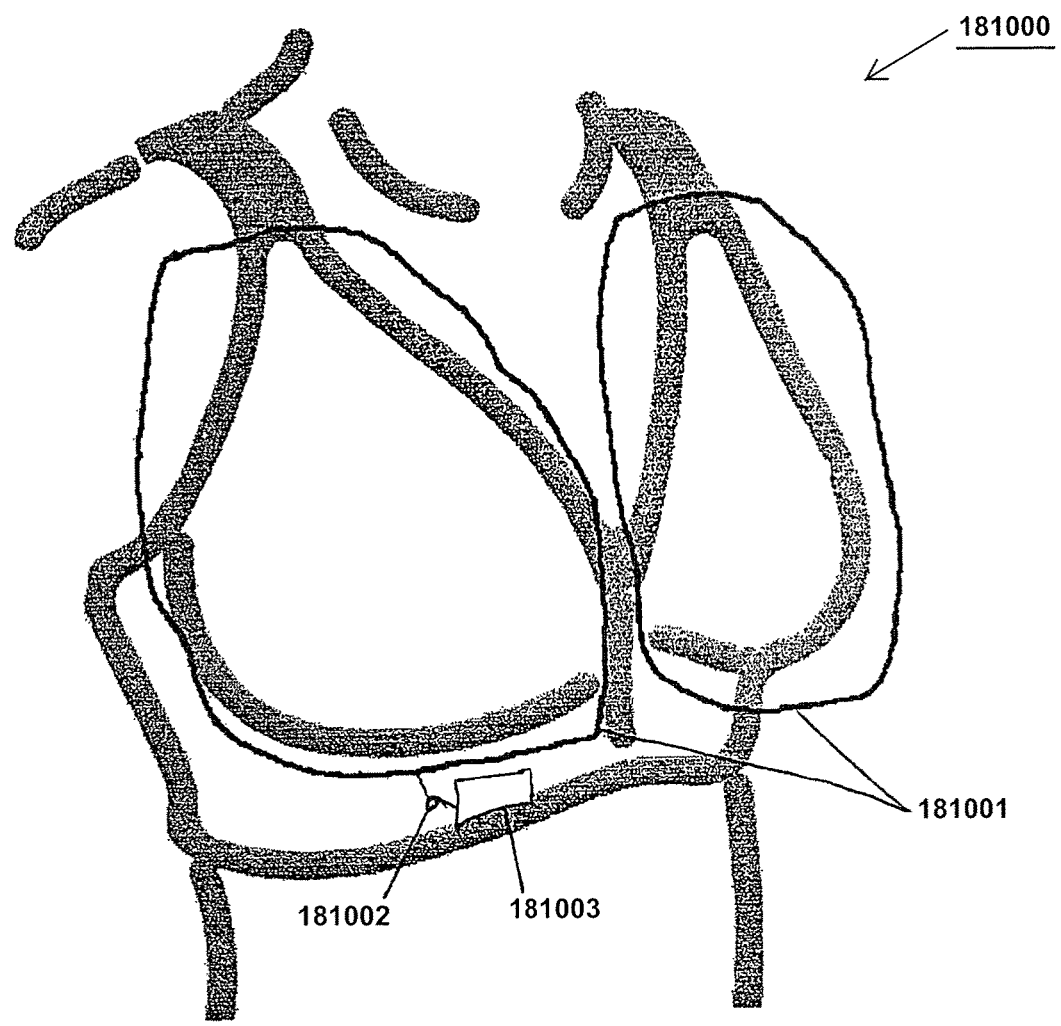

FIG. 9 is a flow diagram of a method for using an electromagnetic treatment inductive apparatus according to an embodiment of the present invention;

FIG. 10 is a view of control circuitry according to a preferred embodiment of the present invention;

FIG. 11 is a block diagram of miniaturized circuitry according to a preferred embodiment of the present invention;

FIG. 12 depicts an electromagnetic treatment inductive apparatus integrated into a hip, thigh, and lower back support garment according to a preferred embodiment of the present invention;

FIG. 13 depicts an electromagnetic treatment inductive apparatus integrated into a head and face support garment according to a preferred embodiment of the present invention;

FIG. 14 depicts an electromagnetic treatment inductive apparatus integrated into a surgical dressing on a human forearm according to a preferred embodiment of the present invention;

FIG. 15 depicts an electromagnetic treatment inductive apparatus integrated into a mattress pad according to a preferred embodiment of the present invention;

FIG. 16A depicts an electromagnetic treatment inductive apparatus integrated into a sock according to a preferred embodiment of the present invention;

FIG. 16B depicts an electromagnetic treatment inductive apparatus integrated into a shoe according to a preferred embodiment of the present invention;

FIG. 17 depicts an electromagnetic treatment inductive apparatus integrated into a therapeutic bed according to a preferred embodiment of the present invention; and FIG. 18 depicts an electromagnetic treatment inductive apparatus integrated into a chest garment according to a preferred embodiment of the present invention.

Part 3

Figure 19:
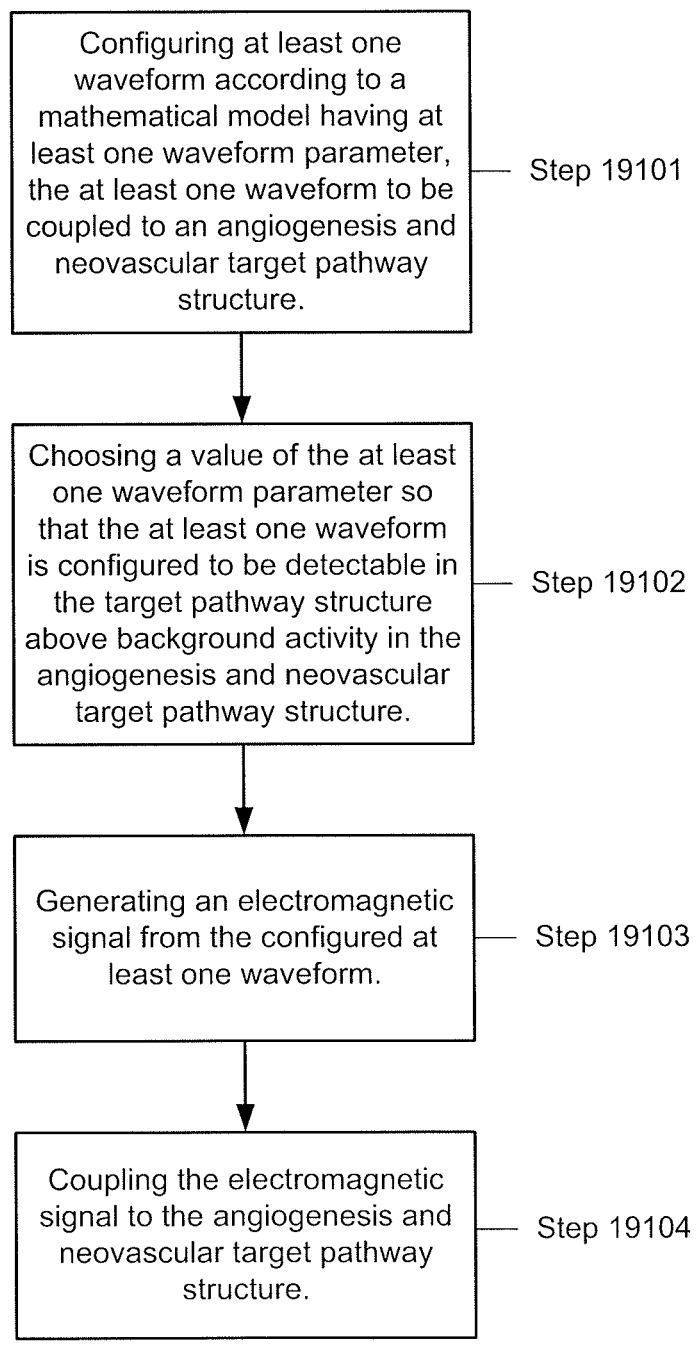
Figure 20:
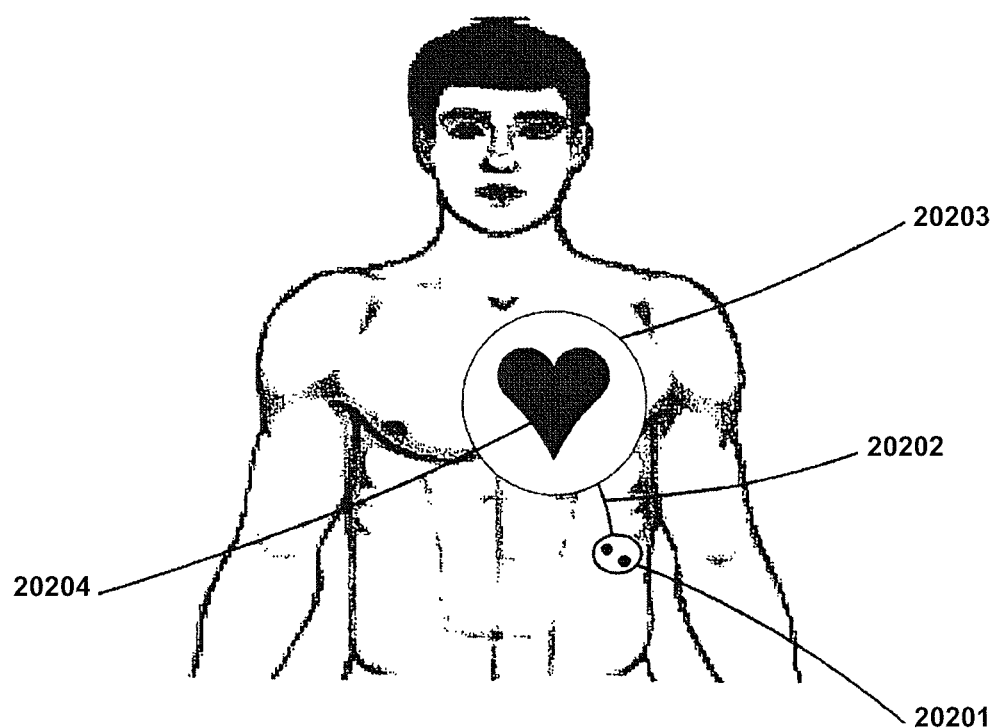
Figure 21:
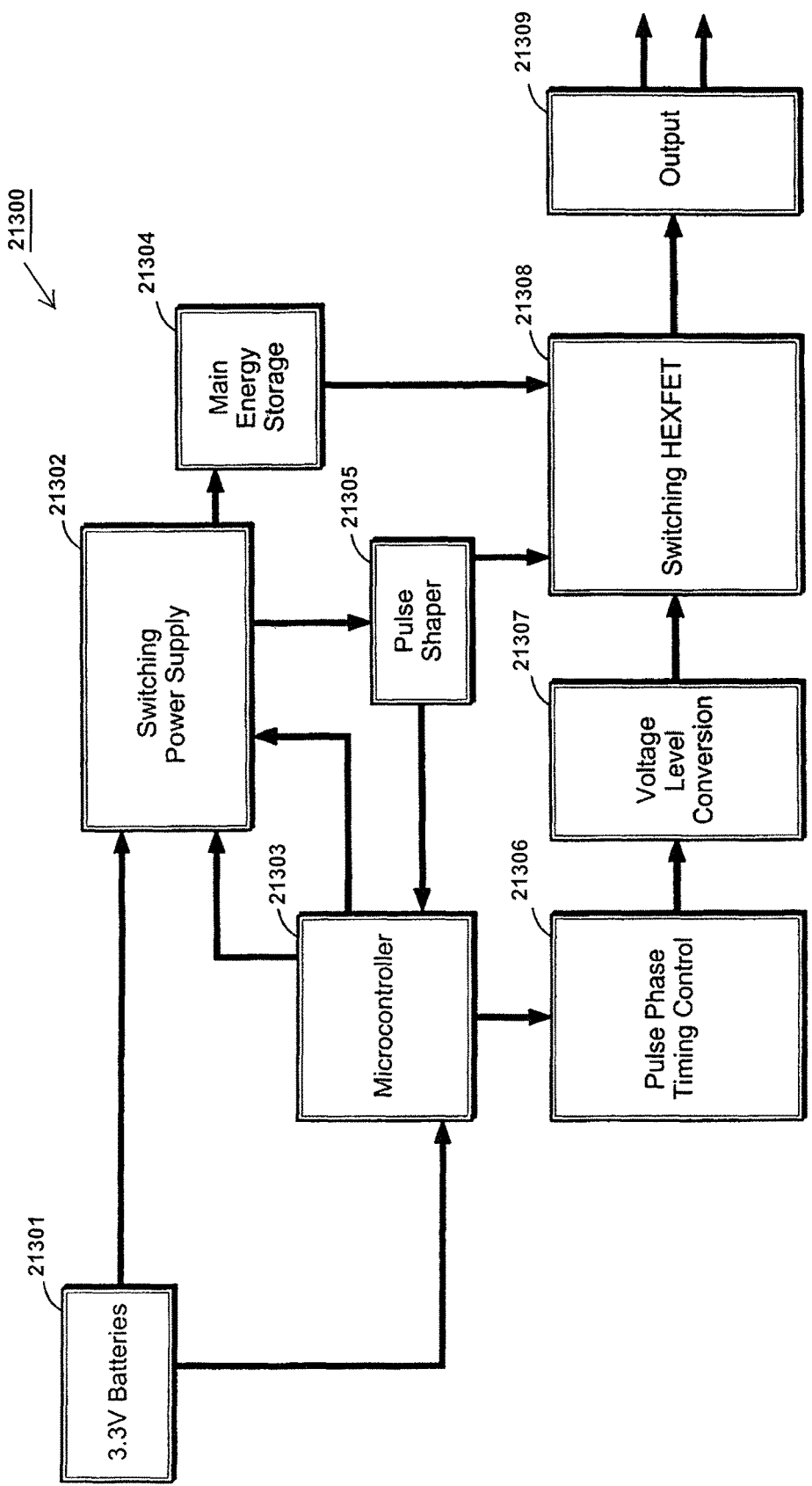
Figure 22:
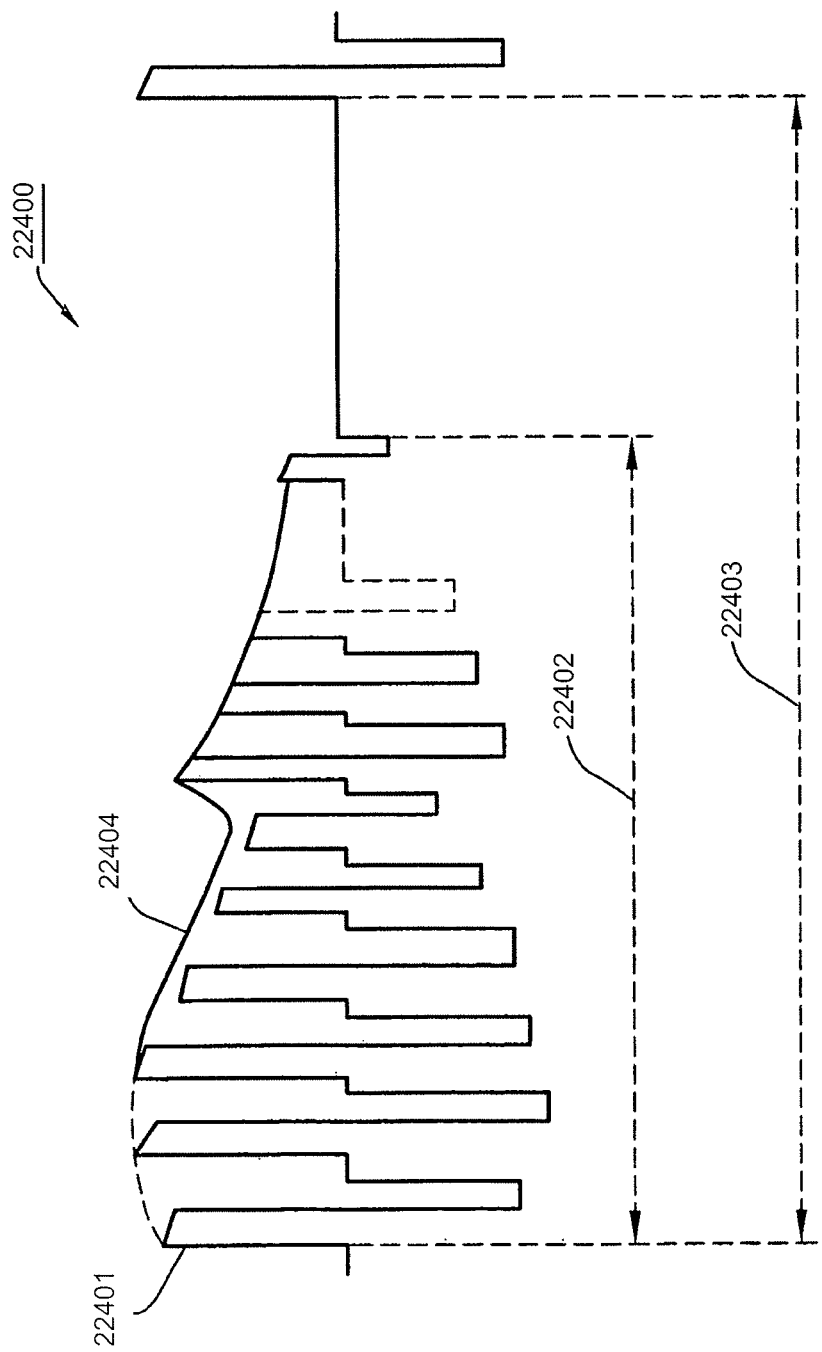

FIG. 19 is a flow diagram of a electromagnetic treatment method for angiogenesis modulation of living tissues and cells according to an embodiment of the present invention;

FIG. 20 is a view of control circuitry according to a preferred embodiment of the present invention;

FIG. 21 is a block diagram of miniaturized circuitry according to a preferred embodiment of the present invention;

FIG. 22 depicts a waveform delivered to a angiogenesis and neovascularization target pathway structure according to a preferred embodiment of the present invention.

Part 4

Figure 23:
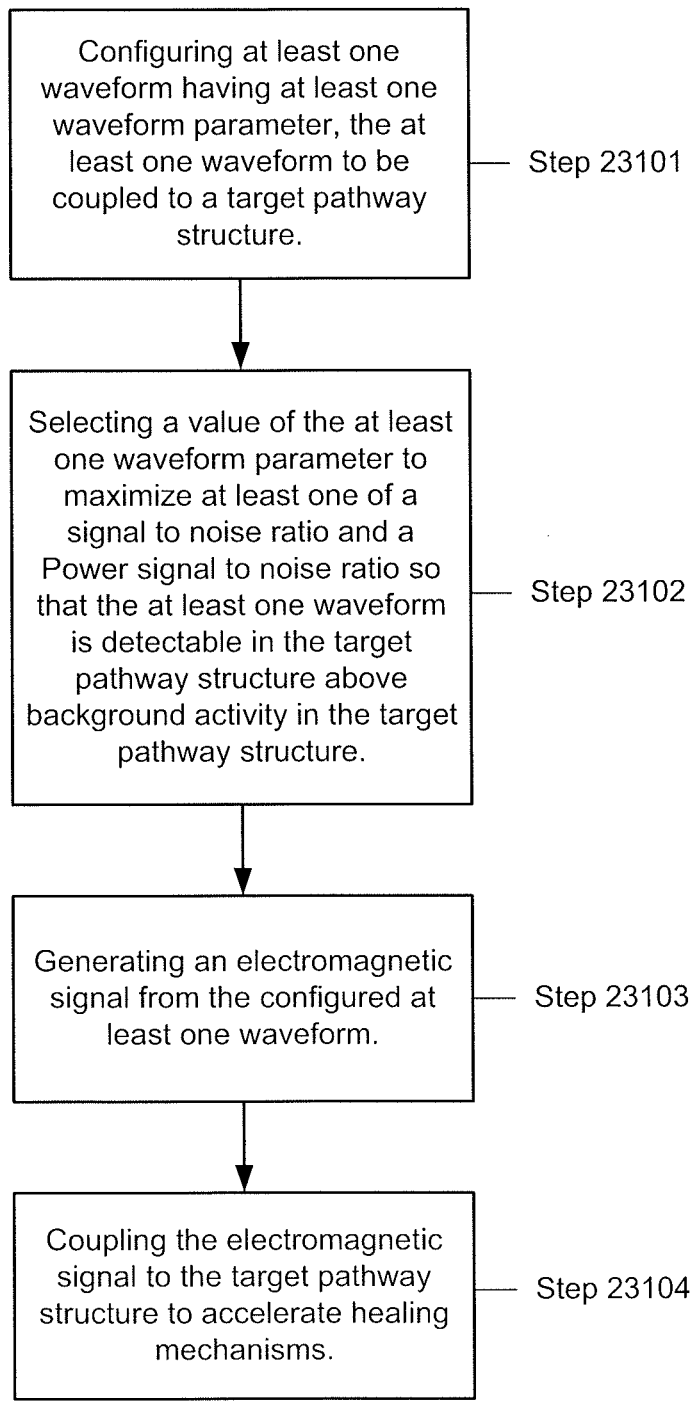
Figure 24:
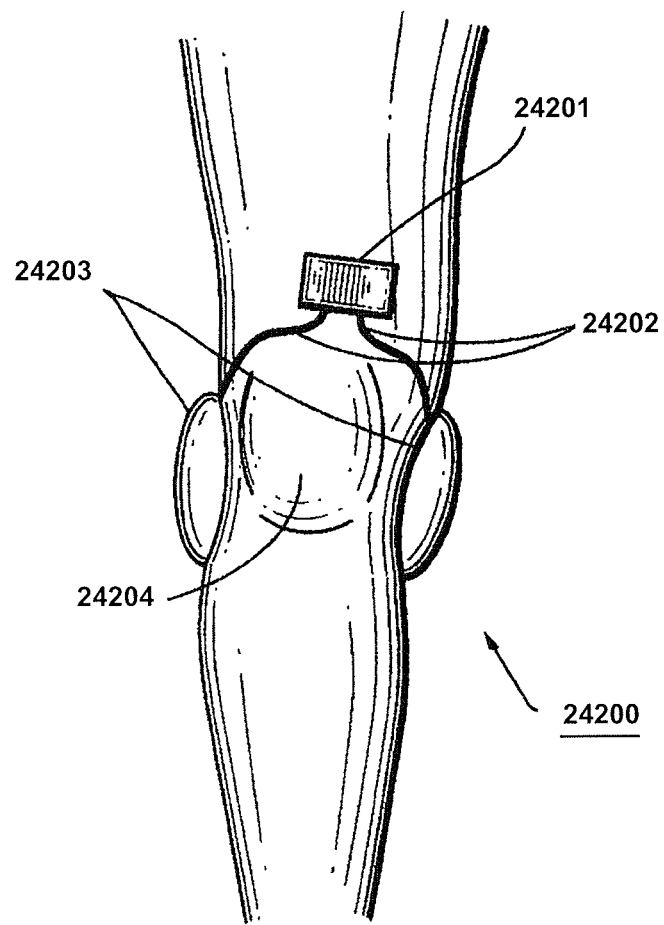
Figure 25:
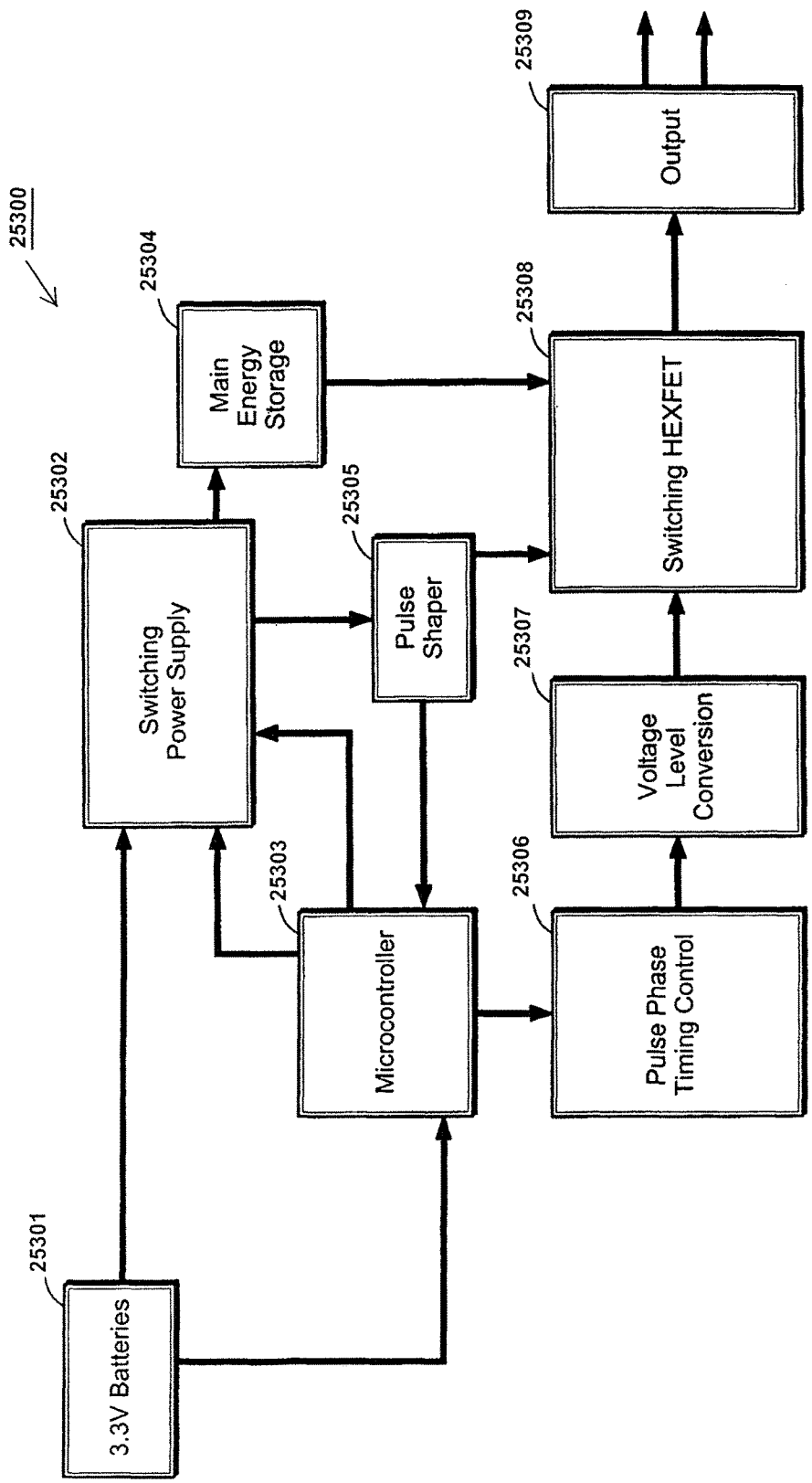
Figure 26A:
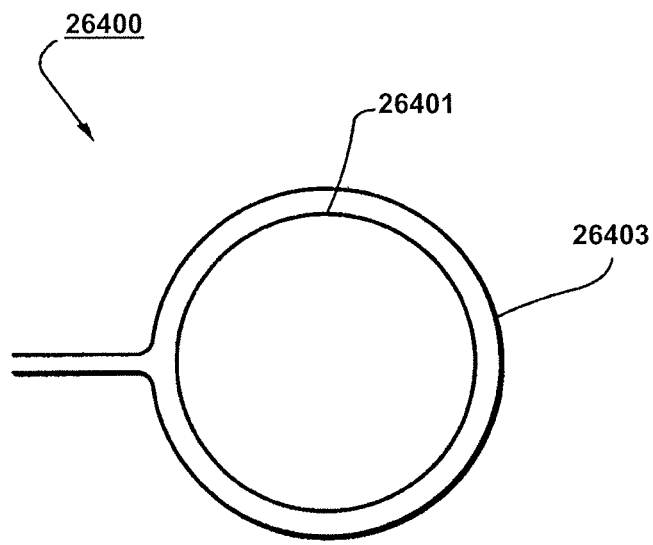
Figure 26B:
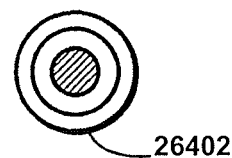
Figure 27:
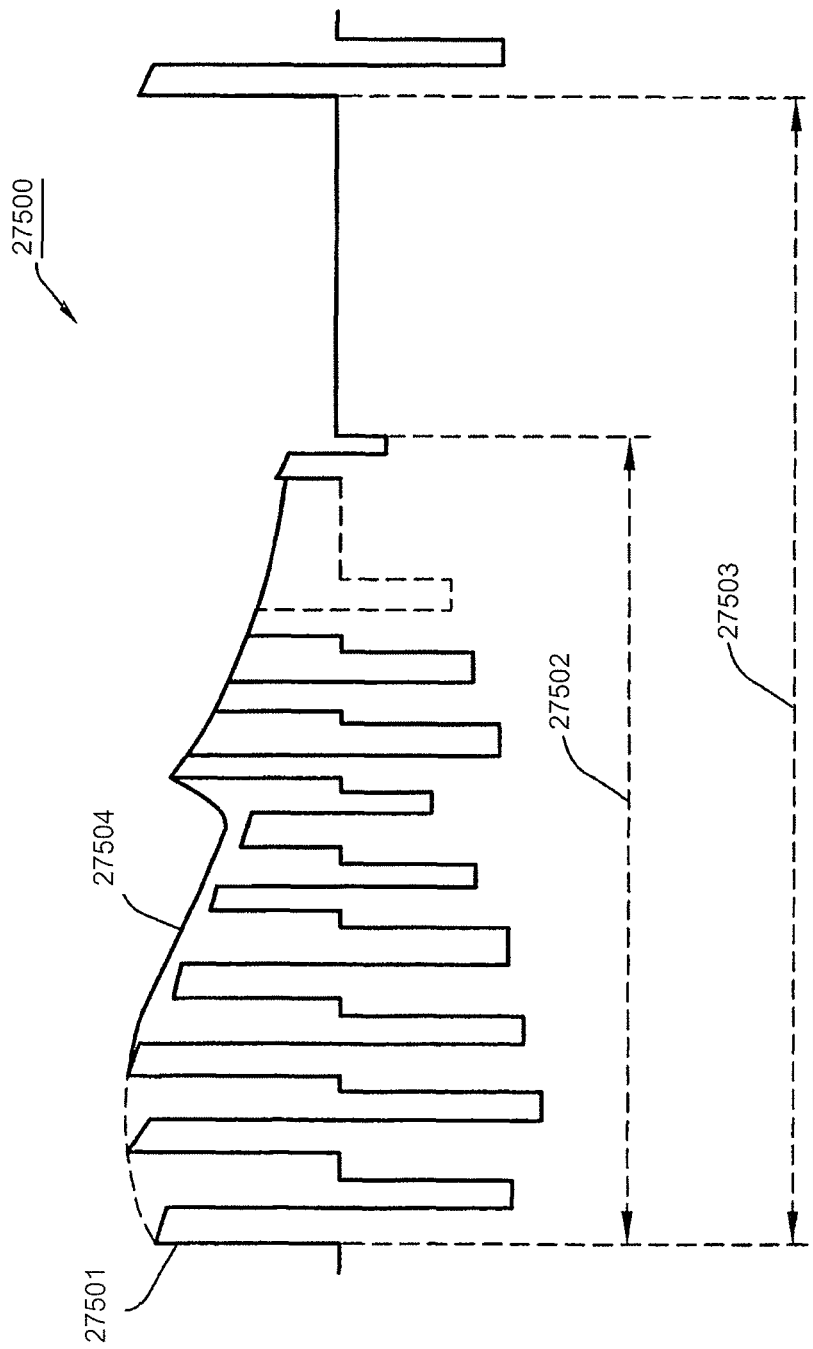
Figure 28:
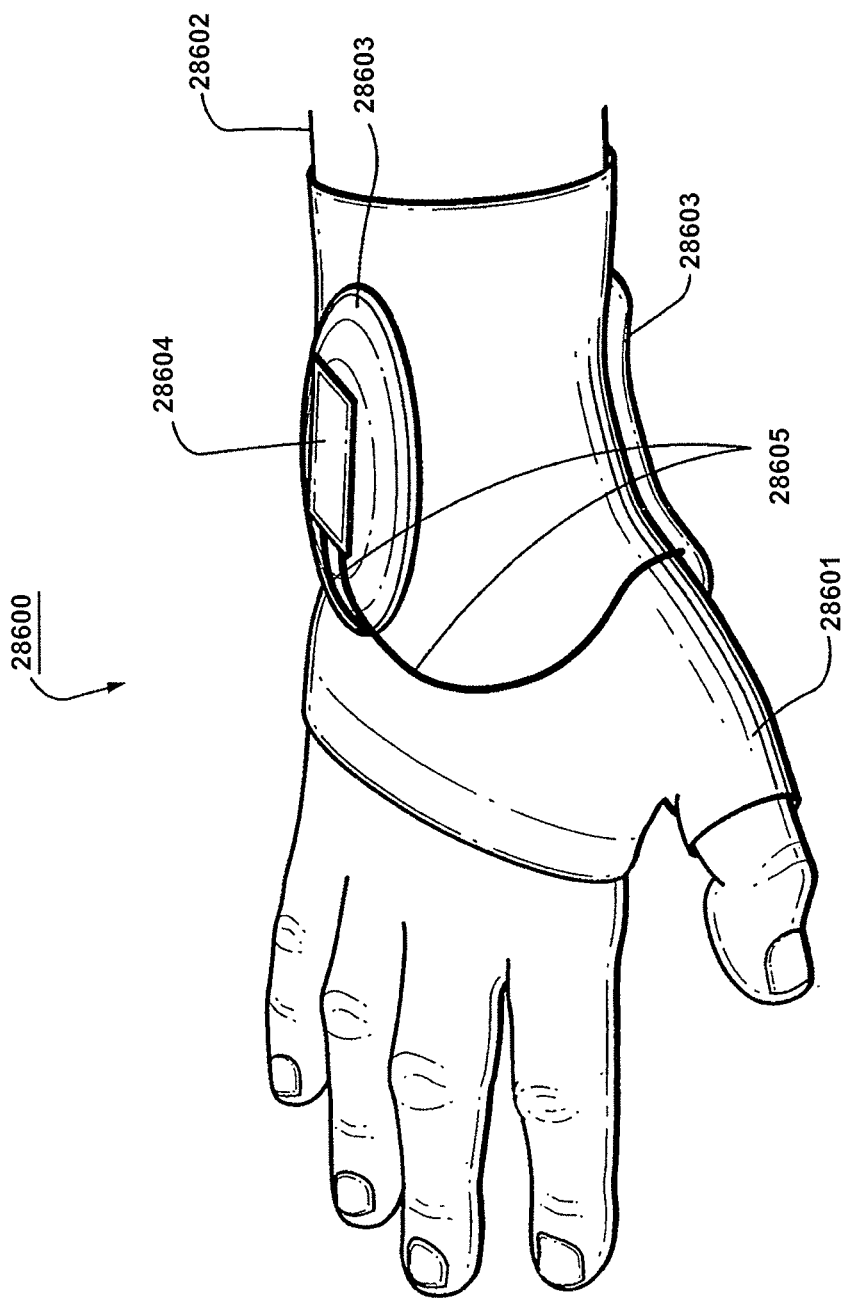
Figure 29:
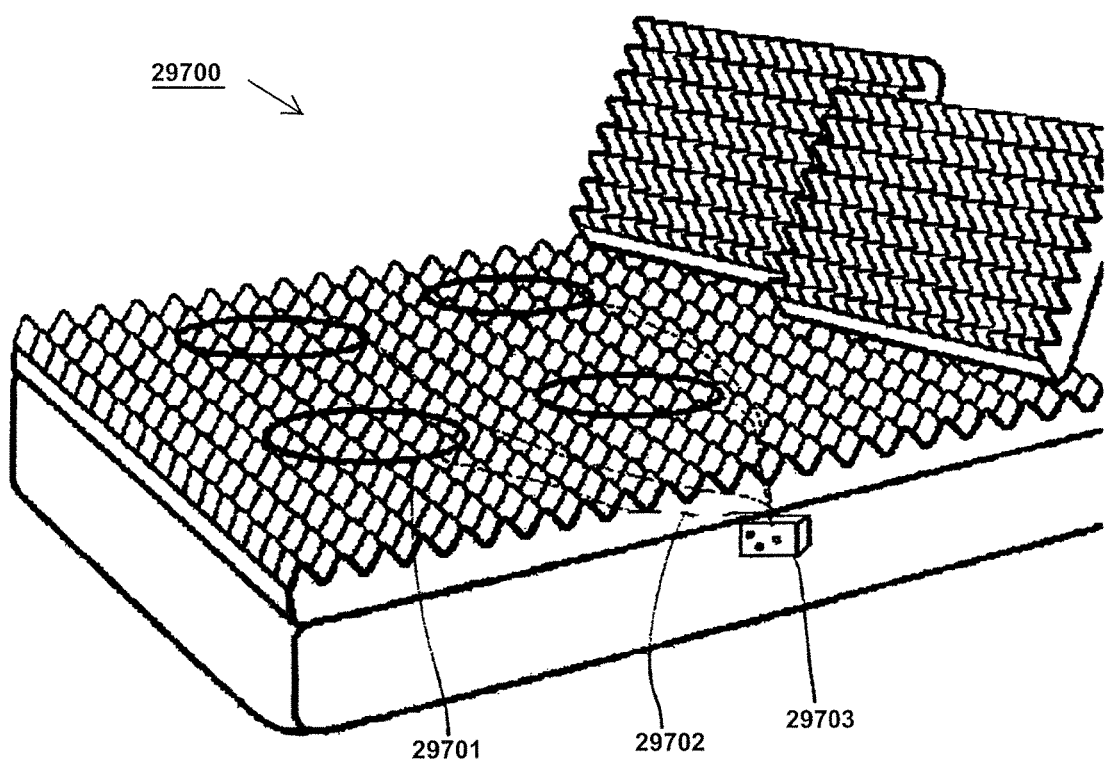
Figure 30:
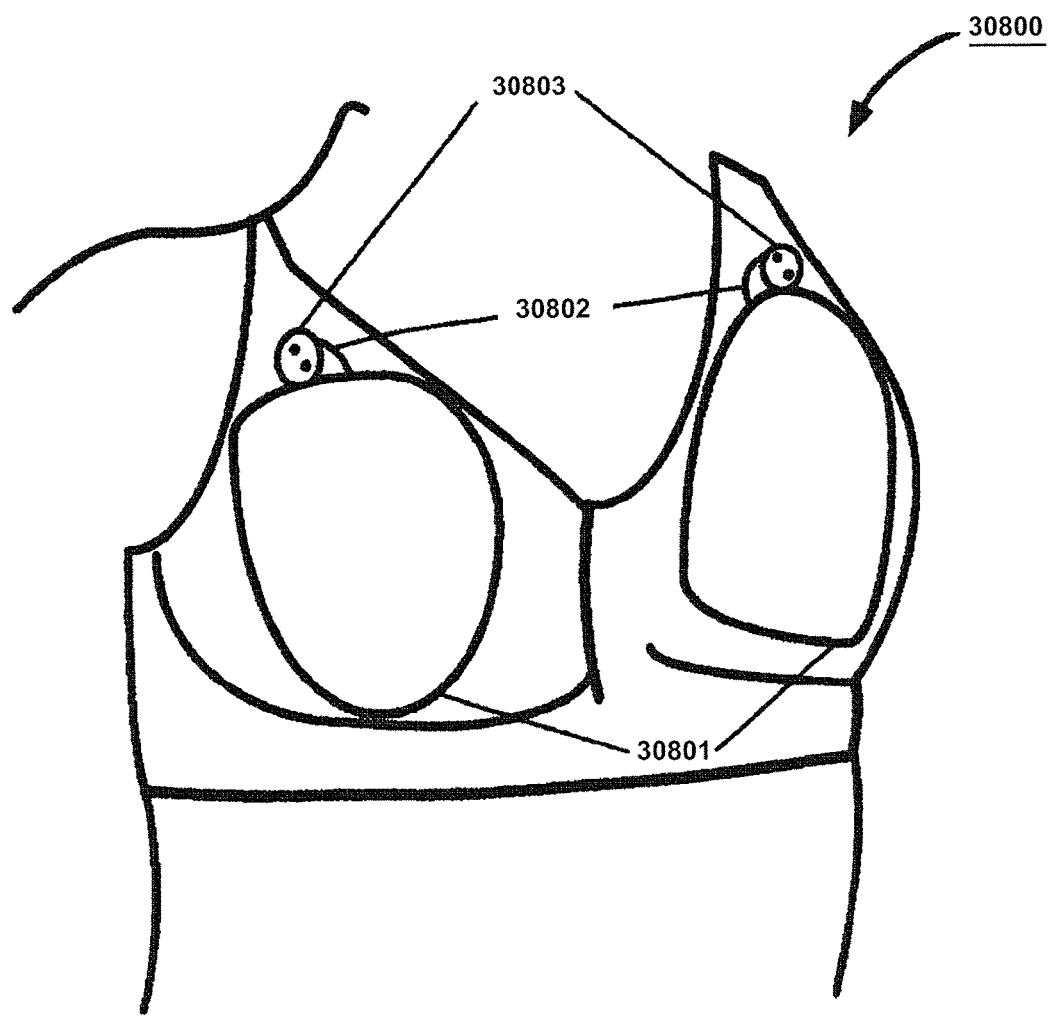
Figure 31:
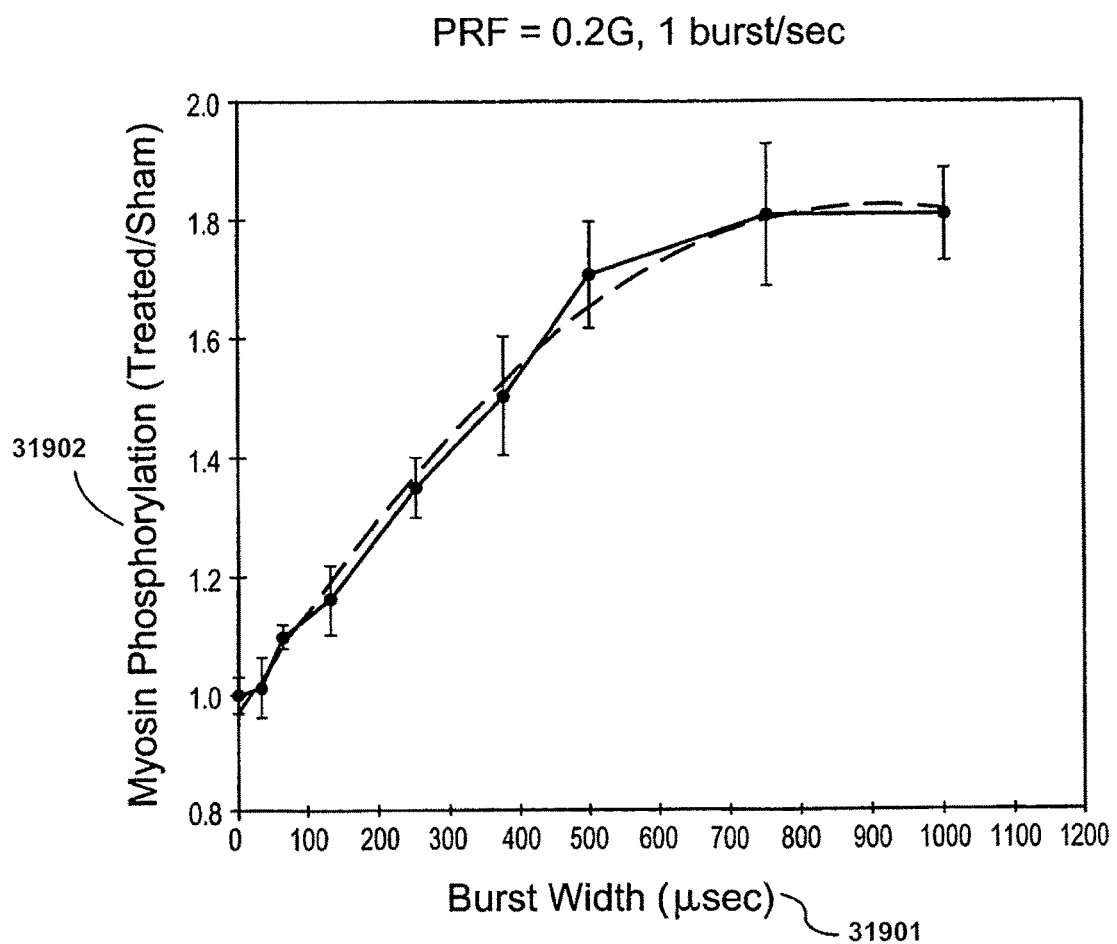

FIG. 23 is a flow diagram of a method for accelerating wound repair in living tissues, cells and molecules according to an embodiment of the present invention;

FIG. 24 is a view of control circuitry and electrical coils applied to a knee joint according to a preferred embodiment of the present invention;

FIG. 25 is a block diagram of miniaturized circuitry according to a preferred embodiment of the present invention;

FIG. 26A is a line drawing of a wire coil such as an inductor according to a preferred embodiment of the present invention;

FIG. 26B is a line drawing of a flexible magnetic wire according to a preferred embodiment of the present invention;

FIG. 27 depicts a waveform delivered to a target pathway structure such as a molecule, cell, tissue or organ according to a preferred embodiment of the present invention;

FIG. 28 is a view of a positioning device such as a wrist support according to a preferred embodiment of the present invention;

FIG. 29 is a view of a positioning device such as a mattress pad according to a preferred embodiment of the present invention;

FIG. 30 is a view of a positioning device such as a chest garment according to an embodiment of the present invention;

FIG. 31 is a graph illustrating maximally increased myosin phosphorylation for a PMRF signal configured according to an embodiment of the present invention.

Part 5

Figure 32:
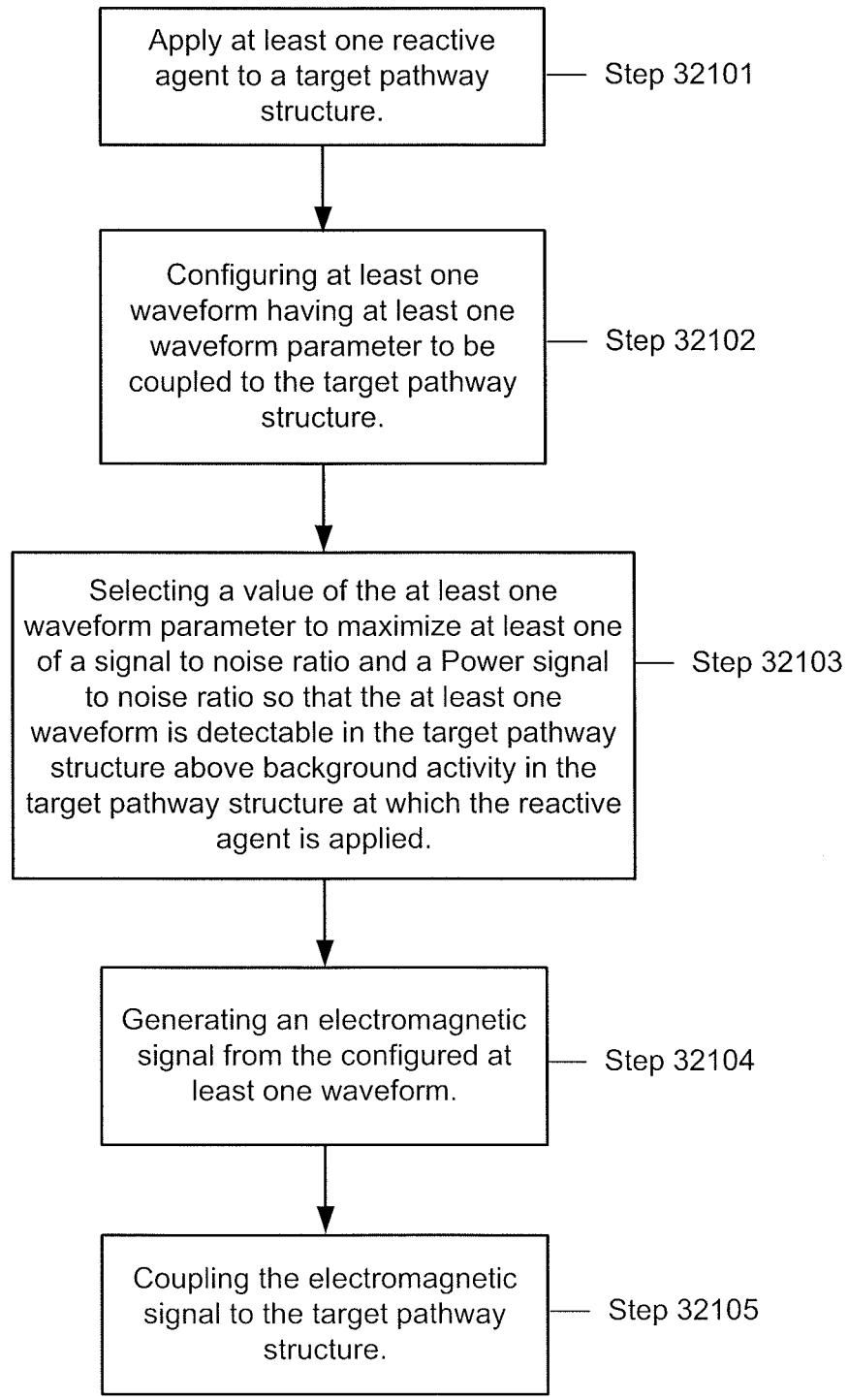
Figure 33:
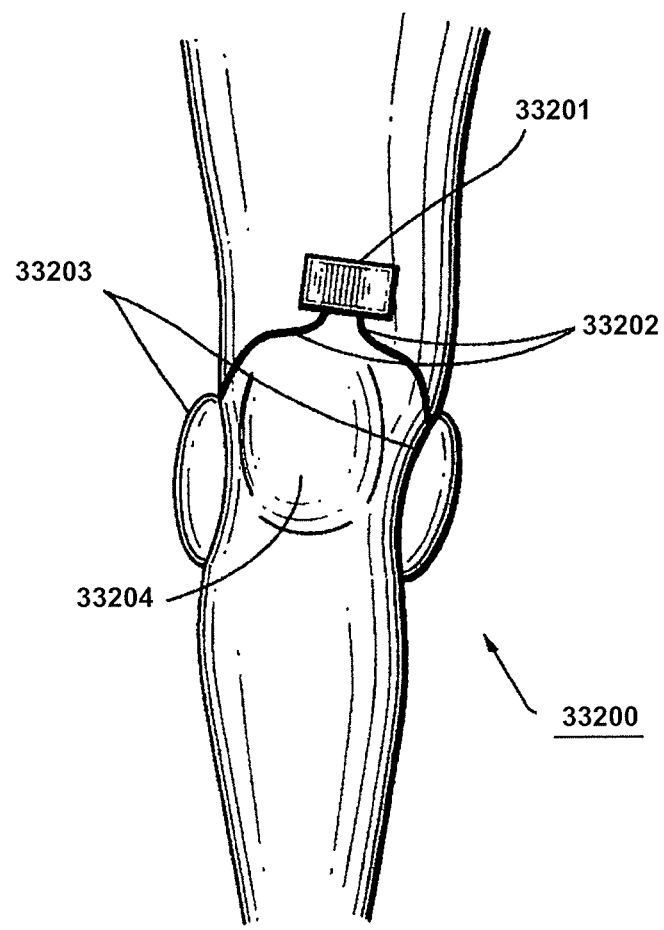
Figure 34:
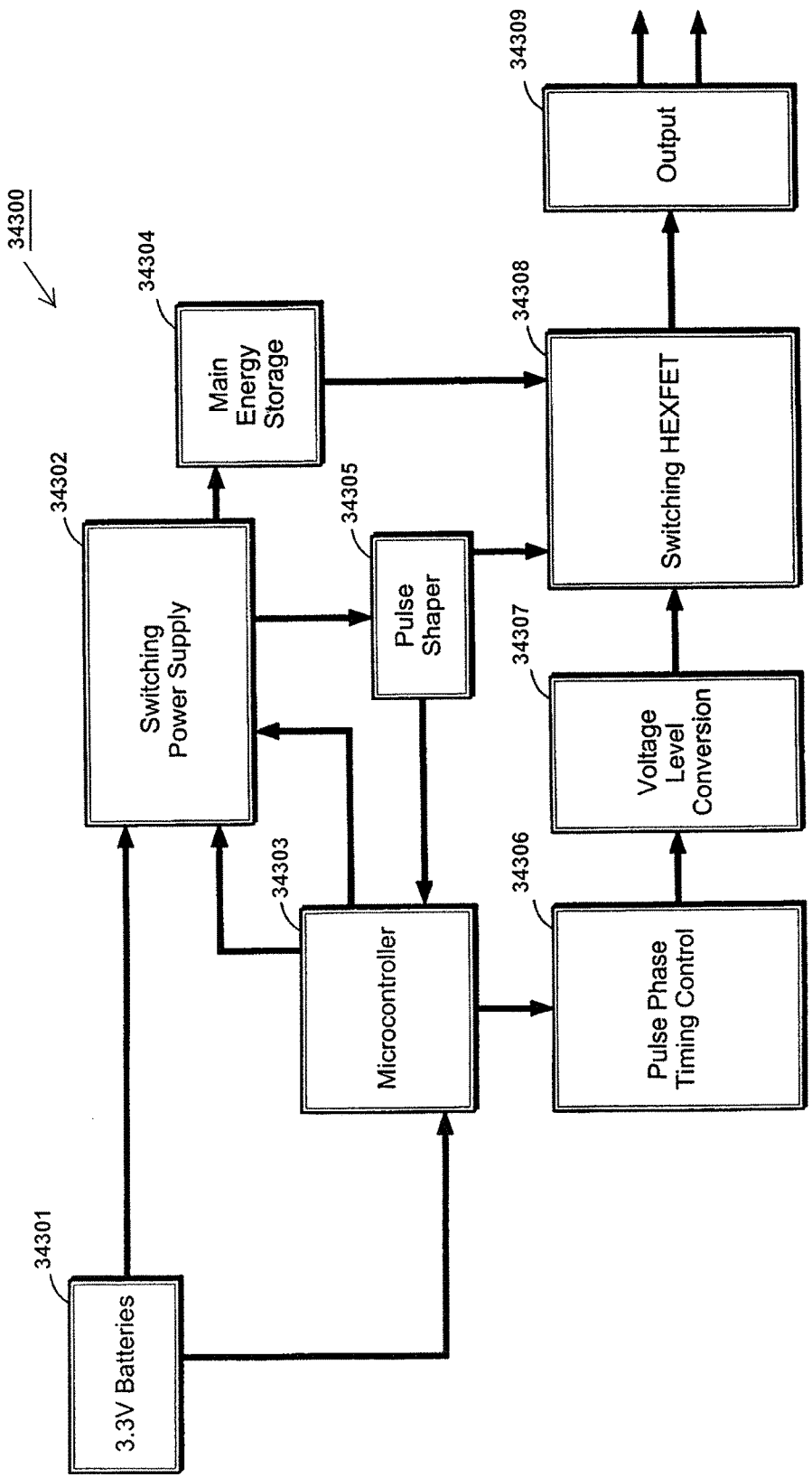
Figure 35A:
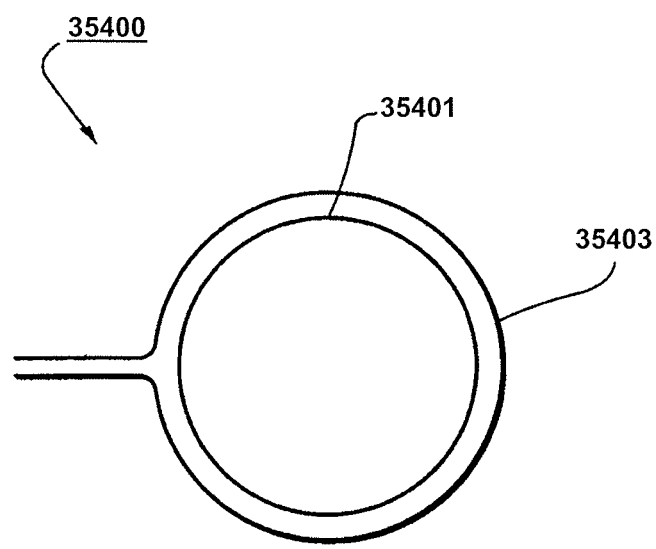
Figure 35B:
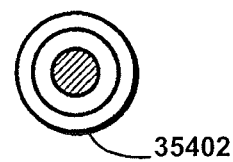
Figure 36:
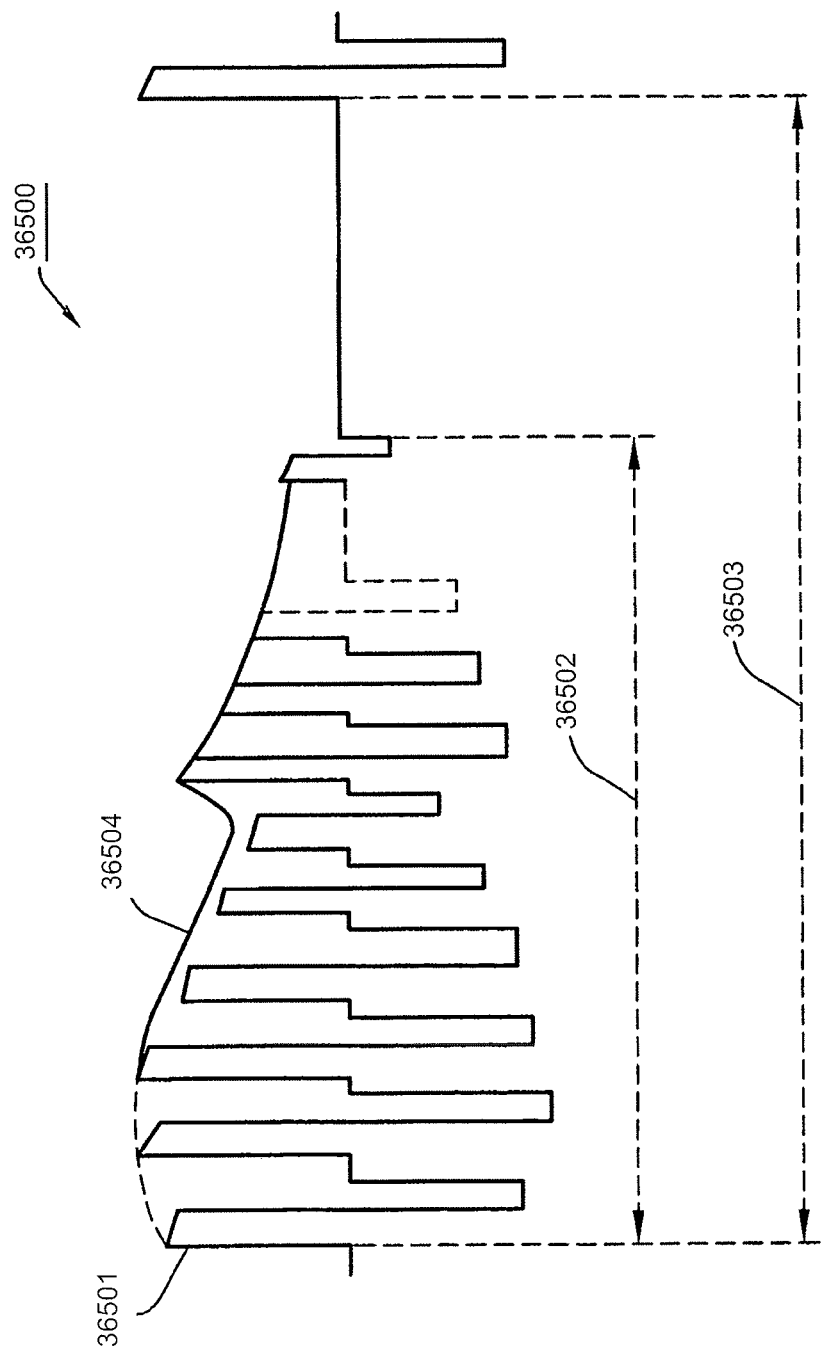
Figure 37:
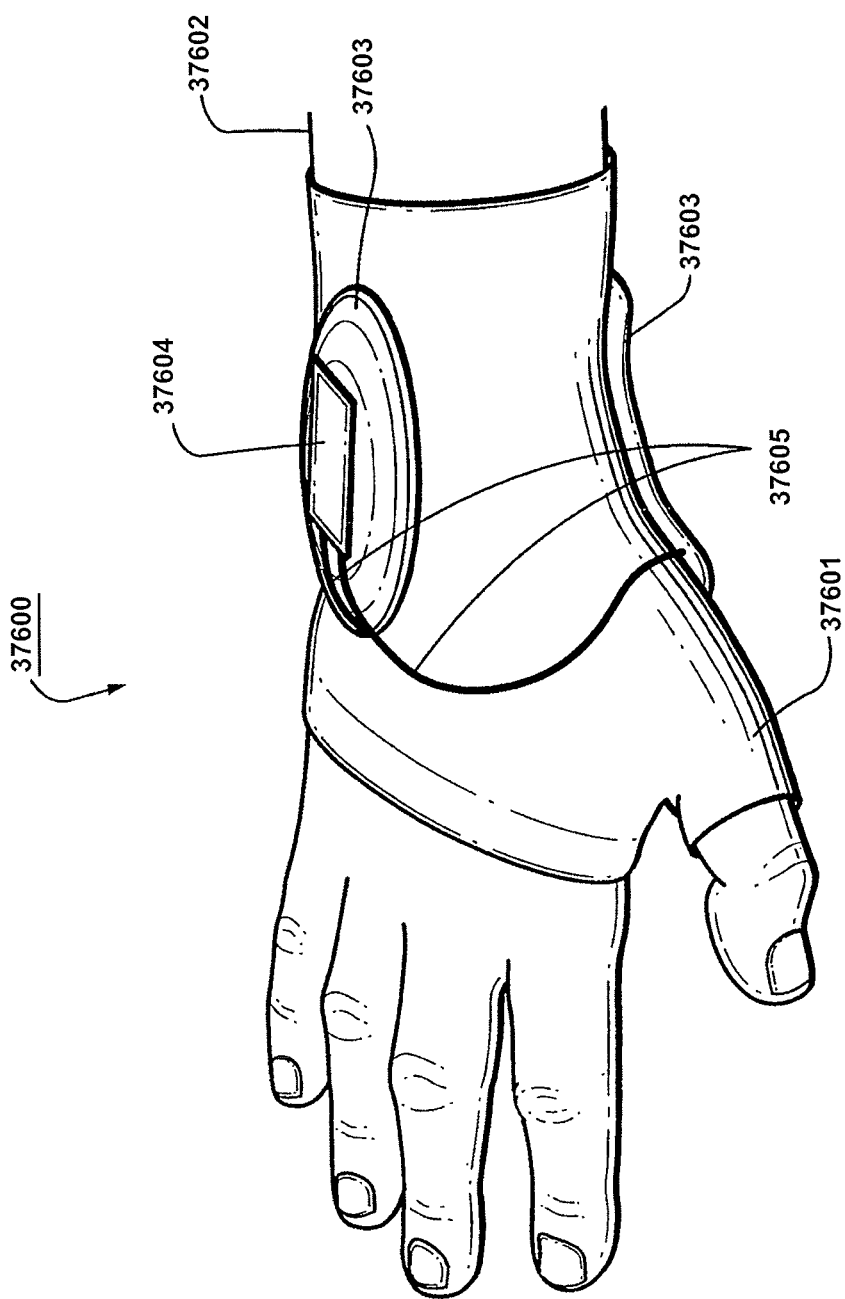
Figure 38:
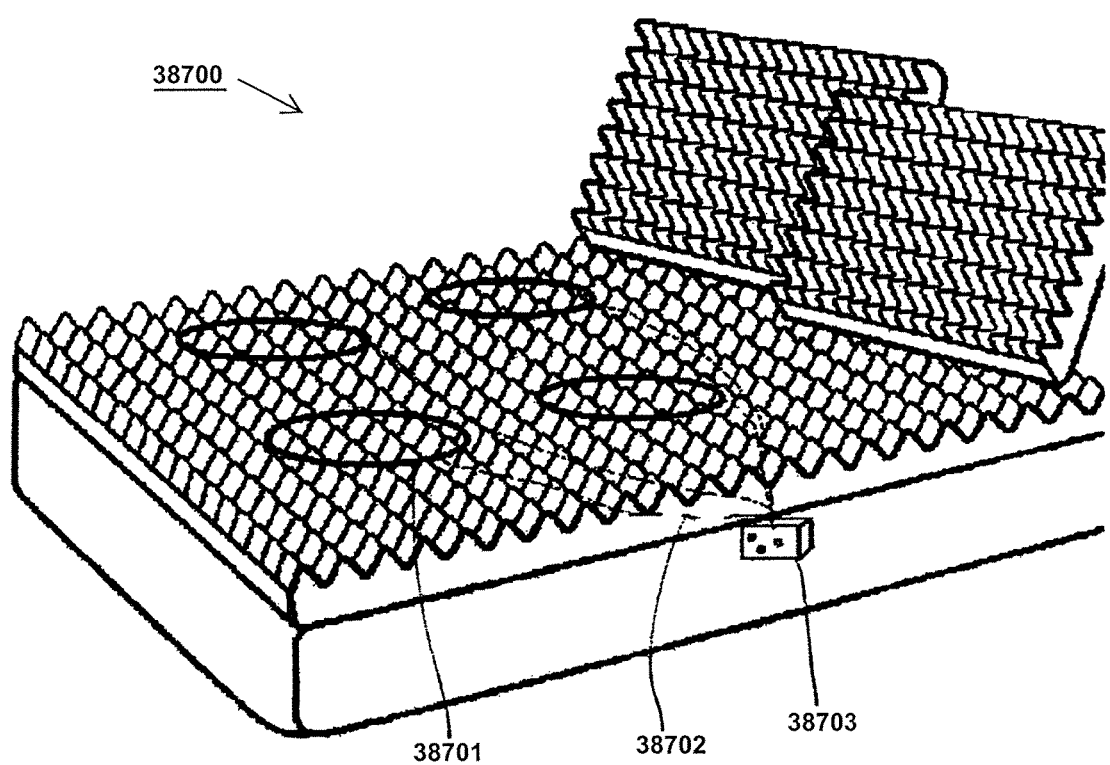
Figure 39:
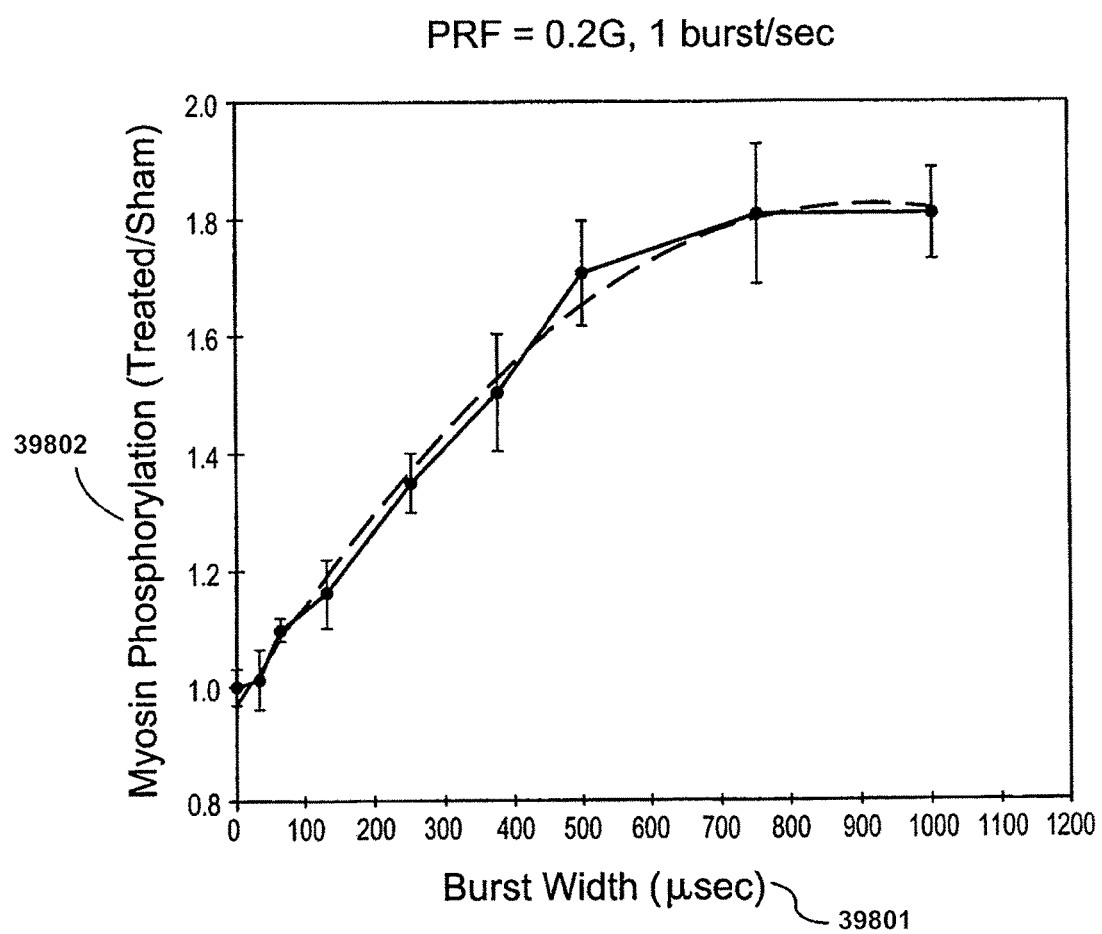
Figure 40:
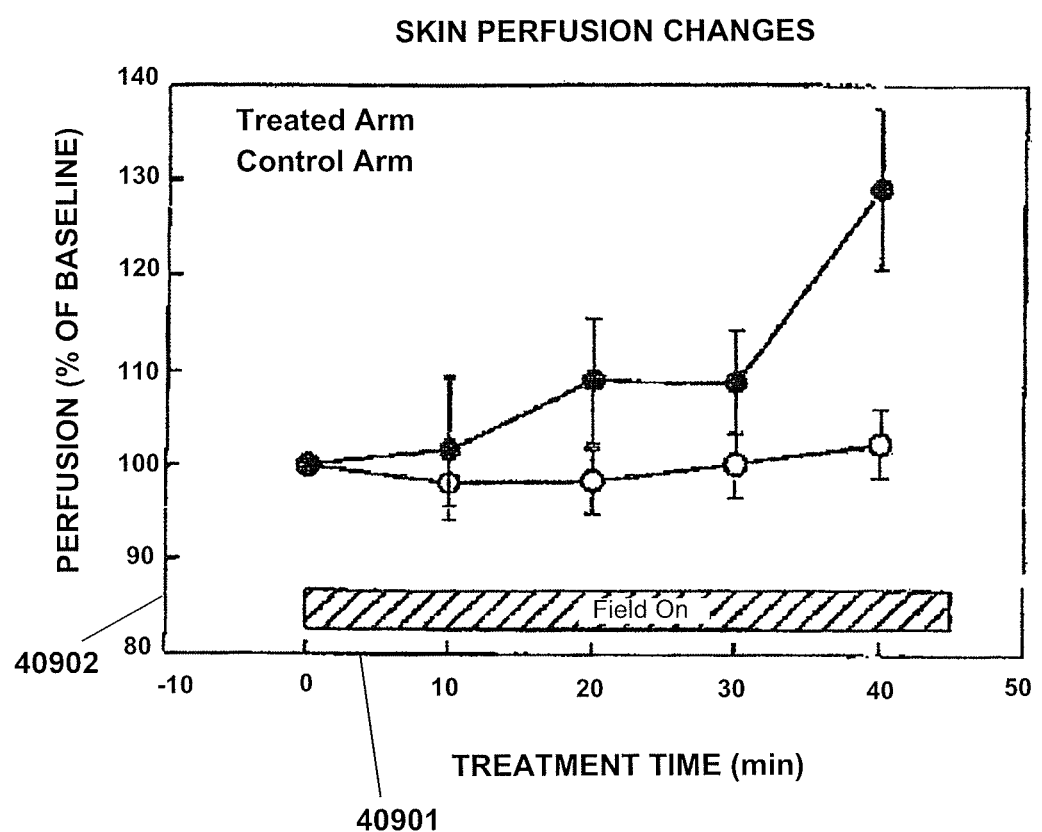

FIG. 32 is a flow diagram of a method for enhancing effectiveness of pharmacological, chemical, cosmetic and topical agents used to treat living tissues, cells and molecules according to an embodiment of the present invention;

FIG. 33 is a view of control circuitry and electrical coils applied to a knee joint according to a preferred embodiment of the present invention;

FIG. 34 is a block diagram of miniaturized circuitry according to a preferred embodiment of the present invention;

FIG. 35A is a line drawing of a wire coil such as an inductor according to a preferred embodiment of the present invention;

FIG. 35B is a line drawing of a flexible magnetic wire according to a preferred embodiment of the present invention;

FIG. 36 depicts a waveform delivered to a target pathway structure such as a molecule, cell, tissue or organ according to a preferred embodiment of the present invention;

FIG. 37 is a view of a positioning device such as a wrist support according to a preferred embodiment of the present invention;

FIG. 38 is a view of a positioning device such as a mattress pad according to a preferred embodiment of the present invention;

FIG. 39 is a graph illustrating effects of increased burst duration according to an embodiment of the present invention; and FIG. 40 is a graph illustrating an increase in skin blood perfusion achieved according to an embodiment of the present invention.

Part 6

Figure 41:
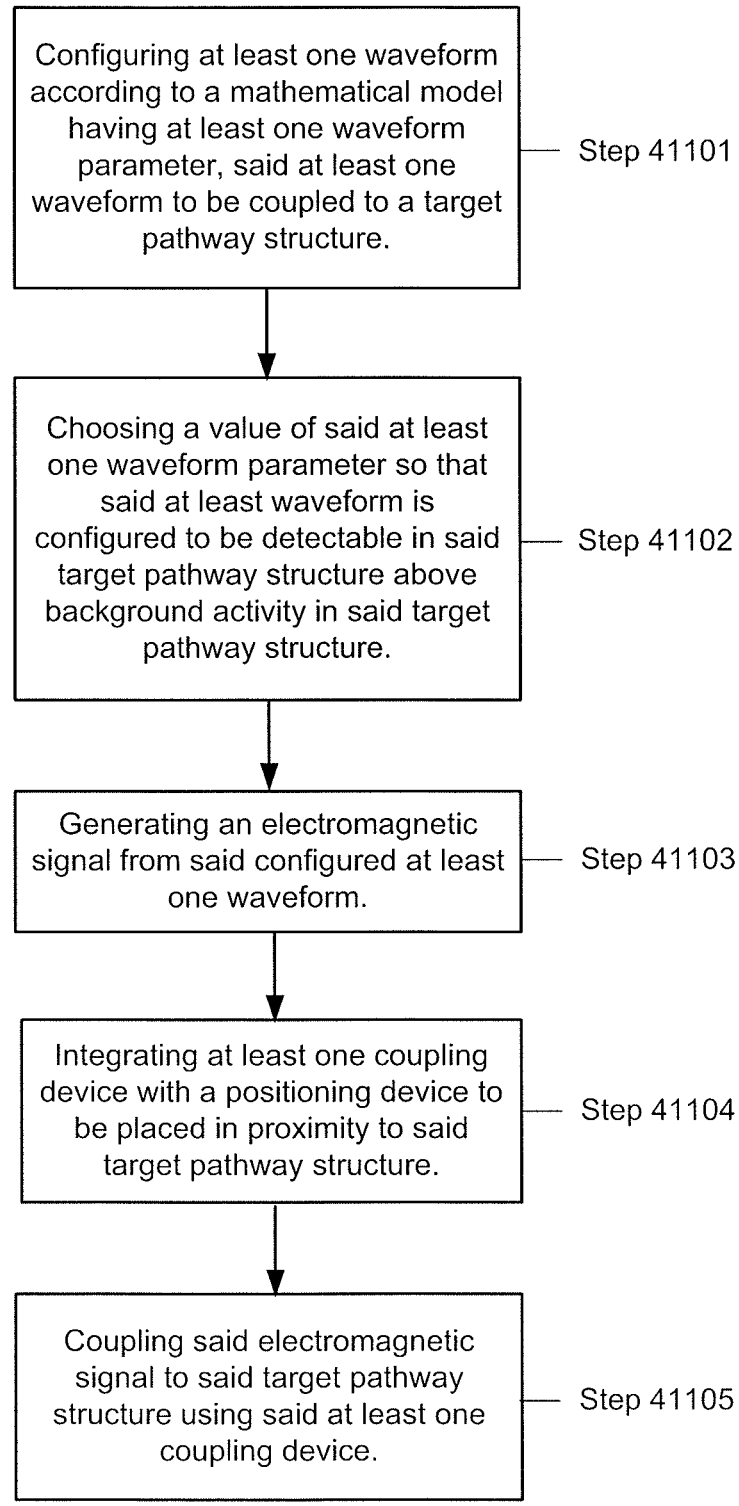
Figure 42:
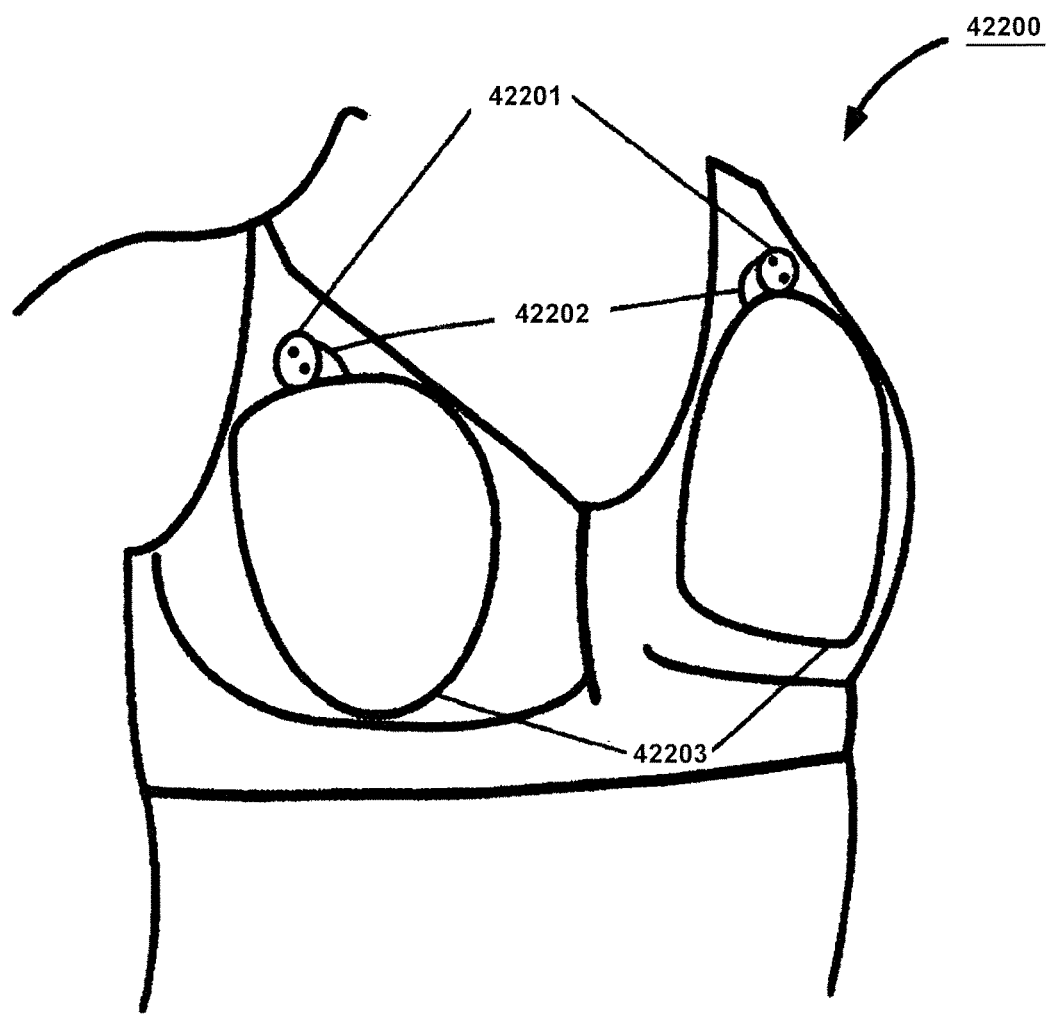
Figure 43:
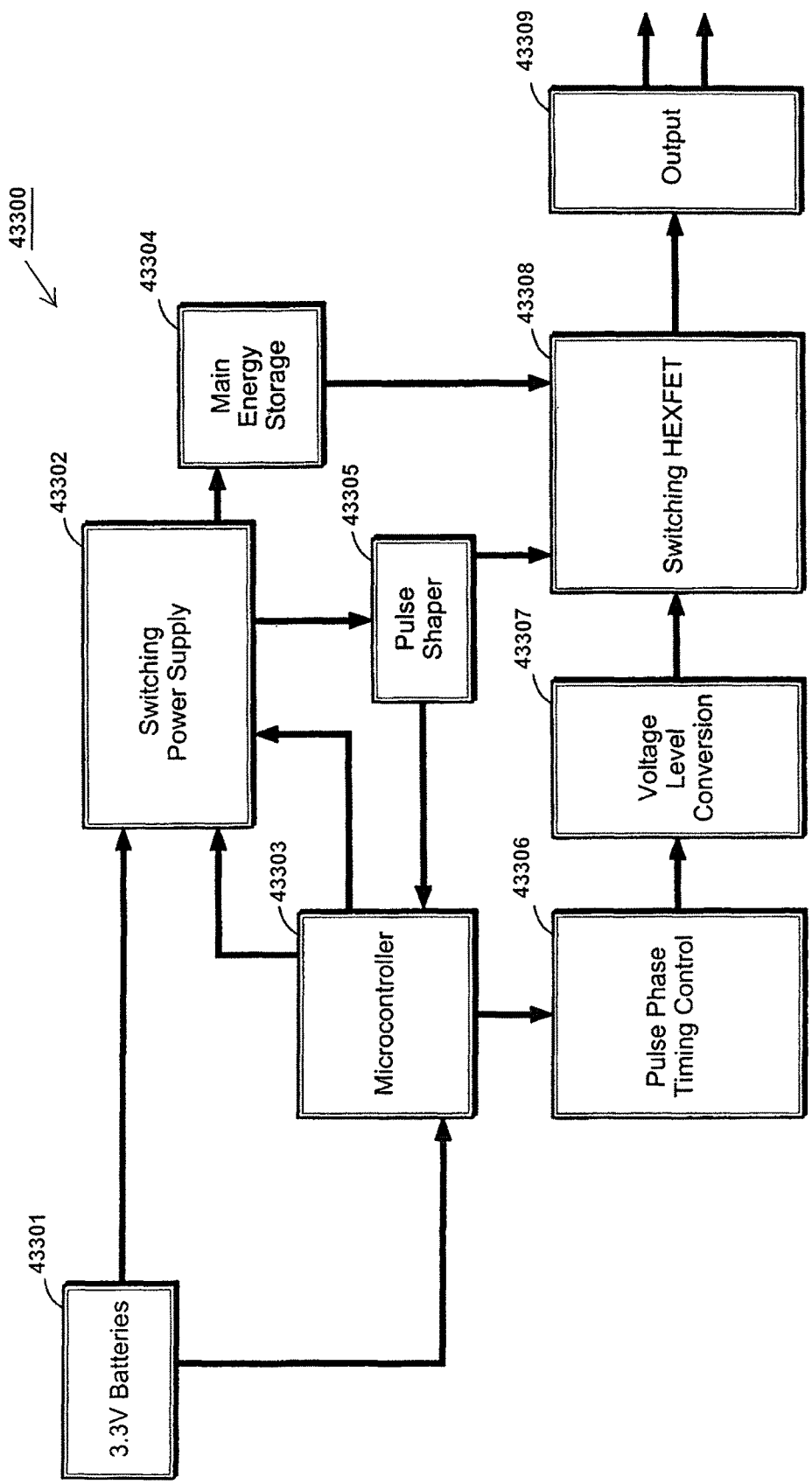
Figure 44:
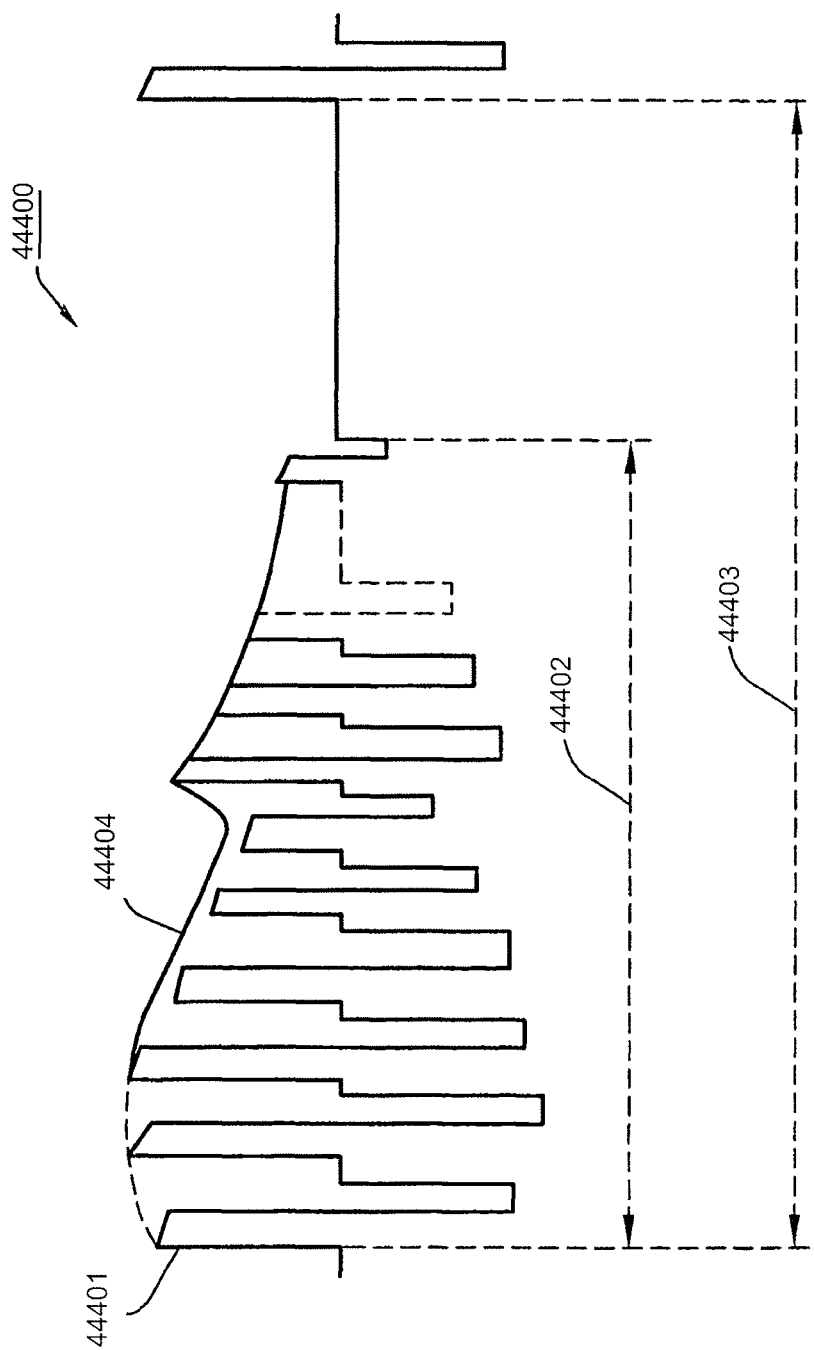

FIG. 41 is a flow diagram of a electromagnetic therapeutic treatment method for using coils integrated into a positioning device according to an embodiment of the present invention;

FIG. 42 is a view of an electromagnetic treatment apparatus according to a preferred embodiment of the present invention;

FIG. 43 is a block diagram of miniaturized circuitry according to a preferred embodiment of the present invention;

FIG. 44 depicts a waveform delivered to a target pathway structure according to a preferred embodiment of the present invention.

Figure 45:
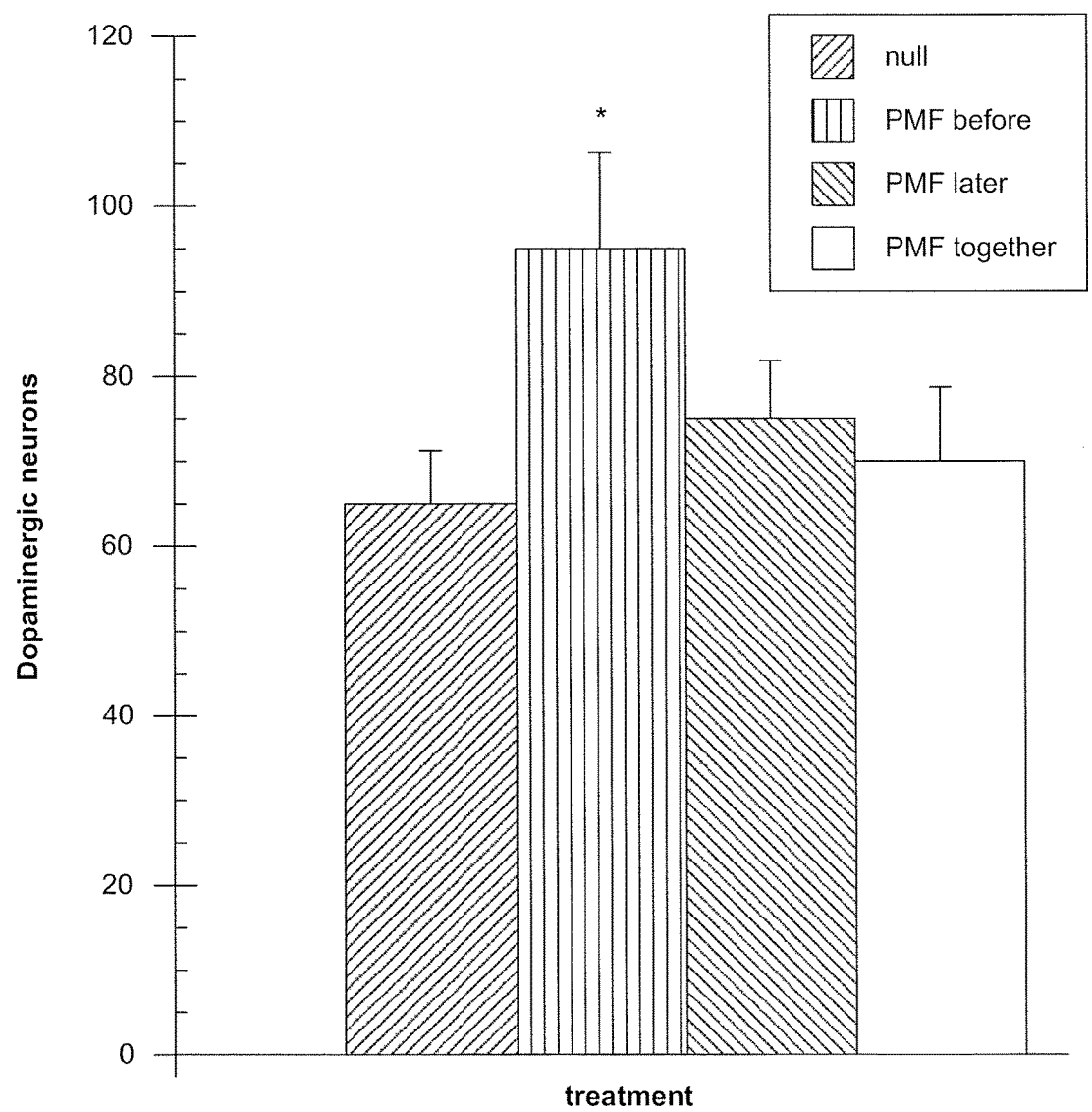
Figure 46:
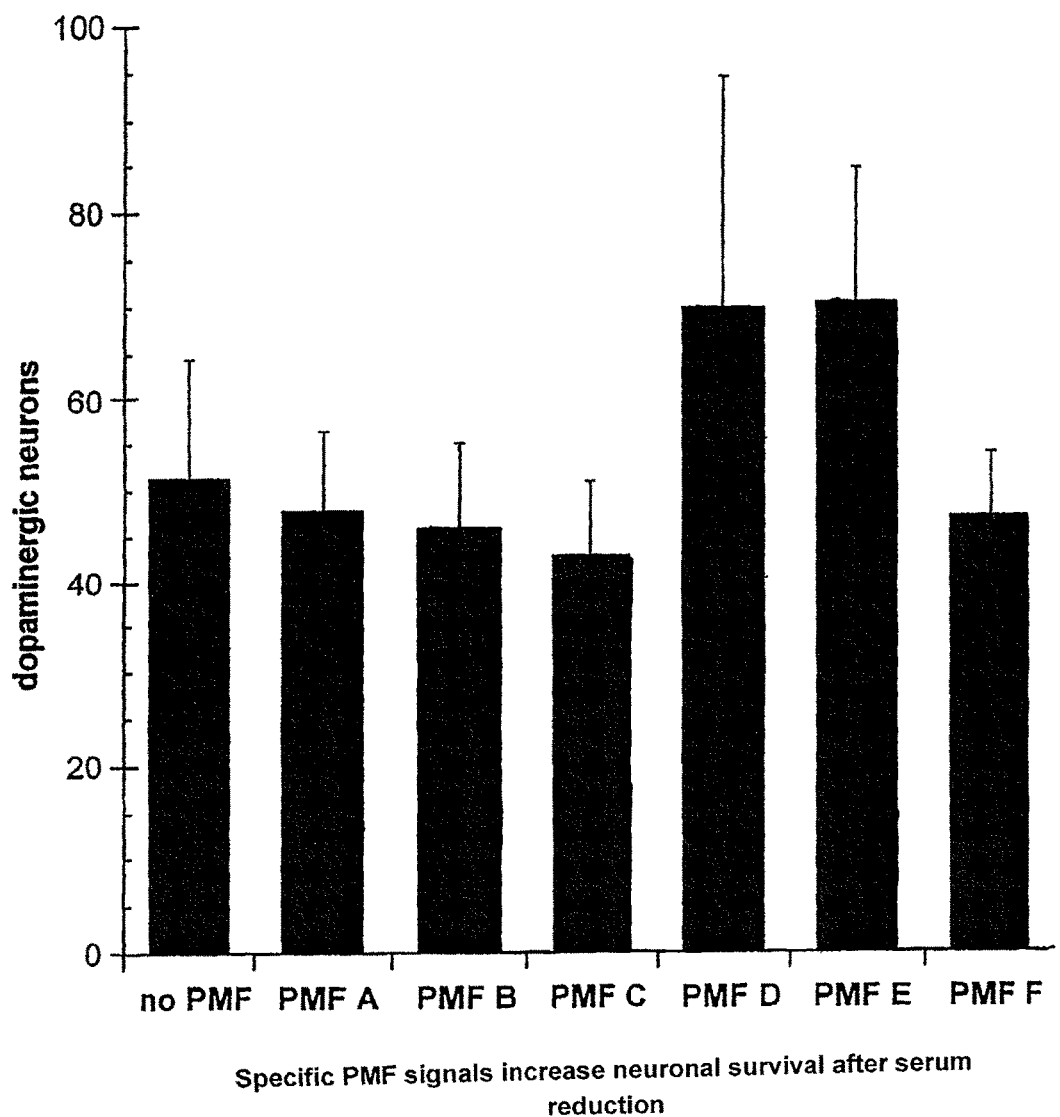

FIG. 45 is a bar graph illustrating PMF pre-treatment results;

FIG. 46 is a bar graph illustrating specific PMF signal results; and

Figure 47:
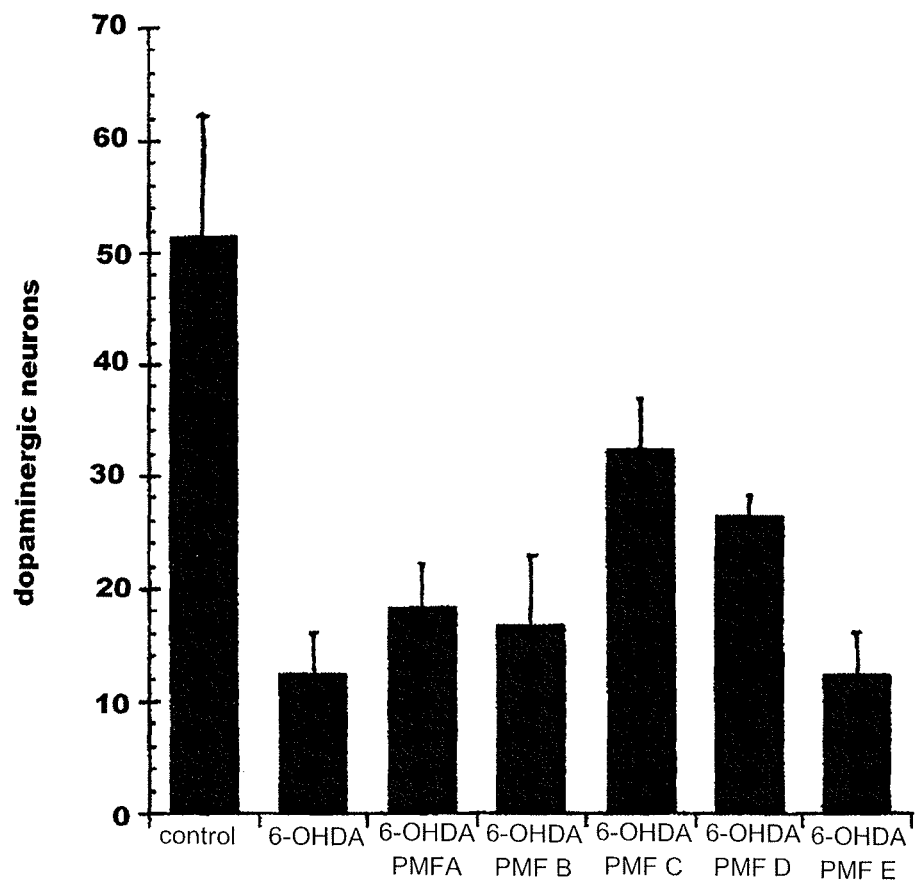

FIG. 47 is a bar graph illustrating chronic PMF results.

Part 7

Figure 48:
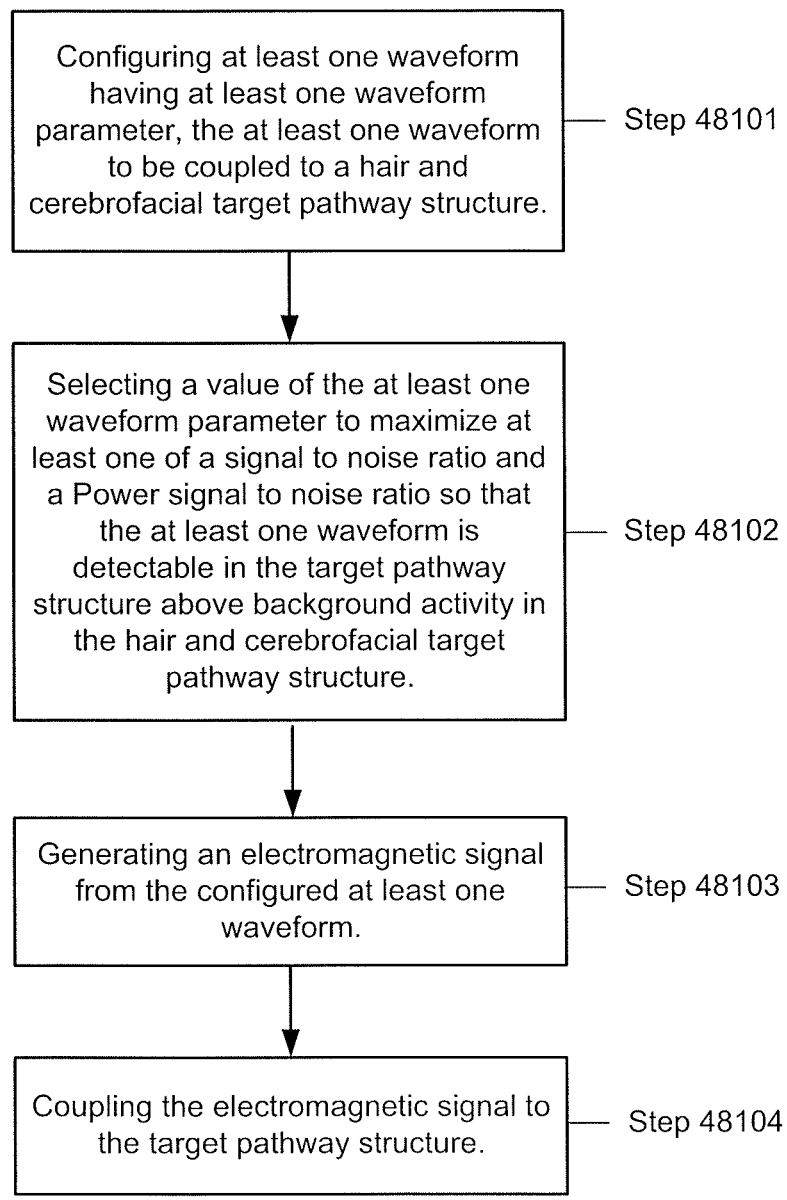
Figure 49:
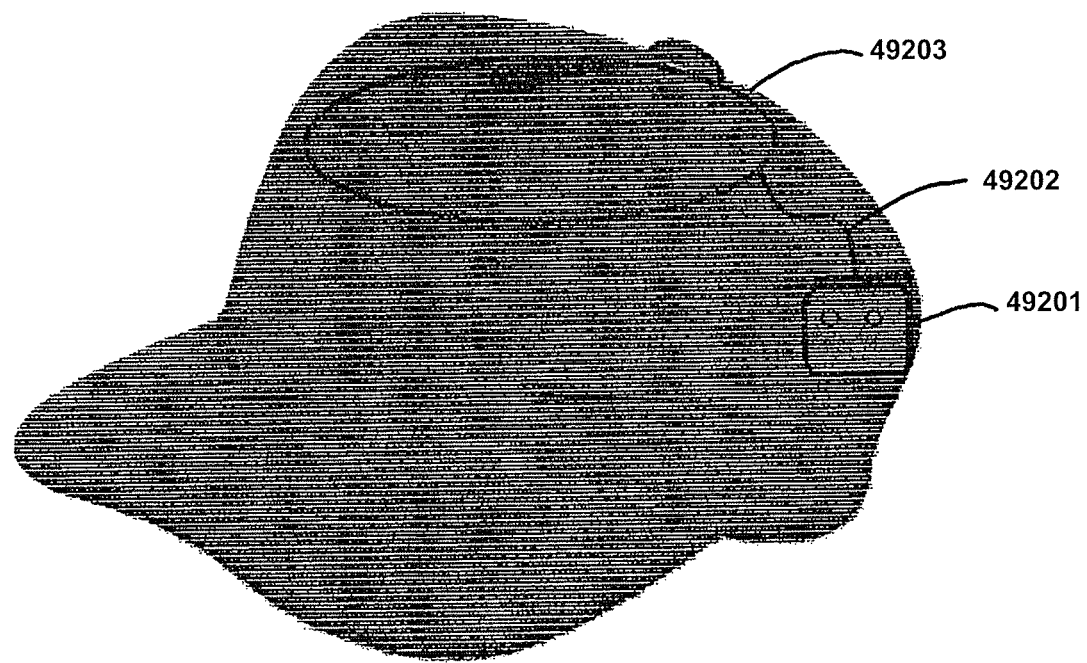
Figure 50:
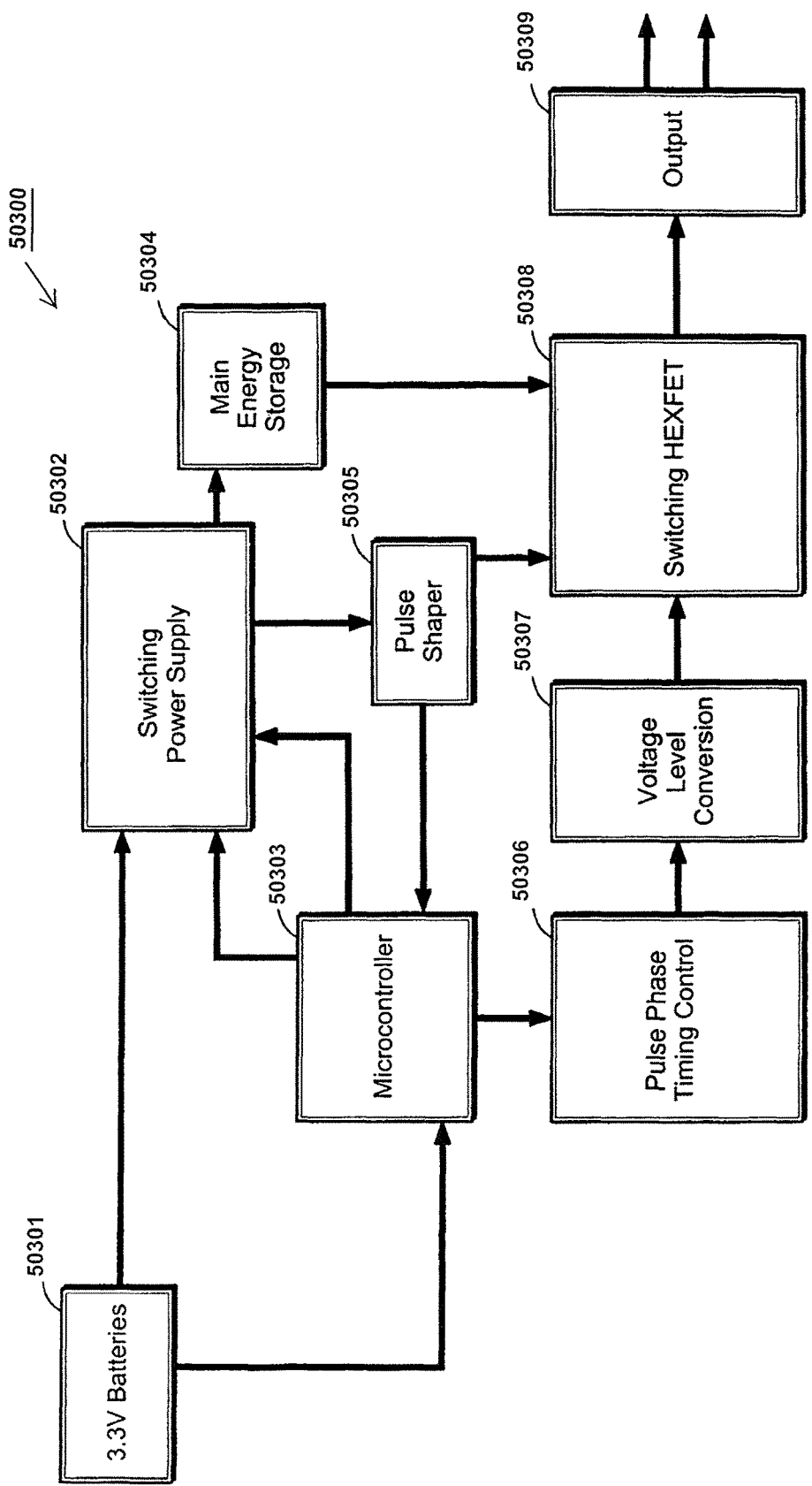
Figure 51:
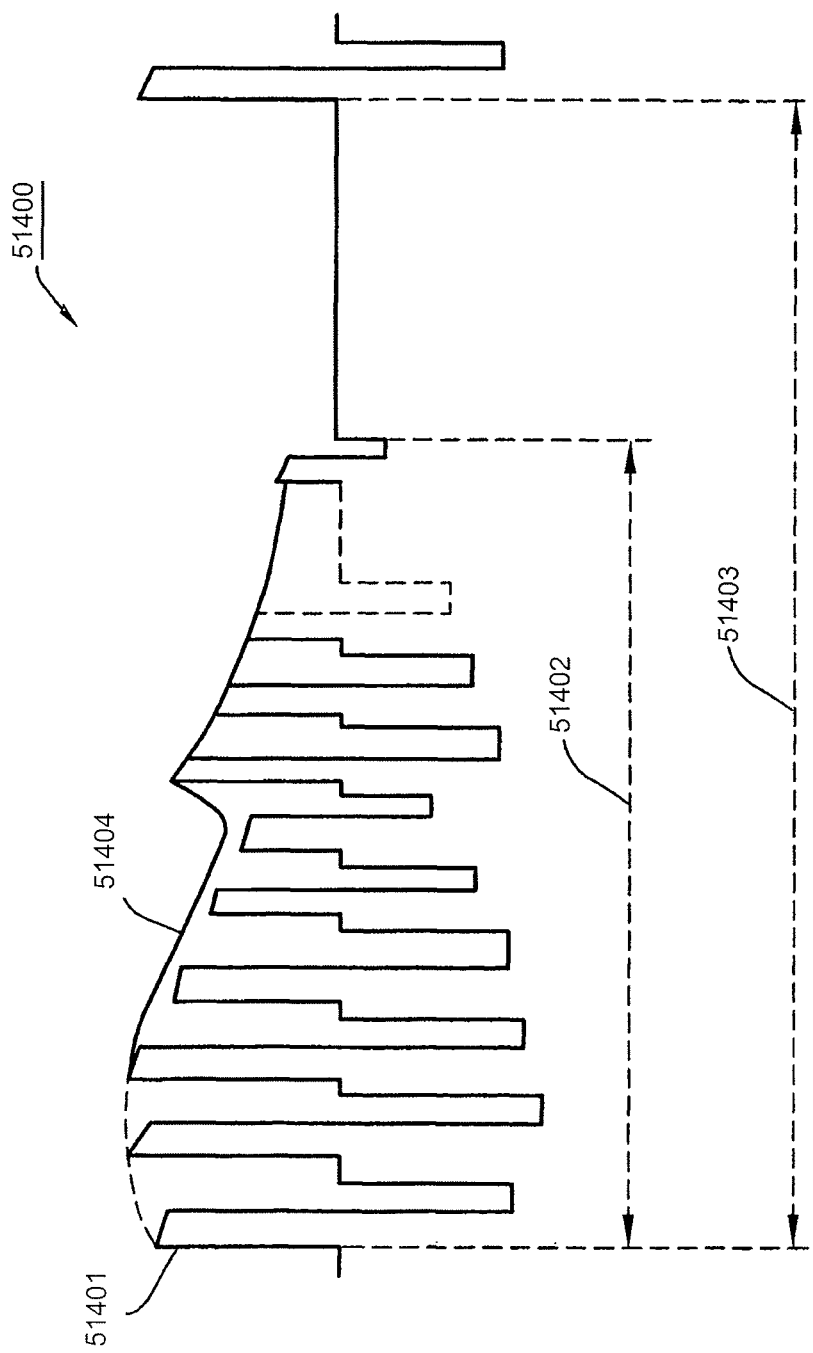
Figure 52:
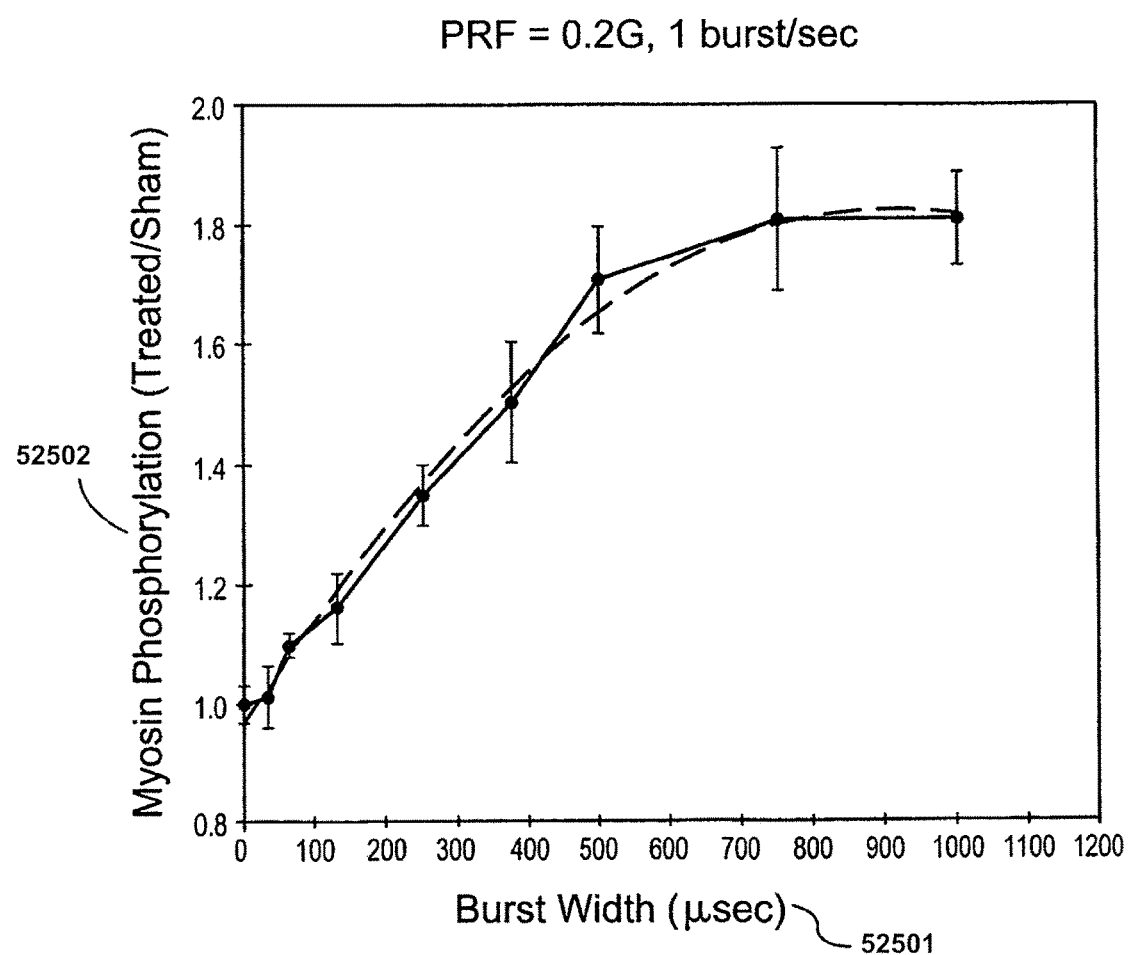
Figure 53:
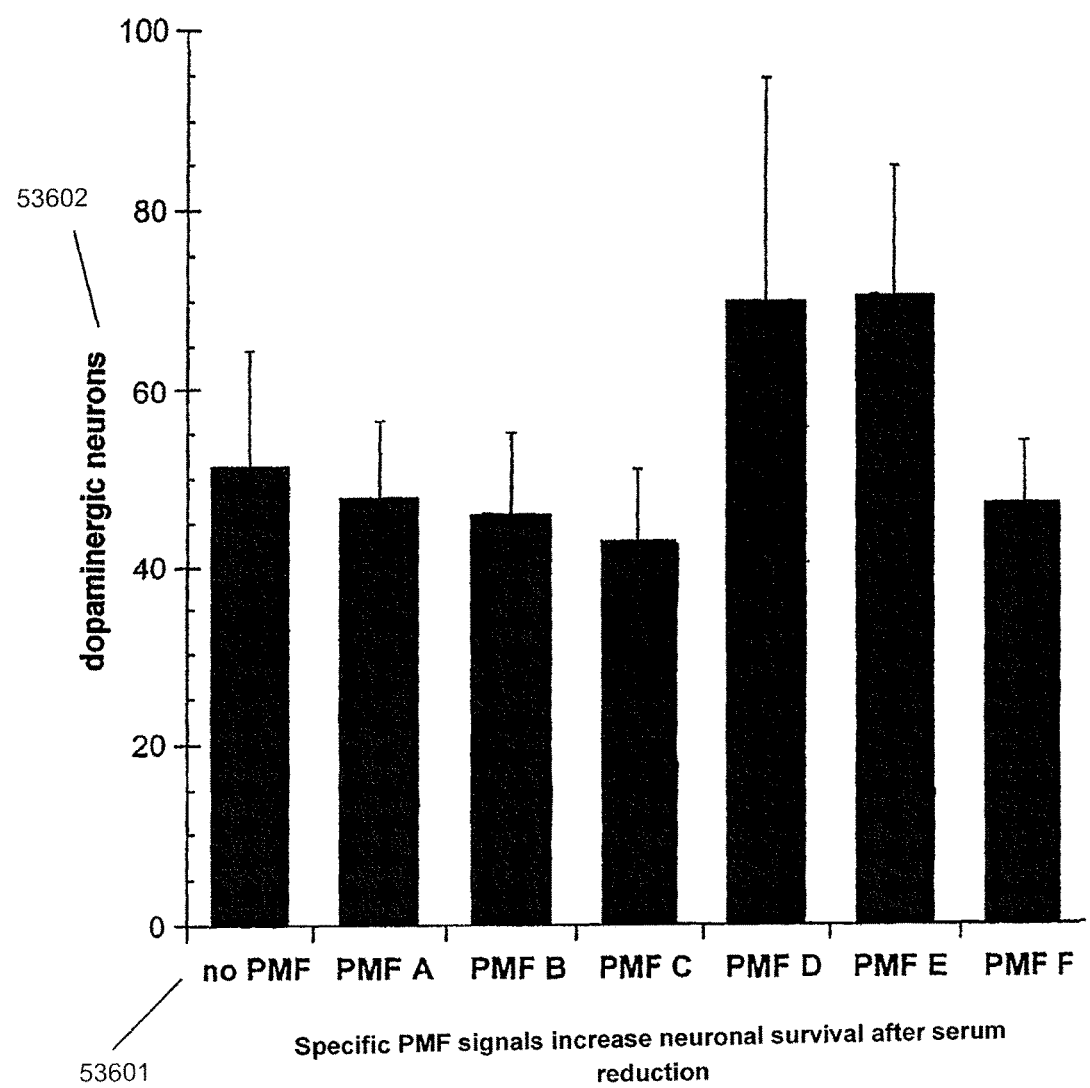

FIG. 48 is a flow diagram of a electromagnetic treatment method for hair restoration and cerebrofacial conditions according to an embodiment of the present invention;

FIG. 49 is a view of an electromagnetic treatment apparatus for hair restoration and cerebrofacial conditions according to a preferred embodiment of the present invention;

FIG. 50 is a block diagram of miniaturized circuitry according to a preferred embodiment of the present invention; and FIG. 51 depicts a waveform delivered to a hair and cerebrofacial target pathway structure according to a preferred embodiment of the present invention;

FIG. 52 is a bar graph illustrating various burst width results;

FIG. 53 is a bar graph illustrating specific PMF signal results; and

Figure 54:
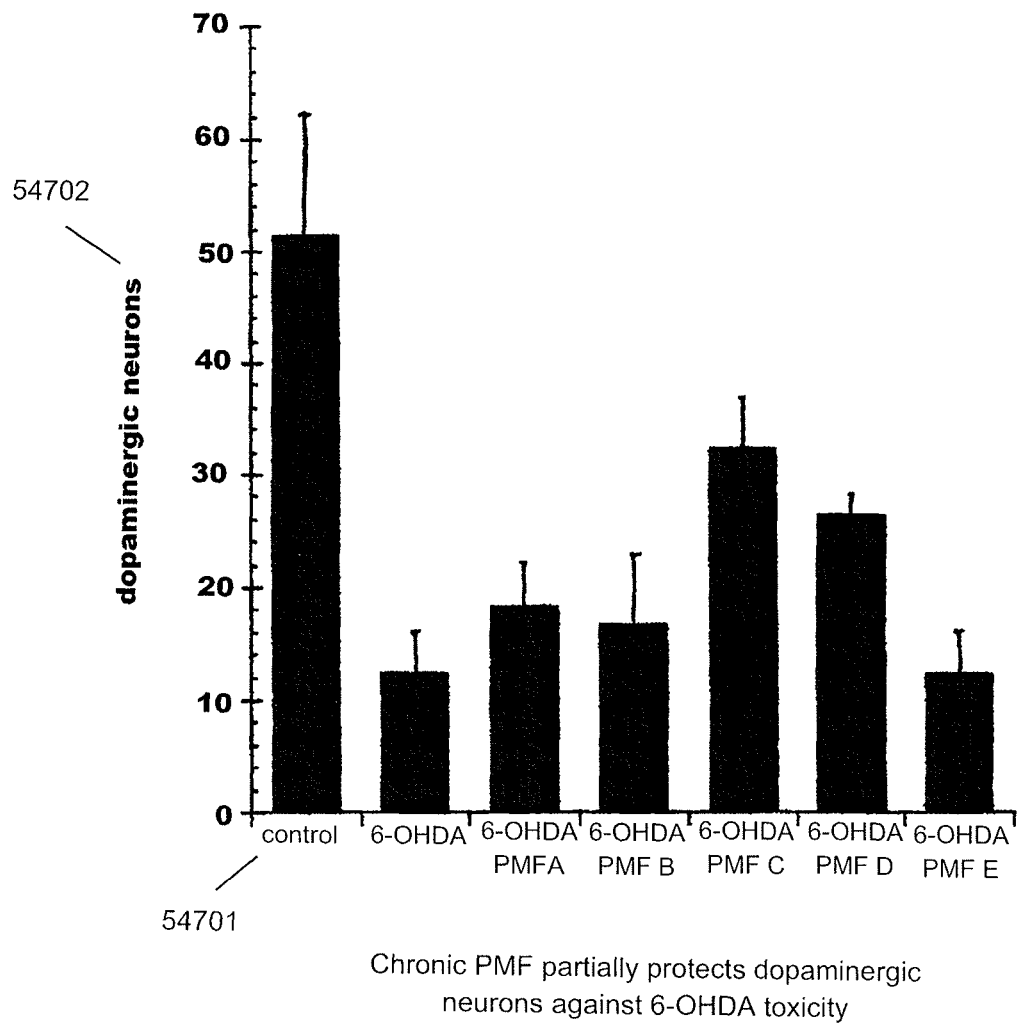

FIG. 54 is a bar graph illustrating chronic PMF results.

Part 8

Figure 55:
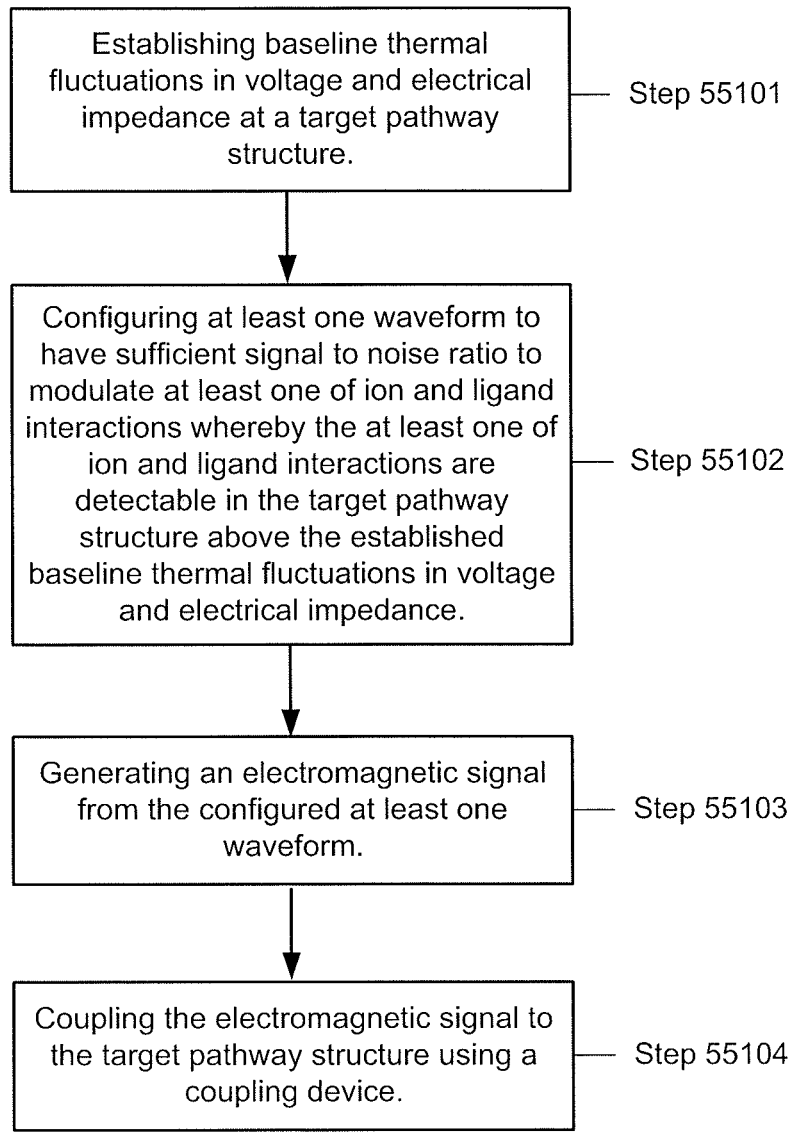
Figure 56:
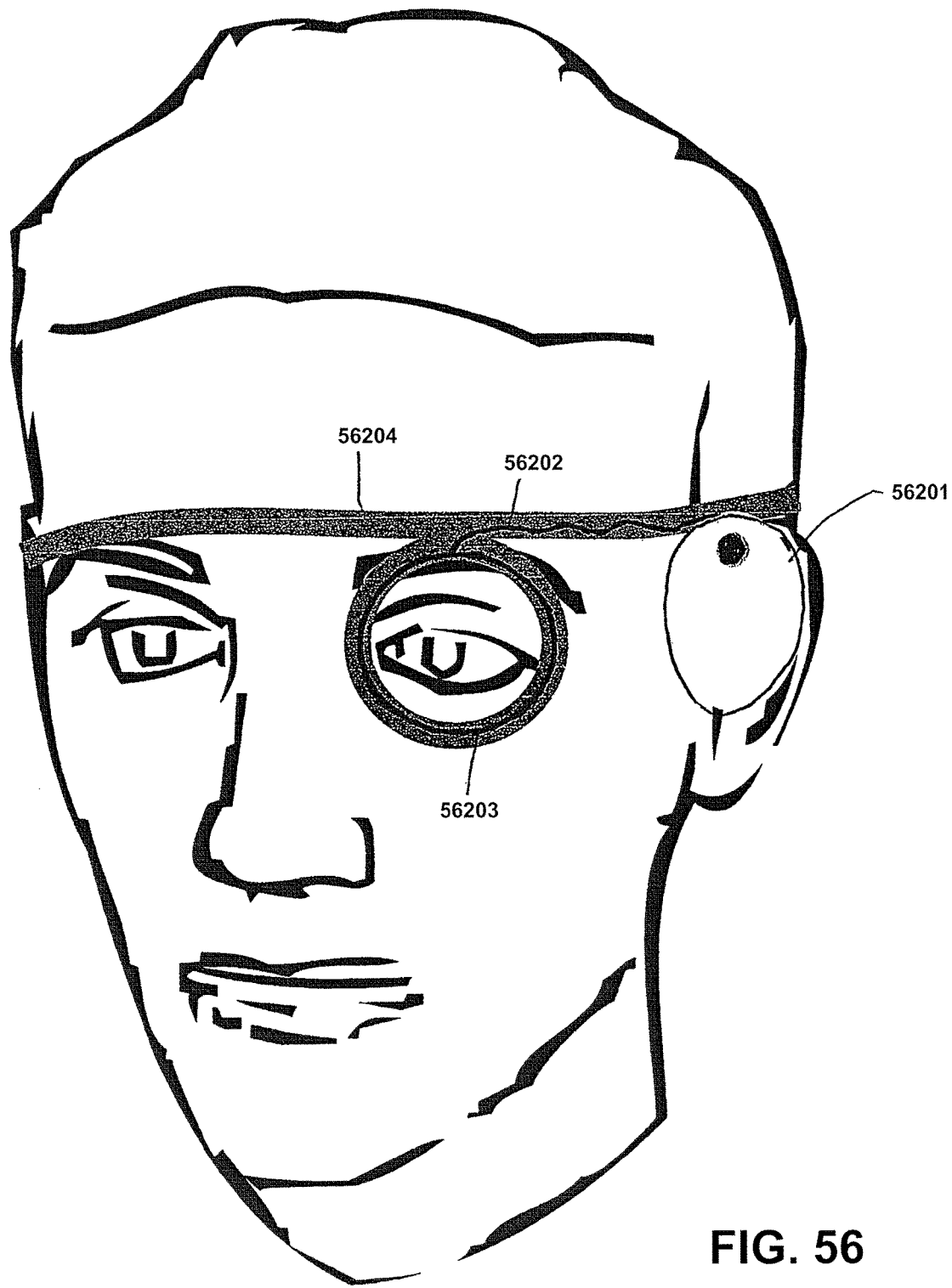
Figure 57:
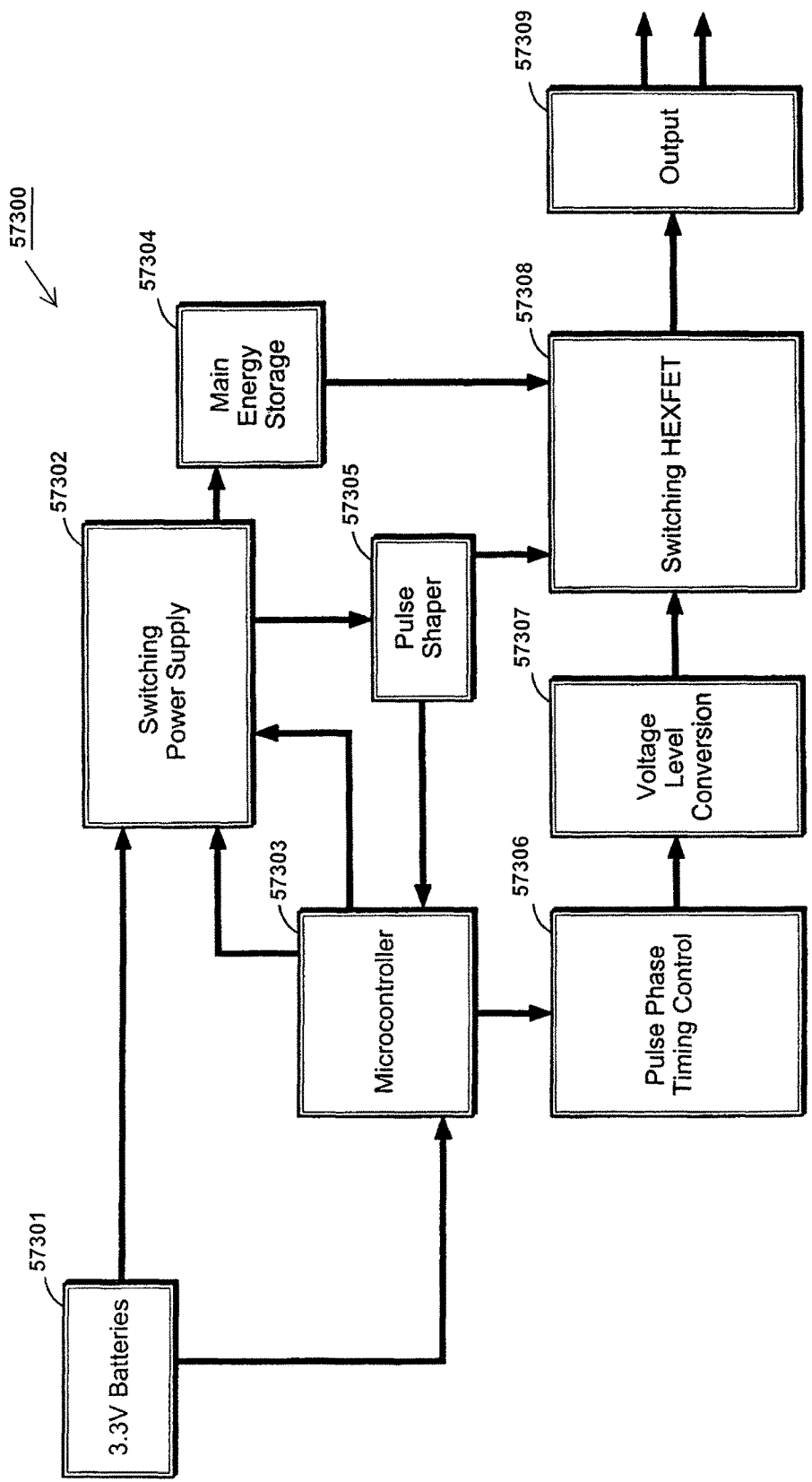
Figure 58:
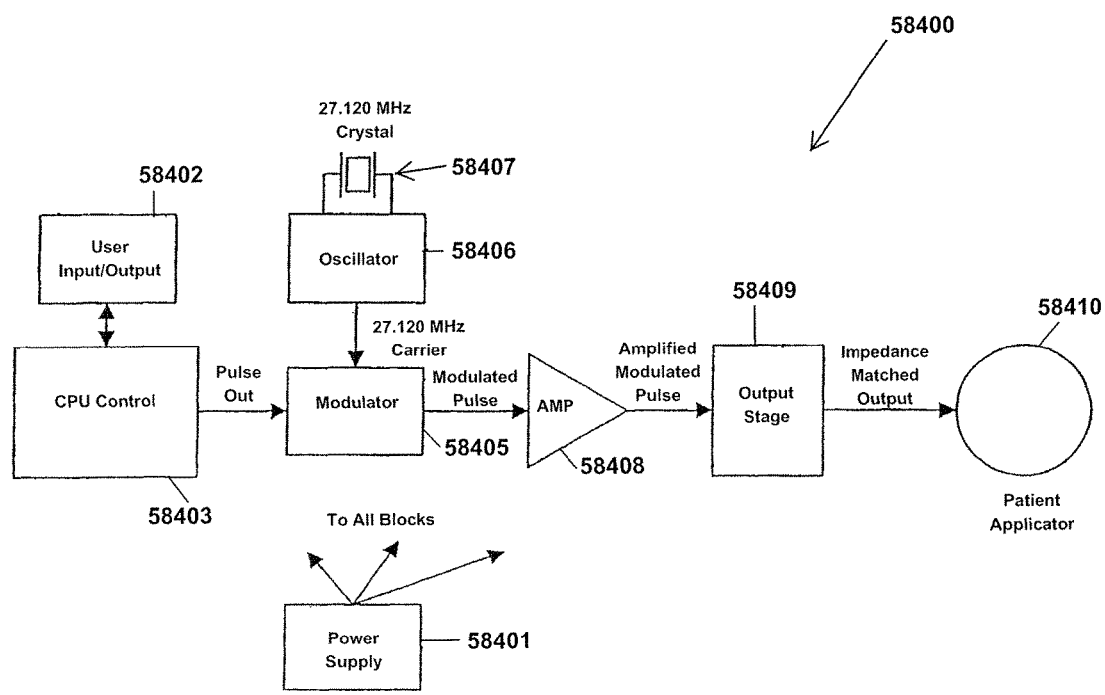
Figure 59:
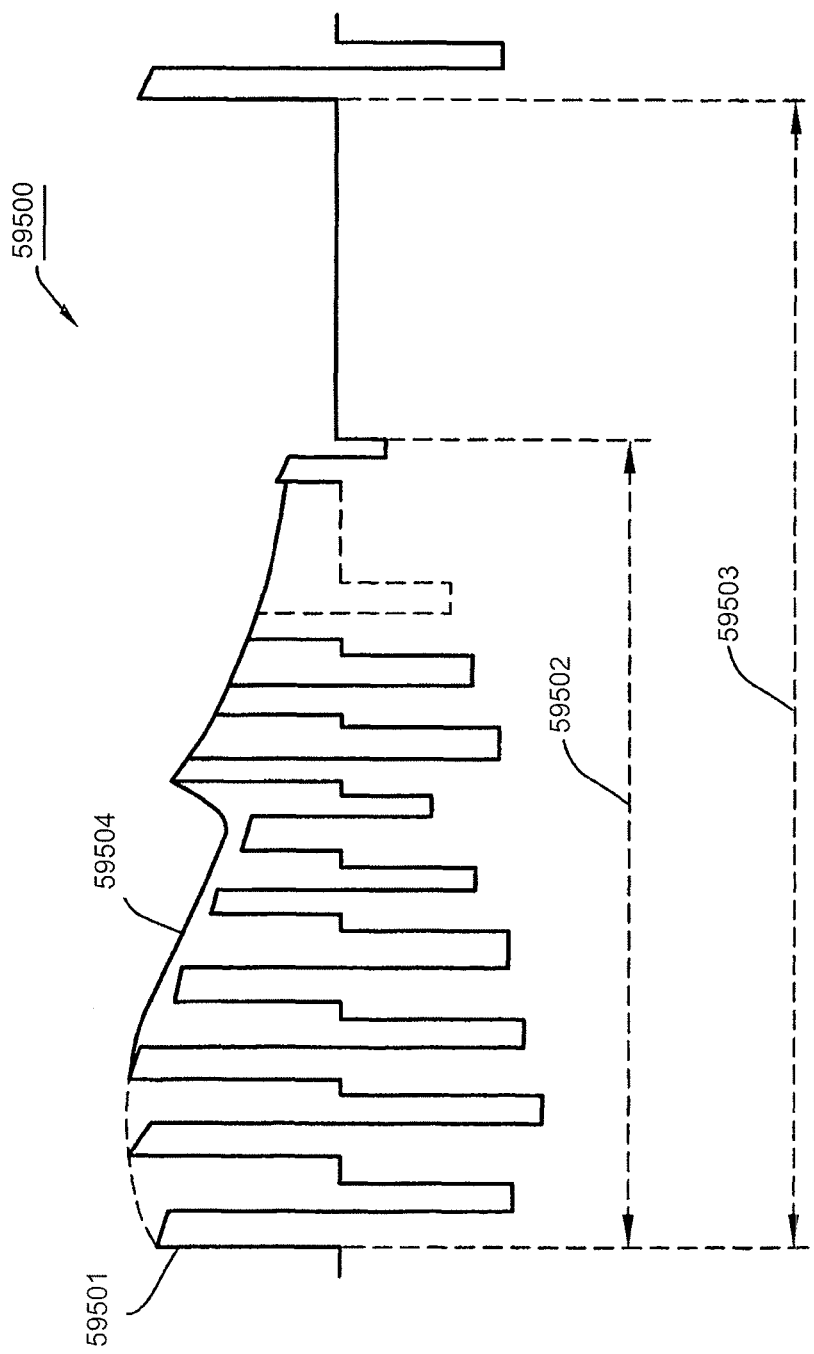
Figure 60:
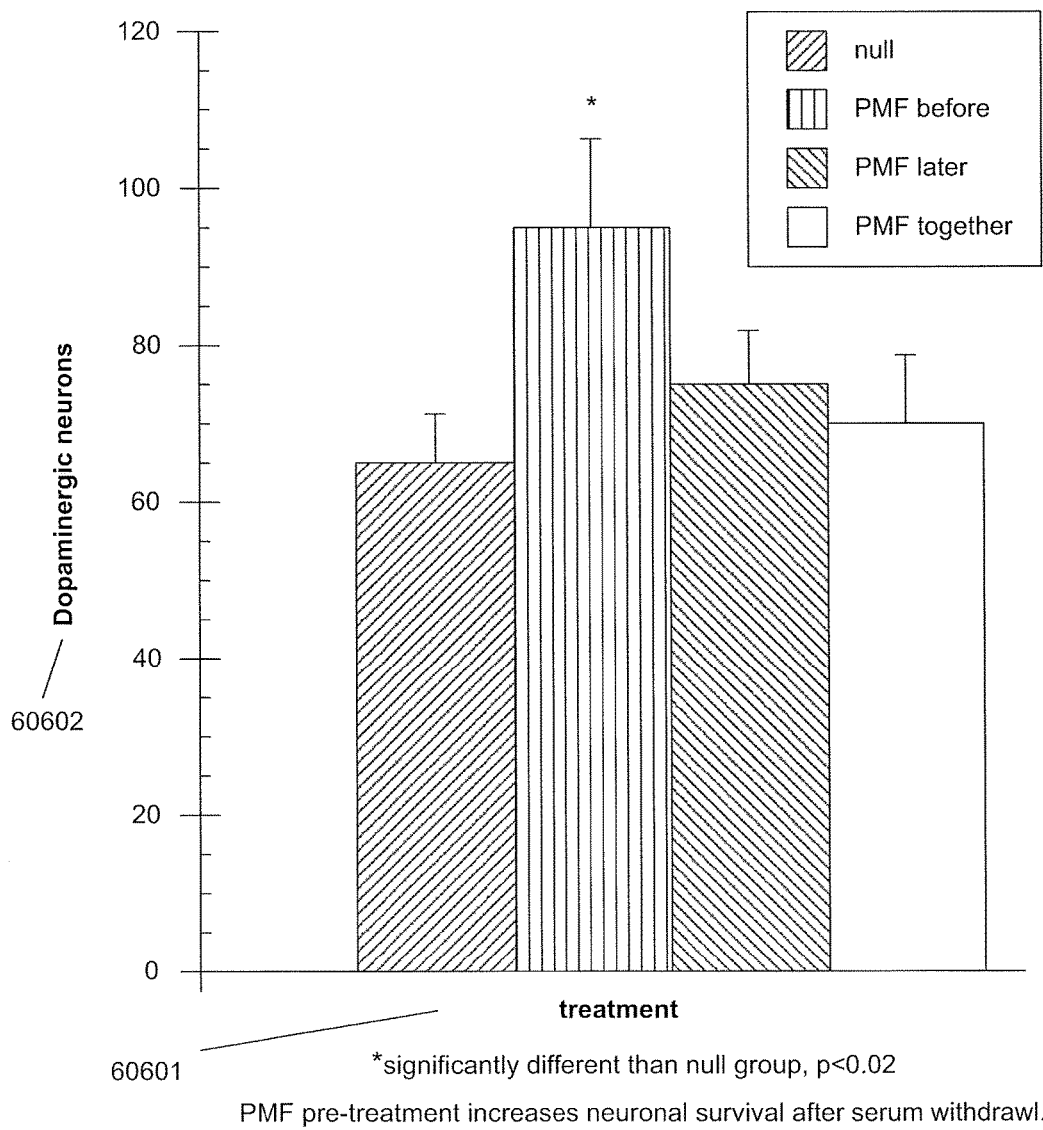
Figure 61:
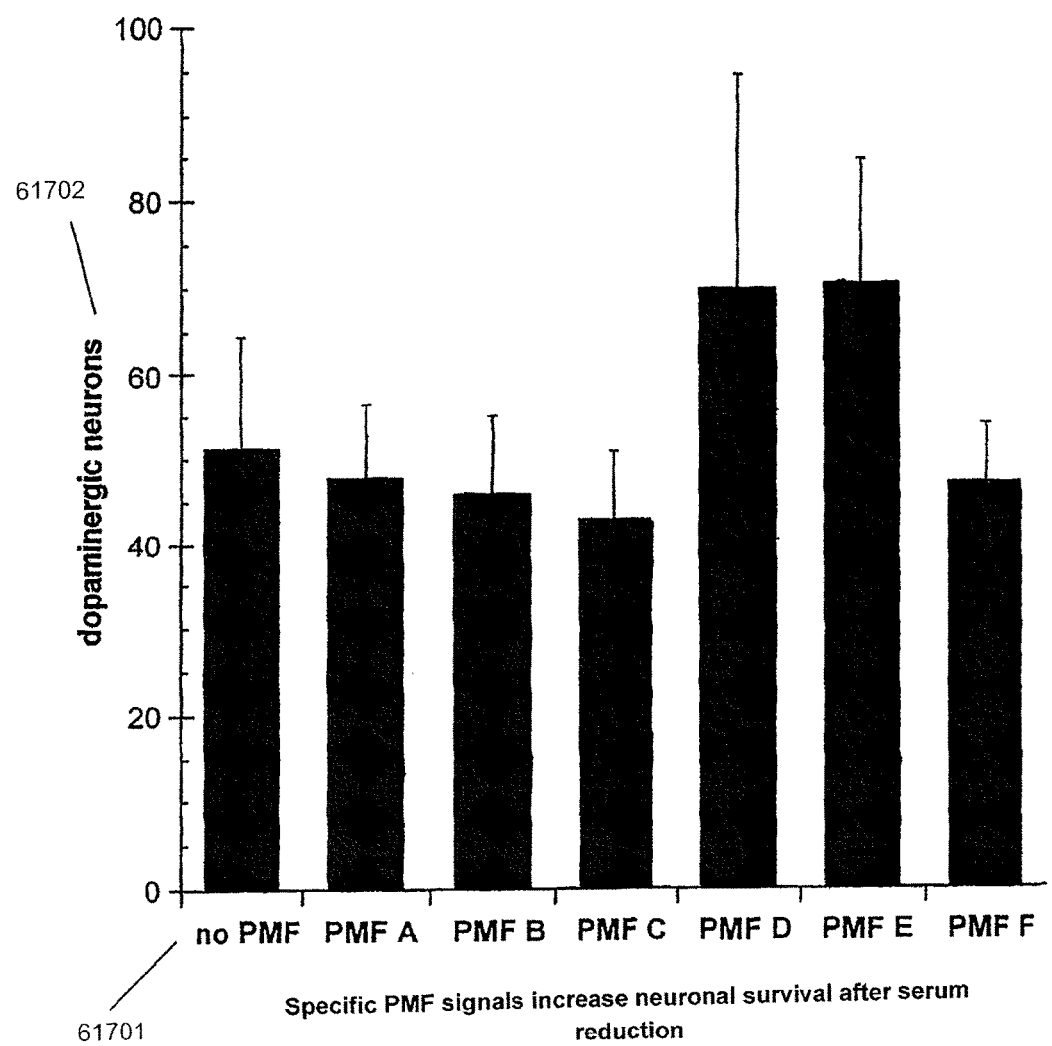

FIG. 55 is a flow diagram of a electromagnetic treatment method for treatment of the ophthalmic tissue area according to an embodiment of the present invention;

FIG. 56 is a view of an electromagnetic treatment apparatus for ophthalmic tissue treatment according to a preferred embodiment of the present invention;

FIG. 57 is a block diagram of miniaturized circuitry according to a preferred embodiment of the present invention;

FIG. 58 is a block diagram of miniaturized circuitry according to another embodiment of the present invention;

FIG. 59 depicts a waveform delivered to eye target pathway structure according to a preferred embodiment of the present invention;

FIG. 60 is a bar graph illustrating PMF pre-treatment results;

FIG. 61 is a bar graph illustrating specific PMF signal results; and

Figure 62:
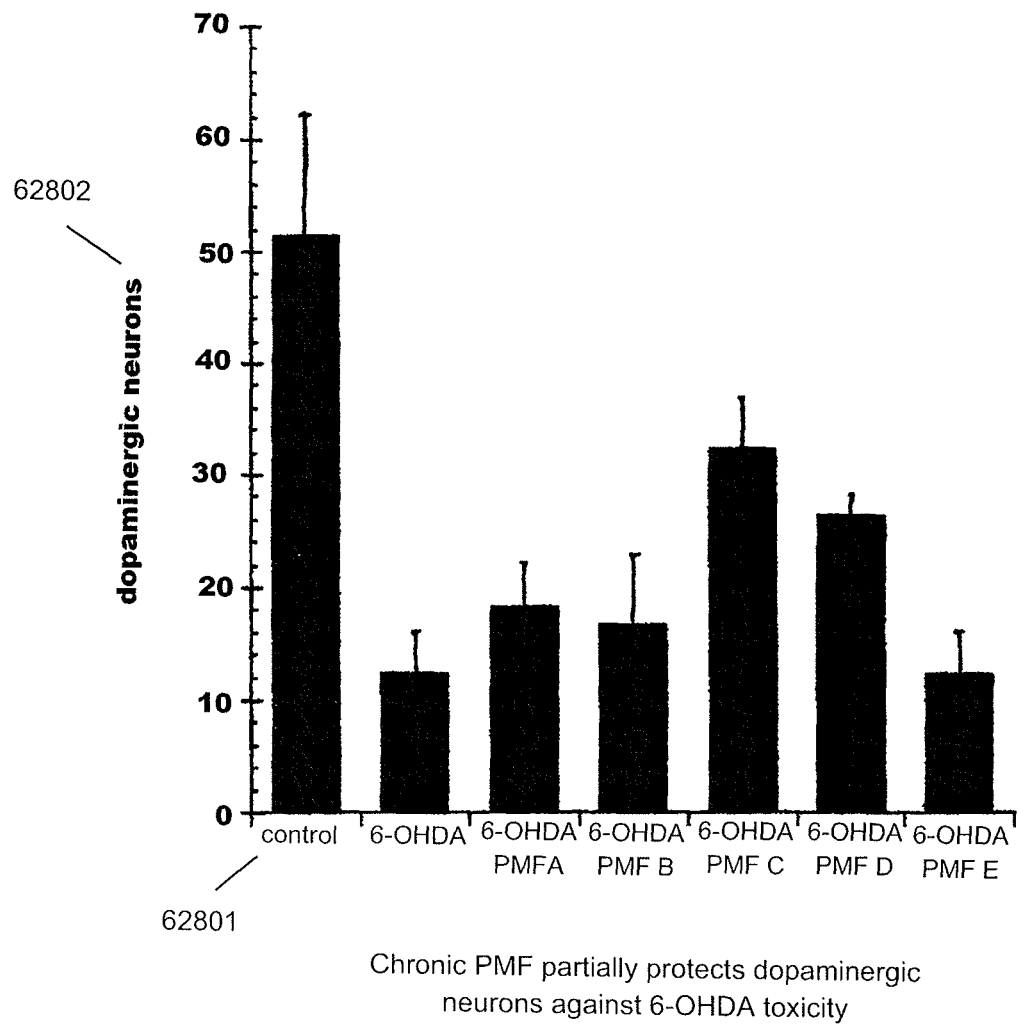

FIG. 62 is a bar graph illustrating chronic PMF results.

Part 9

Figure 64:
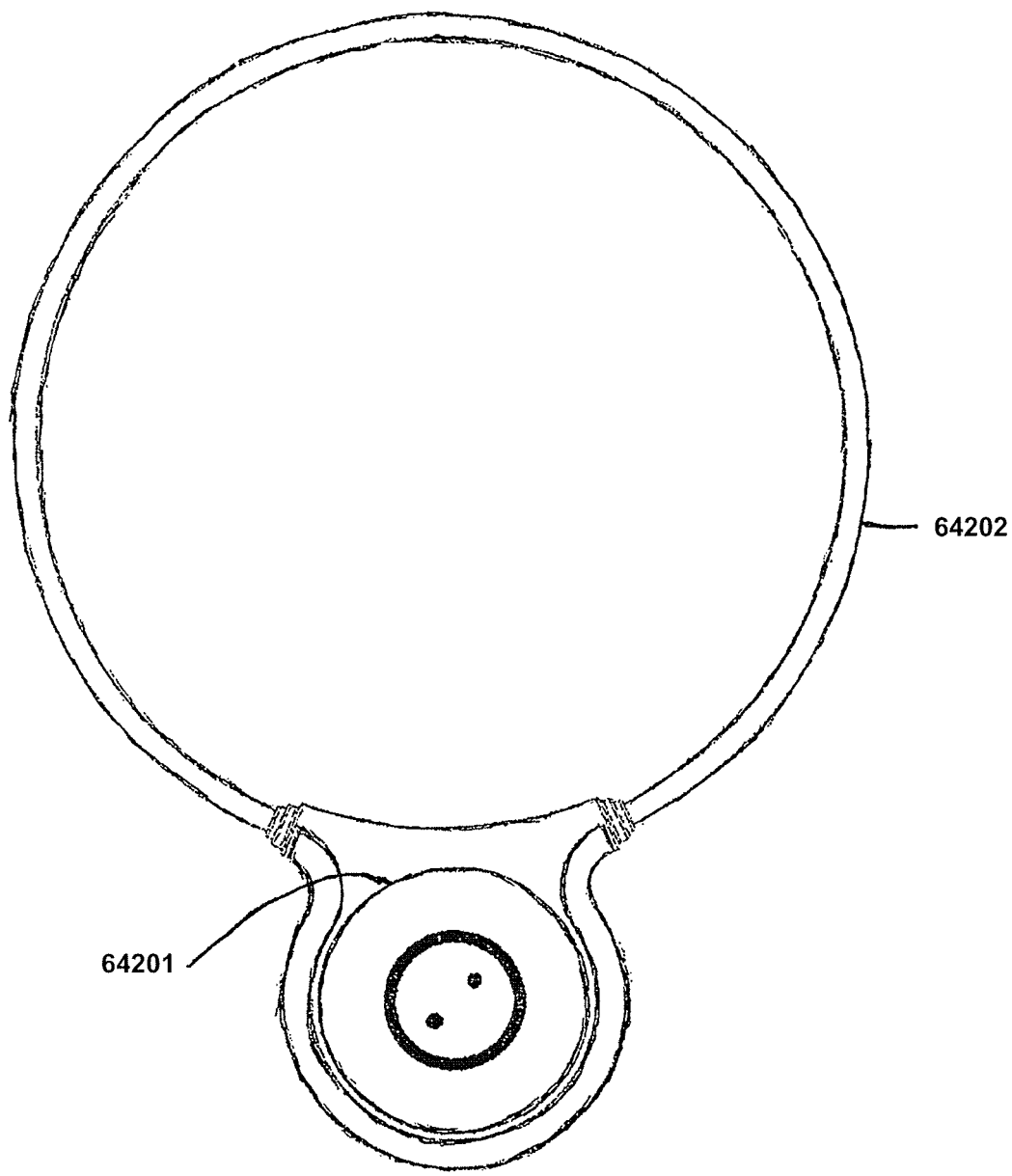
Figure 65:
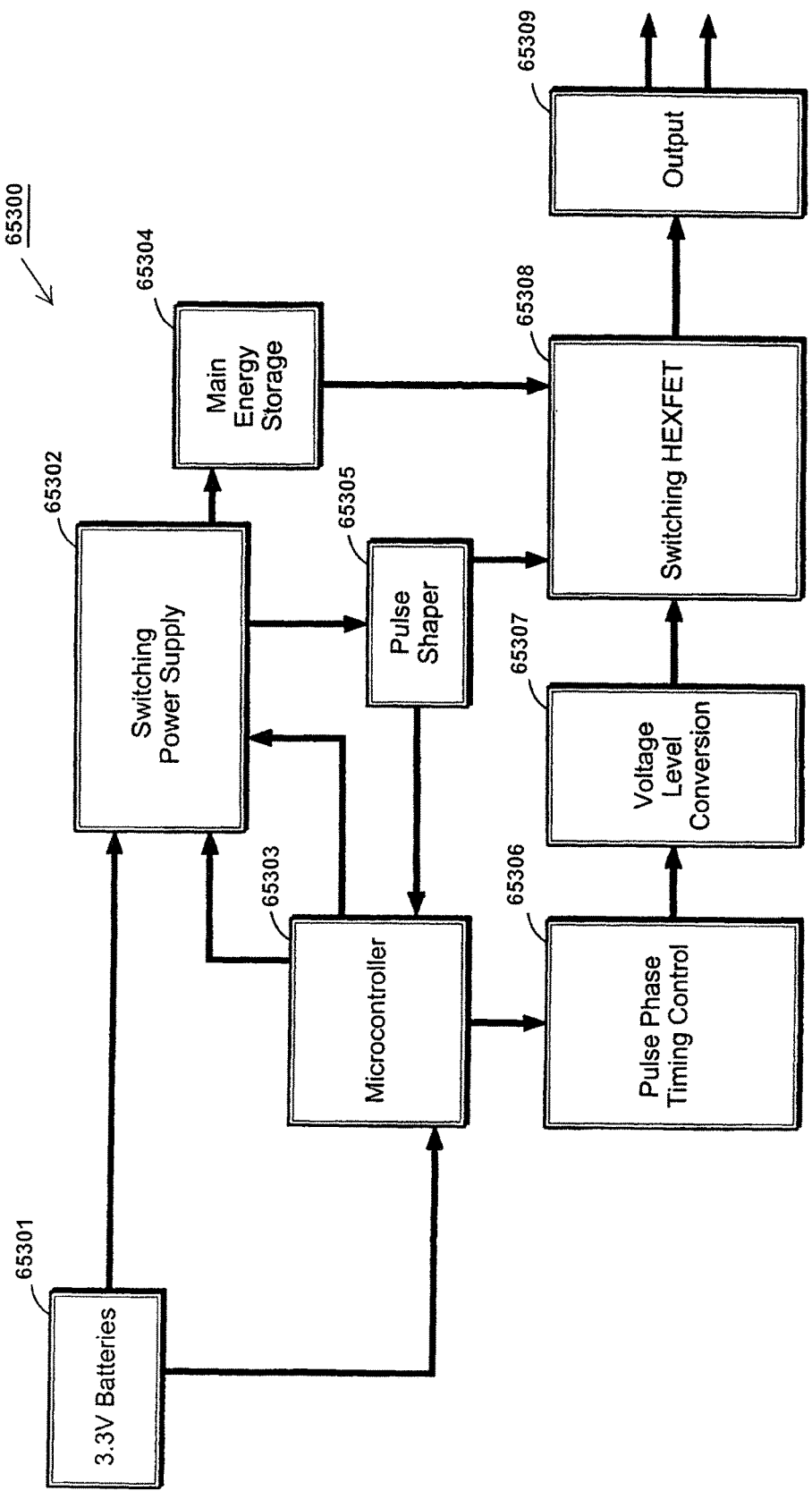
Figure 66:
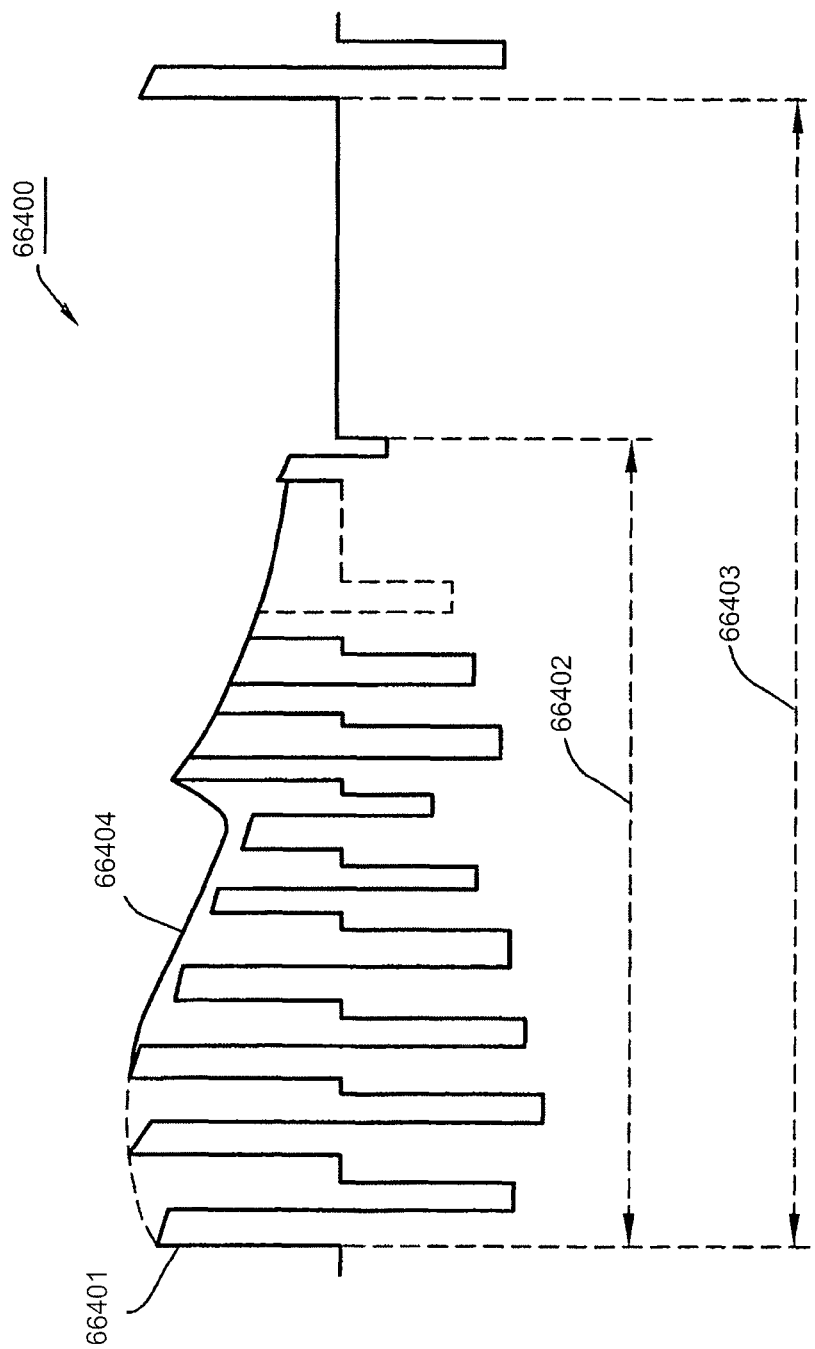
Figure 67:
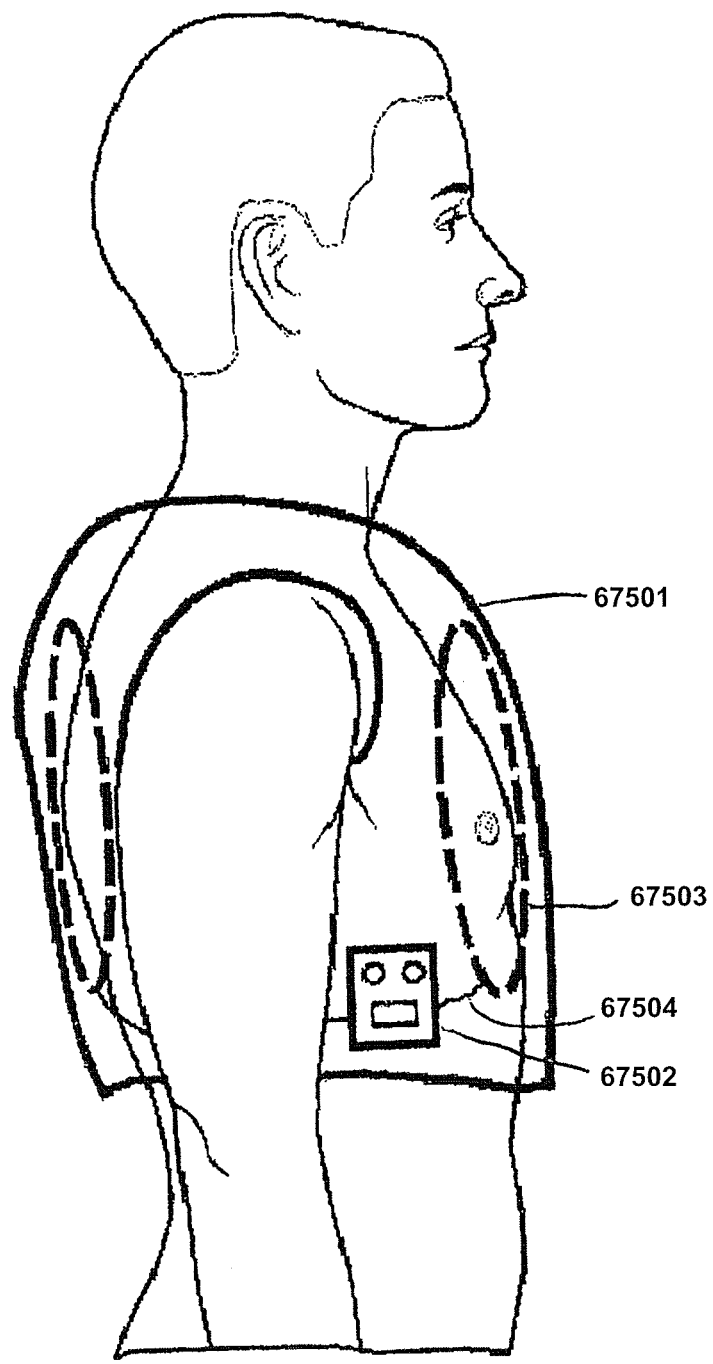
Figure 68:
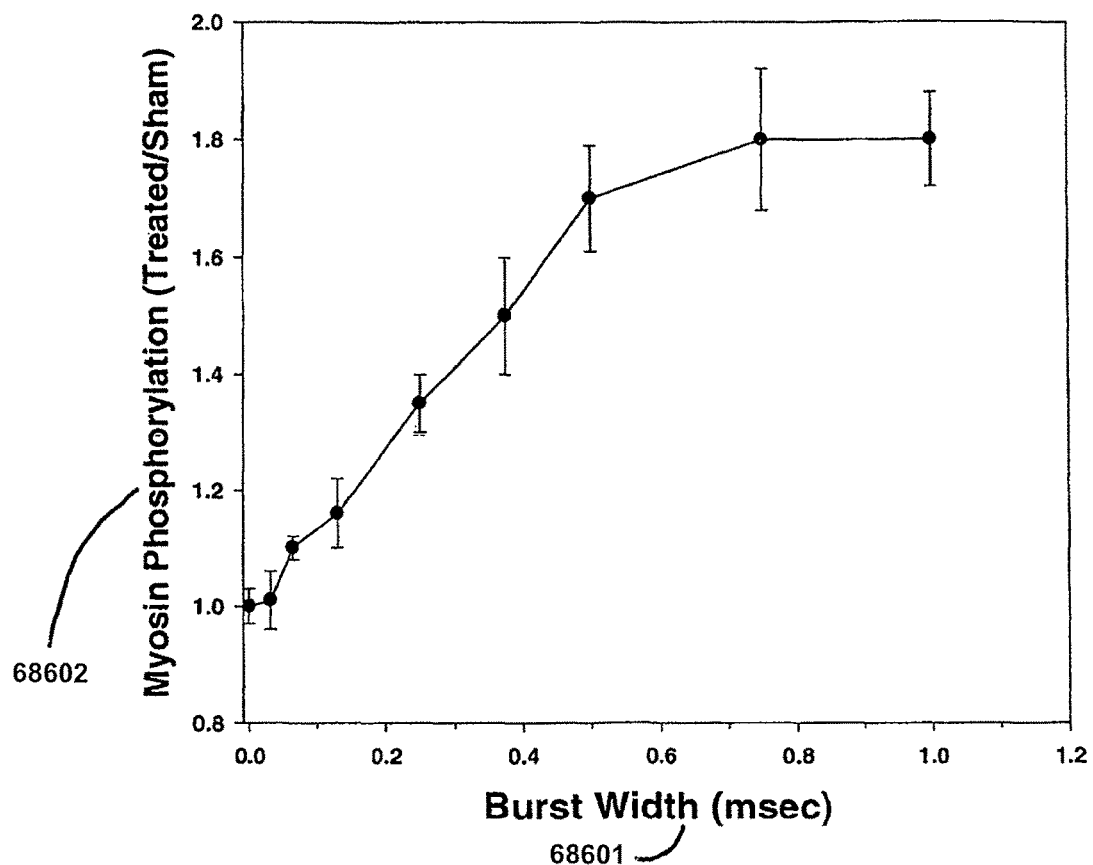
Figure 69:
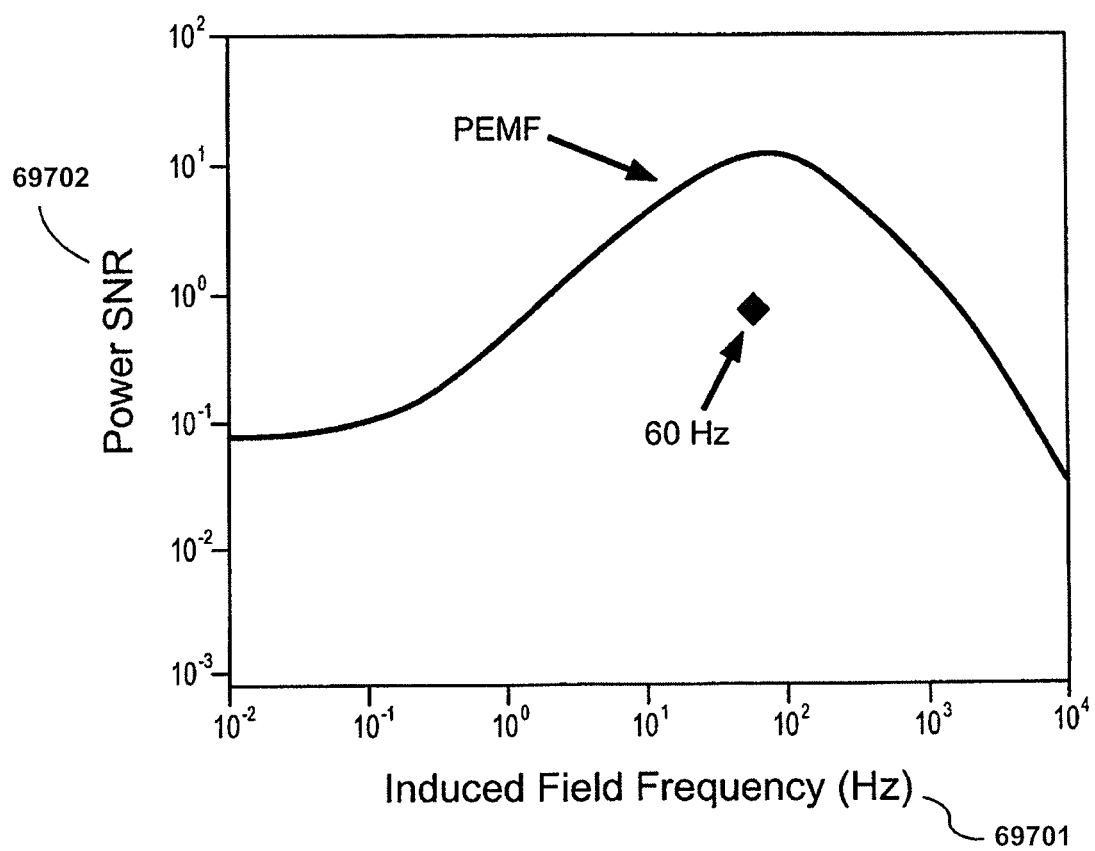

FIG. 63 is a flow diagram of a method for altering an electromagnetic environment of respiratory tissue according to an embodiment of the present invention;

FIG. 64 is a view of an electromagnetic apparatus for respiratory tissue treatment according to an embodiment of the present invention;

FIG. 65 is a block diagram of miniaturized circuitry according to an embodiment of the present invention;

FIG. 66 depicts a waveform delivered to a respiratory target pathway structure according to an embodiment of the present invention;

FIG. 67 is a view of inductors placed in a vest according to an embodiment of the present invention;

FIG. 68 is a bar graph illustrating myosin phosphorylation for a PMF signal configured according to an embodiment of the present invention; and FIG. 69 is a bar graph illustrating SNR signal effectiveness in a cell model of inflammation.

Part 10

Figure 70:
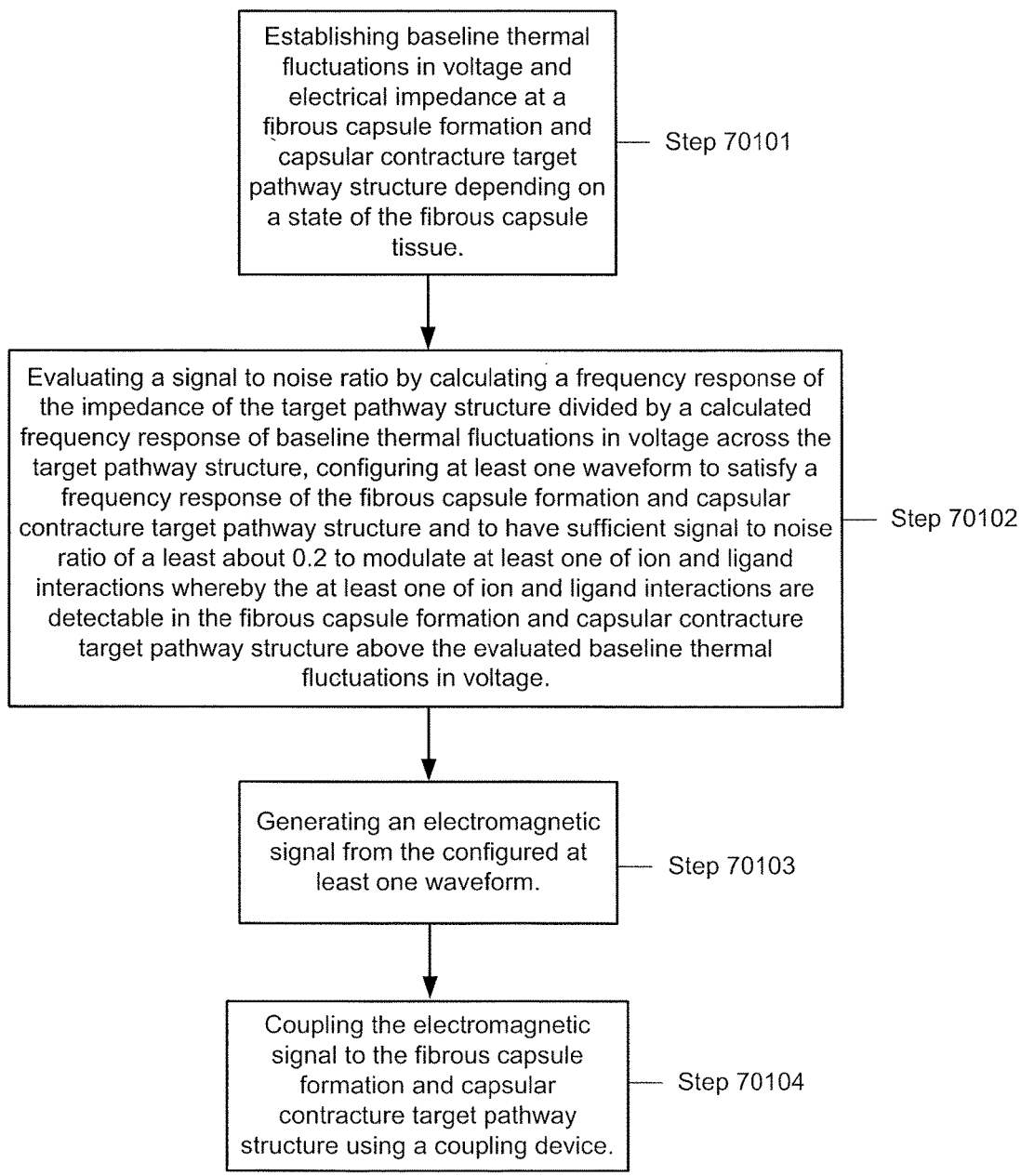
Figure 71:
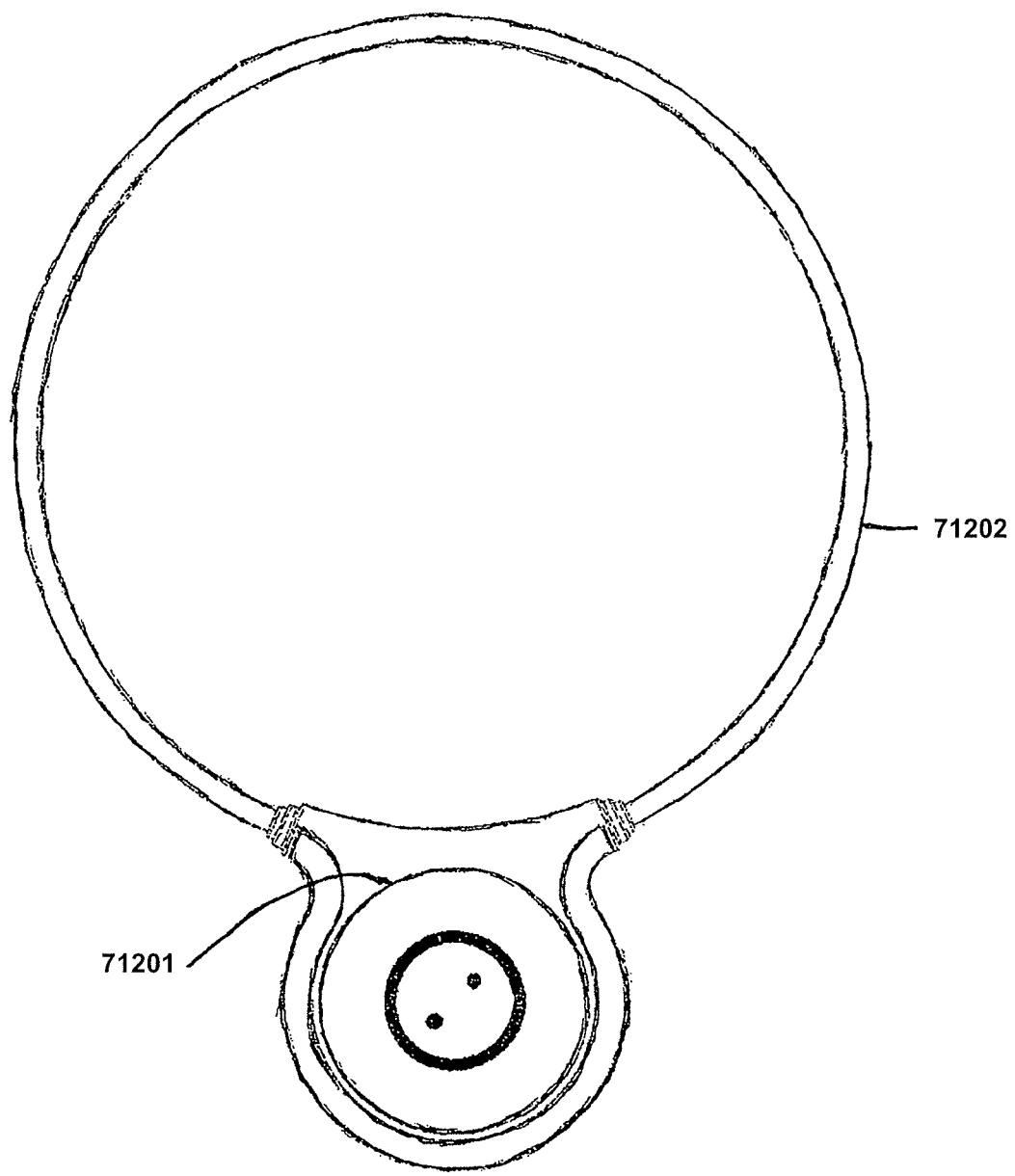
Figure 72:
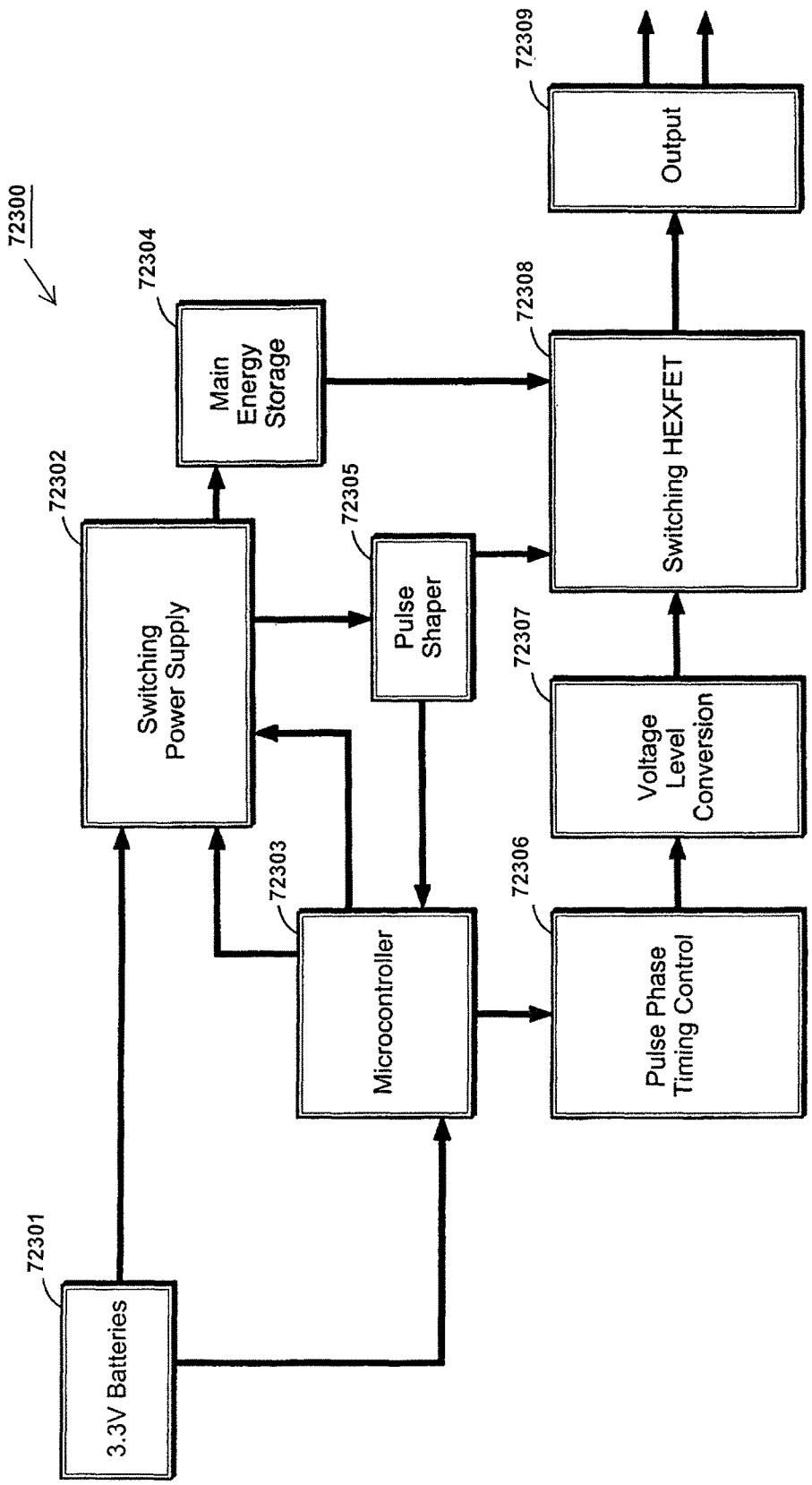
Figure 73:
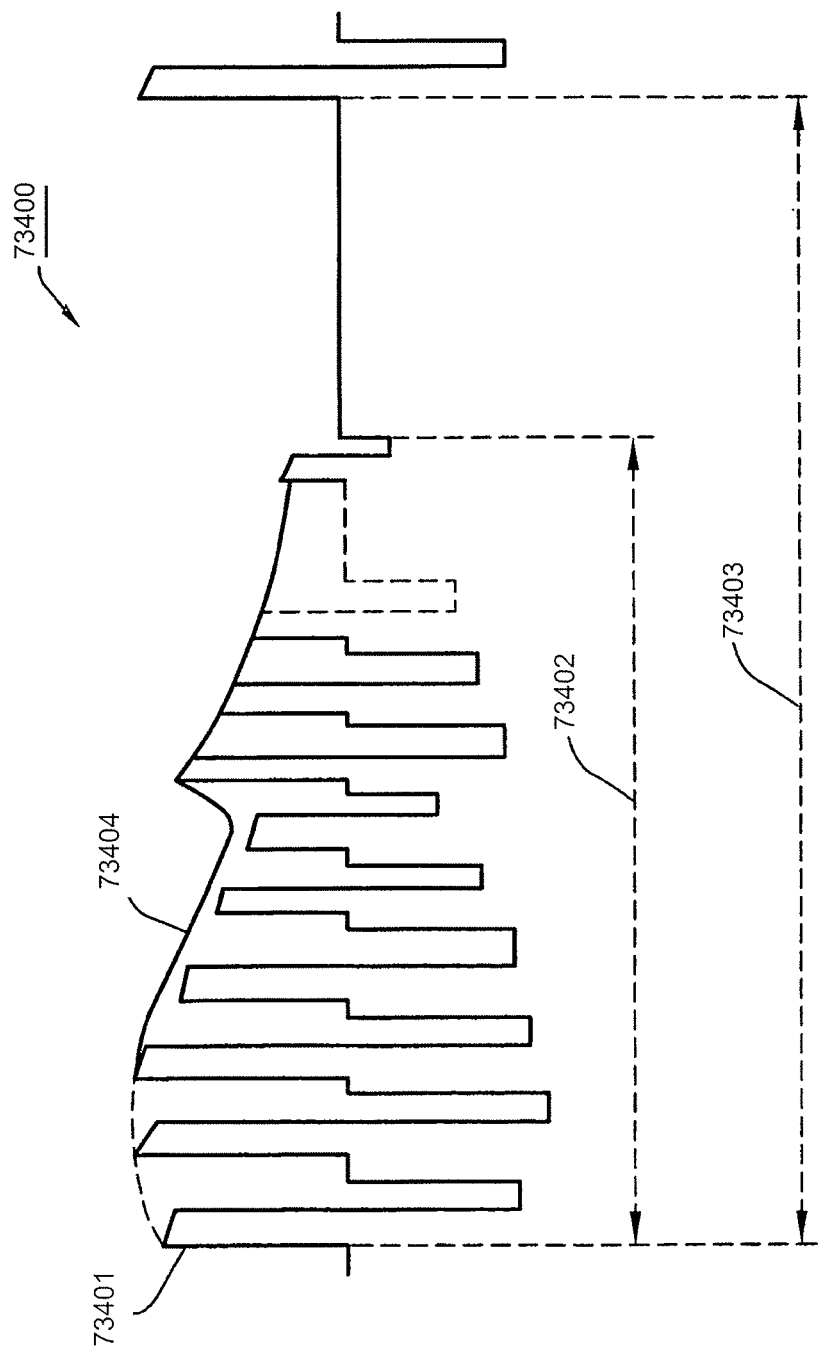
Figure 74:
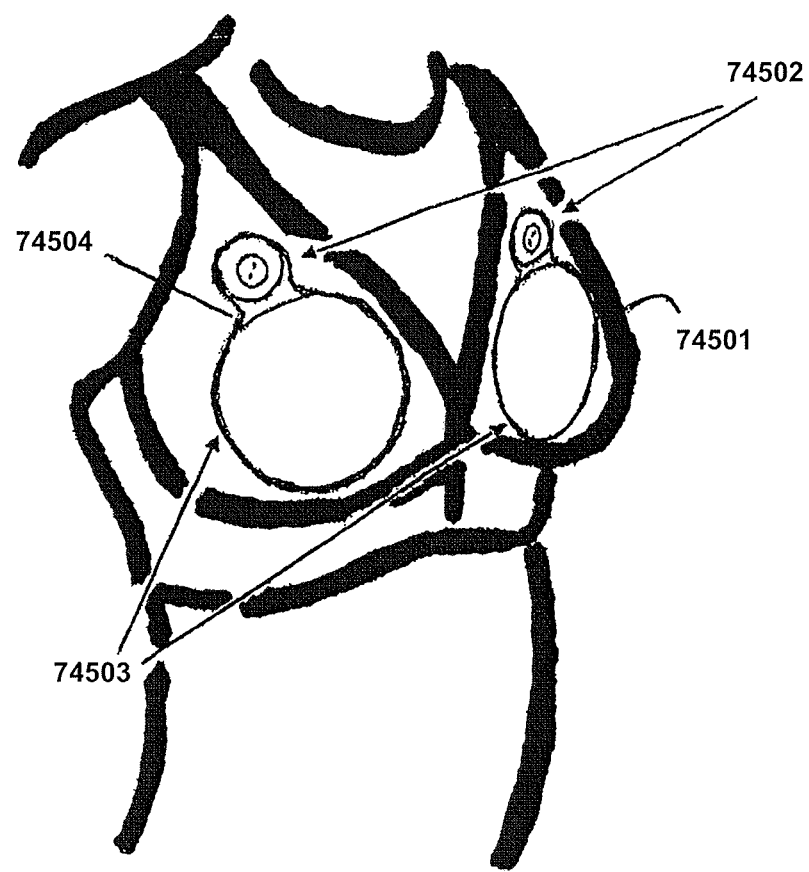
Figure 75:
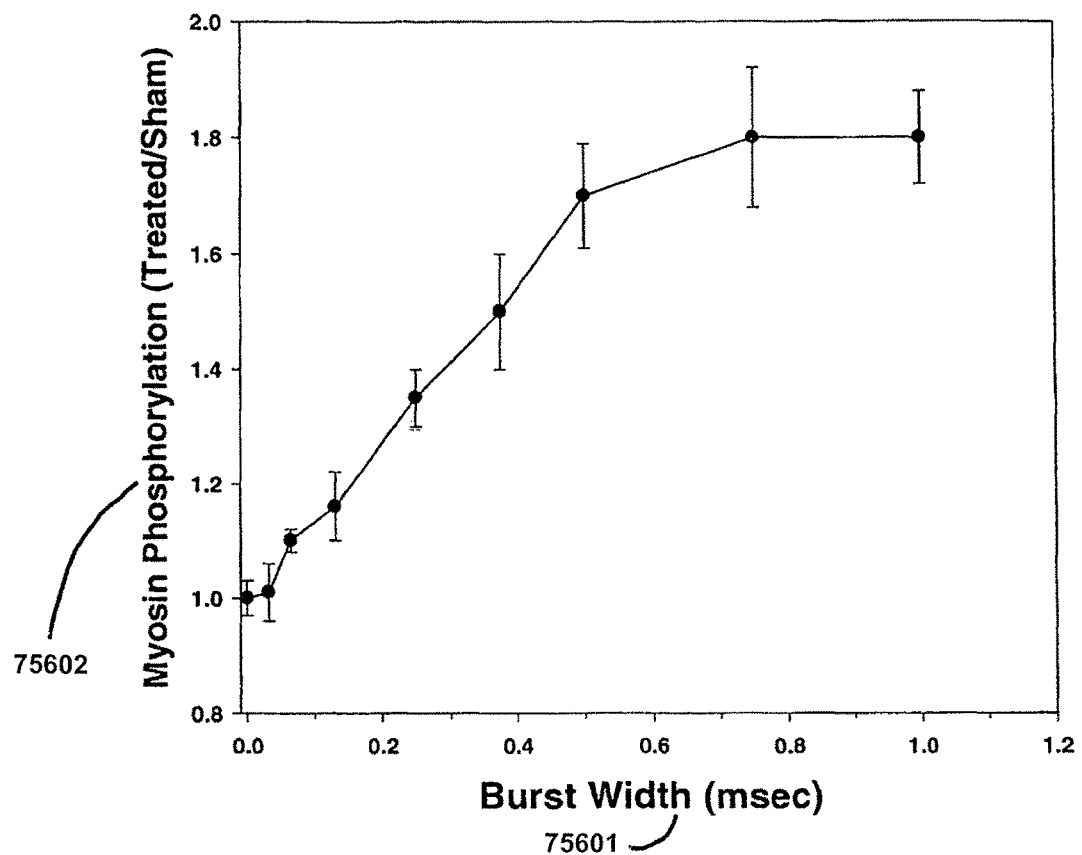
Figure 76:
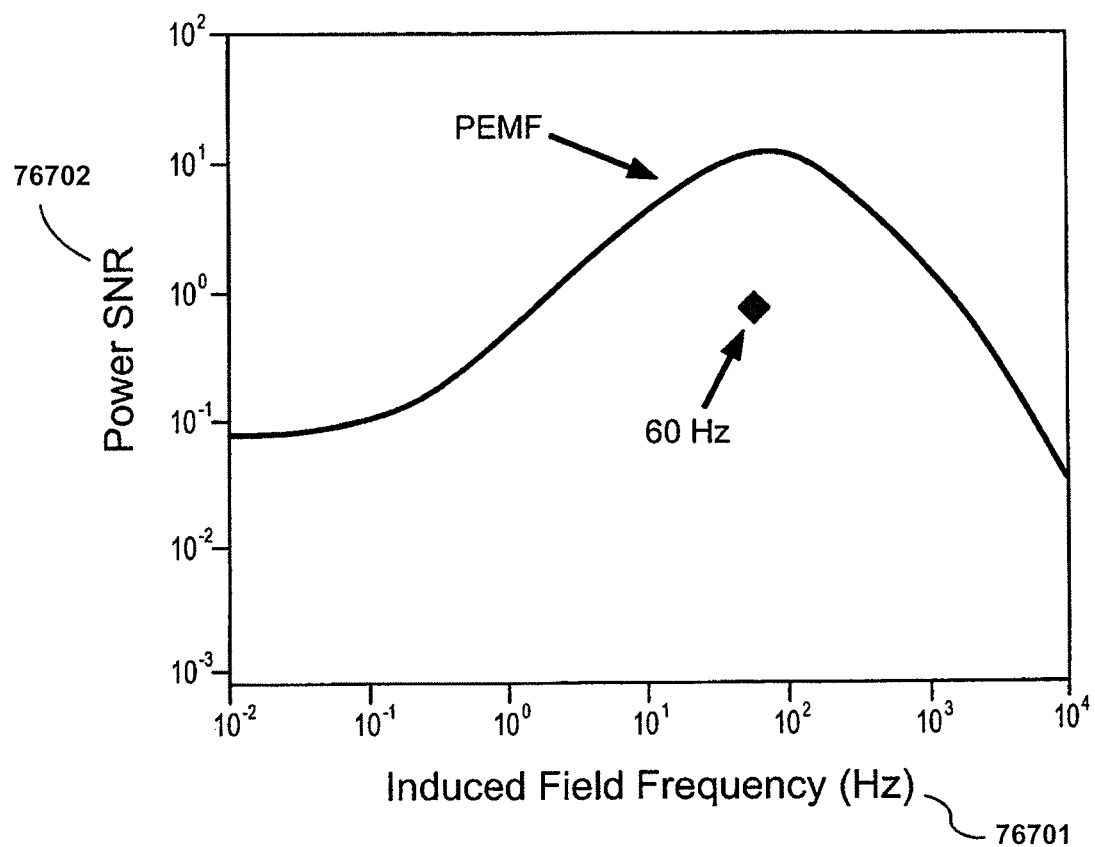

FIG. 70 is a flow diagram of a method for altering fibrous capsule formation and capsular contracture according to an embodiment of the present invention;

FIG. 71 is a view of an apparatus for application of electromagnetic signals according to an embodiment of the present invention;

FIG. 72 is a block diagram of miniaturized circuitry according to an embodiment of the present invention;

FIG. 73 depicts a waveform delivered to a capsule formation and capsule contracture target pathway structure according to an embodiment of the present invention;

FIG. 74 is a view of inductors placed in a vest according to an embodiment of the present invention;

FIG. 75 is a bar graph illustrating myosin phosphorylation for a PMF signal configured according to an embodiment of the present invention; and FIG. 76 is a bar graph illustrating SNR signal effectiveness in a cell model of inflammation.

Part 11

Figure 77A:
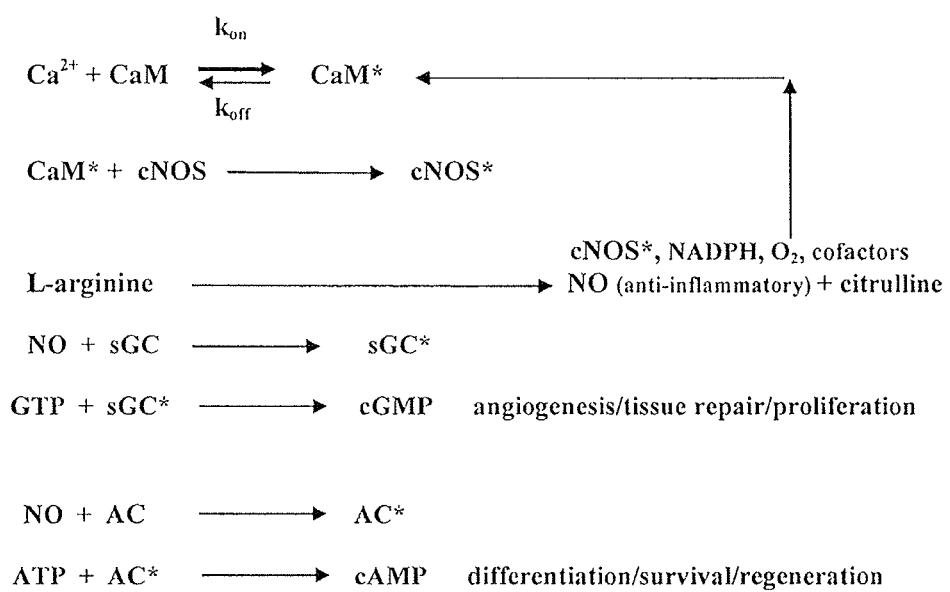

FIG. 77A is a schematic representation of the biological EMF transduction pathway which is a representative target pathway of EMF signals configured according to embodiments described.

Figure 77B:
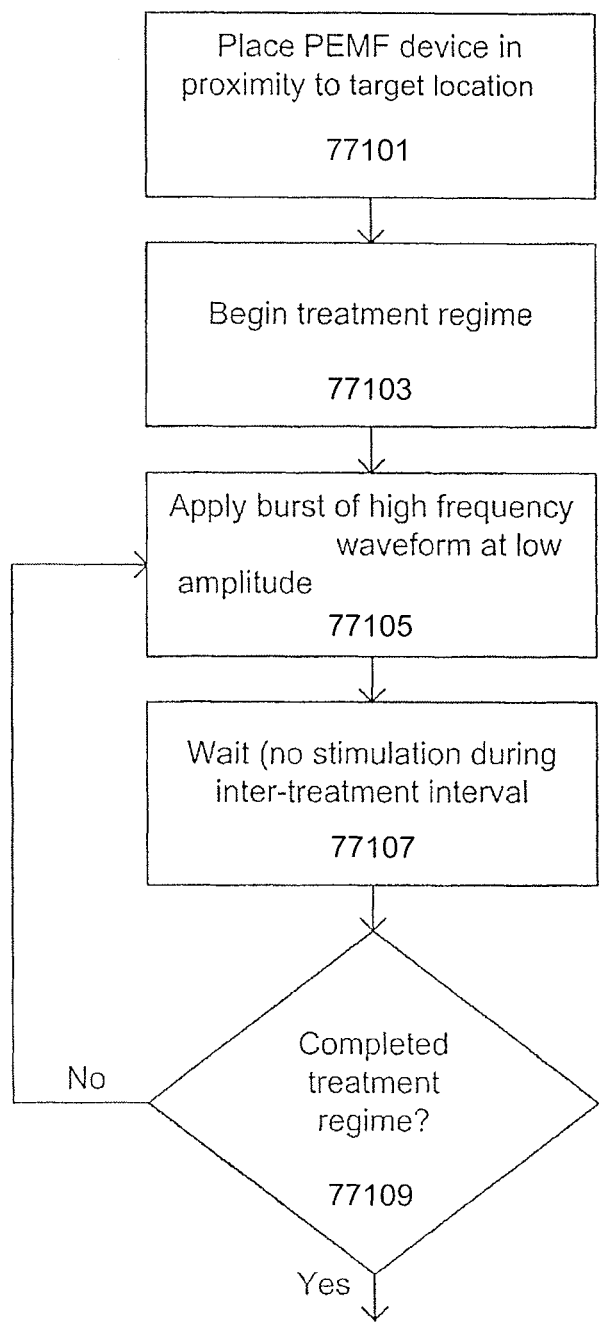

FIG. 77B is a flow diagram of a method for treating a neurological condition/injury according to an embodiment of the devices and methods described herein.

Figure 78A:
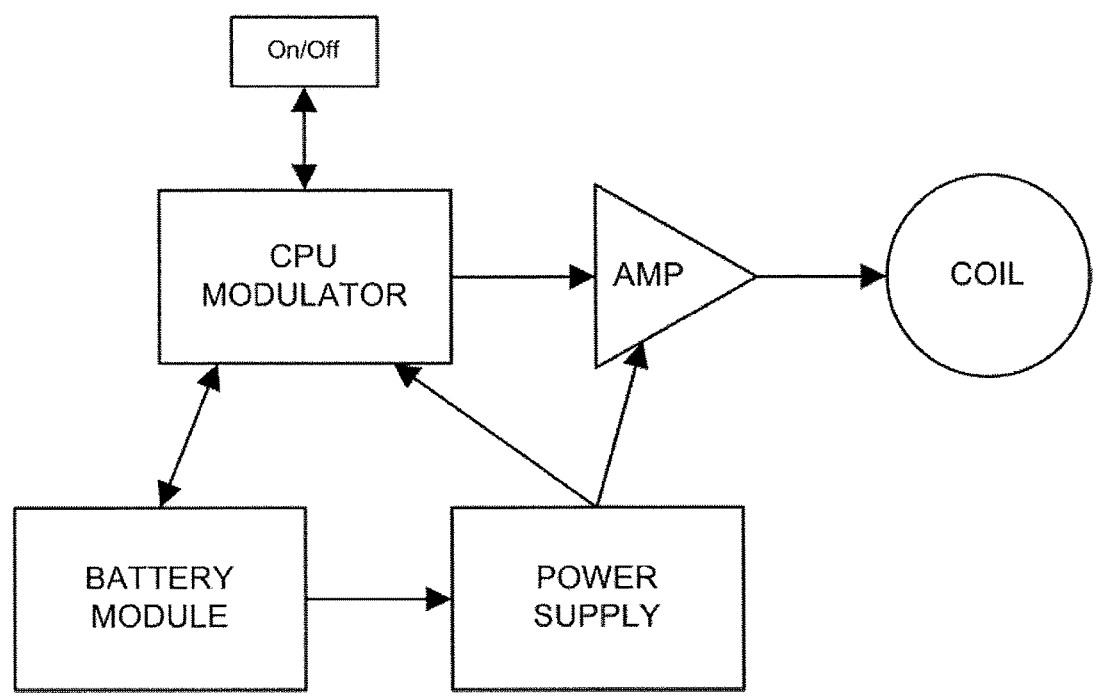

FIG. 78A is a block diagram of miniaturized circuitry for use with a coil applicator according to some embodiments described.

Figure 78B:
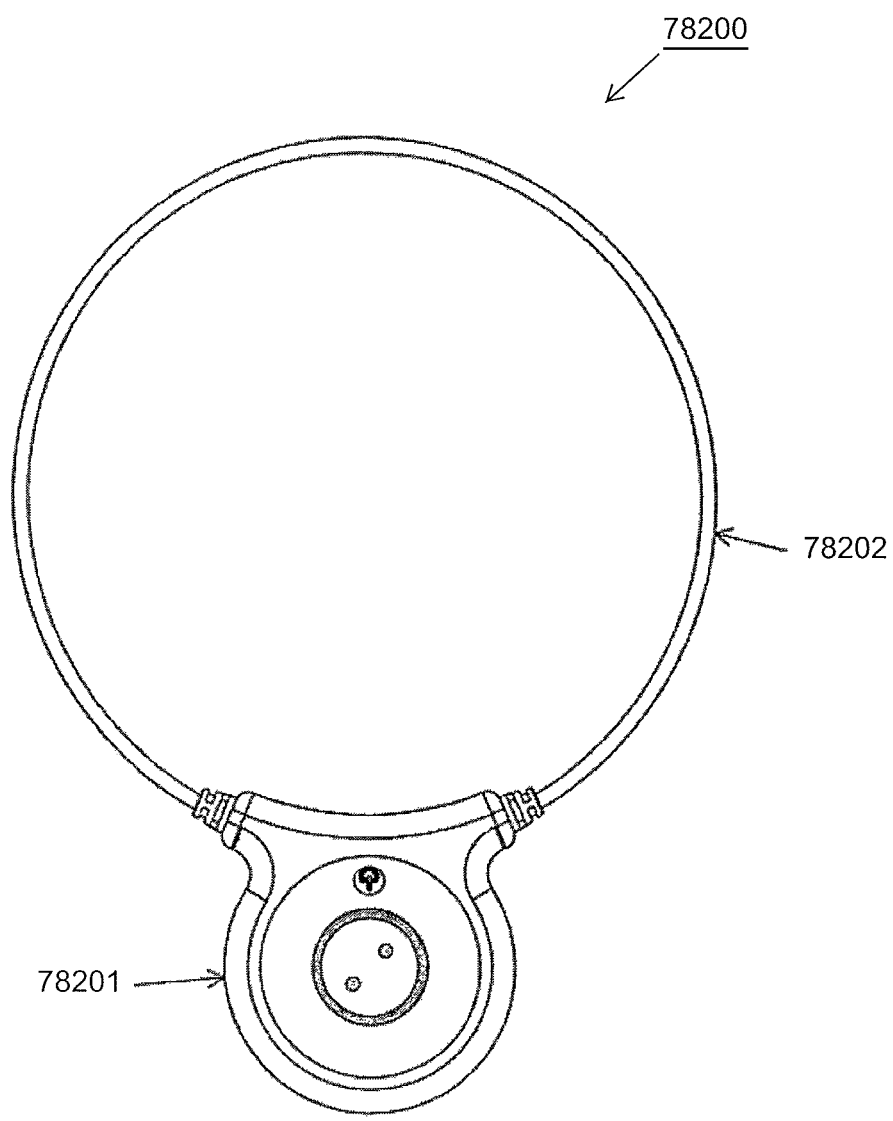

FIG. 78B illustrates a device for application of electromagnetic signals according to an embodiment of the devices and methods described herein.

Figure 78C:
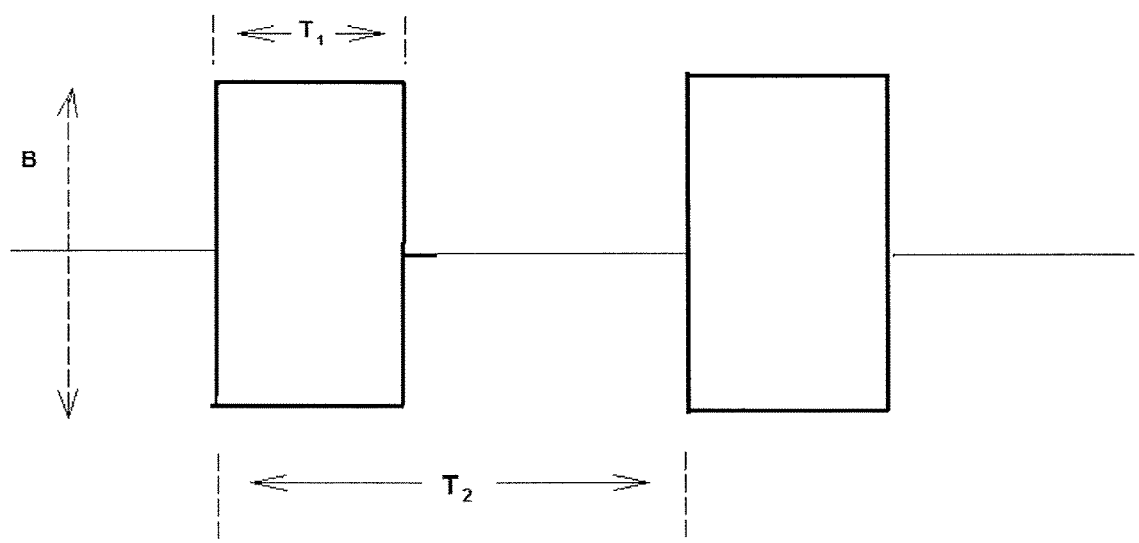

FIG. 78C illustrates a waveform delivered to a target pathway structure of a plant, animal or human, such as a molecule cell, tissue, organ, or partial or entire organism, according to some embodiments described.

Figure 79A:
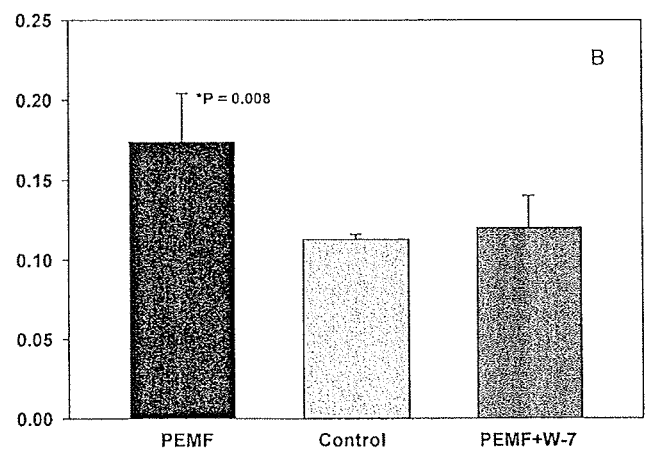
Figure 79B:
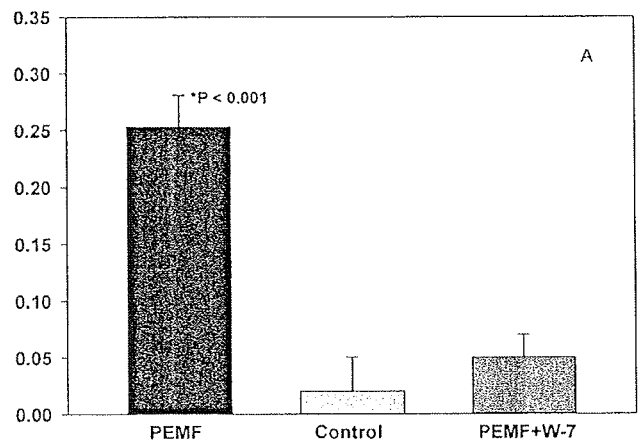

FIGS. 79A and 79B illustrates the effect of a PEMF treatment according to embodiments described on nitric oxide (NO) release from MN9D neuronal cell cultures.

Figure 80:
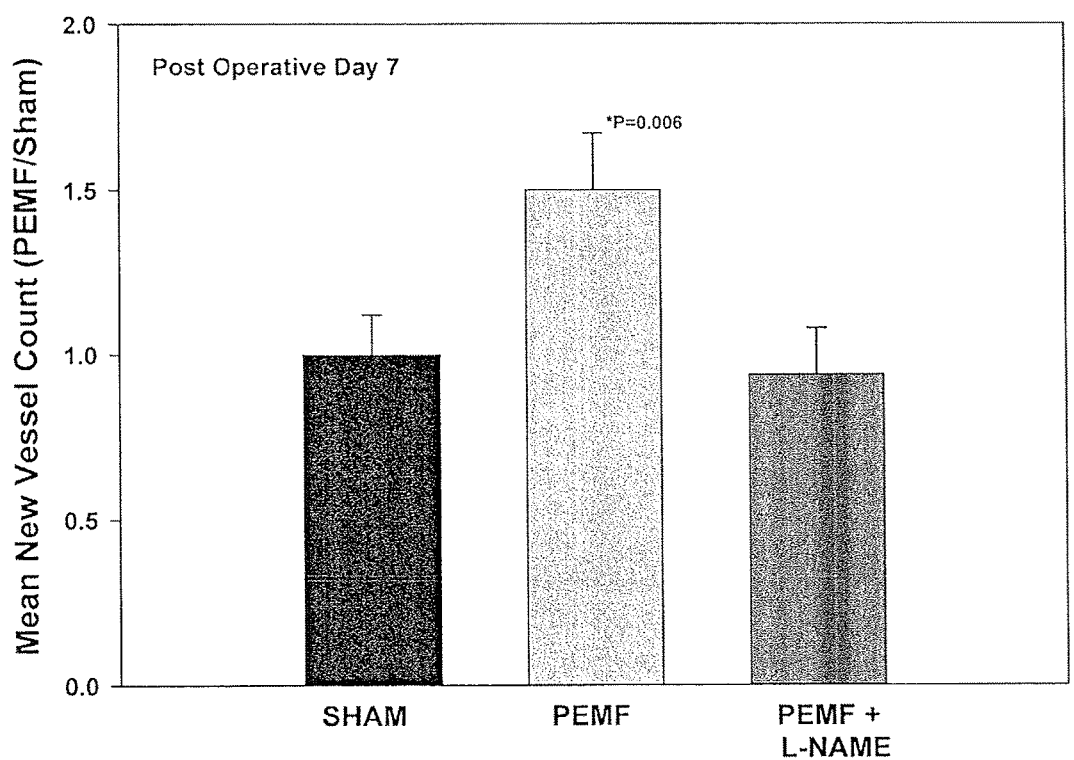

FIG. 80 illustrates the effect of a PEMF treatment according to embodiments described on angiogenesis in thermal myocardial necrosis in a rat model.

Figure 81:
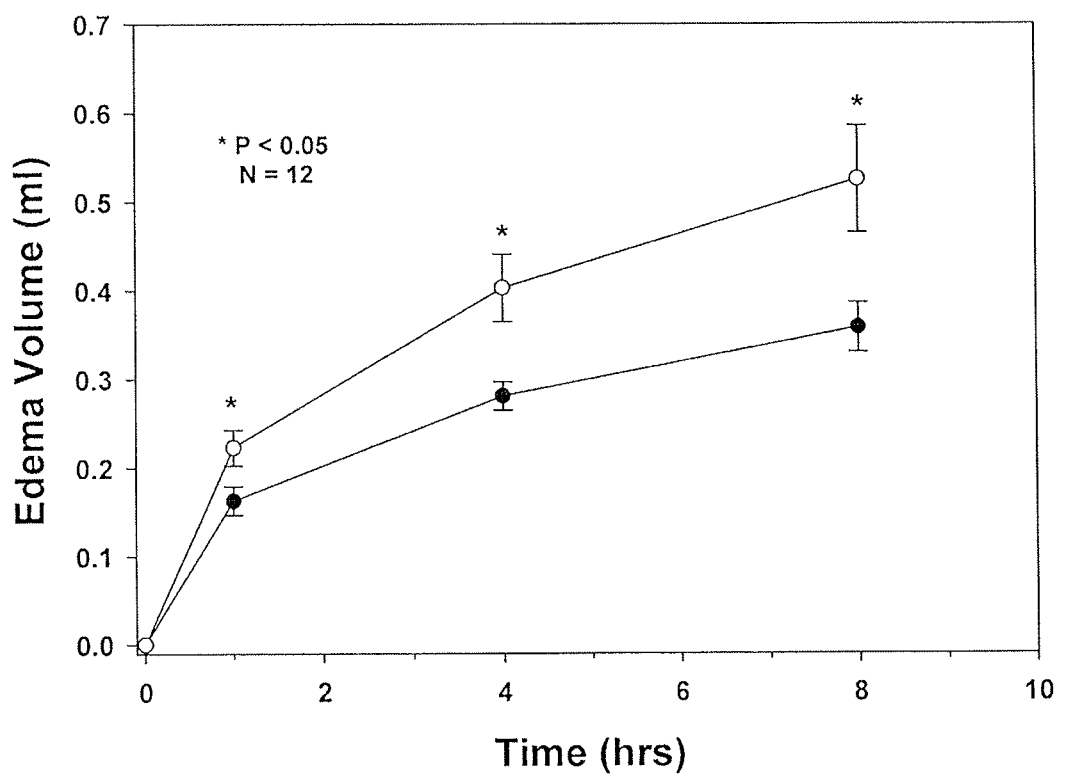

FIG. 81 illustrates the effect of a PEMF treatment according to embodiments described on edema formation in a carrageenan-induced paw edema model of inflammation in the rat.

Figure 82A:
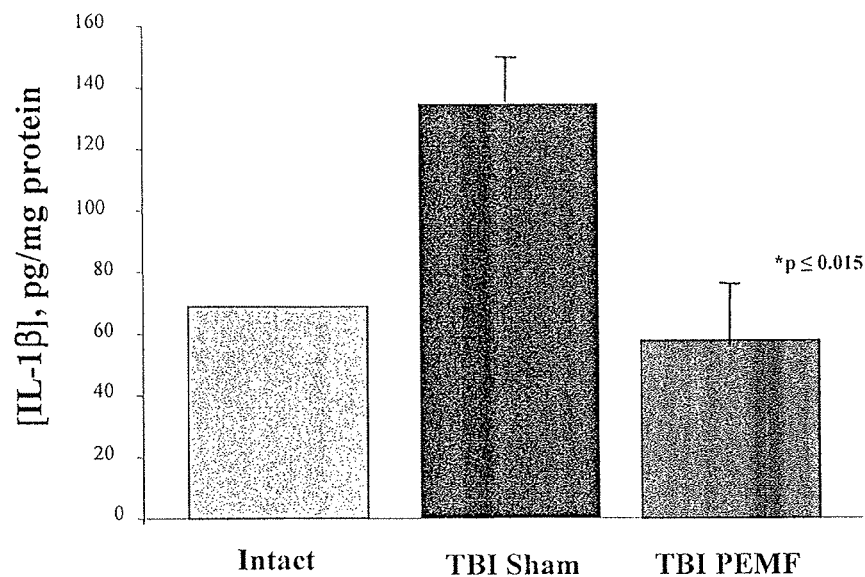
Figure 82B:
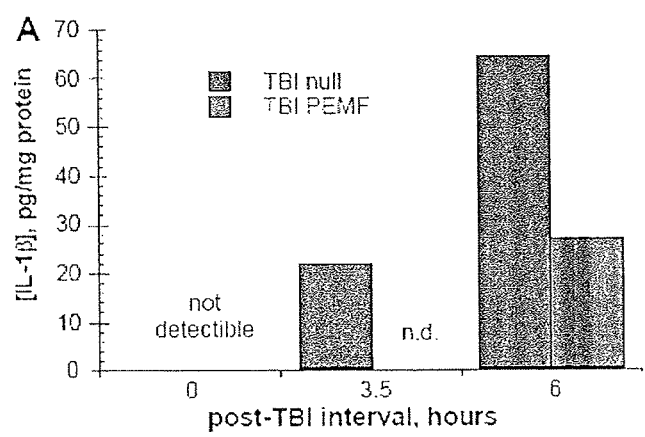
Figure 82C:
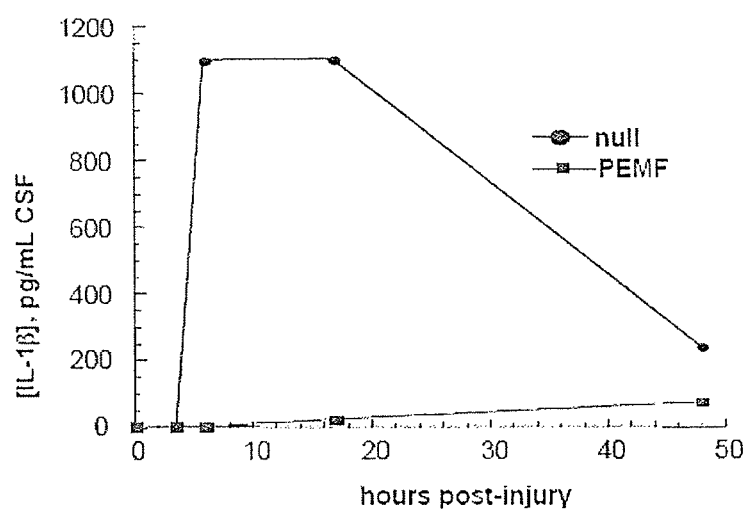

FIGS. 82A-82C illustrate the effect of a PEMF treatment according to embodiments described on rats subjected to contusive traumatic brain injury and invasive brain injury.

FIGS. 83A and 83B illustrate the effect of a PEMF treatment according to embodiments described on post-operative breast reduction patients.

Figure 84:
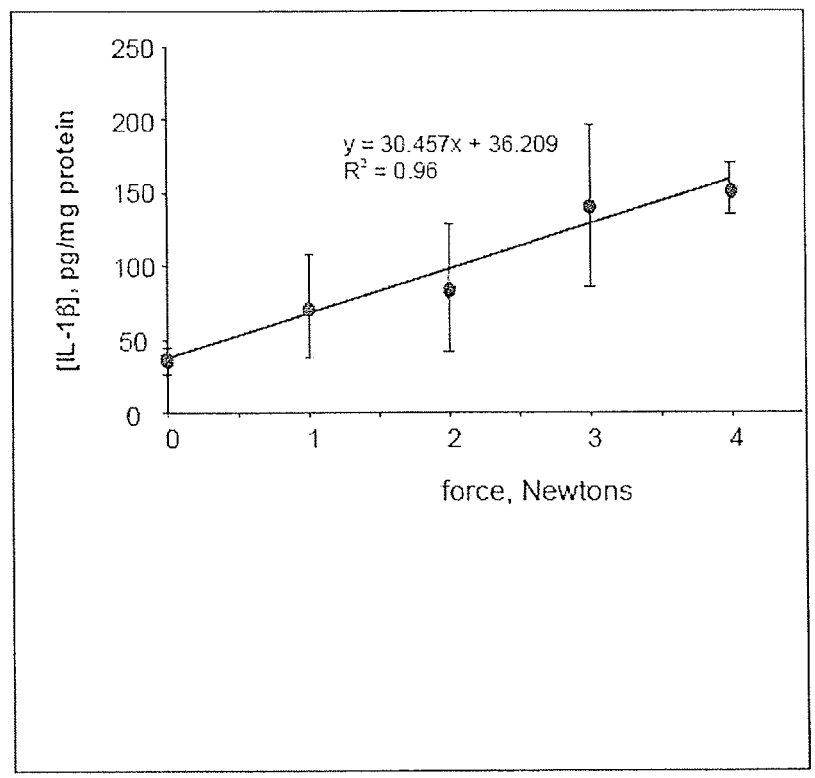

FIG. 84 illustrates the proportional relationship between levels of 1L-1β and force in the Marmarou weight-drop model.

Figure 85:
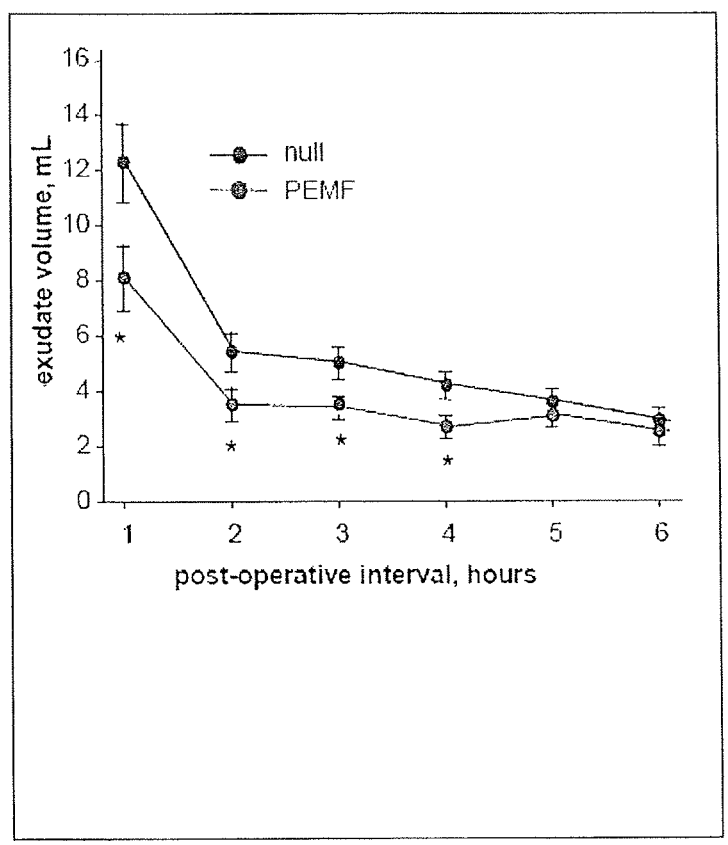

FIG. 85 illustrates the effect of a PEMF treatment according to embodiments described on wound exudate volumes in post-operative patients under breast reduction surgery.

FIGS. 86A and 86B illustrate PEMF signal configurations according to some embodiments described.

Figure 87:
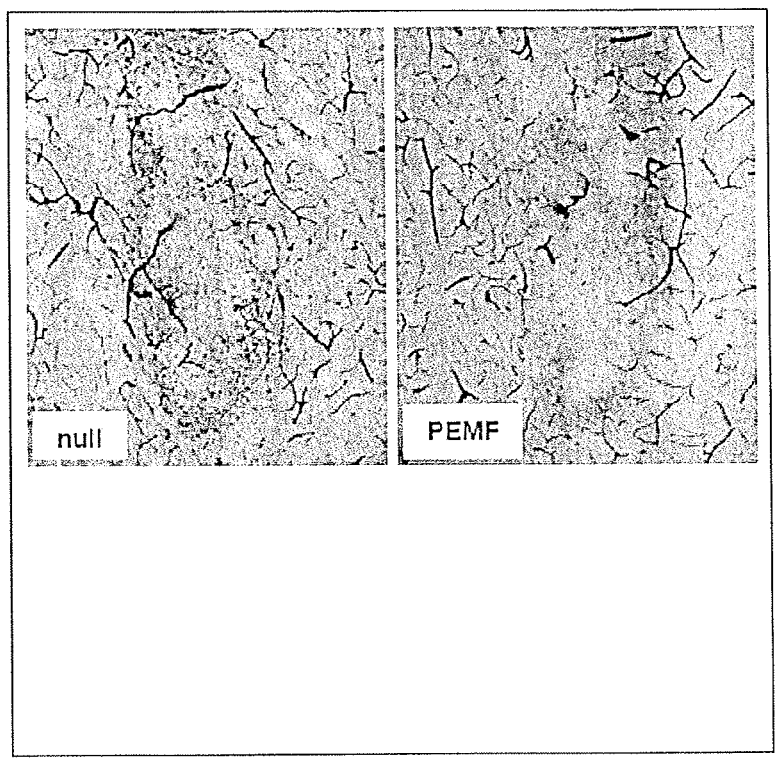

FIG. 87 illustrates the effect of a PEMF treatment according to embodiments described on inflammation in response to transplants of dissociated embryonic midbrain neurons.

Figure 88:
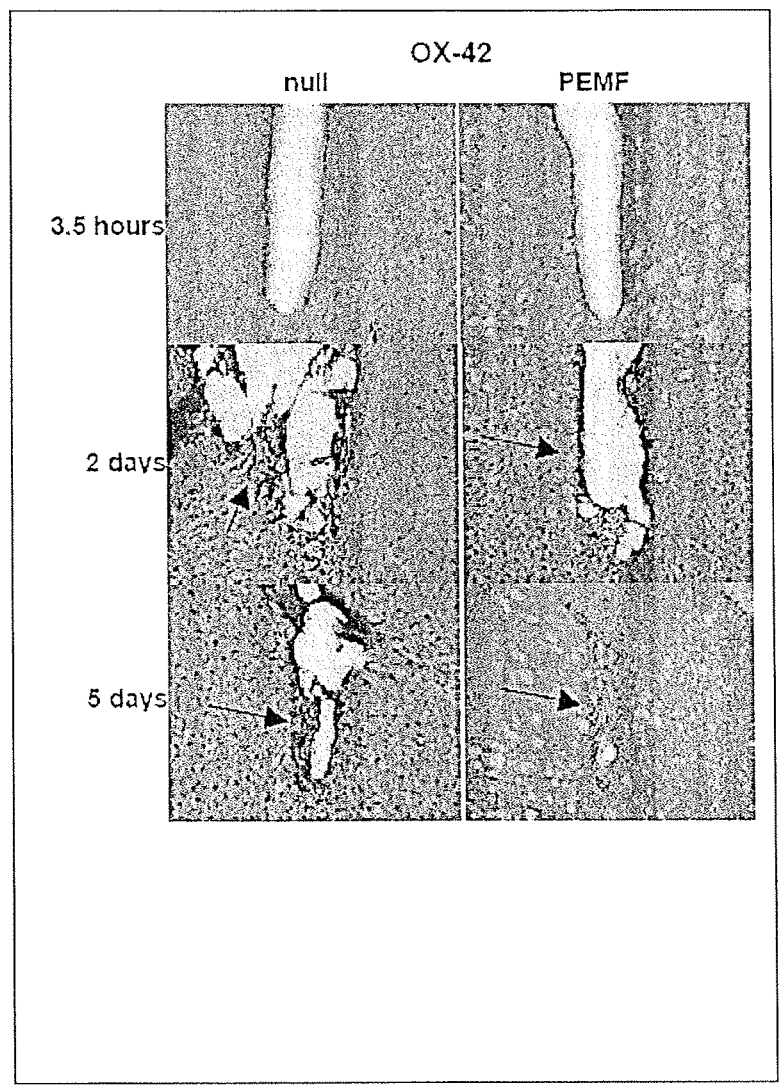

FIG. 88 illustrates the effect of a PEMF treatment according to embodiments described on microglia in rats subjected to penetrating injuries.

Figure 89:
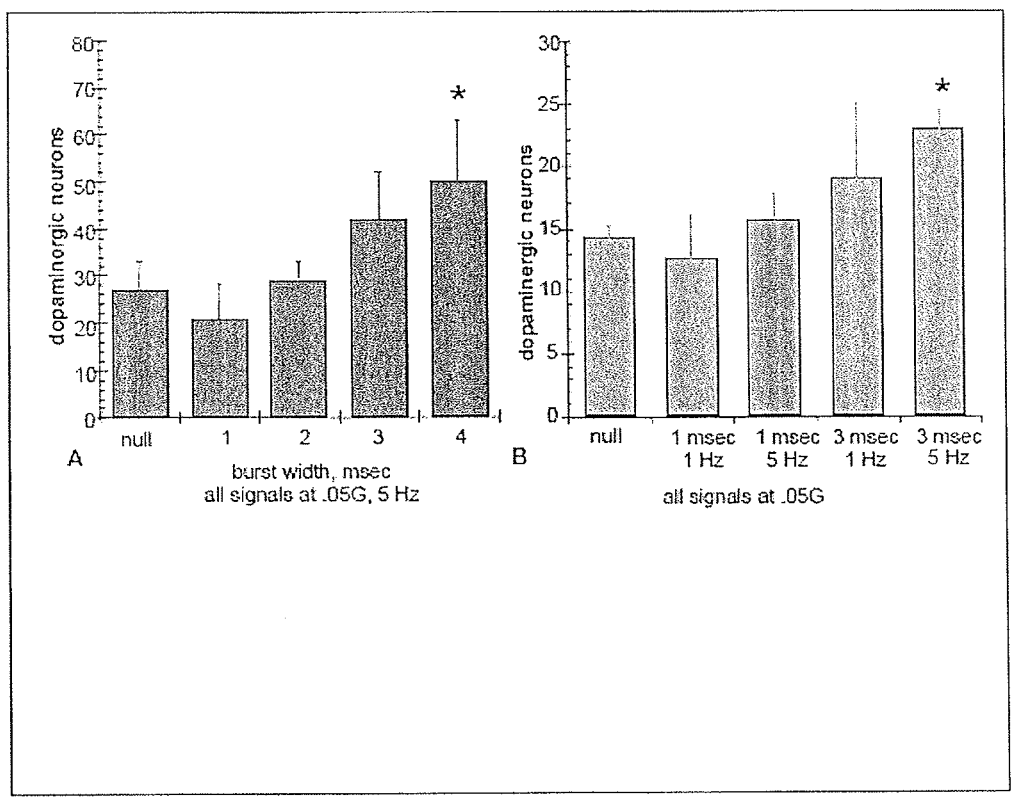

FIG. 89 illustrates the effect of a PEMF treatment according to embodiments described on dopaminergic neurons.

DETAILED DESCRIPTION

Part 1

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("Ca$^{2+}$") binding, the change in concentration of bound Ca$^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of Ca$^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of Ca$^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example Ca$^{2+}$ binding to calmodulin ("CaM"). Use of this pathway is based upon acceleration of wound repair, for example bone repair, that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis is also integral to wound repair and modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of Ca$^{2+}$ binding kinetics at CaM. Within first order binding kinetics, changes in concentration of bound Ca$^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ sec$^{-1}$, =2.5 µM, $K_D$=30 µM, [Ca$^{2+}$CaM]=$K_D$(+[CaM]), yields $k_b$=665 sec$^{-1}$ ($\tau_{ion}$=1.5 msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kTRe[Z_M(x,\omega)]$$

where $Z_M(x, \omega)$ is electrical impedance of a target pathway structure, x is a dimension of a target pathway structure and Re denotes a real part of impedance of a target pathway structure. $Z_M(x, \omega)$ can be expressed as:

$$Z_M(x, \omega) = \left[\frac{R_e + R_i + R_g}{y}\right]\tanh(yx)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)=4$ kT Re $[Z_M(x, \omega)]$ over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

Figure 1:
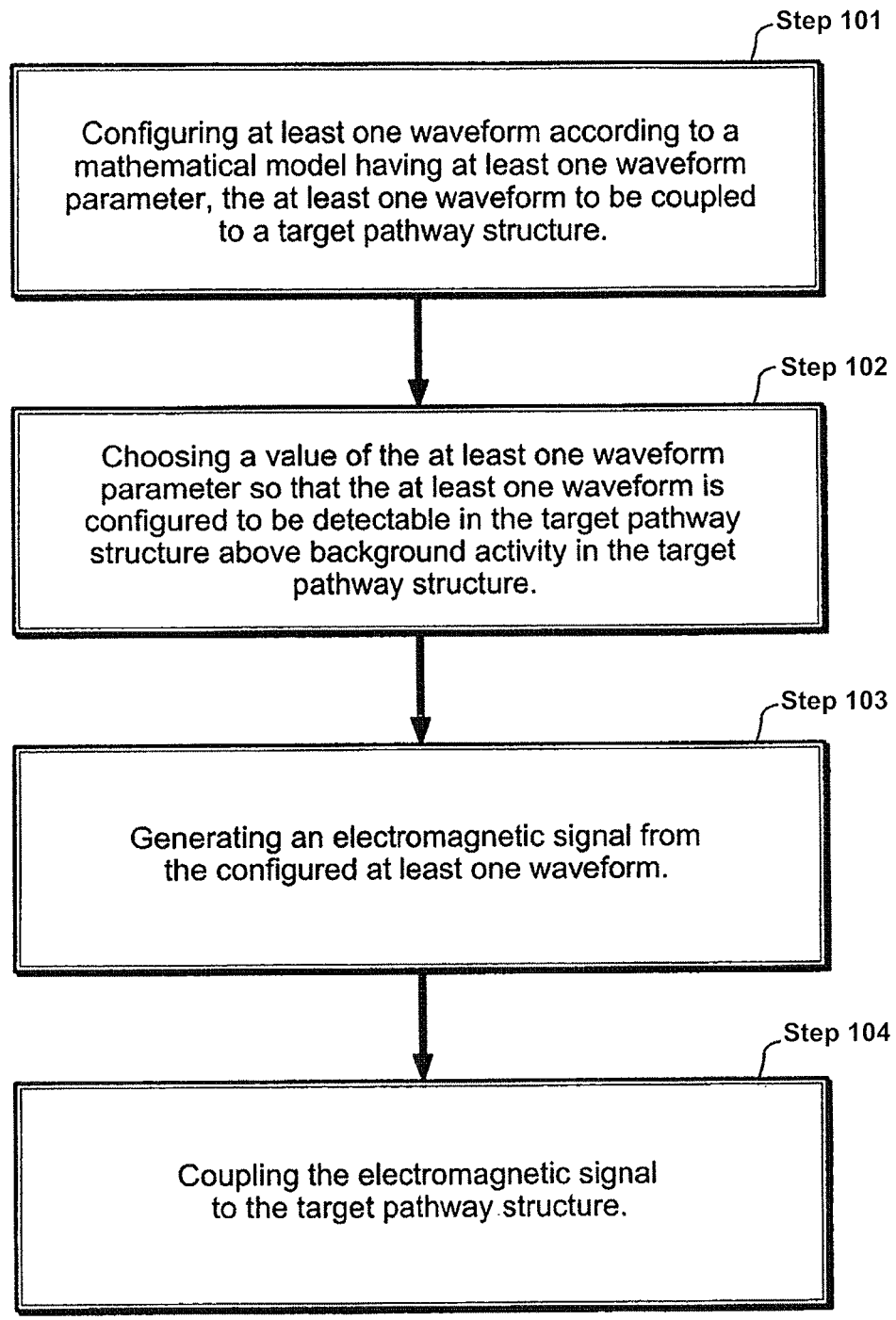
FIG. 1 is a flow diagram of a method for electromagnetic treatment of plant, animal, and human target pathway structures such as tissue, organs, cells, and molecules according to an embodiment of the present invention.

Referring to FIG. 1, wherein FIG. 1 is a flow diagram of a method for delivering electromagnetic signals to target pathway structures such as molecules, cells, tissue and organs of plants, animals, and humans for therapeutic and prophylactic purposes according to an embodiment of the present invention. A mathematical model having at least one waveform parameter is applied to configure at least one waveform to be coupled to a target pathway structure such as a molecule, cell, tissue, and organ (Step 101). The configured waveform satisfies a SNR or Power SNR model so that for a given and known target pathway structure it is possible to choose at least one waveform parameter so that a waveform is detectable in the target pathway structure above its background activity (Step 102) such as baseline thermal fluctuations in voltage and electrical impedance at a target pathway structure that depend upon a state of a cell and tissue, that is whether the state is at least one of resting, growing, replacing, and responding to injury. A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 102). A repetitive electromagnetic signal can be generated for example inductively or capacitively, from said configured at least one waveform (Step 103). The electromagnetic signal is coupled to a target pathway structure such as a molecule, cell, tissue, and organ by output of a coupling device such as an electrode or an inductor, placed in close proximity to the target pathway structure (Step 104). The coupling enhances a stimulus to which cells and tissues react in a physiologically meaningful manner.

Figure 2:
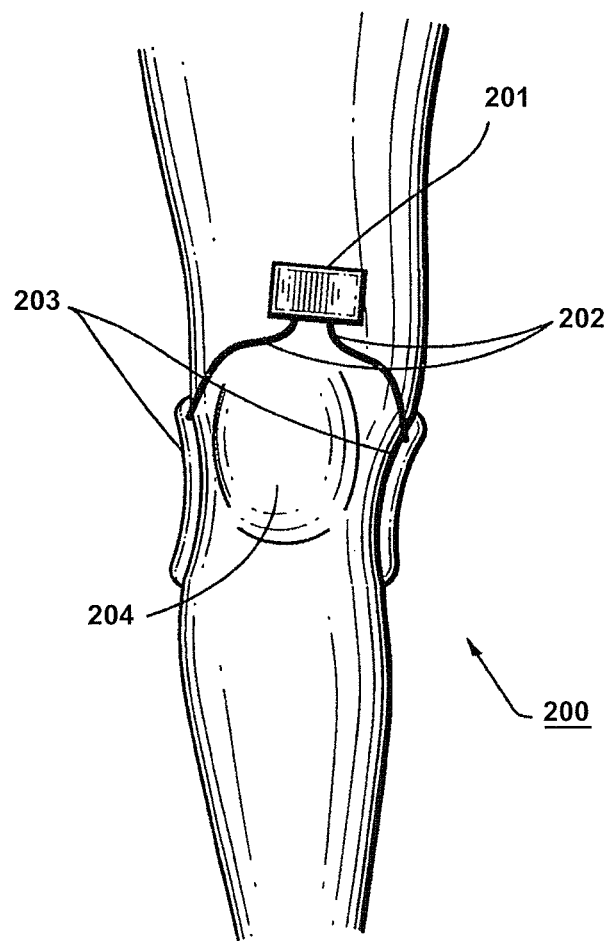
FIG. 2 is a view of control circuitry and electrical coils applied to a knee joint according to a preferred embodiment of the present invention.

FIG. 2 illustrates a preferred embodiment of an apparatus according to the present invention. A miniature control circuit 201 is coupled to an end of at least one connector 202 such as wire. The opposite end of the at least one connector is coupled to a generating device such as a pair of electrical coils 203. The miniature control circuit 201 is constructed in a manner that applies a mathematical model that is used to configure waveforms. The configured waveforms have to satisfy a SNR or Power SNR model so that for a given and known target pathway structure, it is possible to choose waveform parameters that satisfy SNR or Power SNR so that a waveform is detectable in the target pathway structure above its background activity. A preferred embodiment according to the present invention applies a mathematical model to induce a time-varying magnetic field and a time-varying electric field in a target pathway structure such as a molecule, cell, tissue, and organ, comprising about 10 to about 100 msec bursts of about 1 to about 100 microsecond rectangular pulses repeating at about 0.1 to about 10 pulses per second. Peak amplitude of the induced electric field is between about 1 uV/cm and about 100 mV/cm, varied according to a modified 1/f function where f=frequency. A waveform configured using a preferred embodiment according to the present invention may be applied to a target pathway structure such as a molecule, cell, tissue, and organ for a preferred total exposure time of under 1 minute to 240 minutes daily. However other exposure times can be used. Waveforms configured by the miniature control circuit 201 are directed to a generating device 203 such as electrical coils via connector 202. The generating device 203 delivers a pulsing magnetic field configured according to a mathematical model, that can be used to provide treatment to a target pathway structure such as knee joint 204. The miniature control circuit applies a pulsing magnetic field for a prescribed time and can automatically repeat applying the pulsing magnetic field for as many applications as are needed in a given time period, for example 10 times a day. A preferred embodiment according to the present invention can be positioned to treat the knee joint 204 by a positioning device. The positioning device can be portable such as an anatomical support, and is further described below with reference to FIG. 6. Coupling a pulsing magnetic field to a target pathway structure such as a molecule, cell, tissue, and organ, therapeutically and prophylactically reduces inflammation thereby reducing pain and promotes healing. When electrical coils are used as the generating device 203, the electrical coils can be powered with a time varying magnetic field that induces a time varying electric field in a target pathway structure according to Faraday's law. An electromagnetic signal generated by the generating device 203 can also be applied using electrochemical coupling, wherein electrodes are in direct contact with skin or another outer electrically conductive boundary of a target pathway structure. Yet in another embodiment according to the present invention, the electromagnetic signal generated by the generating device 203 can also be applied using electrostatic coupling wherein an air gap exists between a generating device 203 such as an electrode and a target pathway structure such as a molecule, cell, tissue, and organ. An advantage of the preferred embodiment according to the present invention is that its ultra lightweight coils and miniaturized circuitry allow for use with common physical therapy treatment modalities and at any body location for which pain relief and healing is desired. An advantageous result of application of the preferred embodiment according to the present invention is that a living organism's wellbeing can be maintained and enhanced.

Figure 3:
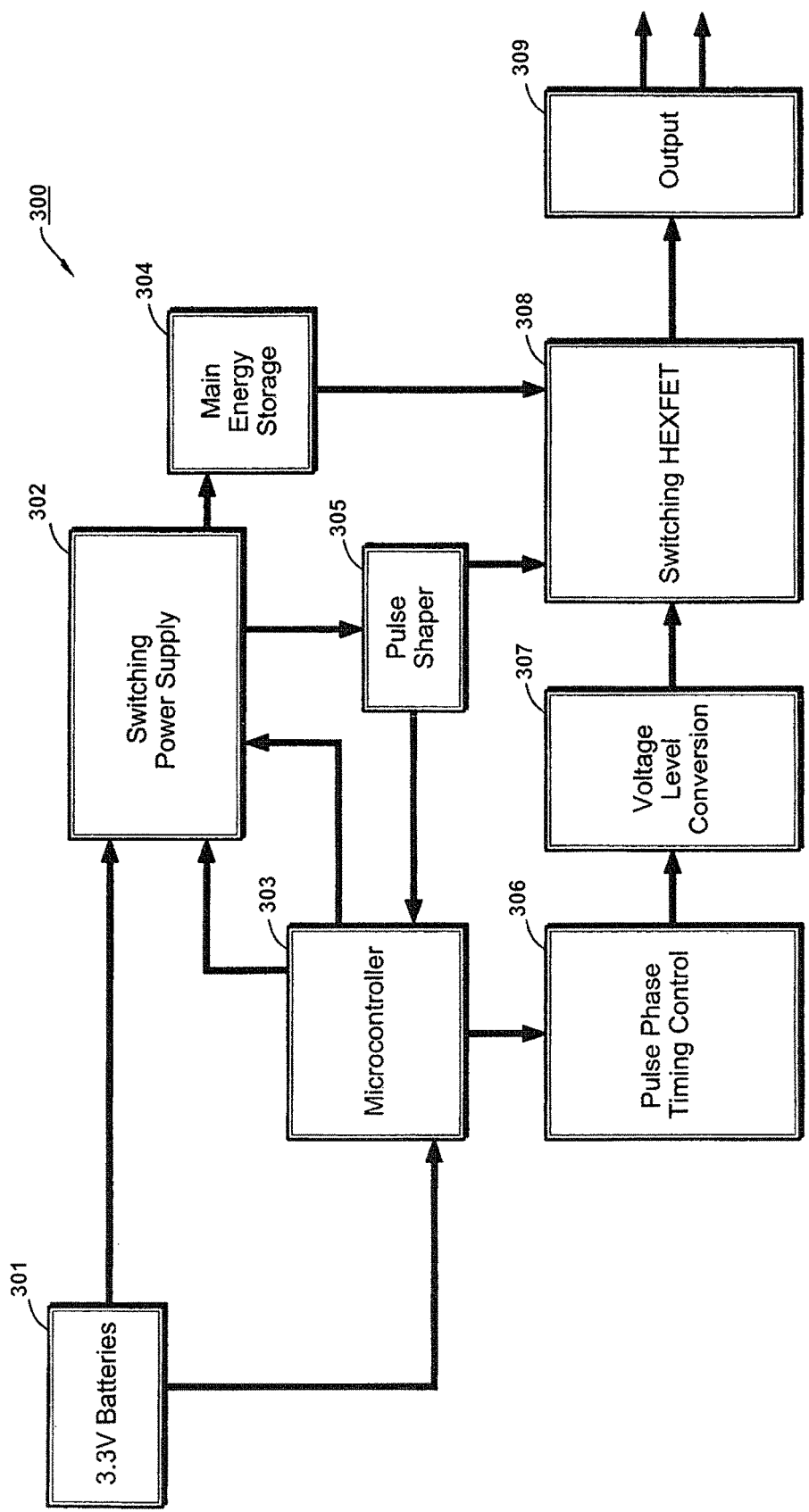
FIG. 3 is a block diagram of miniaturized circuitry according to a preferred embodiment of the present invention.

FIG. 3 depicts a block diagram of a preferred embodiment according to the present invention of a miniature control circuit 300. The miniature control circuit 300 produces waveforms that drive a generating device such as wire coils described above in FIG. 2. The miniature control circuit can be activated by any activation means such as an on/off switch. The miniature control circuit 300 has a power source such as a lithium battery 301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 302 controls voltage to a micro-controller 303. A preferred embodiment of the micro-controller 303 uses an 8 bit 4 MHz micro-controller 303 but other bit MHz combination micro-controllers may be used. The switching power supply 302 also delivers current to storage capacitors 304. A preferred embodiment of the present invention uses storage capacitors having a 220 uF output but other outputs can be used. The storage capacitors 304 allow high frequency pulses to be delivered to a coupling device such as inductors (Not Shown). The micro-controller 303 also controls a pulse shaper 305 and a pulse phase timing control 306. The pulse shaper 305 and pulse phase timing control 306 determine pulse shape, burst width, burst envelope shape, and burst repetition rate. An integral waveform generator, such as a sine wave or arbitrary number generator can also be incorporated to provide specific waveforms. A voltage level conversion sub-circuit 308 controls an induced field delivered to a target pathway structure. A switching Hexfet 308 allows pulses of randomized amplitude to be delivered to output 309 that routes a waveform to at least one coupling device such as an inductor. The micro-controller 303 can also control total exposure time of a single treatment of a target pathway structure such as a molecule, cell, tissue, and organ. The miniature control circuit 300 can be constructed to apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Figure 4A:
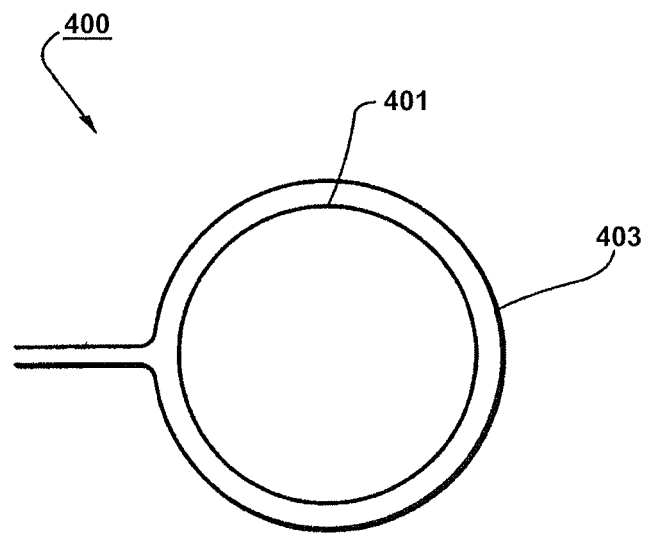
FIG. 4A is a line drawing of a wire coil such as an inductor according to a preferred embodiment of the present invention.
Figure 4B:
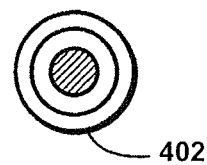
FIG. 4B is a line drawing of a flexible magnetic wire according to a preferred embodiment of the present invention.

Referring to FIGS. 4A and 4B a preferred embodiment according to the present invention of a coupling device 400 such as an inductor is shown. The coupling device 400 can be an electric coil 401 wound with multistrand flexible magnetic wire 402. The multistrand flexible magnetic wire 402 enables the electric coil 401 to conform to specific anatomical configurations such as a limb or joint of a human or animal. A preferred embodiment of the electric coil 401 comprises about 10 to about 50 turns of about 0.01 mm to about 0.1 mm diameter multistrand magnet wire wound on an initially circular form having an outer diameter between about 2.5 cm and about 50 cm but other numbers of turns and wire diameters can be used. A preferred embodiment of the electric coil 401 can be encased with a non-toxic PVC mould 403 but other non-toxic moulds can also be used.

Figure 5:
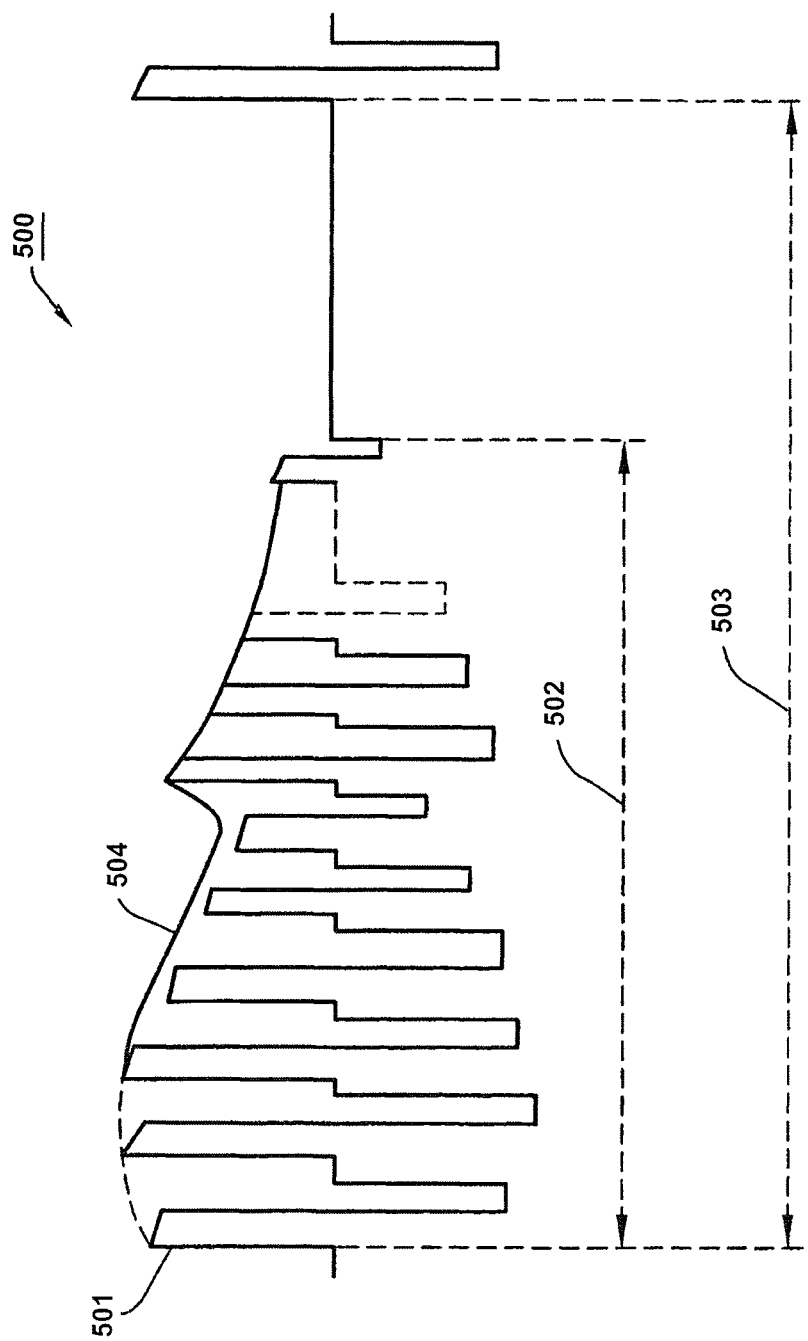
FIG. 5 depicts a waveform delivered to a target pathway structure such as a molecule, cell, tissue or organ according to a preferred embodiment of the present invention.

Referring to FIG. 5 an embodiment according to the present invention of a waveform 500 is illustrated. A pulse 501 is repeated within a burst 502 that has a finite duration 503. The duration 503 is such that a duty cycle which can be defined as a ratio of burst duration to signal period is between about 1 to about $10^{-5}$. A preferred embodiment according to the present invention utilizes pseudo rectangular 10 microsecond pulses for pulse 501 applied in a burst 502 for about 10 to about 50 msec having a modified 1/f amplitude envelope 504 and with a finite duration 503 corresponding to a burst period of between about 0.1 and about 10 seconds.

Figure 6:
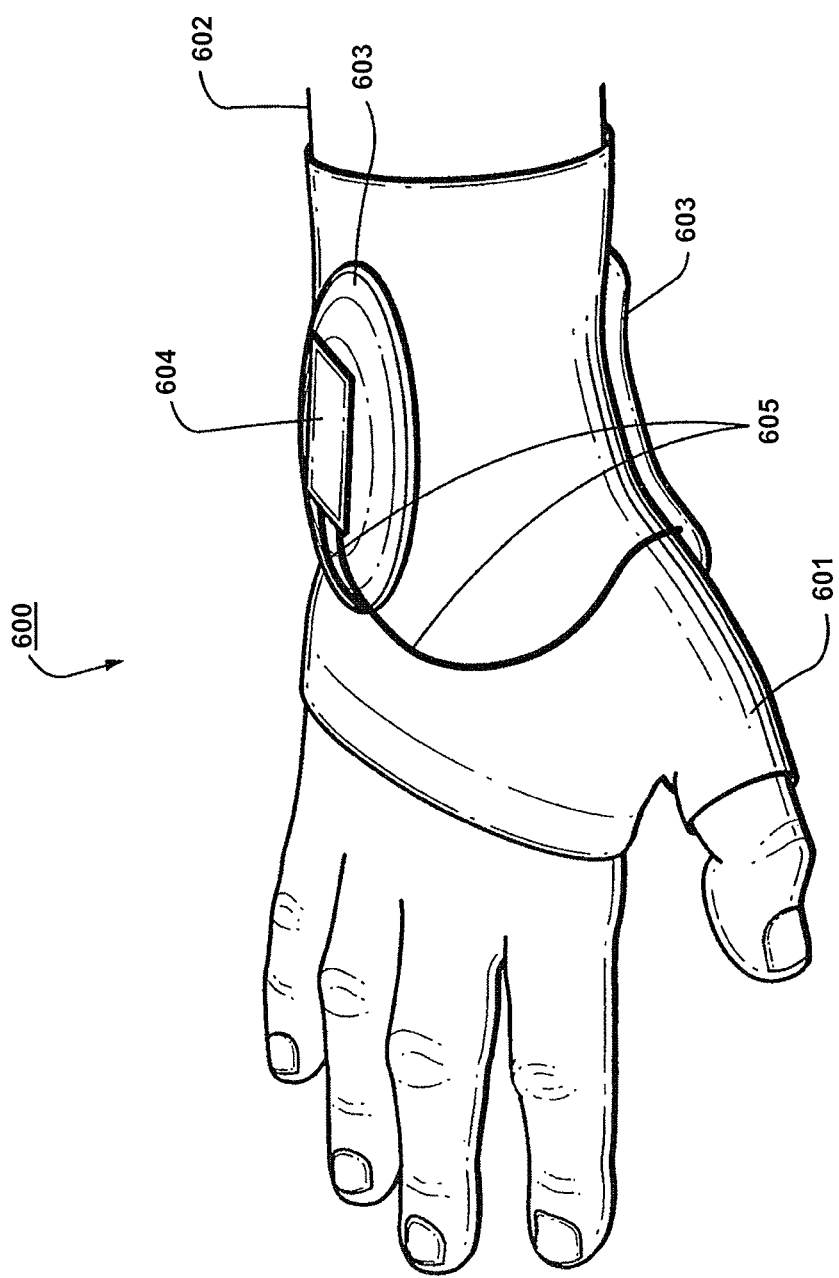
FIG. 6 is a view of a positioning device such as a wrist support according to a preferred embodiment of the present invention.

FIG. 6 illustrates a preferred embodiment according to the present invention of a positioning device such as a wrist support. A positioning device 600 such as a wrist support 601 is worn on a human wrist 602. The positioning device can be constructed to be portable, can be constructed to be disposable, and can be constructed to be implantable. The positioning device can be used in combination with the present invention in a plurality of ways, for example incorporating the present invention into the positioning device for example by stitching, affixing the present invention onto the positioning device for example by Velcro®, and holding the present invention in place by constructing the positioning device to be elastic.

In another embodiment according to the present invention, the present invention can be constructed as a stand-alone device of any size with or without a positioning device, to be used anywhere for example at home, at a clinic, at a treatment center, and outdoors. The wrist support 601 can be made with any anatomical and support material, such as neoprene. Coils 603 are integrated into the wrist support 601 such that a signal configured according to the present invention, for example the waveform depicted in FIG. 5, is applied from a dorsal portion that is the top of the wrist to a plantar portion that is the bottom of the wrist. Micro-circuitry 604 is attached to the exterior of the wrist support 601 using a fastening device such as Velcro® (Not Shown). The micro-circuitry is coupled to one end of at least one connecting device such as a flexible wire 605. The other end of the at least one connecting device is coupled to the coils 603. Other embodiments according to the present invention of the positioning device include knee, elbow, lower back, shoulder, other anatomical wraps, and apparel such as garments, fashion accessories, and footware.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA12. Free $Ca^{2+}$ was varied in the 1-7 µM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 µL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 µM 32P ATP, and was stopped with Laemmli Sample Buffer solution containing 30 µM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

Figure 7:
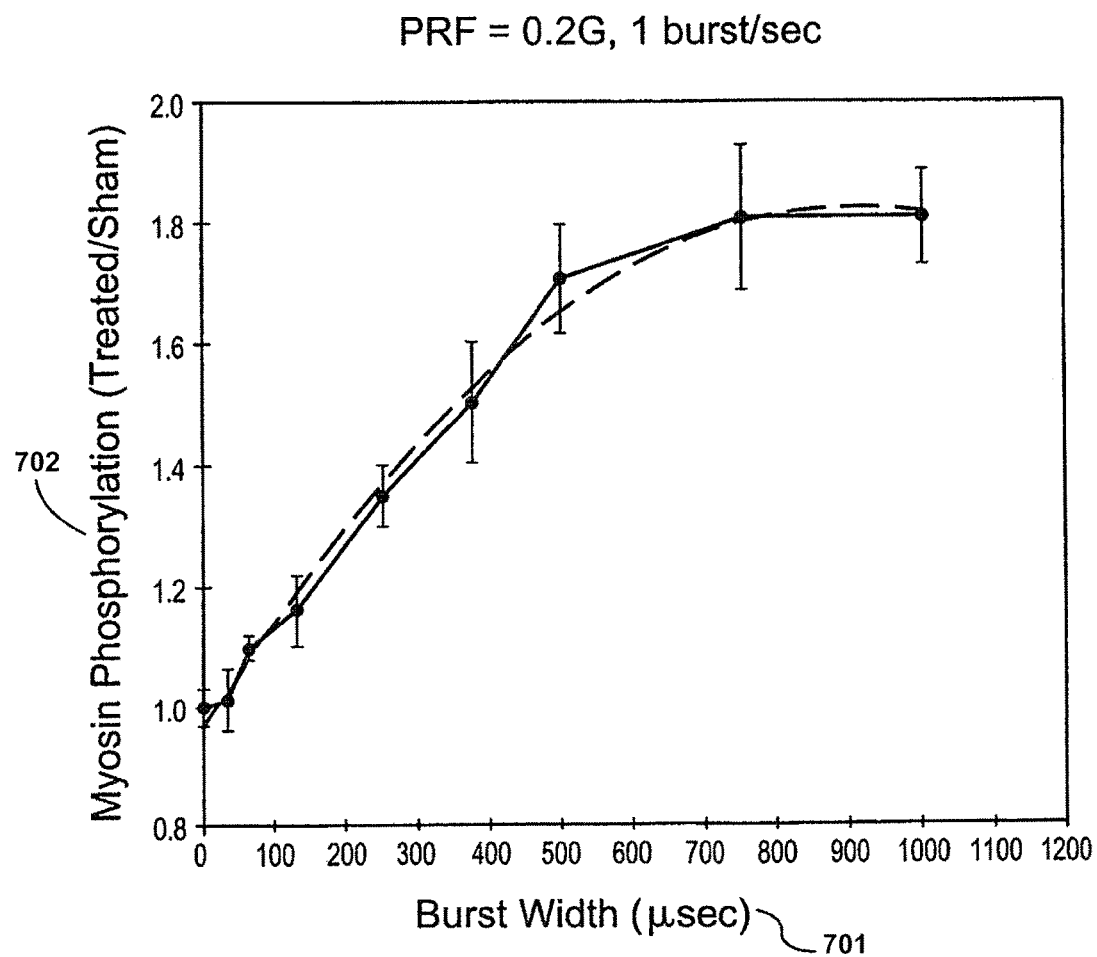
FIG. 7 is a graph illustrating maximally increased myosin phosphorylation for a PMRF signal configured according to an embodiment of the present invention.

The signal comprised repetitive bursts of a high frequency waveform. Amplitude was maintained constant at 0.2 G and repetition rate was 1 burst/sec for all exposures. Burst duration varied from 65 µsec to 1000 µsec based upon projections of Power SNR analysis which showed that optimal Power SNR would be achieved as burst duration approached 500 µsec. The results are shown in FIG. 7 wherein burst width 701 in µsec is plotted on the x-axis and Myosin Phosphorylation 702 as treated/sham is plotted on the y-axis. It can be seen that the PMF effect on $Ca^{2+}$ binding to CaM approaches its maximum at approximately 500 µsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 μsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 μsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in kg/mm². The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per mm² of the two strips from the same wound.

The results showed average tensile strength for the 65 μsec 1 Gauss PRF signal was 19.3±4.3 kg/mm² for the exposed group versus 13.0±3.5 kg/mm² for the control group (p<0.01), which is a 48% increase. In contrast, the average tensile strength for the 2000 μsec 0.2 Gauss PRF signal, configured according to an embodiment of the present invention using a Power SNR model was 21.2±5.6 kg/mm² for the treated group versus 13.7±4.1 kg/mm² (p<0.01) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

In this example Jurkat cells react to PMF stimulation of a T-cell receptor with cell cycle arrest and thus behave like normal T-lymphocytes stimulated by antigens at the T-cell receptor such as anti-CD3. For example in bone healing, results have shown both 60 Hz and PEMF fields decrease DNA synthesis of Jurkat cells, as is expected since PMF interacts with the T-cell receptor in the absence of a costimulatory signal. This is consistent with an anti-inflammatory response, as has been observed in clinical applications of PMF stimuli. The PEMF signal is more effective. A dosimetry analysis performed according to an embodiment of the present invention demonstrates why both signals are effective and why PEMF signals have a greater effect than 60 Hz signals on Jurkat cells in the most EMF-sensitive growth stage.

Comparison of dosimetry from the two signals employed involves evaluation of the ratio of the Power spectrum of the thermal noise voltage that is Power SNR, to that of the induced voltage at the EMF-sensitive target pathway structure. The target pathway structure used is ion binding at receptor sites on Jurkat cells suspended in 2 mm of culture medium. The average peak electric field at the binding site from a PEMF signal comprising 5 msec burst of 200 μsec pulses repeating at 15/sec, was 1 mV/cm, while for a 60 Hz signal it was 50 μV/cm.

Figure 8:
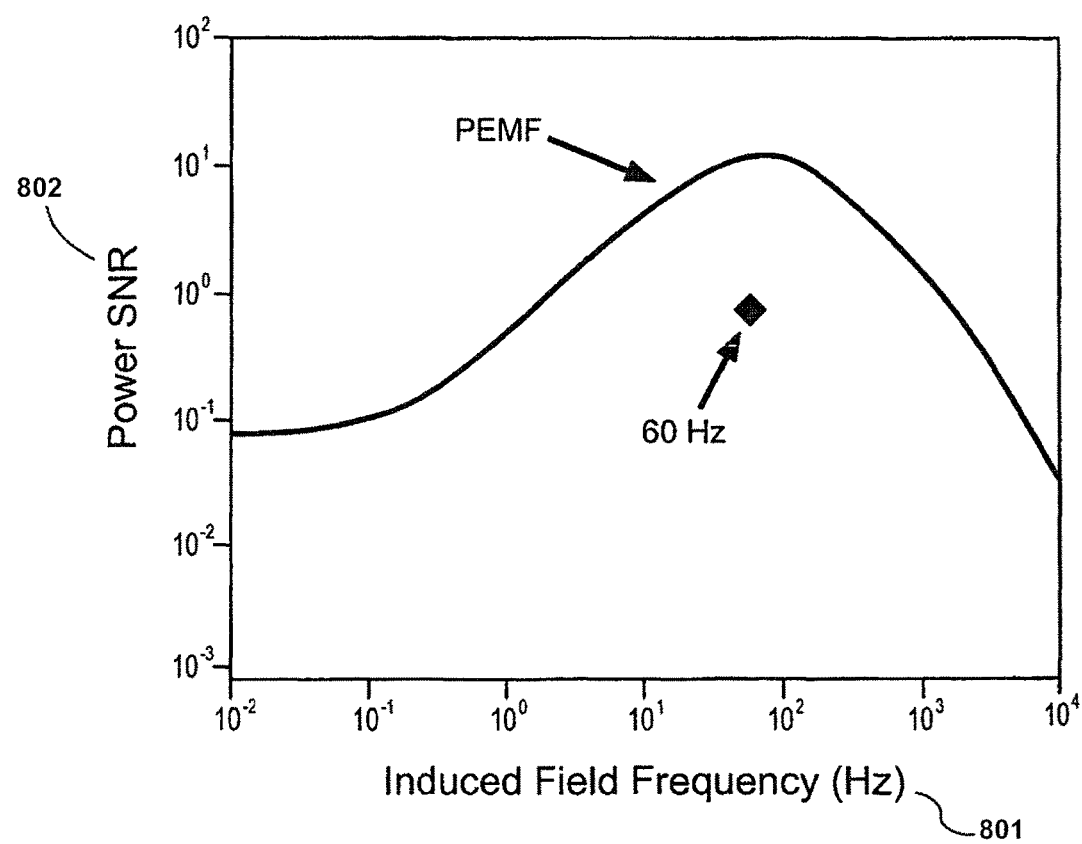
FIG. 8 is a graph illustrating a power consumption comparison between a 60 Hz signal and a PEMF signal configured according to an embodiment of the present invention.

FIG. 8 is a graph of results wherein Induced Field Frequency 801 in Hz is plotted on the x-axis and Power SNR 802 is plotted on the y-axis. FIG. 8 illustrates that both signals have sufficient Power spectrum that is Power SNR≈1, to be detected within a frequency range of binding kinetics. However, maximum Power SNR for the PEMF signal is significantly higher than that for the 60 Hz signal. This is because a PEMF signal has many frequency components falling within the bandpass of the binding pathway. The single frequency component of a 60 Hz signal lies at the mid-point of the bandpass of the target pathway. The Power SNR calculation that was used in this example is dependant upon $\tau_{ion}$ which is obtained from the rate constant for ion binding. Had this calculation been performed a priori it would have concluded that both signals satisfied basic detectability requirements and could modulate an EMF-sensitive ion binding pathway at the start of a regulatory cascade for DNA synthesis in these cells. The previous examples illustrated that utilizing the rate constant for Ca/CaM binding could lead to successful projections for bioeffective EMF signals in a variety of systems.

Having described embodiments for an apparatus and a method for delivering electromagnetic treatment to human, animal and plant molecules, cells, tissue and organs, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Part 2

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where ω is angular frequency defined as 2πf, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of wound repair, for example bone repair, that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to wound repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion} C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion} C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ $sec^{-1}$, =2.5 μM, $K_D$=30 μM, $[Ca^{2+}CaM]=K_D(+[CaM])$, yields $k_b$=665 $sec^{-1}$ ($\tau_{ion}$=1.5 msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kTRe[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x,\omega) = \left[\frac{R_e + R_i + R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)$=4 kT Re[$Z_M(x, \omega)$] over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known healing mechanisms is accessible. According to an embodiment of the present invention applying a random, or other high spectral density envelope, to a pulse burst envelope of mono- or bi-polar rectangular or sinusoidal pulses inducing peak electric fields between about $10^{-6}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 9, wherein FIG. 9 is a flow diagram of a method of using an inductive apparatus to deliver electromagnetic signals to target pathway structures such as such as molecules, cells, tissues, and organs of plants, animals, and humans for therapeutic and prophylactic purposes according to an embodiment of the present invention. A lightweight inductive apparatus is integrated into at least one therapeutic device that will be used for treatment, however the inductive apparatus can also be attached to at least one therapeutic device (Step 9101). Miniaturized circuitry containing logic for a mathematical model having at least one waveform parameter used to configure at least one waveform to be coupled to a target pathway structure such as molecules, cells, tissues, and organs, is attached to the coil by at least one wire (Step 9102). However, the attachment can also be wireless. The configured waveform satisfies a SNR or Power SNR model so that for a given and known target pathway structure it is possible to choose at least one waveform parameter so that a waveform is detectable in the target pathway structure above its background activity (Step 9103) such as baseline thermal fluctuations in voltage and electrical impedance at a target pathway structure that depend upon a state of a cell and tissue, that is whether the state is at least one of resting, growing, replacing, and responding to injury. A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 9104). A repetitive electromagnetic signal can be generated for example inductively, from said configured at least one waveform (Step 9105). The repetitive electromagnetic signal can also be generated conductively. The electromagnetic signal is coupled to a target pathway structure such as molecules, cells, tissues, and organs by output of the inductive apparatus integrated into the support (Step 9106).

FIG. 10 illustrates a preferred embodiment of an apparatus according to the present invention. A miniature control circuit 10201 is coupled to an end of at least one connector 10202 such as wire. The opposite end of the at least one connector is coupled to a generating device such as a pair of electrical coils 10203. The generating device is constructed to have electrical properties that optimize generation of electromagnetic signals from waveforms configured to satisfy at least one of a SNR model, a Power SNR model, and any other mathematical model used for waveform configuration. The miniature control circuit 10201 is constructed in a manner that applies a mathematical model that is used to configure waveforms. The configured waveforms have to satisfy a SNR or Power SNR model so that for a given and known target pathway structure, it is possible to choose waveform parameters that satisfy SNR or Power SNR so that a waveform is detectable in the target pathway structure above its background activity. A preferred embodiment according to the present invention applies a mathematical model to induce a time-varying magnetic field and a time-varying electric field in a target pathway structure such as molecules, cells, tissues, and organs, comprising about 10 to about 100 msec bursts of about 1 to about 100 microsecond rectangular pulses repeating at about 0.1 to about 10 pulses per second. Peak amplitude of the induced electric field is between about 1 uV/cm and about 100 mV/cm, varied according to a modified 1/f function where f=frequency. A waveform configured using a preferred embodiment according to the present invention may be applied to a target pathway structure such as molecules, cells, tissues, and organs for a preferred total exposure time of under 1 minute to 240 minutes daily. However other exposure times can be used. Waveforms configured by the miniature control circuit 10201 are directed to a generating device 10203 such as electrical coils via connector 10202. The generating device 10203 delivers a pulsing magnetic field configured according to a mathematical model, that can be used to provide treatment to a target pathway structure such as a heart in a chest 10204. The miniature control circuit applies a pulsing magnetic field for a prescribed time and can automatically repeat applying the pulsing magnetic field for as many applications as are needed in a given time period, for example 10 times a day. A preferred embodiment according to the present invention can be positioned to treat the heart in a chest 10204 by a positioning device. Coupling a pulsing magnetic field to a angiogenesis and neovascularization target pathway structure such as ions and ligands, therapeutically and prophylactically reduces inflammation thereby reducing pain and promotes healing. When electrical coils are used as the generating device 10203, the electrical coils can be powered with a time varying magnetic field that induces a time varying electric field in a target pathway structure according to Faraday's law. An electromagnetic signal generated by the generating device 10203 can also be applied using electrochemical coupling, wherein electrodes are in direct contact with skin or another outer electrically conductive boundary of a target pathway structure. Yet in another embodiment according to the present invention, the electromagnetic signal generated by the generating device 10203 can also be applied using electrostatic coupling wherein an air gap exists between a generating device 10203 such as an electrode and a target pathway structure such as molecules, cells, tissues, and organs. An advantage of the preferred embodiment according to the present invention is that its ultra lightweight coils and miniaturized circuitry allow for use with common physical therapy treatment modalities and at any body location for which pain relief and healing is desired. An advantageous result of application of the preferred embodiment according to the present invention is that a living organism's angiogenesis and neovascularization can be maintained and enhanced.

FIG. 11 depicts a block diagram of a preferred embodiment according to the present invention of a miniature control circuit 11300. The miniature control circuit 11300 produces waveforms that drive a generating device such as wire coils described above in FIG. 10. The miniature control circuit can be activated by any activation means such as an on/off switch. The miniature control circuit 11300 has a power source such as a lithium battery 11301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 11302 controls voltage to a micro-controller 11303. A preferred embodiment of the micro-controller 11303 uses an 8 bit 4 MHz micro-controller 11303 but other bit MHz combination micro-controllers may be used. The switching power supply 11302 also delivers current to storage capacitors 11304. A preferred embodiment of the present invention uses storage capacitors having a 220 uF output but other outputs can be used. The storage capacitors 11304 allow high frequency pulses to be delivered to a coupling device such as inductors (Not Shown). The micro-controller 11303 also controls a pulse shaper 11305 and a pulse phase timing control 11306. The pulse shaper 11305 and pulse phase timing control 11306 determine pulse shape, burst width, burst envelope shape, and burst repetition rate. An integral waveform generator, such as a sine wave or arbitrary number generator can also be incorporated to provide specific waveforms. A voltage level conversion sub-circuit 11308 controls an induced field delivered to a target pathway structure. A switching Hexfet 11308 allows pulses of randomized amplitude to be delivered to output 11309 that routes a waveform to at least one coupling device such as an inductor. The micro-controller 11303 can also control total exposure time of a single treatment of a target pathway structure such as a molecule, cell, tissue, and organ. The miniature control circuit 11300 can be constructed to apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Referring to FIG. 12 an embodiment according to the present invention of an electromagnetic treatment inductive apparatus integrated into hip, thigh, and lower back support garment 12400 is illustrated. Several lightweight flexible coils 12401 are integrated into the support garment. The lightweight flexible coils can be constructed from fine flexible conductive wire, conductive thread, and any other flexible conductive material. The flexible coils are connected to at least one end of at least one wire 12402. However the flexible coils can also be configured to be directly connected to circuitry 12403 or wireless. Lightweight miniaturized circuitry 12403 that configures waveforms according to an embodiment of the present invention, is attached to at least one other end of said at least on wire. When activated the lightweight miniaturized circuitry 12403 configures waveforms that are directed to the flexible coils (12401) to create PEMF signals that are coupled to a target pathway structure.

Referring to FIG. 13 an embodiment according to the present invention of an electromagnetic treatment inductive apparatus integrated into a head and face support garment 13500 is illustrated. Several lightweight flexible coils 13501 are integrated into the support garment. The lightweight flexible coils can be constructed from fine flexible conductive wire, conductive thread, and any other flexible conductive material. The flexible coils are connected to at least one end of at least one wire 13502. However, the flexible coils can also be configured to be directly connected to circuitry 13503 or wireless. Lightweight miniaturized circuitry 13503 that configures waveforms, according to an embodiment of the present invention, is attached to at least one other end of said at least on wire. When activated the lightweight miniaturized circuitry 503 configures waveforms that are directed to the flexible coils (13501) to create PEMF signals that are coupled to a target pathway structure.

Referring to FIG. 14 an embodiment according to the present invention of an electromagnetic treatment inductive apparatus integrated into surgical dressing applied to a human forearm 14600 is illustrated. Several lightweight flexible coils 14601 are integrated into the dressing. The lightweight flexible coils can be constructed from fine flexible conductive wire, conductive thread, and any other flexible conductive material. The flexible coils are connected to at least one end of at least one wire 14602. However, the flexible coils can also be configured to be directly connected to circuitry 14603 or wireless. Lightweight miniaturized circuitry 14603 that configures waveforms according to an embodiment of the present invention, is attached to at least one other end of said at least one wire. When activated the lightweight miniaturized circuitry 14603 configures waveforms that are directed to the flexible coils (14601) to create PEMF signals that are coupled to a target pathway structure.

Referring to FIG. 15 an embodiment according to the present invention of an electromagnetic treatment inductive apparatus integrated into a mattress pad 15700 is illustrated. Several lightweight flexible coils 15701 are integrated into the mattress pad. The lightweight flexible coils can be constructed from fine flexible conductive wire, conductive thread, and any other flexible conductive material. The flexible coils are connected to at least one end of at least one wire 15702. However, the flexible coils can also be configured to be directly connected to circuitry 15703 or wireless. Lightweight miniaturized circuitry 15703 that configures waveforms according to an embodiment of the present invention, is attached to at least one other end of said at least on wire. When activated the lightweight miniaturized circuitry 15703 configures waveforms that are directed to the flexible coils (15701) to create PEMF signals that are coupled to a target pathway structure.

Referring to FIGS. 16A and 16B an embodiment according to the present invention of an electromagnetic treatment inductive apparatus integrated into a sock 16801 and a shoe 16802 are illustrated. Several lightweight flexible coils 16803 are integrated into the dressing. The lightweight flexible coils can be constructed from fine flexible conductive wire, conductive thread, and any other flexible conductive material. The flexible coils are connected to at least one end of at least one wire 16804. However, the flexible coils can also be configured to be directly connected to circuitry 16805 or wireless. Lightweight miniaturized circuitry 16805 that configures waveforms according to an embodiment of the present invention, is attached to at least one other end of said at least on wire. When activated the lightweight miniaturized circuitry 16805 configures waveforms that are directed to the flexible coils (16806) to create PEMF signals that are coupled to a target pathway structure.

Referring to FIG. 17 an embodiment according to the present invention of an electromagnetic treatment inductive apparatus integrated into a therapeutic bed 17900 is illustrated. Several lightweight flexible coils 17901 are integrated into the bed. The lightweight flexible coils can be constructed from fine flexible conductive wire, conductive thread, and any other flexible conductive material. The flexible coils are connected to at least one end of at least one wire 17902. However, the flexible coils can also be configured to be directly connected to circuitry 17903 or wireless. Lightweight miniaturized circuitry 17903 that configures waveforms according to an embodiment of the present invention, is attached to at least one other end of said at least on wire. When activated the lightweight miniaturized circuitry 17903 configures waveforms that are directed to the flexible coils (17901) to create PEMF signals that are coupled to a target pathway structure.

Referring to FIG. 18 an embodiment according to the present invention of an electromagnetic treatment inductive apparatus integrated into a chest garment 181000, such as a bra is illustrated. Several lightweight flexible coils 181001 are integrated into a bra. The lightweight flexible coils can be constructed from fine flexible conductive wire, conductive thread, and any other flexible conductive material. The flexible coils are connected to at least one end of at least one wire 181002. However, the flexible coils can also be configured to be directly connected to circuitry 181003 or wireless. Lightweight miniaturized circuitry 181003 that configures waveforms according to an embodiment of the present invention, is attached to at least one other end of said at least on wire. When activated the lightweight miniaturized circuitry 181003 configures waveforms that are directed to the flexible coils (181001) to create PEMF signals that are coupled to a target pathway structure.

Having described embodiments for an electromagnetic treatment inductive apparatus and a method for using same, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Part 3

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of wound repair, for example bone repair, that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to wound repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ sec$^{-1}$, $=2.5$ $\mu$M, $K_D=30$ $\mu$M, $[Ca^{2+}CaM]=K_D(+[CaM])$, yields $k_b=665$ sec$^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kTRe[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x,\omega) = \left[\frac{R_e + R_i + R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)=4$ kT Re[$z_M$ (x, $\omega$)] over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known healing mechanisms is accessible. According to an embodiment of the present invention applying a random, or other high spectral density envelope, to a pulse burst envelope of mono- or bi-polar rectangular or sinusoidal pulses inducing peak electric fields between about $10^{-6}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 19, wherein FIG. 19 is a flow diagram of a method for delivering electromagnetic signals to angiogenesis and neovascularization target pathway structures such as ions and ligands of plants, animals, and humans for therapeutic and prophylactic purposes according to an embodiment of the present invention. A mathematical model having at least one waveform parameter is applied to configure at least one waveform to be coupled to a angiogenesis and neovascularization target pathway structure such as ions and ligands (Step 19101). The configured waveform satisfies a SNR or Power SNR model so that for a given and known angiogenesis and neovascularization target pathway structure it is possible to choose at least one waveform parameter so that a waveform is detectable in the angiogenesis and neovascularization target pathway structure above its background activity (Step 19102) such as baseline thermal fluctuations in voltage and electrical impedance at a target pathway structure that depend upon a state of a cell and tissue, that is whether the state is at least one of resting, growing, replacing, and responding to injury. A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 19102). A repetitive electromagnetic signal can be generated for example inductively or capacitively, from said configured at least one waveform (Step 19103). The electromagnetic signal is coupled to a angiogenesis and neovascularization target pathway structure such as ions and ligands by output of a coupling device such as an electrode or an inductor, placed in close proximity to the target pathway structure (Step 19104). The coupling enhances modulation of binding of ions and ligands to regulatory molecule in living tissues and cells.

FIG. 20 illustrates a preferred embodiment of an apparatus according to the present invention. A miniature control circuit 20201 is coupled to an end of at least one connector 20202 such as wire. The opposite end of the at least one connector is coupled to a generating device such as a pair of electrical coils 20203. The miniature control circuit 20201 is constructed in a manner that applies a mathematical model that is used to configure waveforms. The configured waveforms have to satisfy a SNR or Power SNR model so that for a given and known angiogenesis and neovascularization target pathway structure, it is possible to choose waveform parameters that satisfy SNR or Power SNR so that a waveform is detectable in the angiogenesis and neovascularization target pathway structure above its background activity. A preferred embodiment according to the present invention applies a mathematical model to induce a time-varying magnetic field and a time-varying electric field in a angiogenesis and neovascularization target pathway structure such as ions and ligands, comprising about 10 to about 100 msec bursts of about 1 to about 100 microsecond rectangular pulses repeating at about 0.1 to about 10 pulses per second. Peak amplitude of the induced electric field is between about 1 uV/cm and about 100 mV/cm, varied according to a modified 1/f function where f=frequency. A waveform configured using a preferred embodiment according to the present invention may be applied to a angiogenesis and neovascularization target pathway structure such as ions and ligands for a preferred total exposure time of under 1 minute to 240 minutes daily. However other exposure times can be used. Waveforms configured by the miniature control circuit 20201 are directed to a generating device 20203 such as electrical coils via connector 20202. The generating device 20203 delivers a pulsing magnetic field configured according to a mathematical model, that can be used to provide treatment to a angiogenesis and neovascularization target pathway structure such as a heart in a chest 20204. The miniature control circuit applies a pulsing magnetic field for a prescribed time and can automatically repeat applying the pulsing magnetic field for as many applications as are needed in a given time period, for example 10 times a day. A preferred embodiment according to the present invention can be positioned to treat the heart in a chest 20204 by a positioning device. Coupling a pulsing magnetic field to a angiogenesis and neovascularization target pathway structure such as ions and ligands, therapeutically and prophylactically reduces inflammation thereby reducing pain and promotes healing. When electrical coils are used as the generating device 20203, the electrical coils can be powered with a time varying magnetic field that induces a time varying electric field in a target pathway structure according to Faraday's law. An electromagnetic signal generated by the generating device 20203 can also be applied using electrochemical coupling, wherein electrodes are in direct contact with skin or another outer electrically conductive boundary of a target pathway structure. Yet in another embodiment according to the present invention, the electromagnetic signal generated by the generating device 20203 can also be applied using electrostatic coupling wherein an air gap exists between a generating device 20203 such as an electrode and a angiogenesis and neovascularization target pathway structure such as ions and ligands. An advantage of the preferred embodiment according to the present invention is that its ultra lightweight coils and miniaturized circuitry allow for use with common physical therapy treatment modalities and at any body location for which pain relief and healing is desired. An advantageous result of application of the preferred embodiment according to the present invention is that a living organism's angiogenesis and neovascularization can be maintained and enhanced.

FIG. 21 depicts a block diagram of a preferred embodiment according to the present invention of a miniature control circuit 21300. The miniature control circuit 21300 produces waveforms that drive a generating device such as wire coils described above in FIG. 20. The miniature control circuit can be activated by any activation means such as an on/off switch. The miniature control circuit 21300 has a power source such as a lithium battery 21301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 21302 controls voltage to a micro-controller 21303. A preferred embodiment of the micro-controller 21303 uses an 8 bit 4 MHz micro-controller 21303 but other bit MHz combination micro-controllers may be used. The switching power supply 21302 also delivers current to storage capacitors 21304. A preferred embodiment of the present invention uses storage capacitors having a 220 uF output but other outputs can be used. The storage capacitors 21304 allow high frequency pulses to be delivered to a coupling device such as inductors (Not Shown). The micro-controller 21303 also controls a pulse shaper 21305 and a pulse phase timing control 21306. The pulse shaper 21305 and pulse phase timing control 306 determine pulse shape, burst width, burst envelope shape, and burst repetition rate. An integral waveform generator, such as a sine wave or arbitrary number generator can also be incorporated to provide specific waveforms. A voltage level conversion sub-circuit 21308 controls an induced field delivered to a target pathway structure. A switching Hexfet 21308 allows pulses of randomized amplitude to be delivered to output 21309 that routes a waveform to at least one coupling device such as an inductor. The micro-controller 21303 can also control total exposure time of a single treatment of a target pathway structure such as a molecule, cell, tissue, and organ. The miniature control circuit 21300 can be constructed to apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Referring to FIG. 22 an embodiment according to the present invention of a waveform 22400 is illustrated. A pulse 22401 is repeated within a burst 22402 that has a finite duration 22403. The duration 22403 is such that a duty cycle which can be defined as a ratio of burst duration to signal period is between about 1 to about $10^{-5}$. A preferred embodiment according to the present invention utilizes pseudo rectangular 10 microsecond pulses for pulse 22401 applied in a burst 22402 for about 10 to about 50 msec having a modified 1/f amplitude envelope 22404 and with a finite duration 22403 corresponding to a burst period of between about 0.1 and about 10 seconds.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA12. Free $Ca^{2+}$ was varied in the 1-7 μM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 μL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 μM 32P ATP, and was stopped with Laemmli Sample Buffer solution containing 30 μM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 μsec to 1000 μsec based upon projections of Power SNR analysis which showed that optimal Power SNR would be achieved as burst duration approached 500 μsec. The results are shown in FIG. 7 wherein burst width 701 in μsec is plotted on the x-axis and Myosin Phosphorylation 702 as treated/sham is plotted on the y-axis. It can be seen that the PMF effect on $Ca^{2+}$ binding to CaM approaches its maximum at approximately 500 μsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 μsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 μsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in kg/mm$^2$. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per mm$^2$ of the two strips from the same wound.

The results showed average tensile strength for the 65 μsec 1 Gauss PRF signal was 19.3±4.3 kg/mm$^2$ for the exposed group versus 13.0±3.5 kg/mm$^2$ for the control group (p<0.01), which is a 48% increase. In contrast, the average tensile strength for the 2000 μsec 0.2 Gauss PRF signal, configured according to an embodiment of the present invention using a Power SNR model was 21.2±5.6 kg/mm$^2$ for the treated group versus 13.7±4.1 kg/mm$^2$ (p<0.01) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

In this example Jurkat cells react to PMF stimulation of a T-cell receptor with cell cycle arrest and thus behave like normal T-lymphocytes stimulated by antigens at the T-cell receptor such as anti-CD3. For example in bone healing, results have shown both 60 Hz and PEMF fields decrease DNA synthesis of Jurkat cells, as is expected since PMF interacts with the T-cell receptor in the absence of a costimulatory signal. This is consistent with an anti-inflammatory response, as has been observed in clinical applications of PMF stimuli. The PEMF signal is more effective. A dosimetry analysis performed according to an embodiment of the present invention demonstrates why both signals are effective and why PEMF signals have a greater effect than 60 Hz signals on Jurkat cells in the most EMF-sensitive growth stage.

Comparison of dosimetry from the two signals employed involves evaluation of the ratio of the Power spectrum of the thermal noise voltage that is Power SNR, to that of the induced voltage at the EMF-sensitive target pathway structure. The target pathway structure used is ion binding at receptor sites on Jurkat cells suspended in 2 mm of culture medium. The average peak electric field at the binding site from a PEMF signal comprising 5 msec burst of 200 μsec pulses repeating at 15/sec, was 1 mV/cm, while for a 60 Hz signal it was 50 μV/cm.

EXAMPLE 4

In this example electromagnetic field energy was used to stimulate neovascularization in an in vivo model. Two different signal were employed, one configured according to prior art and a second configured according to an embodiment of the present invention.

One hundred and eight Sprague-Dawley male rats weighing approximately 300 grams each, were equally divided into nine groups. All animals were anesthetized with a mixture of ketamine/acepromazine/Stadol at 0.1 cc/g. Using sterile surgical techniques, each animal had a 12 cm to 14 cm segment of tail artery harvested using microsurgical technique. The artery was flushed with 60 U/ml of heparinized saline to remove any blood or emboli.

These tail vessels, with an average diameter of 0.4 mm to 0.5 mm, were then sutured to the transected proximal and distal segments of the right femoral artery using two end-to-end anastomoses, creating a femoral arterial loop. The resulting loop was then placed in a subcutaneous pocket created over the animal's abdominal wall/groin musculature, and the groin incision was closed with 4-0 Ethilon. Each animal was then randomly placed into one of nine groups: groups 1 to 3 (controls), these rats received no electromagnetic field treatments and were killed at 4, 8, and 12 weeks; groups 4 to 6, 30 min. treatments twice a day using 0.1 gauss electromagnetic fields for 4, 8, and 12 weeks (animals were killed at 4, 8, and 12 weeks, respectively); and groups 7 to 9, 30 min. treatments twice a day using 2.0 gauss electromagnetic fields for 4, 8, and 12 weeks (animals were killed at 4, 8, and 12 weeks, respectively).

Pulsed electromagnetic energy was applied to the treated groups using a device constructed according to an embodiment of the present invention. Animals in the experimental groups were treated for 30 minutes twice a day at either 0.1 gauss or 2.0 gauss, using short pulses (2 msec to 20 msec) 27.12 MHz. Animals were positioned on top of the applicator head and confined to ensure that treatment was properly applied. The rats were reanesthetized with ketamine/acepromazine/Stadol intraperitoneally and 100 U/kg of heparin intravenously. Using the previous groin incision, the femoral artery was identified and checked for patency. The femoral/tail artery loop was then isolated proximally and distally from the anastomoses sites, and the vessel was clamped off. Animals were then killed. The loop was injected with saline followed by 0.5 cc to 1.0 cc of colored latex through a 25-gauge cannula and clamped. The overlying abdominal skin was carefully resected, and the arterial loop was exposed. Neovascularization was quantified by measuring the surface area covered by new blood-vessel formation delineated by the intraluminal latex. All results were analyzed using the SPSS statistical analysis package.

The most noticeable difference in neovascularization between treated versus untreated rats occurred at week 4. At that time, no new vessel formation was found among controls, however, each of the treated groups had similar statistically significant evidence of neovascularization at 0 cm2 versus 1.42±0.80 cm2 (p<0.001). These areas appeared as a latex blush segmentally distributed along the sides of the arterial loop. At 8 weeks, controls began to demonstrate neovascularization measured at 0.7±0.82 cm2. Both treated groups at 8 weeks again had approximately equal statistically significant (p<0.001) outcroppings of blood vessels of 3.57±1.82 cm2 for the 0.1 gauss group and of 3.77±1.82 cm2 for the 2.0 gauss group. At 12 weeks, animals in the control group displayed 1.75±0.95 cm2 of neovascularization, whereas the 0.1 gauss group demonstrated 5.95±3.25 cm2, and the 2.0 gauss group showed 6.20±3.95 cm2 of arborizing vessels. Again, both treated groups displayed comparable statistically significant findings (p<0.001) over controls.

These experimental findings demonstrate that electromagnetic field stimulation of an isolated arterial loop according to an embodiment of the present invention increases the amount of quantifiable neovascularization in an in vivo rat model. Increased angiogenesis was demonstrated in each of the treated groups at each of the sacrifice dates. No differences were found between the results of the two gauss levels tested as predicted by the teachings of the present invention.

Having described embodiments for an apparatus and a method for delivering electromagnetic treatment to human, animal and plant molecules, cells, tissue and organs, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Part 4

An embodiment according to the present invention provides a higher spectral density to a pulse burst envelope resulting in enhanced effectiveness of therapy upon relevant dielectric pathways, such as, cellular membrane receptors, ion binding to cellular enzymes and general transmembrane potential changes. An embodiment according to the present invention increases the number of frequency components transmitted to relevant cellular pathways, thereby providing access to a larger range of biophysical phenomena applicable to known healing mechanisms, for example modulation of growth factor and cytokine release, and ion binding at regulatory molecules. By applying a random, or other high spectral density envelope, according to a mathematical model defined by SNR or Power SNR in a transduction pathway, to a pulse burst envelope of mono- or bi-polar rectangular or sinusoidal pulses inducing peak electric fields between $10^{-6}$ and 10 volts per centimeter (V/cm), a greater effect could be accomplished on biological healing processes applicable to both soft and hard tissues.

An advantageous result of the present invention, is that by applying a high spectral density voltage envelope as the modulating or pulse-burst defining parameter, according to a mathematical model defined by SNR or Power SNR in a transduction pathway, the power requirement for such amplitude modulated pulse bursts can be significantly lower than that of an unmodulated pulse burst containing pulses within the same frequency range. Accordingly, the advantages of enhanced transmitted dosimetry to the relevant dielectric target pathways and of decreased power requirement are achieved. Another advantage of the present invention is the acceleration of wound repair.

Known mechanisms of wound repair involve the naturally timed release of the appropriate growth factor or cytokine in each stage of wound repair as applied to humans, animals and plants. Specifically, wound repair involves an inflammatory phase, angiogenesis, cell proliferation, collagen production, and remodeling stages. There are timed releases of specific cytokines and growth factors in each stage. Electromagnetic fields are known to enhance blood flow and to enhance the binding of ions which, in turn, can accelerate each healing phase. It is an object of this invention to provide an improved means to enhance the action and accelerate the intended effects or improve efficacy as well as other effects of the cytokines and growth factors relevant to each stage of wound repair.

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, for example electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of tissue repair, for example bone repair, wound repair, hair repair, and repair of molecules, cells, tissues, and organs that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to tissue growth and repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ $sec^{-1}$, =2.5 µM, $K_D=30$ µM, $[Ca^{2+}CaM]=K_D(+[CaM])$, yields $k_b=665$ $sec^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model for example a mathematical equation and or a series of mathematical equations can be configured to assimilate that thermal noise is present in all voltage dependent processes and represents a minimum threshold requirement to establish adequate SNR. For example a mathematical model that represents a minimum threshold requirement to establish adequate SNR can be configured to include power spectral density of thermal noise such that power spectral density, $S_n(\omega)$, of thermal noise can be expressed as:

$$S_n(\omega)=4kTRe[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x,\omega) = \left[\frac{R_e + R_i + R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structures, all contribute to noise filtering.

A typical approach to evaluation of SNR uses a single value of a root mean square (RMS) noise voltage. This is calculated by taking a square root of an integration of $S_n(\omega)=4$ kT Re[$Z_M(x,\omega)$] over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known tissue growth mechanisms is accessible. According to an embodiment of the present invention applying a random, or other high spectral density envelope, to a pulse burst envelope of mono- or bi-polar rectangular or sinusoidal pulses inducing peak electric fields between about $10^{-8}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 23, wherein FIG. 23 is a flow diagram of a method according to an embodiment of the present invention, for accelerating wound repair by delivering electromagnetic signals that can be pulsed, to target pathway structures such as ions and ligands of animals and humans, for therapeutic and prophylactic purposes. Target pathway structures can also include but are not limited to tissues, cells, organs, and molecules.

Configuring at least one waveform having at least one waveform parameter to be coupled to the target pathway structure such as ions and ligands (Step 23101).

The at least one waveform parameter is selected to maximize at least one of a signal to noise ratio and a Power Signal to Noise ratio in a target pathway structure so that a waveform is detectable in the target pathway structure above its background activity (Step 23102) such as baseline thermal fluctuations in voltage and electrical impedance at a target pathway structure that depend upon a state of a cell and tissue, that is whether the state is at least one of resting, growing, replacing, and responding to injury to produce physiologically beneficial results. To be detectable in the target pathway structure the value of said at least one waveform parameter is chosen by using a constant of said target pathway structure to evaluate at least one of a signal to noise ratio, and a Power signal to noise ratio, to compare voltage induced by said at least one waveform in said target pathway structure to baseline thermal fluctuations in voltage and electrical impedance in said target pathway structure whereby bioeffective modulation occurs in said target pathway structure by said at least one waveform by maximizing said at least one of signal to noise ratio and Power signal to noise ratio, within a bandpass of said target pathway structure.

A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 23103). A repetitive electromagnetic signal can be generated for example inductively or capacitively, from said configured at least one waveform (Step 23104). The electromagnetic signal can also be non-repetitive. The electromagnetic signal is coupled to a target pathway structure such as ions and ligands by output of a coupling device such as an electrode or an inductor, placed in close proximity to the target pathway structure (Step 23105). The coupling enhances blood flow and modulation of binding of ions and ligands to regulatory molecules in molecules, tissues, cells, and organs thereby accelerating wound repair.

FIG. 24 illustrates a preferred embodiment of an apparatus according to the present invention. The apparatus is self-contained, lightweight, and portable. A miniature control circuit 24201 is coupled to an end of at least one connector 24202 such as wire however the control circuit can also operate wirelessly. The opposite end of the at least one connector is coupled to a generating device such as an electrical coil 24203. The miniature control circuit 24201 is constructed in a manner that applies a mathematical model that is used to configure waveforms. The configured waveforms have to satisfy Power SNR so that for a given and known target pathway structure, it is possible to choose waveform parameters that satisfy Power SNR so that a waveform produces physiologically beneficial results, for example bioeffective modulation, and is detectable in the target pathway structure above its background activity. A preferred embodiment according to the present invention applies a mathematical model to induce a time-varying magnetic field and a time-varying electric field in a target pathway structure such as ions and ligands, comprising about 0.1 to about 100 msec bursts of about 1 to about 100 microsecond rectangular pulses repeating at about 0.1 to about 100 pulses per second. Peak amplitude of the induced electric field is between about 1 uV/cm and about 100 mV/cm, varied according to a modified 1/f function where f=frequency. A waveform configured using a preferred embodiment according to the present invention may be applied to a target pathway structure such as ions and ligands for a preferred total exposure time of under 1 minute to 240 minutes daily. However other exposure times can be used. Waveforms configured by the miniature control circuit 24201 are directed to a generating device 24203 such as electrical coils via connector 24202. The generating device 24203 delivers a pulsing magnetic field that can be used to provide treatment to a target pathway structure such as tissue. The miniature control circuit applies a pulsing magnetic field for a prescribed time and can automatically repeat applying the pulsing magnetic field for as many applications as are needed in a given time period, for example 10 times a day. The miniature control circuit can be configured to be programmable applying pulsing magnetic fields for any time repetition sequence. A preferred embodiment according to the present invention can accelerate wound repair by being incorporated into a positioning device 24204, for example a bed. Coupling a pulsing magnetic field to a target pathway structure such as ions and ligands, therapeutically and prophylactically reduces inflammation thereby advantageously reducing pain, promoting healing in targeted areas. When electrical coils are used as the generating device 24203, the electrical coils can be powered with a time varying magnetic field that induces a time varying electric field in a target pathway structure according to Faraday's law. An electromagnetic signal generated by the generating device 24203 can also be applied using electrochemical coupling, wherein electrodes are in direct contact with skin or another outer electrically conductive boundary of a target pathway structure. Yet in another embodiment according to the present invention, the electromagnetic signal generated by the generating device 24203 can also be applied using electrostatic coupling wherein an air gap exists between a generating device 24203 such as an electrode and a target pathway structure such as ions and ligands. An advantage of the preferred embodiment according to the present invention is that its ultra lightweight coils and miniaturized circuitry allow for use with common physical therapy treatment modalities and at any for which growth, pain relief, and tissue and organ healing is desired. An advantageous result of application of the preferred embodiment according to the present invention is that tissue growth, repair, and maintenance can be accomplished and enhanced anywhere and at anytime, for example while driving a car or watching television. Yet another advantageous result of application of the preferred embodiment is that growth, repair, and maintenance of molecules, cells, tissues, and organs can be accomplished and enhanced anywhere and at anytime, for example while driving a car or watching television.

FIG. 25 depicts a block diagram of a preferred embodiment according to the present invention of a miniature control circuit 25300. The miniature control circuit 25300 produces waveforms that drive a generating device such as wire coils described above in FIG. 24. The miniature control circuit can be activated by any activation means such as an on/off switch. The miniature control circuit 25300 has a power source such as a lithium battery 25301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 25302 controls voltage to a micro-controller 25303. A preferred embodiment of the micro-controller 25303 uses an 8 bit 4 MHz micro-controller 25303 but other bit MHz combination micro-controllers may be used. The switching power supply 25302 also delivers current to storage capacitors 25304. A preferred embodiment of the present invention uses storage capacitors having a 220 uF output but other outputs can be used. The storage capacitors 25304 allow high frequency pulses to be delivered to a coupling device such as inductors (Not Shown). The micro-controller 25303 also controls a pulse shaper 25305 and a pulse phase timing control 25306. The pulse shaper 25305 and pulse phase timing control 25306 determine pulse shape, burst width, burst envelope shape, and burst repetition rate. An integral waveform generator, such as a sine wave or arbitrary number generator can also be incorporated to provide specific waveforms. A voltage level conversion sub-circuit 25307 controls an induced field delivered to a target pathway structure. A switching Hexfet 25308 allows pulses of randomized amplitude to be delivered to output 25309 that routes a waveform to at least one coupling device such as an inductor. The micro-controller 25303 can also control total exposure time of a single treatment of a target pathway structure such as a molecule, cell, tissue, and organ. The miniature control circuit 25300 can be constructed to be programmable and apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Referring to FIGS. 26A and 26B a preferred embodiment according to the present invention of a coupling device 26400 such as an inductor is shown. The coupling device 26400 can be an electric coil 26401 wound with single or multistrand flexible wire 26402 however solid wire can also be used. In a preferred embodiment according to the present invention the wire is made of copper but other materials can be used. The multistrand flexible magnetic wire 26402 enables the electric coil 26401 to conform to specific anatomical configurations such as a limb or joint of a human or animal. A preferred embodiment of the electric coil 26401 comprises about 1 to about 1000 turns of about 0.01 mm to about 0.1 mm diameter at least one of single magnet wire and multistrand magnet wire, wound on an initially circular form having an outer diameter between about 2.5 cm and about 50 cm but other numbers of turns and wire diameters can be used. A preferred embodiment of the electric coil 26401 can be encased with a non-toxic PVC mould 403 but other non-toxic moulds can also be used. The electric coil can also be incorporated in dressings, bandages, garments, and other structures typically used for wound treatment.

Referring to FIG. 27 an embodiment according to the present invention of a waveform 27500 is illustrated. A pulse 27501 is repeated within a burst 27502 that has a finite duration 27503. The duration 27503 is such that a duty cycle which can be defined as a ratio of burst duration to signal period is between about 1 to about $10^{-5}$. A preferred embodiment according to the present invention utilizes pseudo rectangular 10 microsecond pulses for pulse 27501 applied in a burst 27502 for about 10 to about 50 msec having a modified 1/f amplitude envelope 27504 and with a finite duration 27503 corresponding to a burst period of between about 0.1 and about 10 seconds but other waveforms, envelopes, and burst periods may be used that conform to a mathematical model such as SNR and Power SNR.

FIG. 28 illustrates a preferred embodiment according to the present invention of a positioning device such as a wrist support. A positioning device 28600 such as a wrist support 28601 is worn on a human wrist 28602. The positioning device can be constructed to be portable, can be constructed to be disposable, and can be constructed to be implantable. The positioning device can be used in combination with the present invention in a plurality of ways, for example incorporating the present invention into the positioning device for example by stitching, affixing the present invention onto the positioning device for example by Velcro®, and holding the present invention in place by constructing the positioning device to be elastic.

In another embodiment according to the present invention, the present invention can be constructed as a stand-alone device of any size with or without a positioning device, to be used anywhere for example at home, at a clinic, at a treatment center, and outdoors. The wrist support 28601 can be made with any anatomical and support material, such as neoprene. Coils 28603 are integrated into the wrist support 28601 such that a signal configured according to the present invention, for example the waveform depicted in FIG. 27, is applied from a dorsal portion that is the top of the wrist to a plantar portion that is the bottom of the wrist. Micro-circuitry 28604 is attached to the exterior of the wrist support 28601 using a fastening device such as Velcro® (Not Shown). The micro-circuitry is coupled to one end of at least one connecting device such as a flexible wire 28605. The other end of the at least one connecting device is coupled to the coils 28603. Other embodiments according to the present invention of the positioning device include knee, elbow, lower back, shoulder, other anatomical wraps, and apparel such as garments, fashion accessories, and footwear.

Referring to FIG. 29 an embodiment according to the present invention of an electromagnetic treatment apparatus integrated into a mattress pad 29700 is illustrated. A mattress can also be used. Several lightweight flexible coils 29701 are integrated into the mattress pad. The lightweight flexible coils can be constructed from fine flexible conductive wire, conductive thread, and any other flexible conductive material. The flexible coils are connected to at least one end of at least one wire 29702. However, the flexible coils can also be configured to be directly connected to circuitry 29703 or wireless. Lightweight miniaturized circuitry 29703 that configures waveforms according to an embodiment of the present invention, is attached to at least one other end of said at least on wire. When activated the lightweight miniaturized circuitry 29703 configures waveforms that are directed to the flexible coils (29701) to create PEMF signals that are coupled to a target pathway structure.

Referring to FIG. 30 an embodiment according to the present invention of an electromagnetic treatment inductive apparatus integrated into a chest garment 30800, such as a bra is illustrated. Several lightweight flexible coils 30801 are integrated into a bra. The lightweight flexible coils can be constructed from fine flexible conductive wire, conductive thread, and any other flexible conductive material. The flexible coils are connected to at least one end of at least one wire 30802. However, the flexible coils can also be configured to be directly connected to circuitry 30803 or wireless. Lightweight miniaturized circuitry 30803 that configures waveforms according to an embodiment of the present invention, is attached to at least one other end of said at least on wire. When activated the lightweight miniaturized circuitry 30803 configures waveforms that are directed to the flexible coils (30801) to create PEMF signals that are coupled to a target pathway structure.

EXAMPLE 1

An embodiment according to the present invention for EMF signal configuration has been used on calcium dependent myosin phosphorylation in a standard enzyme assay. This enzyme pathway is known to enhance the effects of pharmacological, chemical, cosmetic and topical agents as applied to, upon or in human, animal and plant cells, organs, tissues and molecules. The reaction mixture was chosen for phosphorylation rate to be linear in time for several minutes, and for sub-saturation $Ca^{2+}$ concentration. This opens the biological window for $Ca^{2+}$/CaM to be EMF-sensitive, as happens in an injury or with the application of pharmacological, chemical, cosmetic and topical agents as applied to, upon or in human, animal and plant cells, organs, tissues and molecules. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA. Free $Ca^{2+}$ was varied in the 1-7 µM range. Once $Ca^{2+}$ buffering was established, freshly prepared 70 nM CaM, 160 nM MLC and 2 nM MLCK were added to the basic solution to form a final reaction mixture.

The reaction mixture was freshly prepared daily for each series of experiments and was aliquoted in 100 µL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 µM $^{32}P$ ATP, and was stopped with Laemmli Sample Buffer solution containing 30 µM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting $^{32}P$ incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 µsec to 1000 µsec based upon projections of mathematical analysis of the instant invention which showed that optimal Power SNR would be achieved as burst duration approached 500 µsec. The results are shown in FIG. 9 wherein burst width 901 in µsec is plotted on the x-axis and Myosin Phosphorylation 902 as treated/sham is plotted on the y-axis. It can be seen that the PMF effect on $Ca^{2+}$ binding to CaM approaches its maximum at approximately 500 µsec, just as illustrated by the Power SNR model.

These results confirm that an EMF signal, configured according to an embodiment of the present invention, would maximally increase wound repair in human, animal and plant cells, organs, tissues and molecules for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

EMF exposure comprised two pulsed radio frequency waveforms. The first was a standard clinical PRF signal comprising a 65 µsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 µsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in $kg/mm^2$. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per $mm^2$ of the two strips from the same wound.

The results showed average tensile strength for the 65 µsec 1 Gauss PRF signal was 19.3±4.3 $kg/mm^2$ for the exposed group versus 13.0±3.5 $kg/mm^2$ for the control group (p<0.01), which is a 48% increase. In contrast, the average tensile strength for the 2000 µsec 0.2 Gauss PRF signal, configured according to an embodiment of the present invention using a Power SNR model was 21.2±5.6 $kg/mm^2$ for the treated group versus 13.7±4.1 $kg/mm^2$ (p<0.01) for the control group, which is a 54% increase. The results for the two signals were not significantly different from each other.

Non-invasive, non-thermal pulsed magnetic fields are successful therapies for healing non-union fractures, the palliative relief of pain and edema and the healing of chronic wounds. The two radio frequency EMF devices used in this study differed by burst duration, envelope, amplitude and repetition rate. That second radio frequency produced nearly identical results to those produced by first radio frequency demonstrates the validity of the EMF signal configuration according to the present invention.

The results follow the pattern observed in clinical and basic EMF studies. Applying correct dosimetry, that is the signal is detectable in the EMF-sensitive pathway, the state of the target determines the degree of effect. Thus, surrounding normal bone does not respond in a physiologically significant manner even though it receives the same EMF dosage as cells/tissue in the fracture site. The same occurs for cells in culture wherein a dependence upon cell cycle, state of tissue repair and the extracellular concentration of ions/ligands has been reported. Thus EMF has virtually no effect in the later stages of wound repair. By comparison with known biomechanical healing curve for this model, it may be estimated that the EMF treated wounds would have reached the end stage of wound repair, approximately 1.5× faster than the sham group.

At the cellular level PMF have been shown to enhance TGF-β production. EMF of the type used for bone repair significantly increased endothelial cell tubulization and proliferation, as well as fibroblast growth factor β-2, in vitro.

Additionally, EMF signals can modulate anti-CD3 binding at lymphocyte receptors, demonstrating EMF can reduce the inflammatory response. When EMF effects occur in this cutaneous wound model, accelerated healing would be achieved, both from a reduction of time in the inflammatory phase and subsequent acceleration of collagen production. The production of growth factors has been reported to be Ca/CaM (calmodulin) dependent and an EMF signal has been shown to accelerate Ca2+ binding to calmodulin. The electric field induced at tissue level from the EMF signal utilized has been shown to contain the proper frequency spectrum to be detected at Ca/CaM binding pathways. It has also been demonstrated that inductively coupled EMF bone healing signals can increase osteoblast proliferation in-vitro by direct modulation of Ca/CaM.

These results demonstrate that an embodiment of the present invention allowed a EMF signal to be configured that could be produced with significantly lower power. The PRF signal configured according to an embodiment of the present invention, accelerated wound repair in the rat model in a low power manner versus that for a clinical EMF signal which accelerated wound repair but required more than two orders of magnitude more power to produce.

EXAMPLE 3

This study demonstrated the effect of electromagnetic fields configured according an embodiment of the present invention accelerate tendon repair in an in-vivo model.

Young adult male Sprague-Dawley rats, with a mean weight of 350 g, were anesthetized with an intraperitoneal injection of a ketamine/medetomidine 75 mg/kg/0.5 mg/kg mixture. The Achilles tendon was disrupted and repaired. Using sterile surgical technique, a 2-cm midline longitudinal incision was made over the right Achilles tendon while it was stretched by flexing the right foot. Blunt dissection was used to separate the tendon from the surrounding tissue, which was then transected at the middle using a scalpel. The Achilles tendon was then immediately repaired with 6-0 nylon suture using a modified Kessler stitch. The plantaris tendon was divided and not repaired. The skin was sutured over the repaired tendon using interrupted 5-0 Ethilon. The Achilles tendon was not immobilized. Postoperatively, the animals received Ketoprofen for pain control.

On the first postoperative day, all animals were randomly assigned to four treatment groups with 10 animals in each group. Randomization followed the parallel group protocol wherein each animal was randomly assigned to one treatment group until there were ten in each group. Animals remained in their assigned group. There were three active groups that received specific EMF treatments for two 30-min sessions per day over a period of 3 weeks, and one identically treated sham group. The EMF employed in this study was a pulsed radio frequency waveform comprising a repetitive burst of 27.12 MHz sinusoidal waves emitted by a PMF-generating coil. Two configurations were employed. The first, assigned to Group 1, comprised a burst duration of 65 µsec, repeating at 600 bursts/sec with an amplitude at the tendon target of 1 gauss ("G"). The second PRF waveform comprised a burst duration of 2000 µsec, repeating at 5 bursts/sec with an amplitude at the tendon target of 0.05 G, assigned to Group 2, and 0.1 G, assigned to Group 3. Sham animals, no signal, were assigned to Group 4.

The PRF signal was delivered with a single loop coil, mounted to enable a standard rat plastic cage, with all metal portions removed, to be positioned within it. The coil was located 3.5 inches above, and horizontal to, the floor of the cage. Five freely roaming animals were treated with each coil. EMF signal amplitude was checked. Signal amplitude within the rat treatment cage over the normal range of rat movement was uniform to ±10%. Signal consistency was verified weekly. There were two cages each for the sham and active groups, and each cage had its individual coded EMF exposure system. EMF treatment was carried out twice daily for 30-min sessions until sacrifice. Sham animals were treated in identical cages equipped with identical coils.

At the end of the 3-week treatment period, the Achilles tendon was harvested by proximally severing the muscle bellies arising from the tendon and distally disarticulating the ankle, keeping the calcaneous and foot attached. All extraneous soft and hard tissues were removed from the calcaneous-Achilles tendon complex. Tensile strength testing was done immediately after harvest. The tendon, in continuity with the calcaneal bone, was fixed between two metal clamps so as to maintain a physiologically appropriate foot dorsiflexion, compared to the vertically oriented Achilles tendon. The tendons were then pulled apart at a constant speed of 0.45 mm/sec until failure, and the peak tensile strength was recorded. All analyzable tendons failed at the original transection. The tensile strengths from a total of 38 tendons were available for analysis.

Mean tensile strength was compared for each group at 3 weeks post tendon transection and data were analyzed. Tensile strength was calculated as the maximum breaking strength in kilograms per cross-sectional area in square centimeters. Tendons treated with the 65 µsec signal in Group 1 had a mean breaking strength of 99.4±14.6 kg/cm2 compared to 80.6±16.6 kg/cm2 for the sham-treated group in Group 4. This represented a 24% increase in breaking strength vs. the sham group at 21 days, which was not statistically significant ($p=0.055$). Tendons from Groups 2 and 3, treated with the 2000 µsec signals, had significantly higher mean breaking strengths of 129.4±27.8 kg/cm2 and 136.4±31.6 kg/cm2 for the 0.05 G and 0.1 G signals, respectively, vs. the sham exposure group 80.6±16.6 kg/cm2. The mean strengths for both Groups 2 and 3 were 60% and 69% higher, respectively, at the end of 3 weeks of treatment, compared to the sham group. This increase in strength was statistically significant ($p<0.001$); however, the difference in mean tensile strength between Groups 2 and 3 was not statistically significant ($p=0.541$). The differences in mean tensile strength between Group 1 (65 µsec burst) and Groups 2 and 3 (2000 µsec burst) was statistically significant ($p<0.05$).

The results presented here demonstrate that non-invasive pulsed electromagnetic fields can produce up to a 69% increase in rat Achilles tendon breaking strength vs. sham-treated tendons at 21 days post transection. All signals utilized in this study accelerated tendon repair, however greatest acceleration was obtained with waveforms configured according to a transduction mechanism involving Ca2+ binding.

In a manner similar to bone and wound repair, tendon repair for both epitenon and synovial-sheathed tendons begins with an inflammatory stage that generally involves infiltration of inflammatory cells such as macrophages, neutrophils, and T-lymphocytes. This is followed by angiogenesis, fibroblast proliferation, and collagen mainly type III, production. Finally, cells and collagen fibrils orient to achieve maximum mechanical strength. These phases all occur in bone and wound repair, in which EMF has demonstrated effects, particularly in inflammatory, angiogenesis, and cell proliferation stages.

An EMF transduction pathway involves ion binding in regulatory pathways involving growth factor release. Production of many of the growth factors and cytokines involved in tissue growth and repair is dependent on Ca/CaM calmodulin. EMF has been shown to accelerate Ca2+ binding to calmodulin. The 0.05 and 0.1 G signals utilized in this study were configured using a Ca/CaM transduction pathway. The objective was to produce sufficient electric field amplitude that is dose, within the frequency response of Ca2+ binding. This would result in a lower power, more effective signal. The model demonstrated that microsecond range burst durations satisfy these objectives at amplitudes in the 0.05 G range. The 0.1 G signal was added to assure that the small size of the rat tendon target did not limit the induced current pathway and reduce the expected dose.

EMF accelerates bone repair by accelerating return to intact breaking strength. The sham-treated fractures eventually reach the same biomechanical end point, but with increased morbidity. Biomechanical acceleration in a linear full-thickness cutaneous wound in the rat was observed. EMF accelerated wound repair by approximately 60% at 21 days, with intact breaking strength achieved about 50% sooner than the untreated wounds.

Having described embodiments for an apparatus and a method for enhancing pharmacological effects, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Part 5

An embodiment according to the present invention provides a higher spectral density to a pulse burst envelope resulting in enhanced effectiveness of therapy upon relevant dielectric pathways, such as, cellular membrane receptors, ion binding to cellular enzymes and general transmembrane potential changes. An embodiment according to the present invention increases the number of frequency components transmitted to relevant cellular pathways, thereby providing access to a larger range of biophysical phenomena applicable to known healing mechanisms, for example modulation of growth factor and cytokine release, and ion binding at regulatory molecules. By applying a random, or other high spectral density envelope, according to a mathematical model defined by SNR or Power SNR in a transduction pathway, to a pulse burst envelope of mono- or bi-polar rectangular or sinusoidal pulses inducing peak electric fields between 10-6 and 10 volts percentimeter (V/cm), a greater effect could be accomplished on biological healing processes applicable to both soft and hard tissues thereby enhancing effectiveness of pharmacological, chemical, cosmetic and topical agents.

An advantageous result of the present invention, is that by applying a high spectral density voltage envelope as the modulating or pulse-burst defining parameter, according to a mathematical model defined by SNR or Power SNR in a transduction pathway, the power requirement for such amplitude modulated pulse bursts can be significantly lower than that of an unmodulated pulse burst containing pulses within the same frequency range. Accordingly, the advantages of enhanced transmitted dosimetry to the relevant dielectric target pathways and of decreased power requirement are achieved.

An additional advantage of the present invention relates to enhanced effectiveness of pharmacological, chemical, cosmetic and topical agents as applied to, upon or on human, animal and plant cells, organs, tissues and molecules by accelerating the agents intended effects and improving efficacy.

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, for example electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("Ca2+") binding, the change in concentration of bound Ca2+ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of wound repair, for example bone repair, that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis is also integral to wound repair and modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ $sec^{-1}$, $=2.5$ μM, $K_D=30$ μM, $[Ca^{2+}CaM]=K_D(+[CaM])$, yields $k_b=665$ $sec^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kTRe[Z_M(x,\omega)]$$

where $Z_M(x, \omega)$ is electrical impedance of a target pathway structure, x is a dimension of a target pathway structure and Re denotes a real part of impedance of a target pathway structure. $Z_M(x, \omega)$ can be expressed as:

$$Z_M(x, \omega) = \left[\frac{R_e + R_i + R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)=4$ kT Re $[Z_M(x, \omega)]$ over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known tissue growth mechanisms is accessible. According to an embodiment of the present invention applying a random, or other high spectral density envelope, to a pulse burst envelope of mono- or bi-polar rectangular or sinusoidal pulses inducing peak electric fields between about $10^{-8}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 32, wherein FIG. 32 is a flow diagram of a method according to an embodiment of the present invention, for enhancing effectiveness of pharmacological, chemical, cosmetic and topical agents used to treat stem cells, tissues, cells, organs, and molecules by delivering electromagnetic signals that can be pulsed, to target pathway structures such as ions and ligands of animals and humans, for therapeutic and prophylactic purposes. Target pathway structures can also include but are not limited to stem cells, tissues, cells, organs, and molecules. Enhancing effectiveness of pharmacological, chemical, cosmetic and topical agents includes but is not limited to increased absorption rate, decreased effective dosages, faster delivery rates at an organism level; and increased binding kinetics and transport kinetics level at a molecular and cellular level. At least one reactive agent is applied to a target pathway structure (Step 32101). Reactive agents include but are not limited to pharmacological agents, chemical agents, cosmetic agents, topical agents, and genetic agents. Reactive agents can be ingested, applied topically, applied intravenously, intramuscularly, or by any other manner known within the medical community that causes interaction of substances with a target pathway structure, such as iontophoresis, X and light radiation, and heat. Pharmacological agents include but are not limited to antibiotics, growth factors, chemotherapeutic agents, antihistamines, Angiotensin inhibitors, beta blockers, statins, and anti-inflammatory drugs. Chemical agents include but are not limited to hydrogen peroxide, betadine, and alcohol. Topical agents include but are not limited to antibiotics, creams, retinol, benzoyl peroxide, tolnaftate, menthol, emollients, oils, lanolin, squalene, aloe vera, antioxidants, fatty acid, fatty acid ester, cod liver oil, alpha-tocopherol, petroleum, hydrogenated polybutene, vitamin A, vitamin E, topical proteins, and collagens. Cosmetic agents include but are not limited to make-up, eye-liner, and blush. Genetic agents include but are not limited to genes, DNA, and chromosomes.

Configuring at least one waveform having at least one waveform parameter to be coupled to the target pathway structure such as ions and ligands (Step 32102).

The at least one waveform parameter is selected to maximize at least one of a signal to noise ratio and a Power Signal to Noise ratio in a target pathway structure so that a waveform is detectable in the target pathway structure above its background activity (Step 32102) such as baseline thermal fluctuations in voltage and electrical impedance at a target pathway structure that depend upon a state of a cell and tissue, that is whether the state is at least one of resting, growing, replacing, and responding to injury to produce physiologically beneficial results. To be detectable in the target pathway structure the value of said at least one waveform parameter is chosen by using a constant of said target pathway structure to evaluate at least one of a signal to noise ratio, and a Power signal to noise ratio, to compare voltage induced by said at least one waveform in said target pathway structure to baseline thermal fluctuations in voltage and electrical impedance in said target pathway structure whereby bioeffective modulation occurs in said target pathway structure by said at least one waveform by maximizing said at least one of signal to noise ratio and Power signal to noise ratio, within a bandpass of said target pathway structure.

A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 32103). A repetitive electromagnetic signal can be generated for example inductively or capacitively, from said configured at least one waveform (Step 32104). The electromagnetic signal can also be non-repetitive. The electromagnetic signal is coupled to a target pathway structure such as ions and ligands by output of a coupling device such as an electrode or an inductor, placed in close proximity to the target pathway structure (Step 32105). Coupling of the electromagnetic signal to a target pathway structure can occur adjunctively, for example at any time prior to applying a reactive agent, at the same time a reactive agent is being applied, or after the time a reactive agent has been applied. The coupling enhances blood flow and modulation of binding of ions and ligands to regulatory molecules in molecules, tissues, cells, and organs thereby enhancing the reactive agents' bioeffectiveness.

FIG. 33 illustrates a preferred embodiment of an apparatus according to the present invention. The apparatus is self-contained, lightweight, and portable. A miniature control circuit 33201 is coupled to an end of at least one connector 33202 such as wire however the control circuit can also operate wirelessly. The opposite end of the at least one connector is coupled to a generating device such as an electrical coil 33203. The miniature control circuit 33201 is constructed in a manner that applies a mathematical model that is used to configure waveforms. The configured waveforms have to satisfy Power SNR so that for a given and known target pathway structure, it is possible to choose waveform parameters that satisfy Power SNR so that a waveform produces physiologically beneficial results, for example bioeffective modulation, and is detectable in the target pathway structure above its background activity. A preferred embodiment according to the present invention applies a mathematical model to induce a time-varying magnetic field and a time-varying electric field in a target pathway structure such as ions and ligands, comprising about 0.1 to about 100 msec bursts of about 1 to about 100 microsecond rectangular pulses repeating at about 0.1 to about 100 pulses per second. Peak amplitude of the induced electric field is between about 1 uV/cm and about 100 mV/cm, varied according to a modified 1/f function where f=frequency. A waveform configured using a preferred embodiment according to the present invention may be applied to a target pathway structure such as ions and ligands for a preferred total exposure time of under 1 minute to 240 minutes daily. However other exposure times can be used. Waveforms configured by the miniature control circuit 33201 are directed to a generating device 33203 such as electrical coils via connector 33202. The generating device 33203 delivers a pulsing magnetic field that can be used to provide treatment to a target pathway structure such as tissue. The miniature control circuit applies a pulsing magnetic field for a prescribed time and can automatically repeat applying the pulsing magnetic field for as many applications as are needed in a given time period, for example 10 times a day. The miniature control circuit can be configured to be programmable applying pulsing magnetic fields for any time repetition sequence. A preferred embodiment according to the present invention can enhance the pharmacological, chemical, cosmetic and topical agents' effectiveness by being incorporated into a positioning device 33204, for example a bed. Coupling a pulsing magnetic field to a target pathway structure such as ions and ligands, therapeutically and prophylactically reduces inflammation thereby advantageously reducing pain, promoting healing in targeted areas, and enhancing interactions of pharmacological, chemical, cosmetic and topical agents with a target pathway structure. When electrical coils are used as the generating device 33203, the electrical coils can be powered with a time varying magnetic field that induces a time varying electric field in a target pathway structure according to Faraday's law. An electromagnetic signal generated by the generating device 33203 can also be applied using electrochemical coupling, wherein electrodes are in direct contact with skin or another outer electrically conductive boundary of a target pathway structure. Yet in another embodiment according to the present invention, the electromagnetic signal generated by the generating device 33203 can also be applied using electrostatic coupling wherein an air gap exists between a generating device 33203 such as an electrode and a target pathway structure such as ions and ligands. An advantage of the preferred embodiment according to the present invention is that its ultra lightweight coils and miniaturized circuitry allow for use with common physical therapy treatment modalities and at any for which growth, pain relief, and tissue and organ healing is desired. An advantageous result of application of the preferred embodiment according to the present invention is that tissue growth, repair, and maintenance can be accomplished and enhanced anywhere and at anytime, for example while driving a car or watching television. Yet another advantageous result of application of the preferred embodiment is that growth, repair, and maintenance of molecules, cells, tissues, and organs can be accomplished and enhanced anywhere and at anytime, for example while driving a car or watching television.

FIG. 34 depicts a block diagram of a preferred embodiment according to the present invention of a miniature control circuit 34300. The miniature control circuit 34300 produces waveforms that drive a generating device such as wire coils described above in FIG. 33. The miniature control circuit can be activated by any activation means such as an on/off switch. The miniature control circuit 34300 has a power source such as a lithium battery 34301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 34302 controls voltage to a micro-controller 34303. A preferred embodiment of the micro-controller 34303 uses an 8 bit 4 MHz micro-controller 34303 but other bit MHz combination micro-controllers may be used. The switching power supply 34302 also delivers current to storage capacitors 34304. A preferred embodiment of the present invention uses storage capacitors having a 220 uF output but other outputs can be used. The storage capacitors 34304 allow high frequency pulses to be delivered to a coupling device such as inductors (Not Shown). The micro-controller 34303 also controls a pulse shaper 34305 and a pulse phase timing control 34306. The pulse shaper 34305 and pulse phase timing control 34306 determine pulse shape, burst width, burst envelope shape, and burst repetition rate. An integral waveform generator, such as a sine wave or arbitrary number generator can also be incorporated to provide specific waveforms. A voltage level conversion sub-circuit 34307 controls an induced field delivered to a target pathway structure. A switching Hexfet 34308 allows pulses of randomized amplitude to be delivered to output 34309 that routes a waveform to at least one coupling device such as an inductor. The micro-controller 34303 can also control total exposure time of a single treatment of a target pathway structure such as a molecule, cell, tissue, and organ. The miniature control circuit 34300 can be constructed to be programmable and apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Referring to FIGS. 35A and 35B a preferred embodiment according to the present invention of a coupling device 35400 such as an inductor is shown. The coupling device 35400 can be an electric coil 35401 wound with single or multistrand flexible wire 35402 however solid wire can also be used. In a preferred embodiment according to the present invention the wire is made of copper but other materials can be used. The multistrand flexible magnetic wire 35402 enables the electric coil 35401 to conform to specific anatomical configurations such as a limb or joint of a human or animal. A preferred embodiment of the electric coil 35401 comprises about 1 to about 1000 turns of about 0.01 mm to about 0.1 mm diameter at least one of single magnet wire and multistrand magnet wire, wound on an initially circular form having an outer diameter between about 2.5 cm and about 50 cm but other numbers of turns and wire diameters can be used. A preferred embodiment of the electric coil 401 can be encased with a non-toxic PVC mould 35403 but other non-toxic moulds can also be used. The electric coil can also be incorporated in dressings, bandages, garments, and other structures typically used for wound treatment.

Referring to FIG. 36 an embodiment according to the present invention of a waveform 36500 is illustrated. A pulse 36501 is repeated within a burst 36502 that has a finite duration 36503. The duration 36503 is such that a duty cycle which can be defined as a ratio of burst duration to signal period is between about 1 to about $10^{-5}$. A preferred embodiment according to the present invention utilizes pseudo rectangular 10 microsecond pulses for pulse 36501 applied in a burst 36502 for about 10 to about 50 msec having a modified 1/f amplitude envelope 36504 and with a finite duration 36503 corresponding to a burst period of between about 0.1 and about 10 seconds, but other waveforms, envelopes, and burst periods that follow a mathematical model such as SNR and Power SNR, may be used.

FIG. 37 illustrates a preferred embodiment according to the present invention of a positioning device such as a wrist support. A positioning device 37600 such as a wrist support 37601 is worn on a human wrist 37602. The positioning device can be constructed to be portable, can be constructed to be disposable, and can be constructed to be implantable. The positioning device can be used in combination with the present invention in a plurality of ways, for example incorporating the present invention into the positioning device for example by stitching, affixing the present invention onto the positioning device for example by Velcro®, and holding the present invention in place by constructing the positioning device to be elastic.

In another embodiment according to the present invention, the present invention can be constructed as a stand-alone device of any size with or without a positioning device, to be used anywhere for example at home, at a clinic, at a treatment center, and outdoors. The wrist support 601 can be made with any anatomical and support material, such as neoprene. Coils 37603 are integrated into the wrist support 37601 such that a signal configured according to the present invention, for example the waveform depicted in FIG. 36, is applied from a dorsal portion that is, the top of the wrist to a plantar portion that is the bottom of the wrist. Micro-circuitry 37604 is attached to the exterior of the wrist support 37601 using a fastening device such as Velcro®. (Not Shown). The micro-circuitry is coupled to one end of at least one connecting device such as a flexible wire 37605. The other end of the at least one connecting device is coupled to the coils 37603. Other embodiments according to the present invention of the positioning device include knee, elbow, lower back, shoulder, other anatomical wraps, and apparel such as garments, fashion accessories, and footwear.

Referring to FIG. 38 an embodiment according to the present invention of an electromagnetic treatment apparatus integrated into a mattress pad 38700 is illustrated. A mattress can also be used. Several lightweight flexible coils 38701 are integrated into the mattress pad. The lightweight flexible coils can be constructed from fine flexible conductive wire, conductive thread, and any other flexible conductive material. The flexible coils are connected to at least one end of at least one wire 38702. However, the flexible coils can also be configured to be directly connected to circuitry 38703 or wireless. Lightweight miniaturized circuitry 38703 that configures waveforms according to an embodiment of the present invention, is attached to at least one other end of said at least on wire. When activated the lightweight miniaturized circuitry 38703 configures waveforms that are directed to the flexible coils (38701) to create PEMF signals that are coupled to a target pathway structure.

EXAMPLE 1

An embodiment according to the present invention for EMF signal configuration has been used on calcium dependent myosin phosphorylation in a standard enzyme assay. This enzyme pathway is known to enhance the effects of pharmacological, chemical, cosmetic and topical agents as applied to, upon or in human, animal and plant cells, organs, tissues and molecules. The reaction mixture was chosen for phosphorylation rate to be linear in time for several minutes, and for sub-saturation $Ca^{2+}$ concentration. This opens the biological window for $Ca^{2+}$/CaM to be EMF-sensitive, as happens in an injury or with the application of pharmacological, chemical, cosmetic and topical agents as applied to, upon or in human, animal and plant cells, organs, tissues and molecules. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA. Free $Ca^{2+}$ was varied in the 1-7 µM range. Once $Ca^{2+}$ buffering was established, freshly prepared 70 nM CaM, 160 nM MLC and 2 nM MLCK were added to the basic solution to form a final reaction mixture.

The reaction mixture was freshly prepared daily for each series of experiments and was aliquoted in 100 µL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 µM 32P ATP, and was stopped with Laemmli Sample Buffer solution containing 30 µM EDTA. A minimum of five-blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32p incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 µsec to 1000 µsec based upon projections of mathematical analysis of the instant invention which showed that optimal Power SNR would be achieved as burst duration approached 500 µsec. The results are shown in FIG. 39 wherein burst width 39801 in µsec is plotted on the x-axis and Myosin Phosphorylation 39802 as treated/sham is plotted on the y-axis. It can be seen that the PMF effect on $Ca^{2+}$ binding to CaM approaches its maximum at approximately 500 µsec, just as illustrated by the Power SNR model.

These results confirm that an EMF signal, configured according to an embodiment of the present invention, would maximally increase the effect of pharmacological, chemical, cosmetic and topical agents as applied to, upon or in human, animal and plant cells, organs, tissues and molecules for burst durations sufficient to achieve optimal Power SNR for a given magnetic field amplitude.

EXAMPLE 2

This study determined to what extent treatment with pulsed electromagnetic frequency ("PEMF") waveforms affects blood perfusion in a treated region. All testing was done in a temperature controlled room (23 to 24° C.) with the subject seated on a comfortable easy chair. On each arm a non-metallic laser Doppler probe was affixed with double-sided tape to a medial forearm site approximately 5 cm distal to the antecubital space. A temperature sensing thermistor for surface temperature measurements was placed approximately 1 cm distal to the outer edge of the probes and secured with tape. A towel was draped over each forearm to diminish the direct effects of any circulating air currents.

With the subject resting comfortably, the skin temperature of each arm was monitored. During this monitoring interval the excitation coil for producing the PEMF waveform according to the instant invention was positioned directly above the Laser Doppler probe of the right forearm at a vertical distance of approximately 2 cm from the skin surface. When the monitored skin temperature reached a steady state value, the data acquisition phase was begun. This consisted of a 20 minute baseline interval followed by a 45 minute interval in which the PEMF waveform was applied.

Skin temperature was recorded at five minute intervals during the entire protocol. Blood perfusion signals as determined with the Laser Doppler Flowmeter ("LDF") were continuously displayed on a chart recorder and simultaneously acquired by a computer following analog to digital conversion. The LDF signals were time averaged by the computer during each contiguous five minute interval of measurement to produce a single averaged perfusion value for each interval. At the end of the procedure the relative magnetic field strength at the skin site was measured with a 1 cm diameter loop which was coupled to a specially designed and calibrated metering system.

For each subject the baseline perfusion for the treated arm and the control arm was determined as the average during the 20 minute baseline interval. Subsequent perfusion values, following the start of PEMF treatment, was expressed as a percentage of this baseline. Comparison between the treated and control arms were done using analysis of variance with arm (treated vs. control) as the grouping variables and with time as a repeated measure.

FIG. 40 summarizes the time course of the perfusion change found during treatment for the nine subjects studied with time being plotted on the x-axis 40901 and perfusion on the y-axis 40902. Analysis shows significant treatment-time interaction (p=0.03) with a significantly (p<0.01) elevated blood perfusion in the treated arm after 40 minutes of PEMF treatment. The absolute values of baseline perfusion (mv) did not differ between control and treated arms. Analysis of covariance with the baseline perfusion in absolute units (mv) as the covariate also shows an overall difference between treated and control arms (p<0.01).

A main finding of the present investigational study is that PEMF treatment, when applied in the manner described, is associated with a significant augmentation in their resting forearm skin microvascular perfusion. This augmentation, which averages about 30% as compared with resting pretreatment levels, occurs after about 40 minutes of treatment whereas no such augmentation is evident in the contralateral non-treated arm. This allows the increased flow of pharmacological, chemical, topical, cosmetic, and genetic agents to the intended tissue target.

Having described embodiments for an apparatus and a method for enhancing pharmacological effects, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Part 6

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where ω is angular frequency defined as 2πf, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of tissue repair, for example bone repair, wound repair, hair repair, and repair of other molecules, cells, tissues, and organs that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to tissue growth and repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ $sec^{-1}$, $=2.5$ μM, $K_D=30$ μM, $[Ca^{2+}CaM]=K_D(+[CaM])$, yields $k_b=665$ $sec^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kTRe[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x,\omega) = \left[\frac{R_e + R_i + R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to target pathway structures, all contribute to noise filtering.

A typical approach to evaluation of SNR uses a single value of a root mean square (RMS) noise voltage. This is calculated by taking a square root of an integration of $S_n(\omega)=4$ kT $Re[Z_M(x,\omega)]$ over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known tissue growth mechanisms is accessible. According to an embodiment of the present invention applying a random, or other high spectral density envelope, to a pulse burst envelope of mono- or bi-polar rectangular or sinusoidal pulses inducing peak electric fields between about $10^{-8}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 41, wherein FIG. 41 is a flow diagram of a method for delivering electromagnetic signals to tissue target pathway structures such as ions and ligands of animals, and humans for therapeutic and prophylactic purposes according to an embodiment of the present invention. A mathematical model having at least one waveform parameter is applied to configure at least one waveform to be coupled to target pathway structures such as ions and ligands (Step 41101). The configured waveform satisfies a Power SNR model so that for a given and known target pathway structure it is possible to choose at least one waveform parameter so that a waveform is detectable in the target pathway structure above its background activity (Step 41102) such as baseline thermal fluctuations in voltage and electrical impedance at a target pathway structure that depend upon a state of a cell and tissue, that is whether the state is at least one of resting, growing, replacing, and responding to injury.

A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 41102). A repetitive electromagnetic signal can be generated for example inductively or capacitively, from said configured at least one waveform (Step 41103). The electromagnetic signal is coupled to a target pathway structure such as ions and ligands by output of a coupling device such as an electrode or an inductor, placed in close proximity to the target pathway structure (Step 41104) using a positioning device by integrating the coupling device with the positioning device (Step 41105). The coupling enhances modulation of binding of ions and ligands to regulatory molecules tissues, cells, and organs. The coupling device can be integrated into the structure of the positioning device. The positioning device can be surgical dressings, wound dressings, pads, seat cushions, mattress pads, shoes, wheelchairs, chairs, and any other garment and structure that can be juxtaposed to living tissue and cells. An advantage of integrating the coupling device with a positioning device is that therapeutic treatment can be administered in an unnoticeable fashion and can be administered anywhere and at anytime.

FIG. 42 illustrates a preferred embodiment of an apparatus according to the present invention. The apparatus is self-contained, lightweight, and portable. A miniature control circuit 42201 is coupled to an end of at least one connector 42202 such as wire however the control circuit can also operate wirelessly. The opposite end of the at least one connector is coupled to a generating device such as an electrical coil 42203. The miniature control circuit 42201 is constructed in a manner that applies a mathematical model that is used to configure waveforms. The configured waveforms have to satisfy a Power SNR model so that for a given and known target pathway structure, it is possible to choose waveform parameters that satisfy Power SNR so that a waveform is detectable in the target pathway structure above its background activity. A preferred embodiment according to the present invention applies a mathematical model to induce a time-varying magnetic field and a time-varying electric field in a target pathway structure such as ions and ligands, comprising about 0.1 to about 100 msec bursts of about 1 to about 100 microsecond rectangular pulses repeating at about 0.1 to about 100 pulses per second. Peak amplitude of the induced electric field is between about 1 uV/cm and about 100 mV/cm, varied according to a modified 1/f function where f=frequency. A waveform configured using a preferred embodiment according to the present invention may be applied to a target pathway structure such as ions and ligands for a preferred total exposure time of under 1 minute to 240 minutes daily. However other exposure times can be used. Waveforms configured by the miniature control circuit 42201 are directed to a generating device 42203 such as electrical coils via connector 42202. The generating device 42203 delivers a pulsing magnetic field configured according to a mathematical model that can be used to provide treatment to a target pathway structure such as skin tissue. The miniature control circuit applies a pulsing magnetic field for a prescribed time and can automatically repeat applying the pulsing magnetic field for as many applications as are needed in a given time period, for example 10 times a day. The miniature control circuit can be configured to be programmable applying pulsing magnetic fields for any time repetition sequence. A preferred embodiment according to the present invention can be positioned to treat hair 42204 by being incorporated with a positioning device thereby making the unit self-contained. Coupling a pulsing magnetic field to a target pathway structure such as ions and ligands, therapeutically and prophylactically reduces inflammation thereby reducing pain and promotes healing in treatment areas. When electrical coils are used as the generating device 42203, the electrical coils can be powered with a time varying magnetic field that induces a time varying electric field in a target pathway structure according to Faraday's law. An electromagnetic signal generated by the generating device 42203 can also be applied using electrochemical coupling, wherein electrodes are in direct contact with skin or another outer electrically conductive boundary of a target pathway structure. Yet in another embodiment according to the present invention, the electromagnetic signal generated by the generating device 42203 can also be applied using electrostatic coupling wherein an air gap exists between a generating device 42203 such as an electrode and a target pathway structure such as ions and ligands. An advantage of the preferred embodiment according to the present invention is that its ultra lightweight coils and miniaturized circuitry allow for use with common physical therapy treatment modalities and at any location for which tissue growth, pain relief, and tissue and organ healing is desired. An advantageous result of application of the preferred embodiment according to the present invention is that tissue growth, repair, and maintenance can be accomplished and enhanced anywhere and at anytime. Yet another advantageous result of application of the preferred embodiment is that growth, repair, and maintenance of molecules, cells, tissues, and organs can be accomplished and enhanced anywhere and at anytime.

FIG. 43 depicts a block diagram of a preferred embodiment according to the present invention of a miniature control circuit 43300. The miniature control circuit 43300 produces waveforms that drive a generating device such as wire coils described above in FIG. 42. The miniature control circuit can be activated by any activation means such as an on/off switch. The miniature control circuit 43300 has a power source such as a lithium battery 43301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 43302 controls voltage to a micro-controller 43303. A preferred embodiment of the micro-controller 43303 uses an 8 bit 4 MHz micro-controller 43303 but other bit MHz combination micro-controllers may be used. The switching power supply 43302 also delivers current to storage capacitors 43304. A preferred embodiment of the present invention uses storage capacitors having a 220 uF output but other outputs can be used. The storage capacitors 43304 allow high frequency pulses to be delivered to a coupling device such as inductors (Not Shown). The micro-controller 43303 also controls a pulse shaper 43305 and a pulse phase timing control 43306. The pulse shaper 43305 and pulse phase timing control 43306 determine pulse shape, burst width, burst envelope shape, and burst repetition rate. An integral waveform generator, such as a sine wave or arbitrary number generator can also be incorporated to provide specific waveforms. A voltage level conversion sub-circuit 43308 controls an induced field delivered to a target pathway structure. A switching Hexfet 43308 allows pulses of randomized amplitude to be delivered to output 43309 that routes a waveform to at least one coupling device such as an inductor. The micro-controller 43303 can also control total exposure time of a single treatment of a target pathway structure such as a molecule, cell, tissue, and organ. The miniature control circuit 43300 can be constructed to be programmable and apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes. The miniature control circuit 43300 can also be integrated with a positioning device. The positioning device can also include at least one of a therapeutic surface, a therapeutic structure, and a therapeutic device, such as diathermy, ultrasound, TENS, massage, heat compress, cold compress, anatomical support surfaces, structures, and devices.

Referring to FIG. 44 an embodiment according to the present invention of a waveform 44400 is illustrated. A pulse 44401 is repeated within a burst 44402 that has a finite duration 44403. The duration 44403 is such that a duty cycle which can be defined as a ratio of burst duration to signal period is between about 1 to about $10^{-5}$. A preferred embodiment according to the present invention utilizes pseudo rectangular 10 microsecond pulses for pulse 44401 applied in a burst 44402 for about 10 to about 50 msec having a modified 1/f amplitude envelope 44404 and with a finite duration 44403 corresponding to a burst period of between about 0.1 and about 10 seconds.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA12. Free $Ca^{2+}$ was varied in the 1-7 µM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 µL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 µM 32P ATP, and was stopped with Laemmli Sample Buffer solution containing 30 µM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 µsec to 1000 µsec based upon projections of Power SNR analysis which showed that optimal Power SNR would be achieved as burst duration approached 500 µsec. The results are shown in FIG. 7 wherein burst width 701 in µsec is plotted on the x-axis and Myosin Phosphorylation 702 as treated/sham is plotted on the y-axis. It can be seen that the PMF effect on $Ca^{2+}$ binding to CaM approaches its maximum at approximately 500 µsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 μsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 μsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in kg/mm$^2$. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per mm$^2$ of the two strips from the same wound.

The results showed average tensile strength for the 65 μsec 1 Gauss PRF signal was 19.3±4.3 kg/mm$^2$ for the exposed group versus 13.0±3.5 kg/mm$^2$ for the control group (p<0.01), which is a 48% increase. In contrast, the average tensile strength for the 2000 μsec 0.2 Gauss PRF signal, configured according to an embodiment of the present invention using a Power SNR model was 21.2±5.6 kg/mm$^2$ for the treated group versus 13.7±4.1 kg/mm$^2$ (p<0.01) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

This example illustrates the effects of PRF electromagnetic fields chosen via the Power SNR method on neurons in culture.

Primary cultures were established from embryonic days 15-16 rodent mesencephalon. This area is dissected, dissociated into single cells by mechanical trituration, and cells are plated in either defined medium or medium with serum. Cells are typically treated after 6 days of culture, when neurons have matured and developed mechanisms that render them vulnerable to biologically relevant toxins. After treatment, conditioned media is collected.

Enzyme linked immunosorbent assays ("ELISAs") for growth factors such as Fibroblast Growth Factor beta ("FGFb") are used to quantify their release into the medium. Dopaminergic neurons are identified with an antibody to tyrosine hydroxylase ("TH"), an enzyme that converts the amino acid tyrosine to L-dopa, the precursor of dopamine, since dopaminergic neurons are the only cells that produce this enzyme in this system. Cells are quantified by counting TH+ cells in perpendicular strips across the culture dish under 100× magnification.

Serum contains nutrients and growth factors that support neuronal survival. Elimination of serum induces neuronal cell death. Culture media was changed and cells were exposed to PMF (power level 6, burst width 3000 μsec, and frequency 1 Hz). Four groups were utilized. Group 1 used No PMF exposure (null group). Group 2 used Pre-treatment (PMF treatment 2 hours before medium change). Group 3 used Post-treatment (PMF treatment 2 hours after medium change). Group 4 used Immediate treatment (PMF treatment simultaneous to medium change).

Results demonstrate a 46% increase in the numbers of surviving dopaminergic neurons after 2 days when cultures were exposed to PMF prior to serum withdrawal. Other treatment regimes had no significant effects on numbers of surviving neurons. The results are shown in FIG. 6 where type of treatment is shown on the x-axis and number of neurons is shown on the y-axis.

FIG. 7, where treatment is shown on the x-axis and number of neurons is shown on the y-axis, illustrates that PMF signals D and E increase numbers of dopaminergic neurons after reducing serum concentrations in the medium by 46% and 48% respectively. Both signals were configured with a burst width of 3000 μsec, and the repetition rates are 5/sec and 1/sec, respectively. Notably, signal D was administered in a chronic paradigm in this experiment, but signal E was administered only once: 2 hours prior to serum withdrawal, identical to experiment 1 (see above), producing effects of the same magnitude (46% vs. 48%). Since the reduction of serum in the medium reduces the availability of nutrients and growth factors, PMF induces the synthesis or release of these factors by the cultures themselves.

This portion of the experiment was performed to illustrate the effects of PMF toxicity induced by 6-OHDA, producing a well-characterized mechanism of dopaminergic cell death. This molecule enters cells via high affinity dopamine transporters and inhibits mitochondrial enzyme complex I, thus killing these neurons by oxidative stress. Cultures were treated with 25 μM 6-OHDA after chronic, or acute PMF exposure paradigms. FIG. 8 illustrates these results, where treatment is shown on the x-axis and number of neurons is shown on the y-axis. The toxin killed approximately 80% of the dopaminergic neurons in the absence of PMF treatment. One dose of PMF (power=6; burst width=3000 μsec; frequency=1/sec) significantly increased neuronal survival over 6-OHDA alone (2.6-fold; p≤0.02). This result has particular relevance to developing neuroprotection strategies for Parkinson's disease, because 6-OHDA is used to lesion dopaminergic neurons in the standard rodent model of Parkinson's disease, and the mechanism of toxicity is similar in some ways to the mechanism of neurodegeneration in Parkinson's disease itself.

EXAMPLE 4

In this example electromagnetic field energy was used to stimulate neovascularization in an in vivo model. Two different signal were employed, one configured according to prior art and a second configured according to an embodiment of the present invention.

One hundred and eight Sprague-Dawley male rats weighing approximately 300 grams each, were equally divided into nine groups. All animals were anesthetized with a mixture of ketamine/acepromazine/Stadol at 0.1 cc/g. Using sterile surgical techniques, each animal had a 12 cm to 14 cm segment of tail artery harvested using microsurgical technique. The artery was flushed with 60 U/ml of heparinized saline to remove any blood or emboli.

These tail vessels, with an average diameter of 0.4 mm to 0.5 mm, were then sutured to the transected proximal and distal segments of the right femoral artery using two end-to-end anastomoses, creating a femoral arterial loop. The resulting loop was then placed in a subcutaneous pocket created over the animal's abdominal wall/groin musculature, and the groin incision was closed with 4-0 Ethilon. Each animal was then randomly placed into one of nine groups: groups 1 to 3 (controls), these rats received no electromagnetic field treatments and were killed at 4, 8, and 12 weeks; groups 4 to 6, 30 min. treatments twice a day using 0.1 gauss electromagnetic fields for 4, 8, and 12 weeks (animals were killed at 4, 8, and 12 weeks, respectively); and groups 7 to 9, 30 min. treatments twice a day using 2.0 gauss electromagnetic fields for 4, 8, and 12 weeks (animals were killed at 4, 8, and 12 weeks, respectively).

Pulsed electromagnetic energy was applied to the treated groups using a device constructed according to an embodiment of the present invention. Animals in the experimental groups were treated for 30 minutes twice a day at either 0.1 gauss or 2.0 gauss, using short pulses (2 msec to 20 msec) 27.12 MHz. Animals were positioned on top of the applicator head and confined to ensure that treatment was properly applied. The rats were reanesthetized with ketamine/acepromazine/Stadol intraperitoneally and 100 U/kg of heparin intravenously. Using the previous groin incision, the femoral artery was identified and checked for patency. The femoral/tail artery loop was then isolated proximally and distally from the anastomoses sites, and the vessel was clamped off. Animals were then killed. The loop was injected with saline followed by 0.5 cc to 1.0 cc of colored latex through a 25-gauge cannula and clamped. The overlying abdominal skin was carefully resected, and the arterial loop was exposed. Neovascularization was quantified by measuring the surface area covered by new blood-vessel formation delineated by the intraluminal latex. All results were analyzed using the SPSS statistical analysis package.

The most noticeable difference in neovascularization between treated versus untreated rats occurred at week 4. At that time, no new vessel formation was found among controls, however, each of the treated groups had similar statistically significant evidence of neovascularization at 0 cm2 versus 1.42±0.80 cm2 (p<0.001). These areas appeared as a latex blush segmentally distributed along the sides of the arterial loop. At 8 weeks, controls began to demonstrate neovascularization measured at 0.7±0.82 cm2. Both treated groups at 8 weeks again had approximately equal statistically significant (p<0.001) outcroppings of blood vessels of 3.57±1.82 cm2 for the 0.1 gauss group and of 3.77±1.82 cm2 for the 2.0 gauss group. At 12 weeks, animals in the control group displayed 1.75±0.95 cm2 of neovascularization, whereas the 0.1 gauss group demonstrated 5.95±3.25 cm2, and the 2.0 gauss group showed 6.20±3.95 cm2 of arborizing vessels. Again, both treated groups displayed comparable statistically significant findings (p<0.001) over controls.

These experimental findings demonstrate that electromagnetic field stimulation of an isolated arterial loop according to an embodiment of the present invention increases the amount of quantifiable neovascularization in an in vivo rat model. Increased angiogenesis was demonstrated in each of the treated groups at each of the sacrifice dates. No differences were found between the results of the two gauss levels tested as predicted by the teachings of the present invention.

Having described embodiments for an integrated coil apparatus for therapeutically treating human and animal cells, tissues, and organs with electromagnetic fields and method for using same, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Part 7

Induced time-varying currents from PEMF or PRF devices flow in a hair and cerebrofacial target pathway structure such as a molecule, cell, tissue, and organ, and it is these currents that are a stimulus to which cells and tissues can react in a physiologically meaningful manner. The electrical properties of a hair and cerebrofacial target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of tissue repair, for example bone repair, wound repair, hair repair, and repair of other cerebrofacial molecules, cells, tissues, and organs that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to tissue growth and repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ sec$^{-1}$, $=2.5$ μM, $K_D=30$ μM, $[Ca^{2+}CaM]=K_D(+[CaM])$, yields $k_b=665$ sec$^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model for example a mathematical equation and or a series of mathematical equations can be configured to assimilate that thermal noise is present in all voltage dependent processes and represents a minimum threshold requirement to establish adequate SNR. For example a mathematical model that represents a minimum threshold requirement to establish adequate SNR can be configured to include power spectral density of thermal noise such that power spectral density, $S_n(\omega)$, of thermal noise can be expressed as:

$$S_n(\omega)=4kTRe[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x,\omega) = \left[\frac{R_e + R_i + R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a hair and other cerebrofacial target pathway structures, all contribute to noise filtering.

A typical approach to evaluation of SNR uses a single value of a root mean square (RMS) noise voltage. This is calculated by taking a square root of an integration of $S_n(\omega)=4$ kT Re[$Z_M$(x, $\omega$)] over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known hair and other cerebrofacial tissue growth mechanisms is accessible. According to an embodiment of the present invention applying a random, or other high spectral density envelope, to a pulse burst envelope of mono- or bi-polar rectangular or sinusoidal pulses inducing peak electric fields between about $10^{-8}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 48, wherein FIG. 48 is a flow diagram of a method for delivering electromagnetic signals that can be pulsed, to hair and cerebrofacial tissue target pathway structures such as ions and ligands of animals, and humans for therapeutic and prophylactic purposes according to an embodiment of the present invention.

At least one waveform having at least one waveform parameter is configured to be coupled to hair and cerebrofacial target pathway structures such as ions and ligands (Step 48101). Hair and cerebrofacial target pathway structures are located in a cerebrofacial treatment area. Examples of a cerebrofacial treatment area include but are not limited to, hair, a brain, sinuses, adenoids, tonsils, eyes, a nose, ears, teeth, and a tongue.

The at least one waveform parameter is selected to maximize at least one of a signal to noise ratio and a Power Signal to Noise ratio in a hair and cerebrofacial target pathway structure so that a waveform is detectable in the hair and cerebofacial target pathway structure above its background activity (Step 48102) such as baseline thermal fluctuations in voltage and electrical impedance at a target pathway structure that depend upon a state of a cell and tissue, that is whether the state is at least one of resting, growing, replacing, and responding to injury to produce physiologically beneficial results. To be detectable in the hair and cerebrofacial target pathway structure the value of said at least one waveform parameter is chosen by using a constant of said target pathway structure to evaluate at least one of a signal to noise ratio, and a Power signal to noise ratio, to compare voltage induced by said at least one waveform in said target pathway structure to baseline thermal fluctuations in voltage and electrical impedance in said target pathway structure whereby bioeffective modulation occurs in said target pathway structure by said at least one waveform by maximizing said at least one of signal to noise ratio and Power signal to noise ratio, within a bandpass of said target pathway structure.

A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 48102). A repetitive electromagnetic signal can be generated for example inductively or capacitively, from said configured at least one waveform (Step 48103). The electromagnetic signal can also be non-repetitive. The electromagnetic signal is coupled to a hair and cerebrofacial target pathway structure such as ions and ligands by output of a coupling device such as an electrode or an inductor, placed in close proximity to the target pathway structure (Step 48104). The coupling enhances modulation of binding of ions and ligands to regulatory molecules in hair and other cerebrofacial molecules, tissues, cells, and organs.

FIG. 49 illustrates a preferred embodiment of an apparatus according to the present invention. The apparatus is self-contained, lightweight, and portable. A miniature control circuit 49201 is coupled to an end of at least one connector 49202 such as wire however the control circuit can also operate wirelessly. The opposite end of the at least one connector is coupled to a generating device such as an electrical coil 49203. The miniature control circuit 49201 is constructed in a manner that applies a mathematical model that is used to configure waveforms. The configured waveforms have to satisfy Power SNR so that for a given and known hair and cerebrofacial target pathway structure, it is possible to choose waveform parameters that satisfy Power SNR so that a waveform produces physiologically beneficial results, for example bioeffective modulation, and is detectable in the hair and cerebrofacial target pathway structure above its background activity. A preferred embodiment according to the present invention applies a mathematical model to induce a time-varying magnetic field and a time-varying electric field in a hair and cerebrofacial target pathway structure such as ions and ligands, comprising about 0.1 to about 100 msec bursts of about 1 to about 100 microsecond rectangular pulses repeating at about 0.1 to about 100 pulses per second. Peak amplitude of the induced electric field is between about 1 uV/cm and about 100 mV/cm, varied according to a modified 1/f function where f=frequency. A waveform configured using a preferred embodiment according to the present invention may be applied to a hair and cerebrofacial target pathway structure such as ions and ligands for a preferred total exposure time of under 1 minute to 240 minutes daily. However other exposure times can be used. Waveforms configured by the miniature control circuit 49201 are directed to a generating device 49203 such as electrical coils via connector 49202. The generating device 49203 delivers a pulsing magnetic field that can be used to provide treatment to a hair and cerebrofacial target pathway structure such as hair tissue. The miniature control circuit applies a pulsing magnetic field for a prescribed time and can automatically repeat applying the pulsing magnetic field for as many applications as are needed in a given time period, for example 10 times a day. The miniature control circuit can be configured to be programmable applying pulsing magnetic fields for any time repetition sequence. A preferred embodiment according to the present invention can be positioned to treat hair 49204 by being incorporated into a positioning device thereby making the unit self-contained. Coupling a pulsing magnetic field to a hair and cerebrofacial target pathway structure such as ions and ligands, therapeutically and prophylactically reduces inflammation thereby advantageously reducing pain and promoting healing in cerebrofacial areas. When electrical coils are used as the generating device 49203, the electrical coils can be powered with a time varying magnetic field that induces a time varying electric field in a target pathway structure according to Faraday's law. An electromagnetic signal generated by the generating device 49203 can also be applied using electrochemical coupling, wherein electrodes are in direct contact with skin or another outer electrically conductive boundary of a hair and cerebrofacial target pathway structure. Yet in another embodiment according to the present invention, the electromagnetic signal generated by the generating device 49203 can also be applied using electrostatic coupling wherein an air gap exists between a generating device 49203 such as an electrode and a hair and cerebrofacial target pathway structure such as ions and ligands. An advantage of the preferred embodiment according to the present invention is that its ultra lightweight coils and miniaturized circuitry allow for use with common physical therapy treatment modalities and at any cerebrofacial location for which hair growth, pain relief, and tissue and organ healing is desired. An advantageous result of application of the preferred embodiment according to the present invention is that hair growth, repair, and maintenance can be accomplished and enhanced anywhere and at anytime, for example while driving a car or watching television. Yet another advantageous result of application of the preferred embodiment is that growth, repair, and maintenance of cerebrofacial molecules, cells, tissues, and organs can be accomplished and enhanced anywhere and at anytime, for example while driving a car or watching television.

FIG. 50 depicts a block diagram of a preferred embodiment according to the present invention of a miniature control circuit 50300. The miniature control circuit 50300 produces waveforms that drive a generating device such as wire coils described above in FIG. 49. The miniature control circuit can be activated by any activation means such as an on/off switch. The miniature control circuit 50300 has a power source such as a lithium battery 50301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 50302 controls voltage to a micro-controller 50303. A preferred embodiment of the micro-controller 50303 uses an 8 bit 4 MHz micro-controller 50303 but other bit MHz combination micro-controllers may be used. The switching power supply 50302 also delivers current to storage capacitors 50304. A preferred embodiment of the present invention uses storage capacitors having a 220 uF output but other outputs can be used. The storage capacitors 50304 allow high frequency pulses to be delivered to a coupling device such as inductors (Not Shown). The micro-controller 50303 also controls a pulse shaper 50305 and a pulse phase timing control 50306. The pulse shaper 50305 and pulse phase timing control 50306 determine pulse shape, burst width, burst envelope shape, and burst repetition rate. An integral waveform generator, such as a sine wave or arbitrary number generator can also be incorporated to provide specific waveforms. A voltage level conversion sub-circuit 50307 controls an induced field delivered to a target pathway structure. A switching Hexfet 50308 allows pulses of randomized amplitude to be delivered to output 50309 that routes a waveform to at least one coupling device such as an inductor. The micro-controller 50303 can also control total exposure time of a single treatment of a hair and cerebrofacial target pathway structure such as a molecule, cell, tissue, and organ. The miniature control circuit 50300 can be constructed to be programmable and apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

Referring to FIG. 51 an embodiment according to the present invention of a waveform 51400 is illustrated. A pulse 51401 is repeated within a burst 51402 that has a finite duration 51403. The duration 51403 is such that a duty cycle which can be defined as a ratio of burst duration to signal period is between about 1 to about $10^{-5}$. A preferred embodiment according to the present invention utilizes pseudo rectangular 10 microsecond pulses for pulse 51401 applied in a burst 51402 for about 10 to about 50 msec having a modified 1/f amplitude envelope 51404 and with a finite duration 51403 corresponding to a burst period of between about 0.1 and about 10 seconds.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA12. Free $Ca^{2+}$ was varied in the 1-7 μM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 μL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 μM 32P ATP, and was stopped with Laemmli Sample Buffer solution containing 30 μM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 μsec to 1000 μsec based upon projections of Power SNR analysis which showed that optimal Power SNR would be achieved as burst duration approached 500 μsec. The results are shown in FIG. 52 wherein burst width 52501 in μsec is plotted on the x-axis and Myosin Phosphorylation 52502 as treated/sham is plotted on the y-axis. It can be seen that the PMF effect on $Ca^{2+}$ binding to CaM approaches its maximum at approximately 500 μsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 μsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 μsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in kg/mm$^2$. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per mm$^2$ of the two strips from the same wound.

The results showed average tensile strength for the 65 μsec 1 Gauss PRF signal was 19.3±4.3 kg/mm$^2$ for the exposed group versus 13.0±3.5 kg/mm$^2$ for the control group (p<0.01), which is a 48% increase. In contrast, the average tensile strength for the 2000 μsec 0.2 Gauss PRF signal, configured according to an embodiment of the present invention using a Power SNR model was 21.2±5.6 kg/mm$^2$ for the treated group versus 13.7±4.1 kg/mm$^2$ (p<0.01) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

This example illustrates the effects of PRF electromagnetic fields chosen via the Power SNR method on neurons in culture.

Primary cultures were established from embryonic days 15-16 rodent mesencephalon. This area is dissected, dissociated into single cells by mechanical trituration, and cells are plated in either defined medium or medium with serum. Cells are typically treated after 6 days of culture, when neurons have matured and developed mechanisms that render them vulnerable to biologically relevant toxins. After treatment, conditioned media is collected.

Enzyme linked immunosorbent assays ("ELISAs") for growth factors such as Fibroblast Growth Factor beta ("FGFb") are used to quantify their release into the medium. Dopaminergic neurons are identified with an antibody to tyrosine hydroxylase ("TH"), an enzyme that converts the amino acid tyrosine to L-dopa, the precursor of dopamine, since dopaminergic neurons are the only cells that produce this enzyme in this system. Cells are quantified by counting TH+ cells in perpendicular strips across the culture dish under 100× magnification.

Serum contains nutrients and growth factors that support neuronal survival. Elimination of serum induces neuronal cell death. Culture media was changed and cells were exposed to PMF (power level 6, burst width 3000 μsec, and frequency 1 Hz). Four groups were utilized. Group 1 used No PMF exposure (null group). Group 2 used Pre-treatment (PMF treatment 2 hours before medium change). Group 3 used Post-treatment (PMF treatment 2 hours after medium change). Group 4 used Immediate treatment (PMF treatment simultaneous to medium change).

Results demonstrate a 46% increase in the numbers of surviving dopaminergic neurons after 2 days when cultures were exposed to PMF prior to serum withdrawal. Other treatment regimes had no significant effects on numbers of surviving neurons. The results are shown in FIG. 53 where type of treatment is shown on the x-axis and number of neurons is shown on the y-axis.

FIG. 53, where treatment 53601 is shown on the x-axis and number of neurons 53602 is shown on the y-axis, illustrates that PMF signals D and E increase numbers of dopaminergic neurons after reducing serum concentrations in the medium by 46% and 48% respectively. Both signals were configured with a burst width of 3000 μsec, and the repetition rates are 5/sec and 1/sec, respectively. Notably, signal D was administered in a chronic paradigm in this experiment, but signal E was administered only once: 2 hours prior to serum withdrawal, identical to experiment 1 (see above), producing effects of the same magnitude (46% vs. 48%). Since the reduction of serum in the medium reduces the availability of nutrients and growth factors, PMF induces the synthesis or release of these factors by the cultures themselves.

This portion of the experiment was performed to illustrate the effects of PMF toxicity induced by 6-OHDA, producing a well-characterized mechanism of dopaminergic cell death. This molecule enters cells via high affinity dopamine transporters and inhibits mitochondrial enzyme complex I, thus killing these neurons by oxidative stress. Cultures were treated with 25 μM 6-hydroxydopamine ("6-OHDA") after chronic, or acute PMF exposure paradigms. FIG. 54 illustrates these results, where treatment 54701 is shown on the x-axis and number of neurons 54702 is shown on the y-axis. The toxin killed approximately 80% of the dopaminergic neurons in the absence of PMF treatment. One dose of PMF (power=6; burst width=3000 μsec; frequency=1/sec) significantly increased neuronal survival over 6-OHDA alone (2.6-fold; p≤0.02). This result has particular relevance to developing neuroprotection strategies for Parkinson's disease, because 6-OHDA is used to lesion dopaminergic neurons in the standard rodent model of Parkinson's disease, and the mechanism of toxicity is similar in some ways to the mechanism of neurodegeneration in Parkinson's disease itself.

EXAMPLE 4

In this example electromagnetic field energy was used to stimulate neovascularization in an in vivo model. Two different signal were employed, one configured according to prior art and a second configured according to an embodiment of the present invention.

One hundred and eight Sprague-Dawley male rats weighing approximately 300 grams each, were equally divided into nine groups. All animals were anesthetized with a mixture of ketamine/acepromazine/Stadol at 0.1 cc/g. Using sterile surgical techniques, each animal had a 12 cm to 14 cm segment of tail artery harvested using microsurgical technique. The artery was flushed with 60 U/ml of heparinized saline to remove any blood or emboli.

These tail vessels, with an average diameter of 0.4 mm to 0.5 mm, were then sutured to the transected proximal and distal segments of the right femoral artery using two end-to-end anastomoses, creating a femoral arterial loop. The resulting loop was then placed in a subcutaneous pocket created over the animal's abdominal wall/groin musculature, and the groin incision was closed with 4-0 Ethilon. Each animal was then randomly placed into one of nine groups: groups 1 to 3 (controls), these rats received no electromagnetic field treatments and were killed at 4, 8, and 12 weeks; groups 4 to 6, 30 min. treatments twice a day using 0.1 gauss electromagnetic fields for 4, 8, and 12 weeks (animals were killed at 4, 8, and 12 weeks, respectively); and groups 7 to 9, 30 min. treatments twice a day using 2.0 gauss electromagnetic fields for 4, 8, and 12 weeks (animals were killed at 4, 8, and 12 weeks, respectively).

Pulsed electromagnetic energy was applied to the treated groups using a device constructed according to an embodiment of the present invention. Animals in the experimental groups were treated for 30 minutes twice a day at either 0.1 gauss or 2.0 gauss, using short pulses (2 msec to 20 msec) 27.12 MHz. Animals were positioned on top of the applicator head and confined to ensure that treatment was properly applied. The rats were reanesthetized with ketamine/acepromazine/Stadol intraperitoneally and 100 U/kg of heparin intravenously. Using the previous groin incision, the femoral artery was identified and checked for patency. The femoral/tail artery loop was then isolated proximally and distally from the anastomoses sites, and the vessel was clamped off. Animals were then killed. The loop was injected with saline followed by 0.5 cc to 1.0 cc of colored latex through a 25-gauge cannula and clamped. The overlying abdominal skin was carefully resected, and the arterial loop was exposed. Neovascularization was quantified by measuring the surface area covered by new blood-vessel formation delineated by the intraluminal latex. All results were analyzed using the SPSS statistical analysis package.

The most noticeable difference in neovascularization between treated versus untreated rats occurred at week 4. At that time, no new vessel formation was found among controls, however, each of the treated groups had similar statistically significant evidence of neovascularization at 0 cm2 versus 1.42±0.80 cm2 (p<0.001). These areas appeared as a latex blush segmentally distributed along the sides of the arterial loop. At 8 weeks, controls began to demonstrate neovascularization measured at 0.7±0.82 cm2. Both treated groups at 8 weeks again had approximately equal statistically significant (p<0.001) outcroppings of blood vessels of 3.57±1.82 cm2 for the 0.1 gauss group and of 3.77±1.82 cm2 for the 2.0 gauss group. At 12 weeks, animals in the control group displayed 1.75±0.95 cm2 of neovascularization, whereas the 0.1 gauss group demonstrated 5.95±3.25 cm2, and the 2.0 gauss group showed 6.20±3.95 cm2 of arborizing vessels. Again, both treated groups displayed comparable statistically significant findings (p<0.001) over controls.

These experimental findings demonstrate that electromagnetic field stimulation of an isolated arterial loop according to an embodiment of the present invention increases the amount of quantifiable neovascularization in an in vivo rat model. Increased angiogenesis was demonstrated in each of the treated groups at each of the sacrifice dates. No differences were found between the results of the two gauss levels tested as predicted by the teachings of the present invention.

Having described embodiments for an apparatus and a method for treatment of hair restoration and cerebrofacial conditions that is self-contained and delivers electromagnetic treatment to hair and other cerebrofacial tissue, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Part 8

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and ion binding time constants of binding and other voltage sensitive membrane processes such as membrane transport. Knowledge of ion binding time constants allows SNR to be evaluated for any EMF signal configuration. A preferred embodiment according to the present invention uses ion binding time constants in the range of about 1 to about 100 msec.

Equivalent electrical circuit models representing various membrane and charged interface configurations have been derived. For example, in Calcium ("Ca2+") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of tissue repair, for example bone repair, wound repair, hair repair, and repair of other molecules, cells, tissues, and organs that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to tissue growth and repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ $sec^{-1}$, =2.5 μM, $K_D$=30 μM, $[Ca^{2+}CaM]=K_D(+[CaM])$, yields $k_b$=665 $sec^{-1}$ ($\tau_{ion}$=1.5 msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kTRe[Z_M(x,\omega)]$$

where $Z_M(x, \omega)$ is electrical impedance of a target pathway structure, x is a dimension of a target pathway structure and Re denotes a real part of impedance of a target pathway structure. $Z_M(x, \omega)$ can be expressed as:

$$Z_M(x, \omega) = \left[\frac{R_e + R_i + R_g}{y}\right]\tanh(yx)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)=4$ kT Re[$Z_M(x, \omega)$] over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known tissue growth mechanisms is accessible. According to an embodiment of the present invention applying a random, or other high spectral density envelope, to a pulse burst envelope of mono-polar or bi-polar rectangular or sinusoidal pulses inducing peak electric fields between about $10^{-8}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular amplitude and preferably a random amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 55 wherein FIG. 55 is a flow diagram of a method for generating electromagnetic signals to be coupled to an eye according to an embodiment of the present invention, a target pathway structure such as ions and ligands, is identified. Establishing a baseline background activity such as baseline thermal fluctuations in voltage and electrical impedance, at the target pathway structure by determining a state of at least one of a cell and a tissue at the target pathway structure, wherein the state is at least one of resting, growing, replacing, and responding to injury. (STEP 55101) The state of the at least one of a cell and a tissue is determined by its response to injury or insult. Configuring at least one waveform to have sufficient signal to noise ratio to modulate at least one of ion and ligand interactions whereby the at least one of ion and ligand interactions are detectable in the target pathway structure above the established baseline thermal fluctuations in voltage and electrical impedance. (STEP 55102) Generating an electromagnetic signal from the configured at least one waveform. (STEP 55103) The electromagnetic signal can be generated by using at least one waveform configured by applying a mathematical model such as an equation, formula, or function having at least one waveform parameter that satisfies an SNR or Power SNR mathematical model such that ion and ligand interactions are modulated and the at least one configured waveform is detectable at the target pathway structure above its established background activity. Coupling the electromagnetic signal to the target pathway structure using a coupling device. (STEP 55104) The generated electromagnetic signals can be coupled for therapeutic and prophylactic purposes. Since ophthalmic tissue is very delicate, application of electromagnetic signals using an embodiment according to the present invention is extremely safe and efficient since the application of electromagnetic signals is non-invasive.

A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model. A repetitive electromagnetic signal can be generated for example inductively or capacitively, from the configured at least one waveform. The electromagnetic signal is coupled to a target pathway structure such as ions and ligands by output of a coupling device such as an electrode or an inductor, placed in close proximity to the target pathway structure using a positioning device. The coupling enhances modulation of binding of ions and ligands to regulatory molecules tissues, cells, and organs. According to an embodiment of the present invention EMF signals configured using SNR analysis to match the bandpass of a second messenger whereby the EMF signals can act as a first messenger to modulate biochemical cascades such as production of cytokines, Nitric Oxide, Nitric Oxide Synthase and growth factors that are related to tissue growth and repair. A detectable E field amplitude is produced within a frequency response of $Ca^{2+}$ binding.

FIG. 56 illustrates a preferred embodiment of an apparatus according to the present invention. The apparatus is self-contained, lightweight, and portable. A miniature control circuit 56201 is coupled to an end of at least one connector 56202 such as wire however the control circuit can also operate wirelessly. The opposite end of the at least one connector is coupled to a generating device such as an electrical coil 56203. The miniature control circuit 56201 is constructed in a manner that applies a mathematical model that is used to configure waveforms. The configured waveforms have to satisfy a Power SNR model so that for a given and known target pathway structure, it is possible to choose waveform parameters that satisfy Power SNR so that a waveform is detectable in the target pathway structure above its background activity. A preferred embodiment according to the present invention applies a mathematical model to induce a time-varying magnetic field and a time-varying electric field in a target pathway structure such as ions and ligands, comprising about 0.001 to about 100 msec bursts of about 1 to about 100 microsecond rectangular pulses repeating at about 0.1 to about 100 pulses per second. Peak amplitude of the induced electric field is between about 1 uV/cm and about 100 mV/cm, varied according to a modified 1/f function where f=frequency. A waveform configured using a preferred embodiment according to the present invention may be applied to a target pathway structure such as ions and ligands for a preferred total exposure time of under 1 minute to 240 minutes daily. However other exposure times can be used. Waveforms configured by the miniature control circuit 56201 are directed to a generating device 56203 such as electrical coils via connector 56202. The generating device 56203 delivers a pulsing magnetic field configured according to a mathematical model that can be used to provide treatment to a target pathway structure such as eye tissue. The miniature control circuit applies a pulsing magnetic field for a prescribed time and can automatically repeat applying the pulsing magnetic field for as many applications as are needed in a given time period, for example 10 times a day. The miniature control circuit can be configured to be programmable applying pulsing magnetic fields for any time repetition sequence. A preferred embodiment according to the present invention can be positioned to treat ophthalmic tissue by being incorporated with a positioning device 56204 such as an eye-patch, eyeglasses, goggles, and monocles thereby making the unit self-contained. Coupling a pulsing magnetic field to a target pathway structure such as ions and ligands, therapeutically and prophylactically reduces inflammation thereby reducing pain and promotes healing in treatment areas. When electrical coils are used as the generating device 56203, the electrical coils can be powered with a time varying magnetic field that induces a time varying electric field in a target pathway structure according to Faraday's law. An electromagnetic signal generated by the generating device 203 can also be applied using electrochemical coupling, wherein electrodes are in direct contact with skin or another outer electrically conductive boundary of a target pathway structure. Yet in another embodiment according to the present invention, the electromagnetic signal generated by the generating device 56203 can also be applied using electrostatic coupling wherein an air gap exists between a generating device 56203 such as an electrode and a target pathway structure such as ions and ligands. An advantage of the preferred embodiment according to the present invention is that its ultra lightweight coils and miniaturized circuitry allow for use with common physical therapy treatment modalities and at any location for which tissue growth, pain relief, and tissue and organ healing is desired. An advantageous result of application of the preferred embodiment according to the present invention is that tissue growth, repair, and maintenance can be accomplished and enhanced anywhere and at anytime. Yet another advantageous result of application of the preferred embodiment is that growth, repair, and maintenance of molecules, cells, tissues, and organs can be accomplished and enhanced anywhere and at anytime. A preferred embodiment according to the present invention delivers PEMF for application to ophthalmic tissue that is infected with diseases as macular degeneration, glaucoma, retinosa pigmentosa, repair and regeneration of optic nerve prophylaxis, and other related diseases.

FIG. 57 depicts a block diagram of a preferred embodiment according to the present invention of a miniature control circuit 57300. The miniature control circuit 57300 produces waveforms that drive a generating device such as wire coils described above in FIG. 56. The miniature control circuit can be activated by any activation means such as an on/off switch. The miniature control circuit 57300 has a power source such as a lithium battery 57301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 57302 controls voltage to a micro-controller 57303. A preferred embodiment of the micro-controller 57303 uses an 8 bit 4 MHz micro-controller 57303 but other bit MHz combination micro-controllers may be used. The switching power supply 57302 also delivers current to storage capacitors 57304. A preferred embodiment of the present invention uses storage capacitors having a 220 uF output but other outputs can be used. The storage capacitors 57304 allow high frequency pulses to be delivered to a coupling device such as inductors (Not Shown). The micro-controller 57303 also controls a pulse shaper 57305 and a pulse phase timing control 306. The pulse shaper 57305 and pulse phase timing control 57306 determine pulse shape, burst width, burst envelope shape, and burst repetition rate. In a preferred embodiment according to the present invention the pulse shaper 57305 and phase timing control 57306 are configured such that the waveforms configured are detectable above background activity at a target pathway structure by satisfying at least one of a SNR and Power SNR mathematical model. An integral waveform generator, such as a sine wave or arbitrary number generator can also be incorporated to provide specific waveforms. A voltage level conversion sub-circuit 57308 controls an induced field delivered to a target pathway structure. A switching Hexfet 57308 allows pulses of randomized amplitude to be delivered to output 57309 that routes a waveform to at least one coupling device such as an inductor. The micro-controller 57303 can also control total exposure time of a single treatment of a target pathway structure such as a molecule, cell, tissue, and organ. The miniature control circuit 57300 can be constructed to be programmable and apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes.

FIG. 58 depicts a block diagram of an embodiment according to the present invention of a miniature control circuit 58400. The miniature control circuit 58400 produces waveforms that drive a generating device such as wire coils described above in FIG. 56. The miniature control circuit can be activated by any activation means such as an on/off switch. The miniature control circuit 58400 has a power source such as a lithium battery 58401. In another embodiment according to the present invention the power source can be an external power source such as an electric current outlet such as an AC/DC outlet, coupled to the present invention for example by a plug and wire. A user input/output means 58402 such as an on/off switch controls voltage to the miniature control circuit and is connected to a cpu-control 58403. The cpu-control 58403 creates a SNR EMF waveform by processing information provided to it via flash memory programmed having SNR EMF signal parameters such as pulse shape, burst width, burst envelope shape, and burst repetition rate. The waveform is pulse modulated by a modulator 58405 interfacing with an oscillator 58406 having a crystal 58407 controlled by the cpu-control 58403 according to the SNR EMF signal parameters programmed into the flash memory of the cpu-control 58403. The oscillator 58406 having a crystal 58407 provides a carrier frequency. A preferred embodiment of the crystal is a 27.120 MHz crystal but other MHz crystals can be used. The modulated waveform is then amplified by an amp 58408 and sent to an output stage means 58409 where the amplified modulated waveform is matched to impedance via a R C circuit across a patient applicator 58410 such as a coil. The patient applicator generates a SNR EMF signal to be delivered to a patient.

Referring to FIG. 59 an embodiment according to the present invention of a waveform 59500 is illustrated. A pulse 59501 is repeated within a burst 59502 that has a finite duration 59503. The duration 59503 is such that a duty cycle which can be defined as a ratio of burst duration to signal period is between about 1 to about $10^{-5}$. A preferred embodiment according to the present invention utilizes pseudo rectangular 10 microsecond pulses for pulse 59501 applied in a burst 59502 for about 10 to about 50 msec having a modified 1/f amplitude envelope 59504 and with a finite duration 59503 corresponding to a burst period of between about 0.1 and about 10 seconds.

It is further intended that any other embodiments of the present invention that result from any changes in application or method of use or operation, method of manufacture, shape, size or material which are not specified within the detailed written description or illustrations and drawings contained herein, yet are considered apparent or obvious to one skilled in the art, are within the scope of the present invention.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA12. Free $Ca^{2+}$ was varied in the 1-7 µM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 µL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 µM 32P ATP, and was stopped with Laemmli Sample Buffer solution containing 30 µM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 µsec to 1000 µsec based upon projections of Power SNR analysis which showed that optimal Power SNR would be achieved as burst duration approached 500 µsec. The results are shown in FIG. 60 wherein burst width 60601 in µsec is plotted on the x-axis and Myosin Phosphorylation 60602 as treated/sham is plotted on the y-axis. It can be seen that the PMF effect on $Ca^{2+}$ binding to CaM approaches its maximum at approximately 500 µsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 µsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 µsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in kg/mm2. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per mm2 of the two strips from the same wound.

The results showed average tensile strength for the 65 µsec 1 Gauss PRF signal was 19.3±4.3 kg/mm2 for the exposed group versus 13.0±3.5 kg/mm2 for the control group (p<0.01), which is a 48% increase. In contrast, the average tensile strength for the 2000 µsec 0.2 Gauss PRF signal, configured according to an embodiment of the present invention using a Power SNR model was 21.2±5.6 kg/mm2 for the treated group versus 13.7±4.1 kg/mm2 (p<0.01) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

This example illustrates the effects of PRF electromagnetic fields chosen via the Power SNR method on neurons in culture.

Primary cultures were established from embryonic days 15-16 rodent mesencephalon. This area is dissected, dissociated into single cells by mechanical trituration, and cells are plated in either defined medium or medium with serum. Cells are typically treated after 6 days of culture, when neurons have matured and developed mechanisms that render them vulnerable to biologically relevant toxins. After treatment, conditioned media is collected.

Enzyme linked immunosorbent assays ("ELISAs") for growth factors such as Fibroblast Growth Factor beta ("FGFb") are used to quantify their release into the medium. Dopaminergic neurons are identified with an antibody to tyrosine hydroxylase ("TH"), an enzyme that converts the amino acid tyrosine to L-dopa, the precursor of dopamine, since dopaminergic neurons are the only cells that produce this enzyme in this system. Cells are quantified by counting TH+ cells in perpendicular strips across the culture dish under 100.times. magnification.

Serum contains nutrients and growth factors that support neuronal survival. Elimination of serum induces neuronal cell death. Culture media was changed and cells were exposed to PMF (power level 6, burst width 3000 µsec, and frequency 1 Hz). Four groups were utilized. Group 1 used No PMF exposure (null group). Group 2 used Pre-treatment (PMF treatment 2 hours before medium change). Group 3 used Post-treatment (PMF treatment 2 hours after medium change). Group 4 used Immediate treatment (PMF treatment simultaneous to medium change).

Results demonstrate a 46% increase in the numbers of surviving dopaminergic neurons after 2 days when cultures were exposed to PMF prior to serum withdrawal. Other treatment regimes had no significant effects on numbers of surviving neurons. The results are shown in FIG. 60 where type of treatment 60601 is shown on the x-axis and number of neurons 60602 is shown on the y-axis.

FIG. 61, where treatment 61701 is shown on the x-axis and number of neurons 61702 is shown on the y-axis, illustrates that PMF signals D and E increase numbers of dopaminergic neurons after reducing serum concentrations in the medium by 46% and 48% respectively. Both signals were configured with a burst width of 3000 µsec, and the repetition rates are 5/sec and 1/sec, respectively. Notably, signal D was administered in a chronic paradigm in this experiment, but signal E was administered only once: 2 hours prior to serum withdrawal, identical to experiment 1 (see above), producing effects of the same magnitude (46% vs. 48%). Since the reduction of serum in the medium reduces the availability of nutrients and growth factors, PMF induces the synthesis or release of these factors by the cultures themselves.

This portion of the experiment was performed to illustrate the effects of PMF toxicity induced by 6-OHDA, producing a well-characterized mechanism of dopaminergic cell death. This molecule enters cells via high affinity dopamine transporters and inhibits mitochondrial enzyme complex I, thus killing these neurons by oxidative stress. Cultures were treated with 25 µM 6-OHDA after chronic, or acute PMF exposure paradigms. FIG. 62 illustrates these results, where treatment 62801 is shown on the x-axis and number of neurons 62802 is shown on the y-axis. The toxin killed approximately 80% of the dopaminergic neurons in the absence of PMF treatment. One dose of PMF (power=6; burst width=3000 μsec; frequency=1/sec) significantly increased neuronal survival over 6-OHDA alone (2.6-fold; p≤0.02). This result has particular relevance to developing neuroprotection strategies for Parkinson's disease, because 6-OHDA is used to lesion dopaminergic neurons in the standard rodent model of Parkinson's disease, and the mechanism of toxicity is similar in some ways to the mechanism of neurodegeneration in Parkinson's disease itself.

EXAMPLE 4

In this example electromagnetic field energy was used to stimulate neovascularization in an in vivo model. Two different signal were employed, one configured according to prior art and a second configured according to an embodiment of the present invention.

One hundred and eight Sprague-Dawley male rats weighing approximately 300 grams each, were equally divided into nine groups. All animals were anesthetized with a mixture of ketamine/acepromazine/Stadol at 0.1 cc/g. Using sterile surgical techniques, each animal had a 12 cm to 14 cm segment of tail artery harvested using microsurgical technique. The artery was flushed with 60 U/ml of heparinized saline to remove any blood or emboli.

These tail vessels, with an average diameter of 0.4 mm to 0.5 mm, were then sutured to the transected proximal and distal segments of the right femoral artery using two end-to-end anastomoses, creating a femoral arterial loop. The resulting loop was then placed in a subcutaneous pocket created over the animal's abdominal wall/groin musculature, and the groin incision was closed with 4-0 Ethilon. Each animal was then randomly placed into one of nine groups: groups 1 to 3 (controls), these rats received no electromagnetic field treatments and were killed at 4, 8, and 12 weeks; groups 4 to 6, 30 min. treatments twice a day using 0.1 gauss electromagnetic fields for 4, 8, and 12 weeks (animals were killed at 4, 8, and 12 weeks, respectively); and groups 7 to 9, 30 min. treatments twice a day using 2.0 gauss electromagnetic fields for 4, 8, and 12 weeks (animals were killed at 4, 8, and 12 weeks, respectively).

Pulsed electromagnetic energy was applied to the treated groups using a device constructed according to an embodiment of the present invention. Animals in the experimental groups were treated for 30 minutes twice a day at either 0.1 gauss or 2.0 gauss, using short pulses (2 msec to 20 msec) 27.12 MHz. Animals were positioned on top of the applicator head and confined to ensure that treatment was properly applied. The rats were reanesthetized with ketamine/acepromazine/Stadol intraperitoneally and 100 U/kg of heparin intravenously. Using the previous groin incision, the femoral artery was identified and checked for patency. The femoral/tail artery loop was then isolated proximally and distally from the anastomoses sites, and the vessel was clamped off. Animals were then killed. The loop was injected with saline followed by 0.5 cc to 1.0 cc of colored latex through a 25-gauge cannula and clamped. The overlying abdominal skin was carefully resected, and the arterial loop was exposed. Neovascularization was quantified by measuring the surface area covered by new blood-vessel formation delineated by the intraluminal latex. All results were analyzed using the SPSS statistical analysis package.

The most noticeable difference in neovascularization between treated versus untreated rats occurred at week 4. At that time, no new vessel formation was found among controls, however, each of the treated groups had similar statistically significant evidence of neovascularization at 0 cm2 versus 1.42±0.80 cm2 (p<0.001). These areas appeared as a latex blush segmentally distributed along the sides of the arterial loop. At 8 weeks, controls began to demonstrate neovascularization measured at 0.7±0.82 cm2. Both treated groups at 8 weeks again had approximately equal statistically significant (p<0.001) outcroppings of blood vessels of 3.57±1.82 cm2 for the 0.1 gauss group and of 3.77±1.82 cm2 for the 2.0 gauss group. At 12 weeks, animals in the control group displayed 1.75±0.95 cm2 of neovascularization, whereas the 0.1 gauss group demonstrated 5.95±3.25 cm2, and the 2.0 gauss group showed 6.20±3.95 cm2 of arborizing vessels. Again, both treated groups displayed comparable statistically significant findings (p<0.001) over controls.

These experimental findings demonstrate that electromagnetic field stimulation of an isolated arterial loop according to an embodiment of the present invention increases the amount of quantifiable neovascularization in an in vivo rat model. Increased angiogenesis was demonstrated in each of the treated groups at each of the sacrifice dates. No differences were found between the results of the two gauss levels tested as predicted by the teachings of the present invention.

Having described embodiments for an apparatus for applying electromagnetic signals to an eye and method for using same, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Part 9

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and ion binding time constants of binding and other voltage sensitive membrane processes such as membrane transport. Knowledge of ion binding time constants allows SNR to be evaluated for any EMF signal configuration. Preferably ion binding time constants in the range of about 1 to about 100 msec are used.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where ω is angular frequency defined as 2πf, where f is frequency, i=−1½, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by Cion. Electrical charge is directly proportional to a surface concentration of $Ca^{2+}$ ions in the binding site that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of tissue repair, for example bone repair, wound repair, hair repair, and repair of other molecules, cells, tissues, and organs that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis and neovascularization are also integral to tissue growth and repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of Ca2+ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as Vmax=6.5× 10−7 sec−1, =2.5 μM, $K_D$=30 μM, $[Ca^{2+}CaM]=K_D(+[CaM])$, yields $k_b$=665 sec−1 ($\tau_{ion}$=1.5 msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kTRe[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x, \omega) = \left[\frac{R_e + R_i + R_g}{\gamma}\right]\tanh(\gamma x)$$

This equation clearly shows that electrical impedance of the target pathway structure, and contributions from extracellular fluid resistance ("Re"), intracellular fluid resistance ("Ri") and intermembrane resistance ("Rg") which are electrically connected to target pathway structures all contribute to noise filtering.

A typical approach to evaluation of SNR uses a single value of a root mean square (RMS) noise voltage. This is calculated by taking a square root of an integration of $S_n(\omega)=4$ kT $Re[Z_M(x, \omega)]$ over all frequencies relevant to either a complete membrane response, or to bandwidth of a target pathway structure. SNR can be expressed by a ratio:

$$SNR = \frac{|V_M(\omega)|}{\text{RMS}}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known tissue growth mechanisms is accessible. According to an embodiment of the present invention applying a random, or other high spectral density envelope, to a pulse burst envelope of mono-polar or bi-polar rectangular or sinusoidal pulses inducing peak electric fields between about 10−8 and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular amplitude and preferably a random amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 63 wherein FIG. 63 is a flow diagram of a method for generating electromagnetic signals to be coupled to a respiratory target pathway structure according to an embodiment of the present invention, a target pathway structure such as ions and ligands, is identified. Establishing a baseline background activity such as baseline thermal fluctuations in voltage and electrical impedance, at the target pathway structure by determining a state of at least one of a cell and a tissue at the target pathway structure, wherein the state is at least one of resting, growing, replacing, and responding to injury. (STEP 63101) The state of the at least one of a cell and a tissue is determined by its response to injury or insult. Configuring at least one waveform to have sufficient signal to noise ratio to modulate at least one of ion and ligand interactions whereby the at least one of ion and ligand interactions are detectable in the target pathway structure above the established baseline thermal fluctuations in voltage and electrical impedance. (STEP 63102) Repetitively generating an electromagnetic signal from the configured at least one waveform. (STEP 63103) The electromagnetic signal can be generated by using at least one waveform configured by applying a mathematical model such as an equation, formula, or function having at least one waveform parameter that satisfies an SNR or Power SNR mathematical model such that ion and ligand interactions are modulated and the at least one configured waveform is detectable at the target pathway structure above its established background activity. Coupling the electromagnetic signal to the target pathway structure using a coupling device. (STEP 63104) The generated electromagnetic signals can be coupled for therapeutic and prophylactic purposes. The coupling enhances a stimulus that cells and tissues react to in a physiological meaningful manner for example, treatment of lung diseases resulting from inflammatory processes caused by inhalation of foreign material into lung tissue. Since lung tissue is very delicate, application of electromagnetic signals using an embodiment according to the present invention is extremely safe and efficient since the application of electromagnetic signals is non-invasive.

In an aspect of the present invention, a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model. A repetitive electromagnetic signal can be generated for example inductively or capacitively, from the configured at least one waveform. The electromagnetic signal is coupled to a target pathway structure such as ions and ligands by output of a coupling device such as an electrode or an inductor, placed in close proximity to the target pathway structure using a positioning device. The coupling enhances modulation of binding of ions and ligands to regulatory molecules, tissues, cells, and organs. According to an embodiment of the present invention EMF signals configured using SNR analysis to match the bandpass of a second messenger whereby the EMF signals can act as a first messenger to modulate biochemical cascades such as production of cytokines, Nitric Oxide, Nitric Oxide Synthase and growth factors that are related to tissue growth and repair. A detectable E field amplitude is produced within a frequency response of $Ca^{2+}$ binding.

FIG. 64 illustrates an embodiment of an apparatus according to the present invention. The apparatus is self-contained, lightweight, and portable. A miniature control circuit 64201 is connected to a generating device such as an electrical coil 64202. The miniature control circuit 64201 is constructed in a manner that applies a mathematical model that is used to configure waveforms. The configured waveforms have to satisfy a Power SNR model so that for a given and known target pathway structure, it is possible to choose waveform parameters that satisfy Power SNR so that a waveform is detectable in the target pathway structure above its background activity. An embodiment according to the present invention applies a mathematical model to induce a time-varying magnetic field and a time-varying electric field in a target pathway structure such as ions and ligands, comprising about 0.001 to about 100 msec bursts of about 1 to about 100 microsecond rectangular pulses repeating at about 0.1 to about 100 pulses per second. Peak amplitude of the induced electric field is between about 1 uV/cm and about 100 mV/cm, varied according to a modified 1/f function where f=frequency. A waveform configured using an embodiment according to the present invention may be applied to a target pathway structure such as ions and ligands, preferably for a total exposure time of under 1 minute to 240 minutes daily. However other exposure times can be used. Waveforms configured by the miniature control circuit 64201 are directed to a generating device 64202 such as electrical coils. Preferably, the generating device 64202 is a comformable coil for example pliable, comprising one or more turns of electrically conducting wire in a generally circular or oval shape however other shapes can be used. The generating device 64202 delivers a pulsing magnetic field configured according to a mathematical model that can be used to provide treatment to a target pathway structure such as lung tissue. The miniature control circuit applies a pulsing magnetic field for a prescribed time and can automatically repeat applying the pulsing magnetic field for as many applications as are needed in a given time period, for example 12 times a day. The miniature control circuit can be configured to be programmable applying pulsing magnetic fields for any time repetition sequence. An embodiment according to the present invention can be positioned to treat respiratory tissue by being incorporated with a positioning device such as a bandage or a vest thereby making the unit self-contained. Coupling a pulsing magnetic field to a target pathway structure such as ions and ligands, therapeutically and prophylactically reduces inflammation thereby reducing pain and promotes healing in treatment areas. When electrical coils are used as the generating device 64202, the electrical coils can be powered with a time varying magnetic field that induces a time varying electric field in a target pathway structure according to Faraday's law. An electromagnetic signal generated by the generating device 64202 can also be applied using electrochemical coupling, wherein electrodes are in direct contact with skin or another outer electrically conductive boundary of a target pathway structure. Yet in another embodiment according to the present invention, the electromagnetic signal generated by the generating device 64202 can also be applied using electrostatic coupling wherein an air gap exists between a generating device 64202 such as an electrode and a target pathway structure such as ions and ligands. An advantage of the present invention is that its ultra lightweight coils and miniaturized circuitry allow for use with common physical therapy treatment modalities, and at any location for which tissue growth, pain relief, and tissue and organ healing is desired. An advantageous result of application of the present invention is that tissue growth, repair, and maintenance can be accomplished and enhanced anywhere and at anytime. Yet another advantageous result of application of the present invention is that growth, repair, and maintenance of molecules, cells, tissues, and organs can be accomplished and enhanced anywhere and at anytime. Another embodiment according to the present invention delivers PEMF for application to respiratory tissue that is infected with diseases such as sarcoidosis, granulomatous pneumonitis, pulmonary fibrosis, and "World Trade Center Cough."

FIG. 65 depicts a block diagram of an embodiment according to the present invention of a miniature control circuit 65300. The miniature control circuit 65300 produces waveforms that drive a generating device such as wire coils described above in FIG. 64. The miniature control circuit can be activated by any activation means such as an on/off switch. The miniature control circuit 65300 has a power source such as a lithium battery 65301. Preferably the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 65302 controls voltage to a micro-controller 303. Preferably the micro-controller 65303 uses an 8 bit 4 MHz micro-controller 65303 but other bit MHz combination micro-controllers may be used. The switching power supply 65302 also delivers current to storage capacitors 65304. Preferably the storage capacitors 65304 having a 220 uF output but other outputs can be used. The storage capacitors 65304 allow high frequency pulses to be delivered to a coupling device such as inductors (Not Shown). The micro-controller 65303 also controls a pulse shaper 65305 and a pulse phase timing control 65306. The pulse shaper 65305 and pulse phase timing control 65306 determine pulse shape, burst width, burst envelope shape, and burst repetition rate. In an aspect of the present invention the pulse shaper 65305 and phase timing control 65306 are configured such that the waveforms configured are detectable above background activity at a target pathway structure by satisfying at least one of a SNR and Power SNR mathematical model. An integral waveform generator, such as a sine wave or arbitrary number generator can also be incorporated to provide specific waveforms. A voltage level conversion sub-circuit 307 controls an induced field delivered to a target pathway structure. A switching Hexfet 65308 allows pulses of randomized amplitude to be delivered to output 65309 that routes a waveform to at least one coupling device such as an inductor. The micro-controller 65303 can also control total exposure time of a single treatment of a target pathway structure such as a molecule, cell, tissue, and organ. The miniature control circuit 65300 can be constructed to be programmable and apply a pulsing magnetic field for a prescribed time and to automatically repeat applying the pulsing magnetic field for as many applications as are needed in a given time period, for example 10 times a day. Preferably treatments times of about 1 minutes to about 30 minutes are used.

Referring to FIG. 66 an embodiment according to the present invention of a waveform 66400 is illustrated. A pulse 66401 is repeated within a burst 66402 that has a finite duration or width 66403. The duration 66403 is such that a duty cycle which can be defined as a ratio of burst duration to signal period is between about 1 to about $10^{-5}$. Preferably pseudo rectangular 10 microsecond pulses for pulse 66401 applied in a burst 66402 for about 10 to about 50 msec having a modified 1/f amplitude envelope 66404 and with a finite duration 66403 corresponding to a burst period of between about 0.1 and about 10 seconds are utilized.

FIG. 67 illustrates an embodiment of an apparatus according to the present invention. A garment 67501 such as a vest is constructed out of materials that are lightweight and portable such as nylon but other materials can be used. A miniature control circuit 67502 is coupled to a generating device such as an electrical coil 67503. Preferably the miniature control circuit 67502 and the electrical coil 67503 are constructed in a manner as described above in reference to FIG. 64. The miniature control circuit and the electrical coil can be connected with a connecting means such as a wire 57504. The connection can also be direct or wireless. The electrical coil 57503 is integrated into the garment 57501 such that when a user wears the garment 57501, the electrical coil is positioned near a lung or both lungs of the user. An advantage of the present invention is that its ultra lightweight coils and miniaturized circuitry allow for the garment 57501 to be completely self-contained, portable, and lightweight. An additionally advantageous result of the present invention is that the garment 57501 can be constructed to be inconspicuous when worn and can be worn as an outer garment such as a shirt or under other garments, so that only the user will know that the garment 57501 is being worn and treatment is being applied. Use with common physical therapy treatment modalities, and at any respiratory location for which tissue growth, pain relief, and tissue and organ healing is easily obtained. An advantageous result of application of the present invention is that tissue growth, repair, and maintenance can be accomplished and enhanced anywhere and at anytime. Yet another advantageous result of application of the present invention is that growth, repair, and maintenance of molecules, cells, tissues, and organs can be accomplished and enhanced anywhere and at anytime. Another embodiment according to the present invention delivers PEMF for application to respiratory tissue that is infected with diseases such as sarcoidosis, granulomatous pneumonitis, pulmonary fibrosis, and "World Trade Center Cough."

It is further intended that any other embodiments of the present invention that result from any changes in application or method of use or operation, method of manufacture, shape, size or material which are not specified within the detailed written description or illustrations and drawings contained herein, yet are considered apparent or obvious to one skilled in the art, are within the scope of the present invention.

The process of the invention will now be described with reference to the following illustrative examples.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA12. Free $Ca^{2+}$ was varied in the 1-7 μM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 μL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 μM 32P ATP, and was stopped with Laemmli Sample Buffer solution containing 30 μM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 μsec to 1000 μsec based upon projections of Power SNR analysis which showed that optimal Power SNR would be achieved as burst duration approached 500 μsec. The results are shown in FIG. 68 wherein burst width 68601 in msec is plotted on the x-axis and Myosin Phosphorylation 68602 as treated/sham is plotted on the y-axis. It can be seen that the PMF effect on $Ca^{2+}$ binding to CaM approaches its maximum at approximately 500 μsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 μsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 μsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in kg/mm2. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per mm2 of the two strips from the same wound.

The results showed average tensile strength for the 65 μsec 1 Gauss PRF signal was 19.3±4.3 kg/mm2 for the exposed group versus 13.0±3.5 kg/mm2 for the control group (p<0.01), which is a 48% increase. In contrast, the average tensile strength for the 2000 μsec 0.2 Gauss PRF signal, configured according to an embodiment of the present invention using a Power SNR model was 21.2±5.6 kg/mm2 for the treated group versus 13.7±4.1 kg/mm2 (p<0.01) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

This example illustrates the effects of PMF stimulation of a T-cell receptor with cell arrest and thus behave as normal T-lymphocytes stimulated by antigens at the T-cell receptor such as anti-CD3.

In bone healing, results have shown that both 60 Hz and PEMF fields decrease DNA synthesis of Jurkat cells, as is expected since PMF interacts with the T-cell receptor in the absence of a costimulatory signal. This result is consistent with an anti-inflammatory response, as has been observed in clinical applications of PMF stimuli. The PEMF signal is more effective. A dismetry analysis performed according to an embodiment of the present invention demonstrates why both signals are effective and why PEMF signals have a greater effect than 60 Hz signals on Jurkat cells in the most EMF-sensitive growth stage.

Comparison of dosimetry from the two signals employed involves evaluation of the ratio of the Power spectrum of the thermal noise voltage that is Power SNR, to that of the induced voltage at the EMF-sensitive target pathway structure. The target pathway structure used is ion binding at receptor sites on Jurkat cells suspended in 2 mm of culture medium. The average peak electric field at the binding site from a PEMF signal comprising 5 msec burst of 200 μsec pulses repeating at 15/sec was 1 mV/cm, while for a 60 Hz signal the average peak electric field was 100 μV/cm.

FIG. 69 is a graph of results wherein Induced Field Frequency 69701 in Hz is shown on the x-axis and Power SNR 69702 is shown on the y-axis. FIG. 69 illustrates that both signals have sufficient Power spectrum that is Power SNR≥1, to be detected within a frequency range of binding kinetics. However, maximum Power SNR for the PEMF signal is significantly higher than that of the 60 Hz signal.

This is due to a PEMF signal having many frequency components falling within a bandpass of the target pathway structure. The single frequency component of a 60 Hz signal lies at the mid-point of the bandpass of a target pathway structure. The Power SNR calculation that was used in this example is dependent upon $\tau_{ion}$ which is obtained from the rate constant for ion binding. Had this calculation been performed a priori it would have concluded that both signals satisfied basic detectability requirements and could modulate an EMF-sensitive ion binding pathway at the start of a regulatory cascade for DNA synthesis in these cells. The previous examples illustrate that utilizing the rate constant for Ca/CaM binding could lead to successful projections for bioeffective EMF signals in a variety of systems.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

Part 10

Induced time-varying currents from PEMF or PRF devices flow in a fibrous capsule formation and capsular contracture target pathway structure such as a molecule, cell, tissue, and organ, and it is these currents that are a stimulus to which cells and tissues can react in a physiologically meaningful manner. The electrical properties of a fibrous capsule formation and capsular contracture target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent chemical processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and ion binding time constants of binding and other voltage sensitive membrane processes such as membrane transport. Knowledge of ion binding time constants allows SNR to be evaluated for any EMF signal configuration. Preferably ion binding time constants in the range of about 1 to about 100 msec are used.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("CaM"). Use of this pathway is based upon acceleration of wound repair, for example bone repair, that involves modulation of growth factors released in various stages of repair. Growth factors such as platelet derived growth factor ("PDGF"), fibroblast growth factor ("FGF"), and epidermal growth factor ("EGF") are all involved at an appropriate stage of healing. Angiogenesis is also integral to wound repair and modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ $sec^{-1}$, $=2.5$ μM, $K_D=30$ μM, $[Ca^{2+}CaM]=K_D(+[CaM])$, yields $k_b=665$ $sec^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kTRe[Z_M(x,\omega)]$$

where $Z_M(x, \omega)$ is electrical impedance of a target pathway structure, x is a dimension of a target pathway structure and Re denotes a real part of impedance of a target pathway structure. $Z_M(x, \omega)$ can be expressed as:

$$Z_M(x, \omega) = \left[\frac{R_e + R_i + R_g}{y}\right] \tanh(yx)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to a target pathway structure, all contribute to noise filtering.

A typical approach to evaluation of SNR uses a single value of a root mean square (RMS) noise voltage. This is calculated by taking a square root of an integration of $S_n(\omega)=4$ kT Re $[Z_M(x, \omega)]$ over all frequencies relevant to either complete membrane response, or to bandwidth of a target pathway structure. SNR can be expressed by a ratio:

$$SNR = \frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known tissue growth mechanisms is accessible. According to an embodiment of the present invention applying a random, or other high spectral density envelope, to a pulse burst envelope of mono-polar or bi-polar rectangular or sinusoidal pulses inducing peak electric fields between about $10^{-8}$ and about 100 mV/cm, produces a greater effect on biological healing processes applicable to both soft and hard tissues.

An embodiment according to the present invention comprises an electromagnetic signal having a pulse burst envelope of spectral density to efficiently couple to physiologically relevant dielectric pathways, such as cellular membrane receptors, ion binding to cellular enzymes, and general transmembrane potential changes. The use of a burst duration which is generally below 100 microseconds for each PRF burst, limits the frequency components that could couple to the relevant dielectric pathways in cells and tissue. An embodiment according to the present invention increases the number of frequency components transmitted to relevant cellular pathways whereby access to a larger range of biophysical phenomena applicable to known healing mechanisms, including enhanced second messenger release, enzyme activity and growth factor and cytokine release can be achieved. By increasing burst duration and applying a random, or other envelope, to the pulse burst envelope of mono-polar or bi-polar rectangular or sinusoidal pulses which induce peak electric fields between $10^{-8}$ and 100 mV/cm, a more efficient and greater effect can be achieved on biological healing processes applicable to both soft and hard tissues in humans, animals and plants.

Another embodiment according to the present invention comprises known cellular responses to weak external stimuli such as heat, light, sound, ultrasound and electromagnetic fields. Cellular responses to such stimuli result in the production of protective proteins, for example, heat shock proteins, which enhance the ability of the cell, tissue, organ to withstand and respond to such external stimuli. Electromagnetic fields configured according to an embodiment of the present invention enhance the release of such compounds thus advantageously providing an improved means to enhance prophylactic protection and wellness of living organisms. After implant surgery there can be physiological deficiencies such as capsular contraction and excessive fibrous capsule formation states that can have a lasting and deleterious effect on an individual's well being and on the proper functioning of an implanted device. Those physiological deficiencies and states can be positively affected on a non-invasive basis by the therapeutic application of waveforms configured according to an embodiment of the present invention. In addition, electromagnetic waveforms configured according to an embodiment of the present invention can have a prophylactic effect on an implant area whereby formation of excessive fibrous tissue may be prevented.

The present invention relates to a therapeutically beneficial method of and apparatus for non-invasive pulsed electromagnetic treatment for enhanced condition, repair and growth of living tissue in animals, humans and plants. This beneficial method operates to selectively change the bioelectromagnetic environment associated with the cellular and tissue environment through the use of electromagnetic means such as PRF generators and applicator heads. More particularly use of electromagnetic means includes the provision of a flux path to a selectable body region, of a succession of EMF pulses having a minimum width characteristic of at least 0.01 microseconds in a pulse burst envelope having between 1 and 100,000 pulses per burst, in which a voltage amplitude envelope of said pulse burst is defined by a randomly varying parameter. Further, the repetition rate of such pulse bursts may vary from 0.01 to 10,000 Hz. Additionally a mathematically-definable parameter can be employed in lieu of said random amplitude envelope of the pulse bursts.

According to an embodiment of the present invention, by applying a random, or other high spectral density envelope, to a pulse burst envelope of mono-polar or bi-polar rectangular or sinusoidal pulses which induce peak electric fields between $10^{-8}$ and 100 millivolts per centimeter (mV/cm), a more efficient and greater effect can be achieved on biological healing processes applicable to both soft and hard tissues in humans, animals and plants. A pulse burst envelope of higher spectral density can advantageously and efficiently couple to physiologically relevant dielectric pathways, such as, cellular membrane receptors, ion binding to cellular enzymes, and general transmembrane potential changes thereby modulating angiogenesis and neovascularization.

An embodiment according to the present invention utilizes a Power Signal to Noise Ratio ("Power SNR") approach to configure bioeffective waveforms and incorporates miniaturized circuitry and lightweight flexible coils. This advantageously allows a device that utilizes a Power SNR approach, miniaturized circuitry, and lightweight flexible coils, to be completely portable and if desired to be constructed as disposable and if further desired to be constructed as implantable. The lightweight flexible coils can be an integral portion of a positioning device such as surgical dressings, wound dressings, pads, seat cushions, mattress pads, wheelchairs, chairs, and any other garment and structure juxtaposed to living tissue and cells. By advantageously integrating a coil into a positioning device therapeutic treatment can be provided to living tissue and cells in an inconspicuous and convenient manner.

Specifically, broad spectral density bursts of electromagnetic waveforms, configured to achieve maximum signal power within a bandpass of a biological target, are selectively applied to fibrous capsule formation and capsular contracture target pathway structures such as living organs, tissues, cells and molecules that are associated with excessive fibrous capsule formation and capsular contracture. Waveforms are selected using a novel amplitude/power comparison with that of thermal noise in a fibrous capsule formation and capsular contracture target pathway structure. Signals comprise bursts of at least one of sinusoidal, rectangular, chaotic and random wave shapes have frequency content in a range of 0.01 Hz to 100 MHz at 1 to 100,000 bursts per second, with a burst duration from 0.01 to 100 milliseconds, and a burst repetition rate from 0.01 to 1000 bursts/second. Peak signal amplitude at a fibrous capsule formation and capsular contracture target pathway structure such as tissue, lies in a range of 1 µV/cm to 100 mV/cm. Each signal burst envelope may be a random function providing a means to accommodate different electromagnetic characteristics of healing tissue. Preferably the present invention comprises a 20 millisecond pulse burst, repeating at 1 to 10 burst/second and comprising 0.5 to 200 microsecond symmetrical or asymmetrical pulses repeating at $10^{-5}$ to 100 kilohertz within the burst. The burst envelope can be modified 1/f function or any arbitrary function and can be applied at random repetition rates. Fixed repetition rates can also be used between about 0.1 Hz and about 1000 Hz. An induced electric field from about $10^{-8}$ mV/cm to about 100 mV/cm is generated. Another embodiment according to the present invention comprises a 4 millisecond of high frequency sinusoidal waves, such as 27.12 MHz, repeating at 1 to 100 bursts per second. An induced electric field from about $10^{-8}$ mV/cm to about 100 mV/cm is generated. Resulting waveforms can be delivered via inductive or capacitive coupling for 1 to 30 minute treatment sessions delivered according to predefined regimes by which PEMF treatment may be applied for 1 to 12 daily sessions, repeated daily. The treatment regimens for any waveform configured according to the instant invention may be fully automated. The number of daily treatments may be programmed to vary on a daily basis according to any predefined protocol.

According to yet another embodiment of the present invention by applying a high spectral density voltage envelope as a modulating or pulse-burst defining parameter, power requirements for such amplitude modulated pulse bursts can be significantly lower than that of an unmodulated or continuous pulse burst containing pulses within a similar carrier frequency range. This is due to a substantial reduction in duty cycle within repetitive burst trains brought about by imposition of an irregular amplitude and preferably a random amplitude onto what would otherwise be a substantially uniform pulse burst envelope. Accordingly, the dual advantages, of enhanced transmitted dosimetry to the relevant dielectric pathways and of decreased power requirement are achieved.

Referring to FIG. 70 wherein FIG. 70 is a flow diagram of a method for generating electromagnetic signals to be coupled to a fibrous capsule formation and capsular contracture target pathway structure according to an embodiment of the present invention, a fibrous capsule formation and capsular contracture target pathway structure such as ions and ligands, is identified. Establishing a baseline background activity such as baseline thermal fluctuations in voltage and electrical impedance, at the fibrous capsule formation and capsular contracture target pathway structure by determining a state of at least one of a cell and a tissue at the fibrous capsule formation and capsular contracture target pathway structure, wherein the state is at least one of resting, growing, replacing, and responding to injury. (STEP 70101) The state of the at least one of a cell and a tissue is determined by its response to injury or insult. Configuring at least one waveform to have sufficient signal to noise ratio to modulate at least one of ion and ligand interactions whereby the at least one of ion and ligand interactions are detectable in the fibrous capsule formation and capsular contracture target pathway structure above the established baseline thermal fluctuations in voltage and electrical impedance. The EMF signal can be generated by using at least one waveform configured by applying a mathematical model such as an equation, formula, or function having at least one waveform parameter that satisfies an SNR or Power SNR mathematical model of at least about 0.2, to modulate at least one of ion and ligand interactions whereby the at least one of ion and ligand interactions are detectable in a fibrous capsule formation and capsular contracture target pathway structure above baseline thermal fluctuations in voltage and electrical impedance at the fibrous capsule formation and capsular contracture target pathway structure, wherein the signal to noise ratio is evaluated by calculating a frequency response of the impedance of the target path structure divided by a calculated frequency response of baseline thermal fluctuations in voltage across the target path structure (STEP 70102). Repetitively generating an electromagnetic signal from the configured at least one waveform (STEP 70103). Coupling the electromagnetic signal to the fibrous capsule formation and capsular contracture target pathway structure using a coupling device (STEP 70104). The generated electromagnetic signals can be coupled for therapeutic and prophylactic purposes. The coupling enhances a stimulus that cells and tissues react to in a physiological meaningful manner for example, an increase in angiogenesis, neovascularization and vascularogenesis or other physiological effects related to the improvement of excessive fibrous tissue or capsular contracture. Application of electromagnetic signals using an embodiment according to the present invention is extremely safe and efficient since the application of electromagnetic signals configured according to the present invention is non-invasive and athermal.

In the present invention, a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model. A repetitive electromagnetic signal can be generated for example inductively or capacitively, from the configured at least one waveform. The electromagnetic signal is coupled to a fibrous capsule formation and capsular contracture target pathway structure such as ions and ligands by output of a coupling device such as an electrode or an inductor, placed in close proximity to the fibrous capsule formation and capsular contracture target pathway structure using a positioning device. The coupling enhances modulation of binding of ions and ligands to regulatory molecules, tissues, cells, and organs. According to an embodiment of the present invention EMF signals configured using SNR analysis to match the bandpass of a second messenger whereby the EMF signals can act as a first messenger to modulate biochemical cascades such as production of cytokines, Nitric Oxide, Nitric Oxide Synthase and growth factors that are related to tissue growth and repair. A detectable E field amplitude is produced within a frequency response of $Ca^{2+}$ binding.

FIG. 71 illustrates an embodiment of an apparatus according to the present invention. The apparatus is constructed to be self-contained, lightweight, and portable. A miniature control circuit 71201 is connected to a generating device such as an electrical coil 71202. The miniature control circuit 71201 is constructed in a manner that applies a mathematical model that is used to configure waveforms. The configured waveforms have to satisfy a Power SNR model so that for a given and known fibrous capsule formation and capsular contracture target pathway structure, it is possible to choose waveform parameters that satisfy a frequency response of the fibrous capsule formation and capsular contracture target pathway structure and Power SNR of at least about 0.2 to modulate at least one of ion and ligand interactions whereby the at least one of ion and ligand interactions are detectable in a fibrous capsule formation and capsular contracture target pathway structure above baseline thermal fluctuations in voltage and electrical impedance at the fibrous capsule formation and capsular contracture target pathway structure, wherein the signal to noise ratio is evaluated by calculating a frequency response of the impedance of the target path structure divided by a calculated frequency response of baseline thermal fluctuations in voltage across the target path structure. An embodiment according to the present invention applies a mathematical model to induce a time-varying magnetic field and a time-varying electric field in a fibrous capsule formation and capsular contracture target pathway structure such as ions and ligands, comprising about 0.001 to about 100 msec bursts of about 1 to about 100 microsecond rectangular pulses, having a burst duration of about 0.01 to 100,000 microseconds and repeating at about 0.1 to about 100 pulses per second. Peak amplitude of the induced electric field is between about 1 uV/cm and about 100 mV/cm, that can be constant or varied according to a mathematical function, for example a modified 1/f function where f=frequency. A waveform configured using an embodiment according to the present invention may be applied to a fibrous capsule formation and capsular contracture target pathway structure such as ions and ligands, preferably for a total exposure time of under 1 minute to 240 minutes daily. However other exposure times can be used. Waveforms configured by the miniature control circuit 71201 are directed to a generating device 71202 such as electrical coils. Preferably, the generating device 71202 is a conformable coil for example pliable, comprising one or more turns of electrically conducting wire in a generally circular or oval shape however other shapes can be used. The generating device 71202 delivers a pulsing magnetic field configured according to a mathematical model that can be used to provide treatment to a fibrous capsule formation and capsular contracture target pathway structure such as mammary tissue. The miniature control circuit applies a pulsing magnetic field for a prescribed time and can automatically repeat applying the pulsing magnetic field for as many applications as are needed in a given time period, for example 12 times a day. The miniature control circuit can be configured to be programmable applying pulsing magnetic fields for any time repetition sequence. An embodiment according to the present invention can be positioned to treat fibrous capsule tissue by being incorporated with a positioning device such as a bandage, a vest, a brassiere, or an anatomical support thereby making the unit self-contained. Coupling a pulsing magnetic field to a fibrous capsule formation and capsular contracture target pathway structure such as ions and ligands, therapeutically and prophylactically reduces inflammation thereby reducing pain and promotes healing in treatment areas. When electrical coils are used as the generating device 71202, the electrical coils can be powered with a time varying magnetic field that induces a time varying electric field in a fibrous capsule formation and capsular contracture target pathway structure according to Faraday's law. An electromagnetic signal generated by the generating device 202 can also be applied using electrochemical coupling, wherein electrodes are in direct contact with skin or another outer electrically conductive boundary of a fibrous capsule formation and capsular contracture target pathway structure. Yet in another embodiment according to the present invention, the electromagnetic signal generated by the generating device 202 can also be applied using electrostatic coupling wherein an air gap exists between a generating device 202 such as an electrode and a fibrous capsule formation and capsular contracture target pathway structure such as ions and ligands. An advantage of the present invention is that its ultra lightweight coils and miniaturized circuitry allow for use with common physical therapy treatment modalities, and at any location for which tissue growth, pain relief, and tissue and organ healing is desired. An advantageous result of application of the present invention is that tissue growth, repair, and maintenance can be accomplished and enhanced anywhere and at anytime. Yet another advantageous result of application of the present invention is that growth, repair, and maintenance of molecules, cells, tissues, and organs can be accomplished and enhanced anywhere and at anytime. Another embodiment according to the present invention delivers PEMF for application to capsular contracture and excessive fibrous capsule tissue that resulted from implant surgery such as breast augmentation.

FIG. 72 depicts a block diagram of an embodiment according to the present invention of a miniature control circuit 72300. The miniature control circuit 72300 produces waveforms that drive a generating device such as wire coils described above in FIG. 71. The miniature control circuit can be activated by any activation means such as an on/off switch. The miniature control circuit 72300 has a power source such as a lithium battery 72301. Preferably the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 72302 controls voltage to a micro-controller 72303. Preferably the micro-controller 72303 uses an 8 bit 4 MHz micro-controller 72303 but other bit MHz combination micro-controllers may be used. The switching power supply 72302 also delivers current to storage capacitors 72304. Preferably the storage capacitors 72304 having a 220 uF output but other outputs can be used. The storage capacitors 72304 allow high frequency pulses to be delivered to a coupling device such as inductors (Not Shown). The micro-controller 72303 also controls a pulse shaper 72305 and a pulse phase timing control 72306. The pulse shaper 72305 and pulse phase timing control 72306 determine pulse shape, burst width, burst envelope shape, and burst repetition rate. In an embodiment according to the present invention the pulse shaper 72305 and phase timing control 72306 are configured such that the waveforms configured are detectable above background activity at a fibrous capsule formation and capsular contracture target pathway structure by satisfying at least one of a SNR and Power SNR mathematical model. An integral waveform generator, such as a sine wave or arbitrary number generator can also be incorporated to provide specific waveforms. A voltage level conversion sub-circuit 72307 controls an induced field delivered to a fibrous capsule formation and capsular contracture target pathway structure. A switching Hexfet 72308 allows pulses of randomized amplitude to be delivered to output 72309 that routes a waveform to at least one coupling device such as an inductor. The micro-controller 72303 can also control total exposure time of a single treatment of a fibrous capsule formation and capsular contracture target pathway structure such as a molecule, cell, tissue, and organ. The miniature control circuit 72300 can be constructed to be programmable and apply a pulsing magnetic field for a prescribed time and to automatically repeat applying the pulsing magnetic field for as many applications as are needed in a given time period, for example 10 times a day. Preferably treatments times of about 1 minutes to about 30 minutes are used.

Referring to FIG. 73 an embodiment according to the present invention of a waveform 73400 is illustrated. A pulse 73401 is repeated within a burst 73402 that has a finite duration 73403 alternatively referred to as width 73403. The duration 73403 is such that a duty cycle which can be defined as a ratio of burst duration to signal period is between about 1 to about $10^{-5}$. Preferably pseudo rectangular 10 microsecond pulses for pulse 73401 applied in a burst 73402 for about 10 to about 50 msec having a modified 1/f amplitude envelope 73404 and with a finite duration 73403 corresponding to a burst period of between about 0.1 and about 10 seconds are utilized.

FIG. 74 illustrates an embodiment of an apparatus according to the present invention. A garment 74501 such as a brassiere is constructed out of materials that are lightweight and portable such as nylon but other materials can be used. A miniature control circuit 74502 is coupled to a generating device such as an electrical coil 74503. Preferably the miniature control circuit 74502 and the electrical coil 74503 are constructed in a manner as described above in reference to FIG. 71. The miniature control circuit and the electrical coil can be connected with a connecting means such as a wire 74504. The connection can also be direct or wireless. The electrical coil 74503 is integrated into the garment 74501 such that when a user wears the garment 74501, the electrical coil is positioned near an excessive fibrous capsule formation location or capsular contracture location of the user. An advantage of the present invention is that its ultra lightweight coils and miniaturized circuitry allow for the garment 74501 to be completely self-contained, portable, and lightweight. An additionally advantageous result of the present invention is that the garment 74501 can be constructed to be inconspicuous when worn and can be worn as an outer garment such as a shirt or under other garments, so that only the user will know that the garment 74501 is being worn and treatment is being applied. Use with common physical therapy treatment modalities, and at any excessive fibrous capsule location or capsular contracture location for which pain relief, and tissue and organ healing is easily obtained. An advantageous result of application of the present invention is that tissue growth, repair, and maintenance can be accomplished and enhanced anywhere and at anytime. Yet another advantageous result of application of the present invention is that growth, repair, and maintenance of molecules, cells, tissues, and organs can be accomplished and enhanced anywhere and at anytime. Another embodiment according to the present invention delivers PEMF for application to fibrous capsules.

It is further intended that any other embodiments of the present invention that result from any changes in application or method of use or operation, method of manufacture, shape, size or material which are not specified within the detailed written description or illustrations and drawings contained herein, yet are considered apparent or obvious to one skilled in the art, are within the scope of the present invention.

The process of the invention will now be described with reference to the following illustrative examples.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if Ca is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween80; and 1 mM EGTA12. Free $Ca^{2+}$ was varied in the 1-7 µM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 µL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 µM 32P ATP, and was stopped with Laemmli Sample Buffer solution containing 30 µM EDTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

The signal comprised repetitive bursts of a high frequency waveform. Amplitude was maintained constant at 0.2 G and repetition rate was 1 burst/sec for all exposures. Burst duration varied from 65 µsec to 1000 µsec based upon projections of Power SNR analysis which showed that optimal Power SNR would be achieved as burst duration approached 500 µsec. The results are shown in FIG. 75 wherein burst width 75601 in msec is plotted on the x-axis and Myosin Phosphorylation 75602 as treated/sham is plotted on the y-axis. It can be seen that the PMF effect on $Ca^{2+}$ binding to CaM approaches its maximum at approximately 500 µsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 µsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 µsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in kg/mm2. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per mm2 of the two strips from the same wound.

The results showed average tensile strength for the 65 µsec 1 Gauss PRF signal was 19.3±4.3 kg/mm2 for the exposed group versus 13.0±3.5 kg/mm2 for the control group ($p<0.01$), which is a 48% increase. In contrast, the average tensile strength for the 2000 µsec 0.2 Gauss PRF signal, configured according to an embodiment of the present invention using a Power SNR model was 21.2±5.6 kg/mm2 for the treated group versus 13.7±4.1 kg/mm2 ($p<0.01$) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

This example illustrates the effects of PMF stimulation of a T-cell receptor with cell arrest and thus behave as normal T-lymphocytes stimulated by antigens at the T-cell receptor such as anti-CD3.

In bone healing, results have shown that both 60 Hz and PEMF fields decrease DNA synthesis of Jurkat cells, as is expected since PMF interacts with the T-cell receptor in the absence of a costimulatory signal. This result is consistent with an anti-inflammatory response, as has been observed in clinical applications of PMF stimuli. The PEMF signal is more effective. A dosimetry analysis performed according to an embodiment of the present invention demonstrates why both signals are effective and why PEMF signals have a greater effect than 60 Hz signals on Jurkat cells in the most EMF-sensitive growth stage.

Comparison of dosimetry from the two signals employed involves evaluation of the ratio of the Power spectrum of the thermal noise voltage that is Power SNR, to that of the induced voltage at the EMF-sensitive target pathway structure. The target pathway structure used is ion binding at receptor sites on Jurkat cells suspended in 2 mm of culture medium. The average peak electric field at the binding site from a PEMF signal comprising 5 msec burst of 200 µsec pulses repeating at 15/sec was 1 mV/cm, while for a 60 Hz signal the average peak electric field was 100 µV/cm.

FIG. 76 is a graph of results wherein Induced Field Frequency 76701 in Hz is shown on the x-axis and Power SNR 702 is shown on the y-axis. FIG. 76 illustrates that both signals have sufficient Power spectrum that is Power SNR≥1, to be detected within a frequency range of binding kinetics. However, maximum Power SNR for the PEMF signal is significantly higher than that of the 60 Hz signal. This is due to a PEMF signal having many frequency components falling within a bandpass of the target pathway structure. The single frequency component of a 60 Hz signal lies at the mid-point of the bandpass of a target pathway structure. The Power SNR calculation that was used in this example is dependent upon $\tau_{ion}$ which is obtained from the rate constant for ion binding. Had this calculation been performed a priori it would have concluded that both signals satisfied basic detectability requirements and could modulate an EMF-sensitive ion binding pathway at the start of a regulatory cascade for DNA synthesis in these cells. The previous examples illustrate that utilizing the rate constant for Ca/CaM binding could lead to successful projections for bioeffective EMF signals in a variety of systems.

EXAMPLE 4

In this example six patients who had developed capsular contracture after receiving bilateral breast implants were treated with a special support brassiere having embedded coils located in each cup and a generator for each coil located in a special pocket in the strap above each cup as described in FIG. 5 above. PEMF signals generated by the apparatus configured according to an embodiment of the present invention comprised a repetitive burst of radio frequency sinusoidal waves configured according to an embodiment of the present invention. The PEMF signal induced a peak electric field in a range of 1 to 10 mV/cm. All patients were provided a regimen that comprised six thirty minute sessions for days 1 to 3 post implant, four sessions for days 4 to 6 post implant, and two sessions for all subsequent days. Clinical evaluation demonstrated that by day 7 the fibrous capsule was significantly softer and patients reported significantly less pain and discomfort than prior to the treatment. Clinical evaluations at one and three months post PEMF treatment revealed significant resolution of the fibrous capsule and its corresponding symptoms.

Part 11

Basal levels of intracellular $Ca^{2+}$ are typically 50-100 nM, tightly maintained by a number of physiological calcium buffers. It is generally accepted that transient elevations in cytosolic $Ca^{2+}$ from external stimuli as simple as changes in temperature and mechanical forces, or as complex as mechanical disruption of tissue, rapidly activate CaM, which equally rapidly activates the cNOS enzymes, i.e., endothelial and neuronal NOS, or eNOS and nNOS, respectively. Studies have shown that both isoforms are inactive at basal intracellular levels of $Ca^{2+}$, however, their activity increases with elevated $Ca^{2+}$, reaching half-maximal activity at about 300 nM. Thus, nNOS and eNOS are regulated by changes in intracellular $Ca^{2+}$ concentrations within the physiological range. In contrast, a third, inducible isoform of NOS (iNOS), which is upregulated during inflammation by macrophages and/or neutrophils, contains CaM that is tightly bound, even at low resting levels of cytosolic $Ca^{2+}$, and is not sensitive to intracellular $Ca^{2+}$.

Once cNOS is activated by CaM it converts its substrate, L-arginine, to citrulline, releasing one molecule of NO. As a gaseous free radical with a half-life of about 5 sec, NO diffuses locally through membranes and organelles and acts on molecular targets at a distance up to about 200 μm. The low transient concentrations of NO from cNOS can activate soluble guanylyl cyclase (sGC), which catalyzes the synthesis of cyclic guanosine monophosphate (cGMP). The CaM/NO/cGMP signaling pathway is a rapid response cascade which can modulate peripheral and cardiac blood flow in response to normal physiologic demands, as well as to inflammation. This same pathway also modulates the release of cytokines, such as interleukin-1beta (IL-1β) and growth factors such as basic fibroblast growth factor (FGF-2) and vascular endothelial growth factor (VEGF) which have pleiotropic effects on cells involved in tissue repair and maintenance.

Following an injury, e.g., a bone fracture, torn rotator cuff, sprain, strain or surgical incision, repair commences with an inflammatory stage during which the pro-inflammatory cytokine IL-1β is rapidly released. This, in turn, up-regulates iNOS, resulting in the production of large amounts of NO in the wound bed. Continued exposure to NO leads to the induction of cyclooxygenase-2 and increased synthesis of prostaglandins which also play a role in the inflammatory phase. While this process is a natural component of healing, when protracted, it can lead to increased pain and delayed or abnormal healing. In contrast, CaM/eNOS/NO signaling has been shown to attenuate levels of IL-1β and down-regulate iNOS. As tissue further responds to injury, the CaM/NO/cGMP cascade is activated in endothelial cells to stimulate angiogenesis, without which new tissue growth cannot be sustained. Evidence that non-thermal EMF can modulate this cascade is provided by several studies. An early study showed that the original BGS signal promoted the creation of tubular, vessel-like, structures from endothelial cells in culture in the presence of growth factors. Another study using the same BGS signal confirmed a seven-fold increase in endothelial cell tubularization in vitro. Quantification of angiogenic proteins demonstrated a five-fold increase in FGF-2, suggesting that the same BGS signal stimulates angiogenesis by increasing FGF-2 production. This same study also reported increased vascular in-growth more than two-fold when applied to an implanted Matrigel plug in mice, with a concomitant increase in FGF-2, similar to that observed in vitro. The BGS signal significantly increased neovascularization and wound repair in normal mice, and particularly in diabetic mice, through an endogenous increase in FGF-2, which could be eliminated by using a FGF-2 inhibitor.

Similarly, a pulse modulated radio frequency (PRF) signal of the type used clinically for wound repair was reported to significantly accelerate vascular sprouting from an arterial loop transferred from the hind limb to the groin in a rat model. This study was extended to examine free flap survival on the newly produced vascular bed. Results showed 95% survival of PRF-treated flaps compared to 11% survival in the sham-treated flaps, suggesting a significant clinical application for PRF signals in reconstructive surgery.

In some embodiments, the proposed EMF transduction pathway relevant to tissue maintenance, repair and regeneration, begins with voltage-dependent $Ca^{2+}$ binding to CaM, which is favored when cytosolic $Ca^{2+}$ homeostasis is disrupted by chemical and/or physical insults at the cellular level. Ca/CaM binding produces activated CaM that binds to, and activates, cNOS, which catalyzes the synthesis of the signaling molecule NO from L-arginine. This pathway is shown in its simplest schematic form in FIG. 77A.

As shown in FIG. 77A, cNOS* represents activated constitutive nitric oxide synthase (cNOS), which catalyzes the production of NO from L-arginine. The term "sGC*" refers to activated guanylyl cyclase which catalyzes cyclic guanosine monophosphate (cGMP) formation when NO signaling modulates the tissue repair pathway. "AC*" refers to activated adenylyl cyclase, which catalyzes cyclic adenosine monophosphate (cAMP) when NO signaling modulates differentiation and survival.

According to some embodiments, an EMF signal can be configured to accelerate cytosolic ion binding to a cytosolic buffer, such as $Ca^{2+}$ binding to CaM, because the rate constant for binding, $k_{on}$ is voltage-dependent and $k_{on}$ is much greater than the rate constant for unbinding, $k_{off}$, imparting rectifier-like properties to ion-buffer binding, such as $Ca^{2+}$ binding to CaM.

For example, EMF can accelerate the kinetics of $Ca^{2+}$ binding to CaM, the first step of a well characterized cascade that responds to chemical or physical insults. Ca/CaM binding is kinetically asymmetrical, i.e., the rate of binding exceeds the rate of dissociation by several orders of magnitude ($k_{on} \gg k_{off}$), driving the reaction in the forward direction. Ca/CaM binding has been well characterized, with the binding time constant reported to be in the range of $10^{-2}$-$10^{-3}$ sec. In contrast, release of $Ca^{2+}$ from CaM cannot occur until cNOS* has converted L-arginine to citrulline and NO, which takes the better part of a second. Subsequent reactions involving NO depend upon the cell/tissue state. For example, tissue repair requires a temporal sequence of inflammatory, anti-inflammatory, angiogenic and proliferative components. Endothelial cells orchestrate the production of FGF-2 and VEGF for angiogenesis. For each of these phases, early NO production by endothelial cells, leading to increased cGMP by these, as well as other NO targets, such as vascular smooth muscle, would be expected to be modulated by an EMF effect on sGC via Ca/CaM binding. In contrast, nerve or bone regeneration may require other pathways leading to differentiation during development and growth, and prevention of apoptosis, as in response to injury or neurodegenerative diseases. For these cases, early cyclic adenosine monophosphate (cAMP) formation would be modulated by an EMF effect on sAC via Ca/CaM binding.

The substantial asymmetry of Ca/CaM binding kinetics provides a unique opportunity to configure EMF signals that selectively modulate $k_{on}$. In general, if $k_{on} \gg k_{off}$, and $k_{on}$ is voltage-dependent, according to the present invention, ion binding could be increased with an exogenous electric field signal having a carrier period or pulse duration that is significantly shorter than the mean lifetime of the bound ion. This applies to the CaM signaling pathway, causing it to exhibit rectifier-like properties, i.e., to yield a net increase in the population of bound $Ca^{2+}$ because the forward (binding) reaction is favored. The change in surface concentration, $\Delta\Gamma$, of $Ca^{2+}$ at CaM is equal to the net increase in the number of ions that exit the outer Helmholtz plane, penetrate the water dipole layer at the aqueous interface of the binding site, and become bound in the inner Helmoltz plane. For the general case of ion binding, evaluation of Ca/CaM binding impedance, ZA(s), allows calculation of the efficacy of any given waveform in that pathway by evaluating the frequency range over which the forward binding reaction can be accelerated. Thus, binding current, IA(t), is proportional to the change in surface charge (bound ion concentration) via dq(t)/dt, or, in the frequency domain, via sqA(s). IA(s) is, thus, given by:

$$I_A(s) = sq_A(s) = s\Gamma_o f(\Delta\Gamma(s)) \tag{1}$$

where s is the real-valued frequency variable of the Laplace transform. Taking the first term of the Taylor expansion of equation 1 gives:

$$I_A(s) = q_\Gamma s \bar{L}_o \epsilon \bar{I}(s) \tag{2}$$

where $q\Gamma = \partial q/\partial \Gamma$, a coefficient representing the dependence of surface charge on bound ion concentration. $\Delta\Gamma(s)$ is a function of the applied voltage waveform, E(s), and, referring to the reaction scheme in FIG. 77, of the change in concentration of eNOS*, defined as $\Delta\Phi(s)$:

$$\Delta\Gamma(s) = k_{on}/\Gamma_o s[-\Delta\Gamma(s) + aE(s) + \Delta\Phi(s)] \tag{3}$$

where $\Gamma_o$ is the initial surface concentration of $Ca^{2+}$ (homeostasis), and $a = \partial F/\partial E$, representing the voltage dependence of $Ca^{2+}$ binding. Referring to the reaction scheme in FIG. 77, it may also be seen that eNOS* depends only upon $Ca^{2+}$ binding, i.e., $\Delta\Gamma(s)$. Thus:

$$\Delta\Phi(s) = \upsilon\Phi/\Phi_{os}[-\Delta\Phi(s) - \Delta\Gamma(s)] \tag{4}$$

where $\upsilon\Phi$ is the rate constant for Ca/CaM binding to eNOS and $\Phi_o$ is the initial concentration of eNOS* (homeostasis).

Using equations 2, 3 and 4, and for $k_{on} \gg \upsilon_\varphi$, ZA(s) may be written:

$$Z_A(s) = \frac{E(s)}{I_A(s)} = \frac{1}{q_\Gamma a}\left[\frac{1 + \Gamma_o s/k_{on}}{\Gamma_o s}\right] \tag{5}$$

Equation 5 describes the overall frequency response of the first binding step in a multistep ion binding process at an electrified interface, wherein the second step requires that the bound ion remain bound for a period of time significantly longer than the initial binding step. For this case, the first ion binding step is represented by an equivalent electrical impedance which is functionally equivalent to that of a series $R_A$-$C_A$ electric circuit, embedded in the overall dielectric properties of the target. $R_A$ is inversely proportional to the binding rate constant ($k_{on}$), and $C_A$ is directly proportional to bound ion concentration.

Some embodiments provide that a electromagnetic field, for which pulse duration or carrier period is less than about half of the bound ion lifetime can be configured to maximize current flow into the capacitance CA, which will increase the voltage, $E_b(s)$, where s is the LaPlace frequency, across CA. $E_b(s)$ is a measure of the increase in the surface concentration of the binding ion in the binding sites of the buffer, above that which occurs naturally in response to a given physiological state. The result is an increase in the rate of biochemical signaling in plant, animal and human repair, growth and maintenance pathways which results in the acceleration of the normal physiological response to chemical or physical stimuli. The following equation demonstrates the relation between the configured electromagnetic waveform, E(s) and $E_b(s)$.

$$E_b(s) = \frac{(1/sC_A)E(s)}{(R_A^2 + (1/sC_A)^2)^{1/2}} \tag{6}$$

Some embodiments also provide that a time-varying electromagnetic field for which pulse duration or carrier period is less than about half of the bound ion lifetime of $Ca^{2+}$ binding to CaM will maximize the current flow into the Ca/CaM binding pathway to accelerate the CaM-dependent signaling which plants, animals and humans utilize for tissue growth, repair and maintenance. In particular, a time-varying electromagnetic field may be configured to modulate CaM-dependent NO/cGMP signaling which accelerates; pain and edema relief, angiogenesis, hard and soft tissue repair, repair of ischemic tissue, prevention and repair of neurodegenerative diseases, nerve repair and regeneration, skeletal and cardiac muscle repair and regeneration, relief of muscle pain, relief of nerve pain, relief of angina, relief of degenerative joint disease pain, healing of degenerative joint disease, immunological response to disease, including cancer.

Another embodiment according to the present invention is an electromagnetic signal which accelerates the kinetics of $Ca^{2+}$ binding by maximizing non-thermal $E_b(s)$ at its CaM binding sites, consisting of a 1-10 msec pulse burst of 27.12 MHz radio frequency sinusoidal waves, repeating between about 1 and about 5 bursts/sec and inducing a peak electric field between about 1 and about 100 V/m, then coupling the configured waveform using a generating device such as ultra lightweight wire coils that are powered by a waveform configuration device such as miniaturized electronic circuitry which is programmed to apply the waveform at fixed or variable intervals, for example 1 minute every 10 minutes, 10 minutes every hour, or any other regimen found to be beneficial for a prescribed treatment.

In some embodiments, the PEMF signal configuration used may be a sinusoidal wave at 27.12 MHz with peak magnetic field B=0.05 G (Earth=0.5 G), burst width, T1=5 msec, and repetition rate T2=2/sec as shown in FIG. 86A. The PEMF signal configuration may also induce a 1-5 V/m peak electric field in situ with a duty cycle=2%, without heat or excitable membrane activity produced. The field may be applied through an electrical pulse generator to a coil tuned to 27.12 MHz. The burst width and repetition rate may be chosen by comparing the voltage induced across the $Ca^{2+}$ binding site over a broad frequency range to noise fluctuations over the same range. Effects of burst widths of two 27.12 MHz sinusoidal signals at 1 Hz are illustrated in FIG. 86B. As shown in FIG. 10B, high signal-to-noise ratios (SNRs) can be achieved in the relatively low frequency range and at peak magnetic field 0.05 G.

FIG. 78A illustrates a block diagram of an EMF delivery apparatus as described according to some embodiments. As shown in FIG. 78A, the apparatus may have miniaturized circuitry for use with a coil applicator. In some embodiments, the apparatus may include a CPU MODULATOR, a BATTERY MODULE, a POWER SUPPLY, On/Off switch, and an output amplifier, AMP, as illustrated. In further variations, the CPU MODULATOR may be an 8 bit 4 MHz micro-controller; however, other suitable bit-MHz combination micro-controllers may be used as well. For example, in some embodiments, the CPU MODULATOR may be programmed for a given carrier frequency or pulse duration, such as about 27.12 MHz sinusoidal wave. Moreover, the CPU MODULATOR may be programmed for a given burst duration, for example about 3 msec. In further variations, the CPU MODULATOR may be programmed to provide a given in situ peak electric field, for example 20 V/m; or a given treatment time, for example about 15 minutes; and/or a given treatment regimen, for example about 10 minutes about every hour. The CPU MODULATOR may also be programmed to deliver an EMF waveform to the target ion binding pathway.

In further embodiments, the BATTERY MODULE may be rechargeable. In other embodiments, the BATTERY MODULE has an output voltage of 3.3 V; however, other voltages can be used as is understood in the art. In further variations, the BATTERY MODULE supplies DC voltage and current to a POWER SUPPLY which provides operating power to the CPU MODULATOR and the output amplifier AMP.

In some variations, the electromagnetic signal (or a field generated from a electromagnetic signal) is applied inductively to the plant animal or human target with a COIL applicator, or capacitively with electrodes in electrochemical contact with the out conductive surface of the target structure (not shown). In some variations, the COIL applicator is flexible and circular, but may also be anatomically conformable, such as oval or saddle shaped, with a diameter of between about 2 cm to about 50 cm. An electromagnetic treatment, or, if desired, an electromagnetic treatment regimen, can be initiated with the ON/OFF switch, which may be mechanical or electronic.

Some embodiments combine the signal generation and coil or electrode applicator into one portable or disposable unit, such as illustrated in FIG. 78B (which will be described in greater detail below) for the case of an inductively coupled signal. In some variations, when electrical coils are used as the applicator, the electrical coils can be powered with a time varying magnetic field that induces a time varying electric field in a target pathway structure according to Faraday's law. An electromagnetic field generated by a circuit such as shown in FIG. 78A can also be applied using electrochemical coupling, wherein electrodes are in direct contact with skin or another outer electrochemically conductive boundary of a target pathway structure.

In yet another embodiment, the electromagnetic field generated by the generating circuit of FIG. 78A (or FIG. 78B) can also be applied using electrostatic coupling wherein an air gap exists between a generating device such as an electrode and a target pathway structure such as a molecule, cell, tissue, and organ of a plant animal or human. Advantageously, the ultra lightweight coils and miniaturized circuitry, according to some embodiments, allow for use with common physical therapy treatment modalities and at any location on a plant, animal or human for which any therapeutic or prophylactic effect is desired. An advantageous result of application of some embodiments described is that a living organism's wellbeing can be maintained and enhanced.

Referring to FIG. 78C, an embodiment according to the present invention of an induced electric field waveform delivered to a target pathway structure is illustrated. As shown in FIG. 78C, burst duration and period are represented by $T_1$ and $T_2$, respectively. In some embodiments, the signal within the rectangular box designated at $T_1$ can be, rectangular, sinusoidal, chaotic or random, provided that the waveform duration or carrier period is less than one-half of the target ion bound time. The peak induced electric field is related to the peak induced magnetic field, shown as B in FIG. 78C, via Faraday's Law of Induction.

In further variations, the induced electric field waveform provides a burst of duration between about 1 msec and about 30 msec, containing a repetitive rectangular pulse, a sinusoidal wave or a chaotic or random waveform, having, respectively, a period or frequency less than half of the bound time of the target ion binding pathway, repeats between about 1 and about 10 bursts/sec, and induces a peak electric field of 20 V/m which is proportional to a peak applied time varying magnetic field of 50 mG according to Faraday's Law of Induction. The induced electric field illustrated in FIG. 78C can be configured according to embodiments described to modulate biochemical signaling pathways in plant, animal and human targets, such as those illustrated in FIG. 77A.

In addition to the above, induced time-varying electric fields (e.g PEMF) may be configured to affect neurological tissue including specific cellular/molecular pathways in the CNS tissues allowing these tissues to react in a physiologically meaningful manner. For example, a waveform may be configured within a prescribed set of parameters so that a particular pathway, such as CaM-dependent NO synthesis within the neurological tissue target, is modulated specifically. Both the applied waveform and the dosing or treatment regime applied may be configured so that at least this pathway is targeted specifically and effectively. Furthermore, the stimulation protocol and dosing regimen may be configured so that an electromagnetic field applicator device may be portable/wearable, lightweight, require low power, and does not interfere with medical or body support such as wound dressings, orthopedic and other surgical fixation devices, and surgical interventions.

In some embodiments, a method of treating a subject for a neurological condition, injury, or disease includes applying the one or more (or a range of) waveforms that are needed to target the appropriate pathways in the target neuronal tissue. This determination may be made through calculation of mathematical models such as those described in U.S. Patent Publication No. 2011-0112352 filed Jun. 21, 2010 as U.S. patent application Ser. No. 12/819,956 (herein incorporated by reference) to determine the dosing regimen appropriate for modulating a molecular pathway (e.g. Ca/CaM pathway).

For example, as discussed above, it is believed that pathways involved in the maintenance and repair of cerebral tissue include the Ca/CaM pathway. To modulate this pathway, in some variations, the electromagnetic/fields applied are configured to comprise bursts of at least one of sinusoidal, rectangular, chaotic or random wave shapes; burst duration less than about 100 msec, with frequency content less than about 100 MHz at 1 to 100 bursts per second. In other variations, the electromagnetic fields have a 1 to about a 50 msec burst of radio frequency sinusoidal waves in the range of about 1 to about 100 MHz, incorporating radio frequencies in the industrial, scientific, and medical band, for example 27.12 MHz, 6.78 MHz, or 40.68 MHz, repeating between about 0.1 to about 10 bursts/sec. In further variations, a PEMF signal can be applied that consists of a 2 msec burst of 27.12 MHz sinusoidal waves repeating at 2 Hz. In additional embodiments, an applied PEMF signal can consist of a sinusoidal waveform of 27.12 MHz pulse-modulated with 4 msec bursts having an amplitude of 0.001 G to 0.1 G, and repeating at 2 Hz. In additional embodiments, electromagnetic fields applied are configured to have a frequency content in a range of about 0.01 Hz to about 10,000 MHz having a burst duration from about 0.01 to about 100 msec, and having a burst repetition rate from about 0.01 to about 1000 bursts/second.

Alternatively, the carrier signal frequency may be below 1 MHz, such as 100,000 Hz, 10,000 Hz, 100 Hz or 1 Hz. In such variations, the lower carrier signal frequency requires a longer burst duration, e.g. 500 msec for 100 Hz carrier frequency, and a lower amplitude of between about 0.001 G and 0.01 G.

Electromagnetic signals can be applied manually or automatically through application devices to provide a range of electromagnetic fields, treatment ranges and doses. For example, PEMF signals can be applied for 15 minutes, 30 minutes, 60 minutes, etc. as needed for treatment. Electromagnetic signals can also be applied for repeated durations such as for 15 minutes every 2 hours. Treatment duration can also span minutes, days, weeks, etc. For example, PEMF signals can be applied for 15 minutes every 2 hours for 9 days. Furthermore, PEMF treatment can be provided for a therapeutic period of time. As used herein, the term therapeutic period is not limiting to any specific treatment regimen, but rather describes at least the total treatment period and treatment period per each treatment cycle. For example, a PEMF signal may be applied for 15 minutes every 2 hours continuously until levels of intracranial pressure decrease to acceptable levels. The therapeutic period would include at least the treatment interval, any inter-treatment interval, and the total treatment duration.

The electromagnetic applicator devices can also provide a time varying magnetic field (for example, peak=0.001 G to 0.1 G, Average=$10^{-6}$ G to $10^{-3}$ G) to induce a time varying electric field (for example average=0.1V/m to 100V/m) in the tissue target. Moreover, each signal burst envelope may be a random function providing a means to accommodate different electromagnetic characteristics of target tissue. Similarly, the number of treatments and the dose regime may vary depending on the progress of the target location.

In some embodiments, modifying neuronal pathways can result in increased or decreased cerebral blood flow to a target location. For example, modulating the Ca/CaM pathway can cause vasodilation in the target cerebral tissue. Vasodilation of cerebral tissue can result in increased cerebral blood flow which can mitigate inflammation, neuronal degeneration, and tissue death and promote tissue regrowth, repair, and maintenance.

In further embodiments, PEMF can be configured to treat a subject having a metal implant or other foreign object affixed to or penetrating the skull such that the treatment is not affected by the foreign object. Dose regimens such as those described above may still be applied in the presence of foreign metal objects that may have penetrated the skull (e.g. shrapnel) or been implanted (e.g. skull plate) by careful positioning of the applicator coil with respect to the position of the metal in the target, which advantageously allows for treatment of subjects with these conditions.

As is understood by one of ordinary skill in the art, the terms neurological condition, disease, injury etc. as used herein are not intended to be limited to any particular condition or injury described. A neurological injury can mean at least an injury that results from mechanical damage arising from an initial insult or trauma event and/or any secondary injury from secondary physiological responses. In some embodiments, the methods and devices contemplated may be configured to treat patients for whom the trauma event is initiated by medical personnel as part of another treatment. For example, in the case of a craniotomy to remove brain tumors or lesions, the neurological injury would include the surgical incision(s) into brain tissue and subsequent secondary injury from resulting inflammation or swelling that develops after the initial insult. Similarly, neurological conditions or diseases can mean at least, and non-exhaustively, degenerative disorders such as Alzheimer's or neurological, functional, or behavioral impairment(s) resulting from injury. For example, secondary physiological responses such as inflammation can damage healthy brain tissue which can result in impairment of a cognitive or behavioral function associated with that part of the brain.

FIG. 77B is a flow diagram of a method for treating a subject with a neurological condition, disease, or injury. In some variations, before beginning the treatment, one or more (or a range of) waveforms may be determined that target the appropriate pathway for the target tissue. In such embodiments, once this determination is made, electromagnetic fields are applied to the target location.

In further embodiments, the treatment waveform or PEMF signal may be determined by configuring the PEMF waveform to target a rhythm pattern of a physiological system or process. For example, a PEMF signal may be configured to modulate brain rhythms to effect relaxation or alertness depending on the needed physiological response. As is understood in the art, physiological systems like the CNS and the peripheral nervous system (PNS), in particular, the brain or heart emit electrical activity that can be measured and recorded by, for example, electroencephalography (EEG) or electrocardiography (EKG). During particular activities, such as sleep/rest or problem solving, the brain emits electrical/rhythmic activity (e.g. circadian rhythms) in certain frequency bands associated with the activity (e.g. theta, alpha, beta, etc.)

A PEMF waveform can be configured to a specific rhythm of a target location by providing a signal with the frequency, amplitude, burst duration, etc. associated with a particular activity of that target location. For example, for treatment of a neurological condition such as Alzheimer's, a PEMF waveform can be brought in close proximity to a region of the brain associated with problem solving. In such cases, the PEMF waveform provided to the patient can be configured to the rhythm frequency/band that is generally measured when normal problem solving skills are employed. The PEMF waveform may then be used to stimulate the target region while the patient is engaged in a problem solving activity. This treatment may help the patient regain or improve problem solving skills where the target region has exhibited diminished ability to emit normal electrical activity.

In further embodiments, the PEMF waveform may be configured to modulate rhythms associated with a physiological response that arises from a neurological injury. For example, as can be appreciated, neurological damage such as traumatic brain injury results in both secondary physiological responses in the CNS as well as responses in peripheral systems. With brain trauma, a patient's ability to regulate and maintain periphery systems such as the cardiac and pulmonary systems may be indirectly compromised. As such, some embodiments contemplated provide for PEMF configurations that treat a neurological injury by targeting non-neurological systems affected by the injury. In some embodiments, the PEMF waveforms are configured to modulate the rhythms or electrical activity of one or more non-neurological system(s).

In further embodiments, the PEMF waveform may be configured to modulate sleep patterns. In particular, PEMF configurations may increase the duration of slow-wave (Delta) sleep in each sleep cycle which may allow the injured person to maximize the production of human growth hormone, which, in turn, may increase healing for any injury, including CNS and PNS injuries, and provides a prophylactic response to protect from further injury.

As described in FIG. 77B, a method of treating a subject with a neurological injury or condition may include the step of placing the tissue to be treated (e.g. near one or more CNS regions) in contact, or in proximity to, a PEMF device 77101. Any appropriate PEMF device may be used. In general, the device may include an applicator (e.g. inductor applicator) which may be placed adjacent to or in contact with the target location/tissue. The device may also contain a signal conditioner/processor for forming the appropriate waveform to selectively and specifically modulate a pathway (e.g. Ca/CaM pathway). In further embodiments, the device may include a timing element (e.g. circuit) for controlling the timing automatically after the start of the treatment.

In the example shown in FIG. 77B, once treatment begins 77103, the device, in some variations, applies an envelope of high-frequency waveforms at low amplitude (e.g. less than 50 milliGauss, less than 100 milliGaus, less than 200 milliGauss, etc.) 77105. This envelope of high-frequency pulses is then repeated at a particular frequency after an appropriate delay. This series of bursts can be repeated for a first treatment time (e.g. 5 minutes, 15 minutes, 20 minutes, 30 minutes, etc.) and then followed by a delay during which the treatment is "off" 77107. This waiting interval (inter-treatment interval) may last for minutes or hours (15 minutes, 2 hours, 4 hours, 8 hours, 12 hours, etc.) and then the treatment interval may be repeated again until the treatment regime is complete 77109.

In some variations, the treatment device is pre-programmed (or configured to receive pre-programming) to execute the entire treatment regime (including multiple on-periods and/or intra-treatment intervals) punctuated by predetermined off-periods (inter-treatment intervals) when no treatment is applied. In further variations, the device is pre-programmed to emit a PEMF signal at 27.12 MHz at 2 msec bursts repeating at 2 bursts/sec. In other embodiments, the device is pre-programmed to emit a PEMF signal at 27.12 MHz (at about amplitude 250-400 mV/cm) pulsed in 4 msec bursts at 2 Hz.

As discussed, the selection of a treatment regime may be determined by the particular neurological injury or condition etc. at issue. In the case of treating secondary physiological responses from TBI, the treatment parameters may be selected to target any number or combination of physiological responses. For example, some embodiments contemplated provide for devices and methods for reducing intracranial pressure. Oftentimes a trauma event such as brain surgery will induce cerebral edema, the extra- and intracellular accumulation of fluid resulting from changes in vascular endothelium causing vasodilation and leakage as well as surges of extracellular fluid into cells after disturbances in glutamate release and calcium and sodium ion influx. This is potentially fatal as increased intracranial pressure decreases cerebral perfusion pressure and interrupts cerebral blood flow to brain tissue, which can cause ischemia and neuronal death.

To manage intracranial pressure, some embodiments provide a method of reducing intracranial pressure by applying a PEMF signal in close proximity to a target location. Such treatment parameters may include any of those discussed, which are found suitable for the needs of the patient. Moreover, in some embodiments, the selected PEMF signal can be applied continuously to the target area until an acceptable intracranial pressure level is reached. An acceptable intracranial pressure level can be patient-specific depending on the circumstances; however, generally normal intracranial pressure ranges from about 5 mmHg to about 15 mmHg. Additionally, intracranial pressure above about 20 mmHg is generally considered harmful. As such, PEMF treatment may be initiated once intracranial pressure is above an acceptable level.

Alternatively, PEMF treatment may be discontinued once acceptable levels are attained. In some embodiments, the PEMF treatment can be applied as shown in FIG. 77B with inter-treatment intervals. For example, a PEMF signal of 27.12 MHz pulsed in 4 msec bursts at 2 Hz may be applied for 15 minutes every 2 hours for 9 days. In other embodiments, the PEMF signal may be applied continuously without an inter-treatment interval until an acceptable level of intracranial pressure is reached. In further embodiments, the PEMF therapy includes monitoring a neurological factor such as intracranial pressure of the subject such that PEMF treatment can be initiated or discontinued depending on the levels of intracranial pressure.

In some embodiments, the patient may experience intracranial pressure below about 20 mmHg; however, due to lower cerebral perfusion pressure, PEMF therapy may be initiated to mitigate conditions such as ischemia. In further embodiments, the PEMF therapy may be preventative and applied to maintain the subject's pressure levels within a selected range that may or may not be within the normal pressure ranges described above. Additionally, a PEMF device may be pre-programmed with a controller or processor that monitors and adjusts PEMF treatment based on the levels of intracranial pressure. A PEMF device may be configured to communicate with a sensor or other data gathering devices/components that provide information regarding intracranial pressure or other neurological factors.

In addition to intracranial pressure, additional embodiments provide for PEMF methods and devices for treating inflammation resulting as a secondary physiological response to neurological injury (e.g. TBI) Inflammation is a natural and protective systemic physiological response to invading pathogens to preserve tissue viability and function. However, if this process remains unchecked, it can lead to secondary tissue damage in the CNS. In the case of brain injury, inflammation can restrict cerebral blood flow and cause damage or death to healthy brain tissue. Although the complex process involved in inflammation is not completely known, it is understood that following injury, microglia and astrocytes will activate and migrate to the injury site. Once activated, these cells will secrete destructive cytokines (e.g. IL-1α, IL-1β and TNF-α) as well as other inflammatory molecules such as chemokines, which can attract additional immune-mediators. Some of these immune-mediators can penetrate the blood-brain barrier and further add to an inflammatory response. Although microglia, cytokines, chemokines, and other inflammatory promoters are required to some extent to remove invading pathogens, protracted and unremitting inflammation can cause long term damage. As such, some embodiments provide for PEMF treatments and devices to alter the levels of inflammatory factors present in a target location.

Because increased levels of cytokines such as IL-1β have been correlated with high intracranial pressure, inflammation, and breakdown of the blood-brain barrier, some embodiments provide for a PEMF treatment that can reduce or mitigate the levels of cytokines in order to prevent secondary injury to target brain tissue. In such embodiments, a PEMF applicator device such as the one described in FIG. 78B is placed in close proximity to a target tissue location (e.g. brain area). The PEMF applicator device is then activated and generates a PEMF signal configured to reduce the levels of cytokines in the target location. In some embodiments, a PEMF signal of 27.12 MHz pulsed in 4 msec bursts at 2 Hz for about 5 to about 15 minutes every 20 minutes to reduce the quantities of IL-1β present in target location. The PEMF signal may be applied for a selected amount of time before pausing for an inter-treatment interval (see FIG. 77B) and then repeated for a total treatment time. In further embodiments, the PEMF treatment may be applied continuously until acceptable levels of cytokines or inflammation are reached. The PEMF treatment may also be applied continuously or intermittently in response to direct data regarding level of cytokines or inflammation or indirect data such as levels of cerebral blood flow.

In other embodiments, the PEMF treatment may be directed toward altering the levels of microglia or astrocytes present in the target location. As discussed, once activated, microglia not only produce cytokines but also remove damaged or dead tissue and infectious agents. In other words, microglia are dually neuroprotective and neurotoxic. As such, reducing or increasing the levels of microglia at different stages following a neurological injury or condition may modulate the helpful and harmful effects of microglia present in the target location. For example, in the immediate period following injury, an increase in activated microglia may help to clear and collect pathogens and debris from cellular or tissue damage. By doing so, an increased level of microglia can reduce the chances of infection and prevent inflammation before it begins. Moreover, increased activity of microglia may enhance the repair of axons. Alternatively, at a later stage post-injury, reducing the number of activated microglia can reduce inflammation by preventing microglia from producing pro-inflammatory factors such as cytokines and chemokines. As the suitability of increasing or decreasing microglia levels in a target area are dependent on the type of injury/condition and the patient's needs, flexibility will be needed to modify PEMF treatment as needed. In some embodiments, the PEMF device/treatment can be pre-programmed to alter treatment as needed according to monitored conditions such as the levels of inflammation, levels of microglia, or time period after injury. In other variations, the PEMF treatment can be manually modified as needed. In further variations, the PEMF treatment may appear to first decrease microglial activity, but the apparent decrease in microglia may be transitory and microglial activity may actually be increased/accelerated over the course of treatment. As shown in FIGS. 87 and 88 (and further described in detail in Examples 7 and 8), PEMF treatment can effect an increase or decrease in microglial activity.

Further embodiments provide for treatments and devices for preventing neuronal death. Injuries caused by both contusive trauma and by invading foreign objects (e.g. penetrating injury) will kill neurons, which can be responsible for lasting behavioral deficits as well as limbic and cognitive disabilities. Some PEMF treatments contemplated provide for therapies that increase neuronal survival. For example, PEMF signals can be applied to a target location with damaged neuronal cells. The PEMF signals may increase the level of activated microglia present at the site, for example, which can help remove pathogens that could cause infection to already damaged neuronal cells. Moreover, reductions in tissue swelling and inflammation also indirectly increase neuronal survival, as these processes can both initiate and exacerbate acute and chronic neurodegeneration. Treatment parameters may be selected according any of the described regimes as needed for treatment.

In treating neurological conditions and injuries, a primary concern is retaining or recovering cognitive, motor, limbic, and behavioral functions. Tissue damage and death, especially in the brain, can irreversibly affect the ability of patients to function normally after a traumatic event. Some embodiments provide for treatments and devices to improve cognitive, motor, behavioral etc. function after a neurological injury/condition. Some variations provide for short term and long term PEMF treatment where ongoing assessment of the patient's progress is recorded to determine whether treatment should be continued or modified.

As can be appreciated, PEMF signals can be configured to treat one or more of the conditions described. For example, a PEMF treatment may be used to reduce intracranial pressure and inflammation in a patient in need thereof.

FIG. 78B illustrates an embodiment of an apparatus 78200 that may be used. The apparatus is constructed to be self-contained, lightweight, and portable. A circuit control/signal generator 78201 may be held within a (optionally wearable) housing and connected to a generating member such as an electrical coil 78202. In some embodiments, the circuit control/signal generator 78201 is constructed in a manner that given a target pathway within a target tissue, it is possible to choose waveform parameters that satisfy a frequency response of the target pathway within the target tissue. For some embodiments, circuit control/signal generator 78201 applies mathematical models or results of such models that approximate the kinetics of ion binding in biochemical pathways. Waveforms configured by the circuit control/signal generator 78201 are directed to a generating member 78202. In some variations, the generating member 78202 comprises electrical coils that are pliable and comfortable. In further embodiments, the generating member 78202 is made from one or more turns of electrically conducting wire in a generally circular or oval shape, any other suitable shape. In further variations, the electrical coil is a circular wire applicator with a diameter that allows encircling of a subject's cranium. In some embodiments, the diameter is between approximately 6-8 inches. In general, the size of the coil may be fixed or adjustable and the circuit control/signal generator may be matched to the material and the size of the applicator to provide the desired treatment.

The apparatus 78200 may deliver a pulsing magnetic field that can be used to provide treatment of a neurological condition or injury. In some embodiments, the device 78200 may apply a pulsing magnetic field for a prescribed time and can automatically repeat applying the pulsing magnetic field for as many applications as are needed in a given time period, e.g. 6-12 times a day. The device 78200 can be configured to apply pulsing magnetic fields for any time repetition sequence. Without being bound to any theory, it is believed that when electrical coils are used as a generating member 78202, the electrical coils can be powered with a time varying magnetic field that induces a time varying electric field in a target tissue location.

In other embodiments, an electromagnetic field generated by the generating member 78202 can be applied using electrochemical coupling, wherein electrodes are in direct contact with skin or another outer electrically conductive boundary of the target tissue (e.g. skull or scalp). In other variations, the electromagnetic field generated by the generating member 78202 can also be applied using electrostatic coupling wherein an air gap exists between a generating member 78202 such as an electrode and the target tissue. In further examples, a signal generator and battery is housed in the miniature circuit control/signal generator 78201 and the miniature circuit control/signal generator 78201 may contain an on/off switch and light indicator. In further embodiments, the activation and control of the treatment device may be done via remote control such as by way of a fob that may be programmed to interact with a specific individual device. In other variations, the treatment device further includes a history feature that records the treatment parameters carried out by the device such that the information is recorded in the device itself and/or can be transmitted to another device such as computer, smart phone, printer, or other medical equipment/device.

In other variations, the treatment device 78200 has adjustable dimensions to accommodate fit to a variety of patient head sizes. For example, the generating member 78202 may comprise modular components which can be added or removed by mated attaching members. Alternatively, the treatment device 200 may contain a detachable generating member (e.g. detachable circular coil or other configurations) that can be removed and replaced with configurations that are better suited for the particular patient's needs. A circular coil generating member 78202 may be removed and replaced with an elongate generating member such that PEMF treatment can be applied where other medical equipment may obstruct access by a circular generating member 78202. In other variations, the generating member may be made from Litz wire that allows the generating member to flex and fold to accommodate different target areas or sizes.

In other embodiments, the diameter of a circular generating member may be selected based on the desired treatment regimen. In some variations, the depth of penetration for the electromagnetic field increases with increased diameter. In such embodiments, a larger diameter will provide a field with a greater field volume allowing for greater penetration in the target location. Accordingly, by modifying the diameter or size of the generating member, the depth of the treatment field can be adjusted as needed. Greater depth of penetration may be advantageous where the injured target region is below the surface of the target location. Alternatively, where a greater depth of penetration is not needed, generating members of smaller size may be more appropriate where surface application is desired. For example, for treatment of a large surface area, an array of smaller sized generating members can be used to cover a large area without deep penetration beyond the surface.

In further embodiments, the inductive device illustrated in FIG. 78B is flexible, portable and, if desired, disposable; and can be used alone or incorporated into an anatomical positioning device such as a dressing, bandage, compression bandage, compression dressing; knee, elbow, lower back, shoulder, foot, and other body portion wrap and support; garments, footwear, gloves, and fashion accessories; mattress pads, seat cushions, furniture, beds; in seats or beds within cars, motorcycles, bicycles, buses, trains, planes, boats and ships.

In some embodiments, the devices may include a sensor configured to monitor a patient's condition for changes. For example, a device may include a sensor that collects data on the patient's intracranial pressure. Based on the amount of intracranial pressure, the device may automatically turn on for treatment once threshold pressure levels are reached. Similarly, the device may turn off automatically if pressure levels return to normal. Additionally, a device providing treatment may modify and adjust treatment parameters based on the feedback from sensors. For example, a device may change treatment parameters if the sensor registers an increase in intracranial pressure. Moreover, in some variations, medical staff may be notified of changes to treatment parameters where the delivery device can communicate with another device such as computer, smart phone, printer, or other medical equipment/device.

EXAMPLE 1

An EMF signal, configured according to an embodiment of the present invention to modulate CaM-dependent signaling, consisting of a 27.12 MHz carrier, pulse-modulated with a 3 msec burst repeating at 2 Hz and a peak amplitude of 0.05 G, was applied for 30 minutes to the MN9D dopaminergic neuronal cell line and increased NO production by several-fold in a serum depletion paradigm and produced a 45% increase in cGMP. The EMF effects on NO and cGMP were inhibited by the CaM antagonist N-(6-Aminohexyl)-5-chloro-1-naphthalenesulfonamide hydrochloride (W-7), indicating the EMF signal acted in this neuronal culture according to the transduction mechanism illustrated in FIG. 77A. These results are summarized in FIG. 79A.

The effect of the same EMF signal on cAMP production in MN9D cells was also studied. MN9D cells in serum free medium were removed from the incubator (repeatable temperature stress injury to transiently increase intracellular $Ca^{2+}$) and exposed to EMF for 15 min. cAMP was evaluated in cell lysates by ELISA. Results demonstrate that an EMF signal, configured according to an embodiment of the present invention, increased cAMP production by several-fold. Notably, the c-NOS inhibitor L-NAME abolished the PEMF effect on cAMP. The results, summarized in FIG. 79B, indicate EMF signals, configured according to an embodiment of the present invention, affect neuronal differentiation and survival.

EXAMPLE 2

In this example, a highly reproducible thermal myocardial injury was created in the region of the distal aspect of the Left Anterior Descending Artery at the base of the heart of adult male Sprague Dawley rats. The EMF waveform, configured as an embodiment of the present invention, was a 2 msec burst of 27.12 MHz sinusoidal waves repeating at 2 bursts/sec delivering 0.05 G at the tissue target. Five freely roaming animals in a standard rat plastic cage, with all metal portions removed, were placed within a single turn 14×21 inch coil. Exposure was 30 min twice daily for three weeks. Sham animals were identically exposed, but received no EMF signal.

Upon sacrifice, myocardial tissue specimens were stained with CD-31 to evaluate the presence of newly forming blood vessels and capillaries in peri-ischemic tissue. Results at 21 days showed that number of vessels and capillaries in peri-ischemic myocardial tissue was increased by approximately 100% ($p<0.001$) in EMF vs sham exposed animals.

That an EMF signal, configured as an embodiment of the present invention, modulated CaM-dependent NO release, as illustrated in FIG. 77A, was verified by feeding animals L-NAME, a cNOS inhibitor, in their drinking water for 7 days. EMF, configured as an embodiment of the present invention, accelerated angiogenesis at 7 days by 60%. The EMF effect was abolished by L-NAME, as illustrated in FIG. 80.

EXAMPLE 3

In this example, inflammation was induced in the left hind paw of Harlan Sprague-Dawley rats (200-340 g) by injection of 100 μL of a 3.5 mg/mL sterile phosphate buffered saline-based carrageenan solution into the footpad using a 30 gauge tuberculin syringe. The carrageenan dose was carefully calibrated to produce a mild, controllable form of inflammation that could be evaluated for rate of onset. Edema was determined using a plethysmometer volume displacement transducer system (Stoelting Company, Wood Dale, Ill.). Edema was measured pre-carrageenan injection and at 1, 4 and 8 hours post-injection. Rats were exposed to either the PEMF signal or a control, untreated experimental coil configuration for 15 min. EMF exposures were at 0.25, 2, 4 and 8 hours post-injection. The signal consisted of a 2 msec burst of 27.12 MHz sinusoidal waves repeating at 2 bursts/sec, and inducing 20 V/m electric field at a target diameter of 2 cm. This PEMF signal was configured, according to an embodiment of the present invention to accelerate $Ca^{2+}$ binding in a CaM-dependent signaling pathway. Data were analyzed with SigmaStat 3.0 software (SPSS, Chicago, Ill.) using Student's unpaired t-test and one way ANOVA, as appropriate. Differences were also compared using the Mann-Whitney test for two independent groups. Significance was accepted at $P \leq 0.05$.

The results showed mean edema volume in the sham treated animals was 33±7% greater at 1 hour post-injection (P=0.037), 41±8% greater at 4 hours (P=0.005), and 47±9% greater at 8 hours (P=0.009) than edema volume in the PEMF treated animals at these time points. These results, summarized in FIG. 81, demonstrate that a PEMF signal, configured as an embodiment of the present invention, accelerates $Ca^{2+}$ binding to CaM in the NO signaling cascade that regulates lymphatic evacuation of edema from inflammation.

EXAMPLE 4

In this example, groups of rats were subjected to invasive and contusive traumatic brain injury and treated with an EMF signal configured as an embodiment of the present invention consisting of a 27.12 MHz carrier, pulse-modulated with a 3 msec burst repeating at 2 Hz and a peak amplitude of 0.05 G.

Adult male Sprague Dawley rats (350-400 g) were housed in a climate-controlled animal facility with two rats per cage. Food and water were provided ad libitum in a 12-hour light/dark cycle. Animals were maintained, operated on, treated, and euthanized in accordance with federal, state, and IACUC guidelines at the Montefiore Medical Center.

Closed Skull Contusion Injury: Twenty rats (10/group) were subjected to a moderate closed-head injury under anesthesia using the Marmarou impact-acceleration model, with the following modifications. Briefly, rats were anesthetized with ketamine/medetomidine (0.75 mg/0.5 mg/kg, i.p.). After depilation and disinfection, the calvarium was exposed by creating a 1 cm vertical, midline incision through the scalp and displacing the periosteum. To diffuse the impact force and reduce incidence of skull fracture, a metal washer (10 mm diameter, 2 mm thickness) was affixed directly to the skull with epoxy cement midway between the lambda and bregma. Rats were secured directly underneath the weight-drop device on foam bedding (Foam to Size; Ashland, Va.; spring constant=4.0). A diffuse closed-head injury was produced by dropping a 258.7-gram weight in a plexiglass tube from specified heights up to 2 meters, creating forces of impact from 1 to 4 Newtons (4.46N). After impact, the disk was removed from the skull and the periosteum and scalp were approximated with discontinuous nylon sutures. Anesthesia was reversed and animals were either treated with PEMF signals or placed in similar containers in the absence of signals.

The Marmarou weight-drop model was selected for this study partly because it has been found that the levels of 1L-1β closely correlate to the force of the injury in the Marmarou weight-drop model. For example, as shown in FIG. 84, in a previous study, rats were subjected to TBI according to the Marmarou weight-drop model by varying the height from which a 257 g weight was dropped. After six hours, levels of 1L-1β were quantified in brain tissue by ELISA. Points shown on FIG. 84 represent mean values for 3 rats +/−SEM. Data at 0 force was determined from rats receiving sham surgery.

Penetrating Brain Injury: Sixty rats were subjected to bilateral stab injuries to the striatum. Rats were anesthetized with ketamine/medetomidine (0.75 mg/0.5 mg/kg, i.p.) and secured on a stereotaxic frame (David Kopf) with the tooth bar at 3.3 mm below the interaural line. After depilation and disinfection, the calvarium was exposed, as described above, and the separated tissue was secured with hemostats. Two 1 mm burr holes were created by a trephine drill above the striatum at stereotactic coordinates 0.5 mm anterior to and 2.5 mm lateral to Bregma. A 23S gauge blunt-end needle from a Hamilton syringe was inserted 5.2 mm below the dura into each striatum and removed over two minutes. After lesioning, burr holes were sealed with bone wax and the incision site was closed with 4-0, non-absorbable nylon sutures. Rats were reversed from anesthesia with 1 mg/kg medetomidine and placed in containers for PEMF treatment.

PEMF treatment: Animals were exposed to PEMF generated by a sinusoidal 27.12 MHz radiofrequency signal pulse-modulated with 3 millisecond bursts with 0.05 G amplitude, and repeating at 2 Hz beginning immediately after surgery from a coil positioned around a plastic shoebox with a ventilated lid and connected to a PEMF signal generator which automatically provided a signal regimen consisting of signal on for 5 min in every 20 minute time segment for 6 hours. For treatments longer than 6 hours, metal cage inserts were removed, food and hydrogel packs were placed in the cages, and plastic outer cage tops with filters were placed in a larger container equipped with a metal coil around its perimeter on a plastic cart in the animal care facility to avoid signal distortion from surrounding metal.

PEMF signals were delivered externally from a signal generator attached by a wire to the coil. Treatment was administered for 5 minutes every 20 minutes and rats were allowed to move freely in their cages during this time. Identical procedures were followed for the control group, i.e. rats were placed in identical containers in the same room and were fed and handled in an identical manner to rats receiving treatment. Immediately before euthanasia, rats were re-anesthetized and CSF was collected, and after euthanasia, brains were harvested and immediately either fixed in 4% paraformaledhyde or frozen at −80° C. until analysis.

CSF Collection: CSF was obtained utilizing a modification of the Nirogi technique (REF). Briefly, a standard 23 G Vacutainer® Push Button Blood Collection Syringe with 12" (what is the diameter of the hole) tubing (BD) was connected to a 1 cc insulin syringe. Anesthetized rats were positioned on a stereotaxic frame with the tooth bar set to angle the at head 45° in a downward direction. The needle was inserted in an upright position into the medial portion of the cisterna magna until CSF was released into the tubing. Fluid was collected until blood was visible and tubing was clamped with a hemostat to separate clear and blood-tainted CSF. Samples of clear CSF were released into microfuge tubes and cellular material was pelleted by centrifugation (speed and time of centrifuge). Cleared samples were immediately frozen at −80° C.

Tissue Processing: For the weight-drop injury, whole brain hemispheres minus cerebella were frozen. For the penetrating injury, a 5-mm cylinder of brain tissue from the left hemisphere surrounding the stab injury were removed and frozen. The right hemisphere was fixed by immersion in 4% paraformaldehyde for 2 days and stored in 30% sucrose with 0.05% sodium azide.

IL-1β Analysis: Frozen specimens were processed by homogenization using a polytron (model, Manufacturer) in lysis buffer containing tris-buffered saline and centrifuged at 16,000 g for 10 minutes at 4° C. to pellet particulate matter. Supernatants were frozen at −80° C. and triton X-100 was added to a final concentration of 0.1%. IL-1β levels were quantified using a rat IL-1β ELISA duo set (R&D Systems) following manufacturer's recommendations. Results were normalized for protein content determined with the Biorad protein assay.

OX-42 immunohistochemistry: Sixty-micron tissue sections through the striatum were generated using a tissue slicer (Ted Pella) and stored until use in phosphate-buffered saline (150 mM NaCl, 10 mM sodium phosphate, pH 7.4; PBS) with 0.05% sodium azide. For immunostaining, sections belonging to a series consisting of every 2nd-3rd section were permeabilized in 0.25% Trition X-100 in PBS with 3% hydrogen peroxide to extinguish endogenous peroxidase activity. Non-specific binding was blocked with 3% horse serum in PBS with 0.25% Triton X-100 ("block"). Sections were incubated in mouse OX-42 antibody (Serotec; 1:1000) in block overnight at 37° C. After washing in PBS, sections were incubated for 2 hours at 37° C. with biotin anti-mouse in block (Amersham; 1:600). After subsequent washing and 1.5 hours incubation in peroxidase ABC (Vector Laboratories; 1:500), sections were washed and staining was visualized with DAB (Vector). After washing, sections were dehydrated, coverslipped, and photographed at 20× magnification.

Evaluation of microglial activation: OX-42 staining was quantified in a series of every 2-3 sections representing 0.7 mm through the center of the lesion for animals subjected to a penetrating lesion. Initially, the degree of microglial staining in all animals was scored by 4 individuals, where scores (0-5) represented staining intensity and the area occupied by stained cells. Tissue sections from groups that were exposed to PEMF (null) signals for 24 and 48 hours after injury were analyzed further using Image J software. Immuno-stained regions were outlined and areas were measured using a calibrated length. The intensity of immunostaining was quantified by densitometry, defined as an integrated density, calibrated against selected areas from stained tissue sections that represented the entire spectrum of staining.

Statistical Analysis: Data for each group was compared and analyzed for significant differences by Student's t-test and by analysis of variance (ANOVA) followed by Fischer's PLSD test, when more than two groups were compared. Differences between groups generating p-values equal to or less than 0.05 were considered statistically significant.

PEMF treatment reduced levels of IL-1β after contusive TBI. CSF and brain tissue were collected from injured animals in PEMF and control groups as well as from sham and intact animals after 6 hours, when peak IL-1β levels were expected using this injury model. Results demonstrate that intact animals had the lowest levels of IL-1β (29±4 pg/mg protein), which increased 34% in the sham group to 39±7 pg/mg protein. After injury, mean levels of IL-1β in the group that did not receive PEMF treatment was 55±3 pg/mg protein, which was not significantly different from levels of this inflammatory cytokine in animals that received sham surgery. Mean levels of IL-1β in animals that received PEMF treatment were 50±4 pg/mg protein, indicating that there were no significant effects on levels of this peptide in brain homogenates.

Results also demonstrated that levels of IL-1β in CSF changed dramatically in response to both injury and PEMF treatment. Mean levels of this cytokine in CSF from intact animals was 19±7 pg/mL CSF, increasing to 25±21 pg/mL in the sham group (31%). Levels in animals receiving a contusive 3N injury rose to 252±91 pg/mL, a 10-fold increase over the sham group. Moreover, animals receiving PEMF treatment demonstrated significantly lower concentrations (44±25 pg/mL), or levels that were 83% lower than those of animals receiving the injury, and less than twice the mean concentration of IL-1β in animals receiving sham surgery.

Results for PEMF reduced levels of IL-1β after penetrating brain injury: Results illustrating the time course of IL-1β expression demonstrate similarly low levels of IL-1β in brain homogenates from intact and sham animals; 24±5 and 24±6 pg/mg protein, respectively. In addition, two animals from the sham group were treated with PEMF signals for 6 hours before they were euthanized. Animals in this group demonstrated mean IL-1β levels of 15.4 and 16.6 pg/mg protein for PEMF and sham animals respectively, but the number of animals in this group was too low to compare with either intact or sham rats (n=5 and n=2, respectively). At 3.5 hours after injury, IL-10 levels increased approximately 2-fold and attained their highest levels of any time point measured at 6 hours after injury in PEMF treated and control groups at 93±15 and 99±11 pg/mg protein, approximately 4 times basal levels. Importantly, at 17 hours after injury, levels of IL-1β were significantly lower in the PEMF group (42±5 pg/mg protein) than those of the control group (61±5 pg/mg protein; p≤0.04). Control levels decreased and values at later time points were similar in both groups up to 9 days after injury.

In CSF, levels of IL-1β followed a more protracted time course. In intact naive animals, basal levels of IL-1β were 32±32 pg/mL CSF, demonstrating wide and average levels in the sham group were 56±51 and 39±10 pg/mL (control and PEMF-treated, respectively). Levels stayed fairly low at 6 hours after injury, but rose approximately 5-fold to reach a maximum of 224±23 pg/mL at 17 hours after injury, a 7 to 8-fold increase over basal levels, and to a similar degree as IL-1β levels in CSF from animals receiving the closed-skull contusion. In contrast, animals that received PEMF treatment did not exhibit significant increases in IL-1β, which was maintained at approximately basal levels (23±18 pg/mL CSF), or ten-fold lower than rats that received an injury and were not exposed to PEMF signals. Concentrations of IL-1β remained high in the injured control group at 24 hours (122±56 pg/mL), and decreased to baseline levels at 4 to 9 days after injury (31-45 pg/mL), which persisted throughout this period. IL-1β concentrations were lowest in both groups at 9 days (0-2 pg/mL). Taken together, results demonstrate that PEMF treatment suppressed IL-1β levels in CSF throughout a 9-day period after penetrating brain injury.

PEMF treatment increased OX-42 expression after penetrating injury. The CNS responds to focal penetrating injuries by mounting a local inflammatory response. Using the penetrating injury TBI model, the effects of PEMF treatment on microglial activation were examined. Animals received bilateral penetrating injuries and were assigned to PEMF or null treatment groups, where they received continuous treatment until sacrifice at 3.5 hours to 9 days after lesioning. Results demonstrate that OX-42 staining was absent in the area of the lesion at 3.5 and 6 hours. Beginning at 17 hours after injury, OX-42 immunoreactivity was detected increasing in intensity and size over 5 days. At 9 days, the last time point, staining was most intense and appeared more focal, encompassing the lesion itself a compacted surrounding area with a well-defined perimeter. Initially, the extent of staining was analyzed in a semi-quantitative by rating the intensity and area of staining on a scale of 1 to 5 in 0.25 increments by four blinded observers. The overall degree of OX-42 expression, a combination of staining intensity and the area of staining, increased over the 9 days of the experiment.

Significantly, PEMF signals increased the intensity of OX-42 staining at 24 and 48 hours after injury. This increase was transient, as values were higher, but similar to control levels at both 5 and 9 days after injury. The area occupied by OX-42+ cells at 9 days was smaller than at 5 days, indicating that microglia had arrived at their destination. Image analysis was employed to confirm our observations. Areas (mm2) and mean gray values (average value of pixels over the area in which OX-42 staining was found) were measured on Image J for groups of animals receiving PEMF (null) signals for 24 and 48 hours. Interestingly, the area of OX-42 staining at 24 hours after injury significantly decreased in the PEMF-treated animals compared to controls, but in contrast, the mean intensity of OX-42 immunoreactivity was significantly higher, suggesting that PEMF signals accelerated microglial activation and migration. The intensity of OX-42 immunoreactivity increased in both groups at 48 hours after injury, but neither differences in staining intensity nor the area encompassed by microglia were statistically significant. After 5 days, both staining intensity and areas of microglial activation were essentially the same for both groups of animals.

In addition, FIGS. 82A-82C illustrate some results discussed above. In the contusive study, animals were sacrificed and brains homogenized to determine the EMF effect on the master pro-inflammatory cytokine. FIG. 82A shows the results from the contusive study where EMF reduced IL-1β by approximately 10-fold in CSF in treated vs control animals.

In the invasive injury study, brains were collected in intact animals at 0, 3.5, and 6 hours and assayed for levels of 1L-1β by ELISA. Results shown in FIG. 82B demonstrate that IL-1β levels in brain tissue were lower in injured rats treated with PEMF than that of the null group for both models.

Similarly, FIG. 82C shows data from the same study where rats were subjected to bilateral invasive penetrating needle injuries into the striatum. CSF samples were collected under anesthesia from single rats at time specified by the symbols shown in FIG. 82C and analyzed by ELISA. The results suggest that IL-1β appears in CSF 6 hours after invasive trauma and, importantly, levels appear to be suppressed by PEMF treatment.

These results indicate that EMF, configured according to embodiments described, produced a very rapid drop in the inflammatory response to traumatic brain and cervical injury which no other pharmacological or physical modality has been able to achieve. An important factor is that these results were obtained with a portable disposable device which can be incorporated in kits for field response to brain trauma, stroke and other neurological injuries.

EXAMPLE 5

In this example, the effect of a radio frequency EMF signal, configured according to an embodiment of the present invention consisting of a 27.12 MHz carrier, pulse-modulated with a 3 msec burst repeating at 2 Hz and a peak amplitude of 0.05 G, on post-operative pain was studied in a randomized double-blind clinical study on breast reduction patients. Patients were treated with EMF, configured according to an embodiment of the present invention, delivered to the target tissue with a disposable device, similar to that illustrated in FIG. 78B, which was incorporated in the post-surgical dressing.

Treatment regimen for active patients was 30 min every 4 hours for three days. Sham patients received the same EMF device which did not deliver a signal. Wound exudates were collected and pain was assessed by participants using a validated Visual Analog Scale (VAS). Concentrations of IL-1β, a major pro-inflammatory cytokine, were approximately 3-fold lower at 5 hours post-op ($P<0.001$) in wound exudates from EMF-treated patients compared to those of the control group. EMF also produced a concomitant 2-fold decrease in pain at 1 hour ($P<0.01$) and a 2.5-fold decrease at 5 hours post-op ($P<0.001$), persisting to 48 hours post-op. No significant changes in VAS scores were observed in the control group. Furthermore, the increased levels of analgesia were reflected in a 2.2-fold reduction in narcotic use in patients receiving active treatment over the first 24 hours post-op ($P=0.002$). Importantly, the time course for both pain and IL-1β reduction were concomitant, showing that EMF, configured to modulate CaM/NO signaling in an embodiment according to the present invention, produced endogenous changes in the dynamics of IL-10 availability, which impacts the many known subsequent inflammatory events that are mediated by this cytokine, including those leading to post-operative pain. These results, which are illustrated in FIGS. 83A-B, demonstrate that EMF, configured according to an embodiment of the present invention produced a rapid, non-pharmacological, non-invasive post-operative anti-inflammatory response which significantly reduced patient morbidity and the cost of health care, and enhanced healing.

EXAMPLE 6

This example studies PEMF treatment to attenuate post-traumatic edema. PEMF signals, including a radiofrequency signals, have been shown to reduce the edema associated with various types of peripheral tissue injury. For example, in a double-blinded study of human subjects undergoing breast-reduction surgery, post-operative subjects were treated with a PEMF signal consisting of a 27.12 MHz carrier, pulse-modulated with a 3 msec burst repeating at 2

Hz and a peak amplitude of 0.05 G. As shown in FIG. 85, wound exudates were collected for analysis and volumes were measured at regular post-operative intervals. Results demonstrate a 30% reduction in volumes in the first 4 hours after surgery. Asterisks in FIG. 85 indicate lower volumes in the group of post-operative subjects receiving PEMF treatment (*p≤0.03).

With this current example, PEMF signals will be shown to attenuate increases in brain volume, intracranial pressure, and T2-weighted MRI signals. Animals will be subjected to the weight-drop injury and randomly assigned to receive PEMF (or null) signals. Thirty rats will be implanted with a Codman micro-sensor ICP probe (Codman, Raynham, Mass.) at the same time that the scalp is prepared for the weight-drop injury, as described for use in rats by Williams.

Using a stereotactic frame, a burr hole will be made at −4 mm posterior to and 5 mm lateral to Bregma and the probe will be inserted to a depth of 2 mm. Baseline ICP will be monitored 10 minutes before the injury. The protruding part of the probe will be removed during impact. After injury, 2 groups (n=15) will be treated with PEMF or null signals for 5 minutes every 20 minutes for 8 hours and the sham group will be maintained under similar conditions. The PEMF signal configuration used may be a sinusoidal wave at 27.12 MHz with peak magnetic field B=0.05 G (Earth=0.5 G), burst width, T1=5 msec, and repetition rate T2=2/sec as shown in FIG. 86A. The PEMF signal configuration may also induce a 1-5 V/m peak electric field in situ with a duty cycle=2%, without heat or excitable membrane activity produced. The field may be applied through an electrical pulse generator to a coil tuned to 27.12 MHz. The burst width (5 msec) and repetition rate (2 Hz) were chosen by comparing the voltage induced across the $Ca^{2+}$ binding site over a broad frequency range to noise fluctuations over the same range. Effects of burst widths of two 27.12 MHz sinusoidal signals at 1 Hz are illustrated in FIG. 86B. As shown in FIG. 86B, high signal-to-noise ratios (SNRs) can be achieved in the relatively low frequency range and at peak magnetic field 0.05 G.

Animals will be re-anesthetized at 30 minutes, 1 hour, 4 hours, and 8 hours and the probe will be re-inserted for ICP measurement. After the final measurement, animals will be euthanized. ICP of both injury groups will be compared over time with respect to pre- and post-injury values and effects of PEMF (vs. null) to determine the extent and kinetics of ICP for this model and to determine whether PEMF signals can attenuate the magnitude of ICP or protract the rise in ICP over time.

T2-weighted Magnetic Resonance Imaging: Thirty rats will undergo contusive injuries and will be randomly assigned to receive PEMF or null signals (n=15) using a regimen of 5 minutes of treatment every 20 minutes. T2-weighted MRI will be performed at the Gruss Magnetic Resonance Research Center (MRRC) at the Albert Einstein College of Medicine, both before injury and after injury at 3 time points that bracket peak ICP, as established in the pilot experiment (see above). Edema will be calculated using standard MRI algorithms and protocols established at the MRRC. MRI is a validated method of following edema in post injury neurotrauma models. Animals will be transported to the MRRC on a staggered basis. Under isofluorane anesthesia, each animal will be connected to a ventilator and anesthesia will be maintained at 1.5% isofluorane. Ventilation rate will be maintained at 60 breaths/minute, and volume pressure settings will be adjusted to produce stable end-tidal CO2 and regular respiratory movements. Core temperature will be monitored by rectal thermometer and a feedback-controlled water pump will warm the animal while in the MRI cradle. The animal will then be placed into the magnet and imaging data are collected. The animal will then be removed from the magnet, extubated, placed on a feedback-controlled warming pad, and allowed to recover from anesthesia, when it will be returned to its home cage and transported to the Animal Care Facility.

Each T2W slice will be displayed on a workstation and edema will be quantified using the MEDx package after manually outlining areas of signal hyper-intensity that are consistent with edema. Volume will be computed as the sum of area outlined on each slice multiplied by slice thickness. Longitudinal comparison and quantification of edema will allow values for each animal to be compared and normalized to its own baseline. Information from this analysis will include the determination of areas of brain that are most affected by the injury and the ability of PEMF to suppress brain swelling over the period of edema formation. Animals from this study will also be used for $^1$H-MRS imaging.

ICP has been evaluated in response to severe injury in the weight-drop model. Normally, ICP ranges between 5 and 15 mm Hg. A 450 g weight dropped over 2 meters will result in a rise in ICP to 28±3 mm Hg after 30 min, followed by a gradual decline, measured over 4 hours. Based on PEMF-mediated reductions of wound exudate volumes (FIG. 85), the study results are expected to show that PEMF to has immediate effects on reducing edema. Moreover, the ability to obtain whole brain images with T2-weighted MRI will allow us to identify regions of interest in our model that incur the worst injury and follow them over time.

EXAMPLE 7

In one study, a group of rats received neural transplants of dissociated embryonic midbrain neurons and were treated twice a day with PEMF or null signals for 1 week. As shown in FIG. 87, OX-42 labeled activated microglia form a "cuff" surrounding the transplant. Alkaline phosphatase-labeled blood vessels were stained in purple. Results of the microglial staining, shown in FIG. 87, demonstrate that microglial activation was less intense in the PEMF group. This study showed that PEMF may attenuate inflammation in response to transplantation. However, the apparent decrease in microglia may be transitory and that microglial activity may actually be increased/accelerated.

EXAMPLE 8

In this example, rats were subject to penetrating injuries and exposed to PEMF signals according to embodiments described. Brain tissue was processed for OX-42 IHC at specified times after injury to identify activated microglia. As shown in FIG. 88, results demonstrate that the pattern of OX-42 staining in rats that received penetrating injuries was localized to the site of the trauma. Most importantly, staining intensity appears higher with PEMF treatment at 2 and 5 days after injury, indicating activation of microglial cells was accelerated.

EXAMPLE 9

As shown in FIG. 89, neuronal cultures were treated with PEMF signals for 6 days before challenge by (1) reduced serum 1% or (2) 5 µM quisqualic acid, a non-NMDA glutamate receptor agonist. Dopaminergic neurons were identified by tyrosine hydroxylase immunocytochemistry and quantified at 8 days. The bars shown in FIG. 89 indicate mean neuronal numbers (+/−SEM) in triplicate cultures. Asterisk denotes groups with significant differences from the null group (P<0.05). Results indicate that PEMF signals according to embodiments describe provide neuroprotective treatment to prevent neural death.

EXAMPLE 10

This example will study the ability of PEMF signals to prevent neural death. Animals will be subjected to contusive (weight-drop) TBI. Eighty rats will be randomly assigned to PEMF or null groups and treated for 5 minutes every 20 minutes. A group of rats receiving sham surgery will serve as controls. At 1, 2, 5 and 10 days and after injury, CSF will be collected from 10 animals from each treatment group immediately prior to euthanasia, at which time blood will be collected peri-mortem. Brains will be fixed, cryoprotected, 50 µm vibratome sections will be generated through the cerebrum from approximately −7 to +4 mm with respect to Bregma on the anteroposterior axis. Multiple series of every 6th section will be prepared for analyses described below.

Tissue Necrosis: The overall extent of tissue damage will be assessed on a series of sections after hematoxylin and eosin (H&E) histochemistry, first qualitatively, by observations of astrocytic, neuronal, or dendritic swelling, pyknotic nuclei, and necrosis and then quantitatively, by measuring the area abnormal histology. Regions of damaged tissue will be captured by digital photography and the volume will be assessed by outlining the perimeter using Image J software, calculating the area with calibrated markers, and multiplying by section thickness. Histological abnormalities, as described above, will be quantified within a specified volume of these regions. Data from each group will be compared to determine whether PEMF signals reduce the volume of tissue damage and numbers of cells with abnormal morphology.

Neuronal Injury: Proton Magnetic Resonance Spectroscopy: This study will be conducted on the same animals that will be used for T2-MRI studies (see Example 6), as they will provide information on regions of interest, and to avoid duplications of time and costs associated with live-animal studies. Based on information obtained from T2-weighted MRI (see Example 6), several regions of interest (ROI), defined by anatomical landmarks and changes on T2 maps, will be selected and further analyzed. Studies by other groups suggest that both cortical and hippocampal regions may be the most vulnerable to the injury made in the weight-drop model. Afterwards, computerized graphical analysis of specific, localized spectra in the ROIs will be utilized to determine resonance corresponding to NAA, Cr, Cho, lactate and taurine. Quantitative analysis of the spectroscopic metabolite ratios will be compared among the pre-injury, TBI null, and TBI PEMF groups to determine changes in concentrations of these biochemical markers.

Neuronal Death: Fluoro-Jade staining: Fluoro-jade stain is a fluorochrome derived from fluorescein and is commonly used to label degenerating neurons including neurons injured from TBI as an alternative to other methods, such as silver and Nissl stains. Fluoro-jade stained tissue can be visualized with epifluorescence using filters designed for fluorescein or fluorescein isothiocynate (excitation 495 nm; emission 521 nm). Multiple morphological features can be detected using fluoro-jade including; cell bodies, dendrites, axons, and axon terminals. Even though all fluoro-jade derivatives can detect these specific morphological features, fluoro-jade C has greater specificity and resolution. A series of every 6th serial section will be processed stained with fluoro-jade-C to identify dying neurons. Sections will be dehydrated in ethanol and rinsed in distilled water, followed by oxidation in 0.06% potassium permanganate for 15 minutes, followed by several water washes. Sections will then be placed in 0.1% acetic acid containing 0.001% fluoro-jade C (Millipore) for 1 hour at room temperature. After washing, sections will be dehydrated, cleared and coverslipped for viewing. Areas demonstrating the greatest generalized damage by H&E will be assessed for neuronal damage. Neurons within a defined anatomical structure can be quantified on a series of sections by stereological analysis (i.e. optical dissector) using Neurolucida software (Microbrightfield).

Data from PEMF-treated and null groups will be compared. UCH-L1: Ubiquitin C-terminal hydrolase-L1 (UCH-L1), a neuron-specific protein (also called protein gene product 9.5 or Park 5) involved in protein degradation via the ATP-dependent proteosomal pathway, is abundant in neuronal cell bodies. Mice bearing a spontaneous mutation in this gene demonstrate behavioral disturbances and neuronal loss, and mutations in humans are associated with Parkinson's disease, supporting a sustaining role for this protein in neurons. Importantly, UCL-L1 was identified in a proteomic screen of CSF as a biomarker for neuronal injury. Studies have shown that UCH-L1 is released following severe cortical impact injury and ischemia. This marker has recently gained attention in the general press as a potential CSF marker for brain injury in humans. Therefore, we will evaluate the effects of PEMF on UCH-L1 in CSF, and we will also assess levels in blood, as they can easily be obtained before euthanasia. Although not commercially available, we will devise an ELISA to quantify UCH-L1 using chicken and rabbit UCH-L1 polyclonal antibodies (Cell Signaling and Thermo Scientific, respectively), as described by others. Plates will be coated with anti-UCH-LI, followed by washing and aliquots of CSF, or blood. Protein will be identified with HRP-anti UCH-L1 and a soluble substrate for peroxidase. Western blots for UCH-L1 (a 24 kD protein) will be run with selected samples to validate ELISA data. Levels of UCH-L1 should be inversely proportional to the extent of neuronal death.

Axonal Injury: A series of sections from injured animals in PEMF and null groups and sham controls will be processed for silver staining with this method. Briefly, mounted tissue sections are pre-incubated in an alcoholic solution containing silver and copper nitrates, washed in acetone, and impregnated in silver nitrate with lithium and ammonium hydroxides, followed by reduction in formalin, citric acid and ethanol. After acidification, bleaching, and fixation, slides will be coverslipped for viewing. Tissue sections will be processed commercially (Neuroscience Associates, Knoxville, Tenn.), as this technique requires a number of hazardous solutions that require special processing and disposal. Silver-impregnated, degenerating neurons and processes will stain black, progressing to a Golgi-like intensity. More lightly stained terminals and lysosomes may only be apparent at earlier time points, as these structures often degenerate prior to axonal loss. For quantification of degeneration, images will be digitized and the density of optical staining over an assigned area of cortex will be quantified by densitometry with Image J Software. This method has been validated by others.

Predicted Results: The time course of pathological events following TBI are the direct destruction of tissue (including neurons) if the injury is invasive, followed by edema, inflammation, axonal injury, and subsequently delayed neuronal death. The Marmarou weight-drop method induces all of these events in a more protracted fashion. Cell culture experiments indicate that neuronal survival is increased with PEMF directly in response to an excitotoxic insult, suggesting that neurotoxicity due to ischemia and subsequent release of glutamate may also be attenuated by PEMF signals in vivo. Because brain swelling and inflammation result in indirect neurotoxicity, increased survival by PEMF is also predicted for this pathway. Positive results will confirm that treatment with PEMF signals can be used to attenuate the damage caused by traumatic, closed head injury and may have therapeutic implications for other types of TBI as well as more acute and chronic neurodegenerative diseases, such as stroke, Alzheimer's disease, and Parkinson's disease where many of these same mechanisms are known to be involved.

EXAMPLE 11

In this example, rats will be subjected to the Marmarou weight-drop TBI model to produce moderate behavioral deficits. Individual naive animals will be subjected to general assessments and sensorimotor behavioral testing. Those animals whose behavior falls in the normal range will receive moderate TBI using the weight-drop model and will be randomly assigned to receive PEMF or null signals using the regimen of 5 minutes every 20 minutes. At 1, 2, 7, 14, and 21 days after injury, animals will be re-assessed for general behaviors and neurological function to quantify the magnitude of these basic deficits. At 1 month after surgery, animals will be transported to the Bronx VA for long-term cognitive testing. After acclimation to the VA animal holding facility (2 weeks), testing will take place over 8 weeks for each animal by the same technician.

Rats will first be evaluated for general health and spontaneous and elicited behavior. These basic observations will be supplemented with an assessment of motor, sensory and general activity level using rotarod, grip strength, balance beam, and tail-flick analgesia tasks to determine whether the injury has affected the general health status and overt behavioral profile of the rat in a way that would make its general behavior incompatible with more complex behavioral assays. Moreover, if specific deficits are identified in the basic screen, we may be able to alter the choice of more complex behavioral assays to account for the deficit. We will then proceed to more detailed testing. Rats will be observed in an open field assay to assess both general motor activity and anxiety related behavior, and an elevated plus maze as an additional indicator of anxiety related behavior. In the cognitive domain we will administer at least three tests designed to measure learning and memory related functions: 1) the Morris water maze, a standard test of hippocampal dependent spatial memory 2) a test of contextual and cued fear conditioning, which is highly dependent on amygdaloid function and requires a set of motor and sensory abilities distinct from those required for spatial navigation, and 3) a Y-maze task, a test of working memory. We will also measure response to acoustic startle and pre-pulse inhibition as measures of auditory function and sensory gating, physiological functions that can be affected in TBI.

Order of testing and timetable: Carryover effects can significantly confound behavioral testing in rodents. The testing order will be as described except that the cued fear conditioning and Morris water maze tests will be performed last in the sequence, as these include the most demanding and stressful tasks. Based on our prior experience in rodent behavioral work, testing will require: Basic screen (SHIRPA) (7 days), Rotarod (2 days), Grip strength (1 day), Tail flick (1 day), open field (3 days), elevated plus maze (2 days), Morris water maze (4 weeks), contextual/cued fear conditioning (2 days), Y-maze (2 days) and acoustic startle/PPI (2 days) or approximately 8 weeks of testing.

Data analysis: Data will be analyzed using GraphPad Prism 5.0 (GraphPad Software, San Diego, Calif.) or SPSS 18.0 (SPSS, Chicago, Ill.) software as in previous studies. Depending on the behavioral test, statistics will employ univariate or repeated measures analysis of variance (ANOVA), unpaired t-tests or linear regression. Equality of variance will be assessed using the Levene test and when it is not significant ($p>0.05$) between-group comparisons will be made with unpaired t-tests (Student's) or Tukey post-hoc tests. If the Levene statistic is significant ($p<0.05$) unpaired t-tests will be used using the Welch correction for unequal variances. For repeated-measures ANOVA, sphericity will be assessed using Mauchly's test. If the assumption of sphericity is violated ($p<0.05$, Mauchly's test), significance will be determined using the Greenhouse-Geisser correction.

Predicted Results: Data from PEMF and null groups will be compared with naive animals to determine the degree of deficit and with each other to determine whether PEMF signals improve neurological function. It is expected that PEMF treatment will show a decrease in the degree of initial deficits and/or accelerate or enhance the degree of recovery.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A method for treating a neurological injury or condition caused by a stroke in a patient in need thereof, the method comprising:
   providing a treatment apparatus including
      a signal generator connected to a circular wire applicator having a diameter that allows encircling the patient's head, and
      a sensor configured to detect the patient's intracranial pressure;
   placing the circular wire applicator over and around the patient's head and in proximity to a target region for treatment through the patient's skull;
   activating the signal generator to generate a pulsed electromagnetic field in the circular wire applicator, wherein the pulsed electromagnetic field comprises a burst of between 15-40 MHz, wherein the burst repeats at between 0.01 and 100 Hz; and
   reducing the patient's intracranial pressure by applying the pulsed electromagnetic field until the sensor detects that the patient's intracranial pressure has been reduced to a desired level.

2. The method of claim 1, wherein the desired level is below about 20 mmHg.

3. The method of claim 1, wherein the burst comprises a 2 msec burst of 27.12 MHz sinusoidal waves repeating at 2 Hz.

4. The method of claim 1, wherein the burst comprises a 3 msec burst of 27.12 MHz sinusoidal waves repeating at 2 Hz.

5. The method of claim 1, wherein the burst comprises a 4 msec burst of 27.12 MHz sinusoidal waves repeating at 2 Hz.

6. The method of claim 1, wherein the burst comprises about a 1 msec to about a 10 msec burst of 27.12 MHz sinusoidal waves repeating at about 1 Hz to about 10 Hz.

7. The method of claim 1, wherein the pulsed electromagnetic field burst comprises an ISM carrier frequency modulated at about a 1 msec to about a 10 msec burst repeating at about 1 Hz to about 10 Hz.

8. The method of claim 1, wherein the pulsed electromagnetic field comprises a waveform that modulates at least one biological signaling pathway.

9. The method of claim 1, wherein the target region is a brain of the patient.

* * * * *